(12) United States Patent
Stolz-Dunn et al.

(10) Patent No.: US 7,332,607 B2
(45) Date of Patent: *Feb. 19, 2008

(54) PROCESSES FOR THE PREPARATION OF (R)-α-(2,3-DIMETHOXYPHENYL)-1-[2-(4-FLUOROPHENYL)ETHYL]-4-PIPERIDINEMETHANOL

(75) Inventors: Sandra K. Stolz-Dunn, Midland, MI (US); Jonathan Evans, Midland, MI (US); Ian A. Tomlinson, Midland, MI (US)

(73) Assignees: Aventis Holdings Inc., Bridgewater, NJ (US); Sanofi Aventis Deutschland GmbH, Frankfurt am Main (DE)

( * ) Notice: Subject to any disclaimer, the term of this patent is extended or adjusted under 35 U.S.C. 154(b) by 595 days.

This patent is subject to a terminal disclaimer.

(21) Appl. No.: 10/840,586

(22) Filed: May 6, 2004

(65) Prior Publication Data

US 2005/0010051 A1    Jan. 13, 2005

Related U.S. Application Data

(60) Continuation of application No. 10/757,113, filed on Jan. 14, 2004, now abandoned, which is a division of application No. 10/043,498, filed on Jan. 11, 2002, now Pat. No. 6,713,627, which is a division of application No. 09/670,005, filed on Sep. 25, 2000, now abandoned, which is a continuation of application No. 09/266,471, filed on Mar. 11, 1999, now abandoned.

(60) Provisional application No. 60/266,298, filed on Feb. 16, 1999, provisional application No. 60/155,197, filed on Mar. 13, 1998.

(51) Int. Cl.
*C07C 211/22* (2006.01)

(52) U.S. Cl. ...................... 546/225; 546/314

(58) Field of Classification Search ............ 546/225, 546/314

See application file for complete search history.

(56) References Cited

U.S. PATENT DOCUMENTS

| | | | |
|---|---|---|---|
| 3,580,923 A | 5/1971 | Leigh et al. | |
| 3,608,063 A | 9/1971 | Banker | |
| 4,757,076 A | 7/1988 | Hirsch et al. | |
| 4,783,471 A | 11/1988 | Carr et al. | |
| 4,839,353 A | 6/1989 | Hosoi et al. | |

(Continued)

FOREIGN PATENT DOCUMENTS

EP    0208235    1/1987

(Continued)

OTHER PUBLICATIONS

Greene "Protective groups in Organic Synthesis" (1982) p. 10-11.*

Chi-Hsin R. King et al., Immobilization of Substrates in Enzyme-Catalyzed Hydrolysis, Tetrahedron: Asymmetry vol. 4, No. 5 pp. 943-946 1993.

Doepke, W. Schwertner et al., The resolution of racemates of the .beta. -receptor blocking agent propranolol, Chem. pp. 673-675 vol. 45 (9).

Efange, S.M.N. et al., Flexible N-Methyl-4-phenyl-1,2,3,6-tetrahydropyridine Analogues; Synthesis and Monoamine Oxidase Catalyzed Bioactivation, J. Med. Chem. pp. 3133-3138, vol. 33, 1990.

(Continued)

*Primary Examiner*—Celia Chang
(74) *Attorney, Agent, or Firm*—Balaram Gupta

(57) ABSTRACT

The present invention provides various processes for the preparation of (R)-α-(2,3-dimethoxyphenyl)-1-[2-(4-fluorophenyl)ethyl]-4-piperidinemethanol. These processes may be characterized by the following scheme:

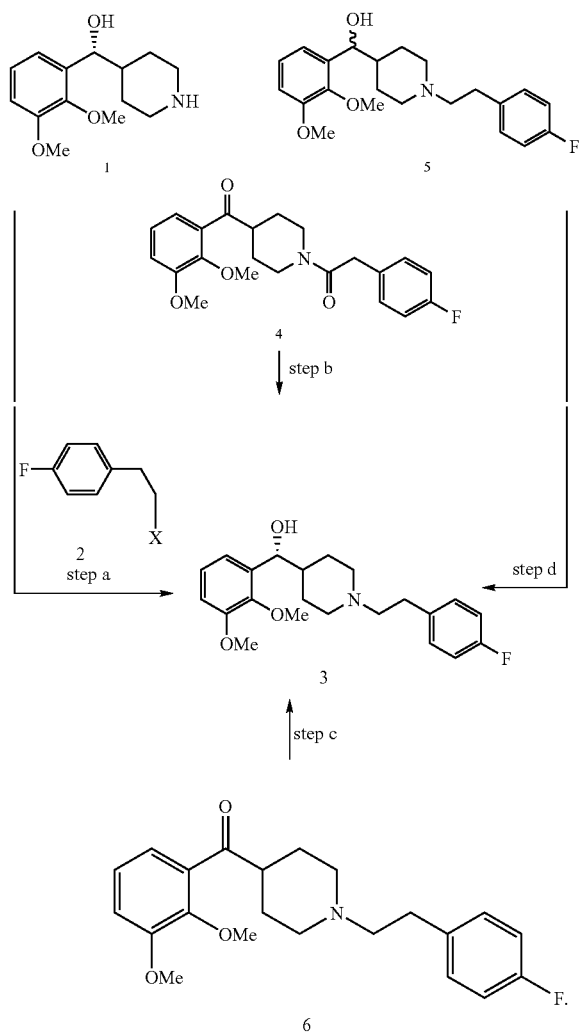

2 Claims, No Drawings

U.S. PATENT DOCUMENTS

| | | | |
|---|---|---|---|
| 4,877,798 | A | 10/1989 | Sorensen |
| 4,908,369 | A | 3/1990 | Schechter et al. |
| 4,912,117 | A | 3/1990 | Carr et al. |
| 4,990,511 | A | 2/1991 | Nakajima et al. |
| 5,021,428 | A | 6/1991 | Carr et al. |
| 5,064,838 | A | 11/1991 | Carr et al. |
| 5,106,855 | A | 4/1992 | McLees |
| 5,134,149 | A | 7/1992 | Carr et al. |
| 5,169,096 | A | 12/1992 | Carr et al. |
| 5,227,526 | A | 7/1993 | Duchek |
| 5,338,742 | A | 8/1994 | Hackler et al. |
| 5,478,846 | A | 12/1995 | Carr et al. |
| 5,541,201 | A | 7/1996 | Carr et al. |
| 5,561,144 | A | 10/1996 | Carr et al. |
| 5,618,824 | A | 4/1997 | Schmidt et al. |
| 5,635,510 | A | 6/1997 | Brukholder et al. |
| 5,700,812 | A | 12/1997 | Carr et al. |
| 5,700,813 | A | 12/1997 | Carr et al. |
| 5,721,249 | A | 2/1998 | Carr et al. |
| 6,716,986 | B2 * | 4/2004 | Bernotas et al. ............ 546/240 |

FOREIGN PATENT DOCUMENTS

| | | |
|---|---|---|
| EP | 0264883 | 4/1988 |
| EP | 0319962 | 6/1989 |
| EP | 0337136 | 10/1989 |
| EP | 0706795 | 4/1996 |
| EP | 0742207 | 11/1996 |
| EP | 0838448 | 4/1998 |
| FR | 2350341 | 12/1977 |
| JP | 394255 | 4/1994 |
| WO | WO 91/18602 | 12/1991 |
| WO | WO 91/18603 | 12/1991 |
| WO | WO 93/04579 | 3/1993 |
| WO | WO 94/12461 | 6/1994 |
| WO | WO 95/24194 | 9/1995 |
| WO | WO 97/19074 | 5/1997 |
| WO | WO 97/34603 | 9/1997 |

OTHER PUBLICATIONS

Herbert A. Lieberman et al., Pharmaceutical Dosage Forms, Marcel Dekker, Inc. 1989 vol. 2.

Jounela A.J. et al., Effect of Particle Size on The Bioavailability of Digoxin , Eur. J. Clin. Pharmacol. 1975, 8/5 365-370.

Paul J. Gilligan et al., Novel Piperidine o Receptor Ligands as Potential Antipsychotic Drugs, J. Med. Chem. 1992, vol. 35, pp. 4344-4361.

Sauter, Fritz, Synthese Substituierter Pheny-pyridinyl- und Phenyl-pyrimidinyl-methanone, J. Chem. Research, pp. 2001-2009.

Timothy P. Burkholder et al., Identification and Chemical Synthesis of MDL 105,212, a Non-Peptide Tachykinin Antagonist with High Affinity for NK1 and NK2 Receptors, Bioorganic & Medicinal Chemistry Letters, vol. 6, No. 8, pp. 951-956 1996.

Villari A. et al., Methods for the Particle-Size Analysis of Pharmaceutical Powders I, Journal Farm Ed Prat vol. 42, Issue 10, year 1987 pp. 253-260.

Matsumura M. et al., Computer Optimization for the Formulation of Controlled Release Theophylline Tablet Made of Micronized Low-substituted Hydroxypropylcellulose and Methylcellulose, Chemical & Pharmaceutical Bulletin, vol. 42, Issue 9 , 1999, pp. 1902-1908.

* cited by examiner

PROCESSES FOR THE PREPARATION OF (R)-α-(2,3-DIMETHOXYPHENYL)-1-[2-(4-FLUOROPHENYL)ETHYL]-4-PIPERIDINEMETHANOL

CROSS REFERENCE TO RELATED CASES

This application is a continuation of U.S. application Ser. No. 10/757,113 filed Jan. 14, 2004 now abandoned, which is a divisional of U.S. application Ser. No. 10/043,498 filed Jan. 11, 2002, now U.S. Pat. No. 6,713,627, issued Mar. 30, 2004, which is a divisional of U.S. application Ser. No. 09/670,005, filed, Sep. 25, 2000, now abandoned, which is a continuation of U.S. application Ser. No. 09/266,471, filed Mar. 11, 1999, now abandoned, which claims the benefit of U.S. Provisional Application No. 60/266,298, filed, Feb. 16, 1999 and U.S. Provisional Application No. 60/155,197, filed, Mar. 13, 1998.

FIELD OF THE INVENTION

The present invention is directed toward novel processes for the preparation of (R)-α-(2,3-dimethoxyphenyl)-1-[2-(4-fluorophenyl)ethyl]-4-piperidinemethanol.

BACKGROUND OF THE INVENTION

α-(2,3-Dimethoxyphenyl)-1-[2-(4-fluorophenyl)ethyl]-4-piperidinemethanol has been generically described in U.S. Pat. No. 5,169,096, issued Dec. 8, 1992, the disclosure of which is hereby incorporated by reference. (R)-α-(2,3-dimethoxyphenyl)-1-[2-(4-fluorophenyl)ethyl]-4-piperidinemethanol was thereafter described in U.S. Pat. No. 5,134,149, issued Jul. 28, 1992, the disclosure of which is hereby incorporated by reference. U.S. Pat. No. 5,700,813, issued Dec. 23, 1997, U.S. Pat. No. 5,700,812, issued Dec. 23, 1997, and U.S. Pat. No. 5.561,144, issued Oct. 1, 1996, the disclosure of each which is hereby incorporated by reference, describe the use of (R)-α-(2,3-dimethoxyphenyl)-1-[2-(4-fluorophenyl)ethyl]-4-piperidinemethanol as $5HT_2$ receptor antagonists in the treatment of a number of disease states, including schizophrenia, anxiety, variant angina, anorexia nervosa, Raynaud's phenomenon, intermittent claudication, coronary or peripheral vasospasms, fibromyalgia, cardiac arrhythmia's, thrombotic illness and in controlling the extrapyramidal symptoms associated with neuroleptic therapy.

The preparation of (R)-α-(2,3-dimethoxyphenyl)-1-[2-(4-fluorophenyl)ethyl]-4-piperidinemethanol reported previously involved the esterification of α-(2,3-dimethoxyphenyl)-1-[2-(4-fluorophenyl)ethyl]-4-piperidinemethanol with the (+)-isomer of α-methoxyphenylacetic acid to produce a diastereomeric mixture. The diastereomers were then separated by chromatography and the (+,+)-diastereomer hydrolyzed to give (R)-α-(2,3-dimethoxyphenyl)-1-[2-(4-fluorophenyl)ethyl]-4-piperidinemethanol.

SUMMARY OF THE INVENTION

The present invention provides various processes for the preparation of (R)-α-(2,3-dimethoxyphenyl)-1-[2-(4-fluorophenyl)ethyl]-4-piperidinemethanol (3).

Thus, in one embodiment, there is provided a process for preparing (R)-α-(2,3-dimethoxyphenyl)-1-[2-(4-fluorophenyl)ethyl]-4-piperidinemethanol (3) comprising reacting (R)-α-(2,3-dimethoxyphenyl)-4-piperidinemethanol (1) with a suitable 4-fluorophenylethyl alkylating agent of the structure:

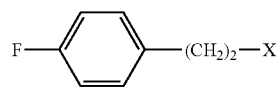

(2)

wherein X is halide or methanesulfonate.

In another embodiment of the present invention there is provided a process for preparing (R)-α-(2,3-dimethoxyphenyl)-1-[2-(4-fluorophenyl)ethyl]-4-piperidinemethanol (3) comprising reacting 4-[1-oxo-1-(2,3-dimethoxyphenyl)methyl]-N-2-(4-fluorophen-1-oxo -ethyl)piperidine (4) with a suitable chiral reducing agent, such as (+)-β-chlorodiisopinocamphenylborane.

In yet another embodiment, there is provided a process for preparing (R)-α-(2,3-dimethoxyphenyl)-1-[2-(4-fluorophenyl)ethyl]-4-piperidinemethanol (3) comprising reacting 4-[1-oxo-1-(2,3-dimethoxyphenyl)methyl]-N-2-(4-fluorophenylethyl)piperidine (6) with a suitable chiral reducing agent, such as (+)-β-chlorodiisopinocamphenylborane.

In yet another embodiment of the present invention, there is provided a process for preparing (R)-α-(2,3-dimethoxyphenyl)-1-[2-(4-fluorophenyl)ethyl]-4-piperidinemethanol (3) comprising the steps of: a) reacting α-(2,3-dimethoxyphenyl)-1-[2-(4-fluorophenyl)ethyl]-4-piperidinemethanol (5) with (2S,3S)-(+)-di-(p-anisoyl)tartaric acid to give a racemic mixture of (R)-α-(2,3-dimethoxyphenyl)-1-[2-(4-fluorophenyl)ethyl]-4-piperidinemethanol, (2S,3S) -(+)-di-(p-anisoyl)tartaric acid salt (3a) and (S)-α-(2,3-dimethoxyphenyl)-1-[2-(4-fluorophenyl)ethyl]-4-piperidinemethanol, (2S,3S)-(+)-di-(p-anisoyl)tartaric acid salt (3b); b) separating the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) from the (S)-α-(2,3-dimethoxyphenyl)-1-[2-(4-fluorophenyl)ethyl]-4-piperidinemethanol, (2S,3S)-(+)-di-(p -anisoyl)tartaric acid salt (3b) by selective crystallization; and c) reacting the (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a) with a suitable base, extracting with a suitable solvent and isolating in the usual manner to give (R)-α-(2,3-dimethoxyphenyl)-1-[2-(4-fluorophenyl)ethyl]-4-piperidinemethanol (3).

In still another embodiment of the present invention, there is provided a process for preparing (R)-α-(2,3-dimethoxyphenyl)-1-[2-(4-fluorophenyl)ethyl]-4-piperidinemethanol (3) comprising the steps of: a) subjecting α-(2,3-dimethoxyphenyl)-1-[2-(4-fluorophenyl)ethyl]-4-piperidinemethanol, butyrate ester (5a) to a selective enzymatic hydrolysis, using for example lipase of *Candida cylindracea*, to provide a mixture of (R)-α-(2,3-dimethoxyphenyl)-1-[2-(4-fluorophenyl)ethyl]-4-piperidinemethanol (3) and (S)-α-(2,3-dimethoxyphenyl)-1-[2-(4-fluorophenyl)ethyl]-4-piperidinemethanol, butyrate ester (5b); and b) separating the (R)-α-(2,3-dimethoxyphenyl)-1-[2-(4-fluorophenyl)ethyl]-4-piperidinemethanol (3) from the (S)-α-(2,3-dimethoxyphenyl)-1-[2-(4-fluorophenyl)ethyl]-4-piperidinemethanol, butyrate ester (5b).

In yet another embodiment, there is provided a process for preparing (R)-α-(2,3-dimethoxyphenyl)-1-[2-(4-fluorophenyl)ethyl]-4-piperidinemethanol (3) comprising using ethyl N-(4-fluorophenylthioacetyl)-4-carboxylpiperidine (24).

In yet still another embodiment, there is provided a process for preparing (R)-α-(2,3-dimethoxyphenyl)-1-[2-(4- fluorophenyl)ethyl]-4-piperidinemethanol (3) comprising using N -4-fluorophenylacetyl)-4-carboxylpiperidine (21).

In yet another embodiment, there is provided a process for preparing (R)-α-(2,3-dimethoxyphenyl)-1-[2-(4-fluorophenyl)ethyl]-4-piperidinemethanol (3) comprising using 1-(4-carboethoxypiperidine)-2-(4-fluorophenyl)ethane (25).

In yet another embodiment, there is provided a process for preparing (R)-α-(2,3-dimethoxyphenyl)-1-[2-(4-fluorophenyl)ethyl]-4-piperidinemethanol (3) comprising the steps of: a) reacting lithiated veratrole with 4-pyridinecarboxaldehyde (9) in the presence of a suitable aprotic solvent to provide 4-[1-hydroxy-1-(2,3-dimethoxyphenyl)methyl]pyridine (10); b) subjecting 4-[1-hydroxy-1-(2,3-dimethoxyphenyl)methyl]pyridine (10) to catalytic hydrogenation to provide 4-[1-hydroxy-1-(2,3-dimethoxyphenyl)methyl]piperidine (11); c) reacting 4-[1-hydroxy-1-(2,3-dimethoxyphenyl)methyl]piperidine (11) with a suitable 4-fluorophenylacetylating reagent, in the presence of a suitable base and a suitable solvent to provide 4-[1-hydroxy-1-(2,3-dimethoxyphenyl)methyl]-N-2-(4-fluorophen-1-oxo-ethyl)piperidine (20); d) reacting 4-[1-hydroxy-1-(2,3-dimethoxyphenyl)methyl]-N-2-(4-fluorophen-1-oxo-ethyl)piperidine (20) with a suitable reducing agent in the presence of a suitable solvent to provide α-(2,3-dimethoxyphenyl)-1-[2-(4-fluorophenyl)ethyl]-4-piperidinemethanol (5); e) reacting α-(2,3-dimethoxyphenyl)-1-[2-(4-fluorophenyl)ethyl]-4-piperidinemethanol (5) with (2S,3S)-(+)-di-(p-anisoyl)tartaric acid to give a racemic mixture of (R)-α-(2,3-dimethoxyphenyl)-1-[2-(4-fluorophenyl)ethyl]-4-piperidinemethanol, (2S,3S)-(+) -di-(p-anisoyl)tartaric acid salt (3a) and (S)-α-(2,3-dimethoxyphenyl)-1-[2-(4-fluorophenyl)ethyl]-4-piperidinemethanol, (2S,3S)-(+)-di-(p-anisoyl)tartaric acid salt (3b); f) separating the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3b) from the (S)-α-(2,3-dimethoxyphenyl)-1-[2-(4-fluorophenyl)ethyl]-4-piperidinemethanol, (2S,3S)-(+)-di-(p -anisoyl)tartaric acid salt (3a) by selective crystallization; and g) reacting the (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a) with a suitable base to give (R)-α-(2,3-dimethoxyphenyl)-1-[2-(4-fluorophenyl)ethyl]-4-piperidinemethanol (3).

Another embodiment of the present invention provides (R)-α-(2,3-dimethoxyphenyl)-1-[2-(4-fluorophenyl)ethyl]-4-piperidinemethanol (3) having a particle size range of approximately 25 μm to approximately 250 μm and a process for preparing same comprising: a) in one vessel, using from approximately 4% to approximately 20% of the (R)-α-(2,3-dimethoxyphenyl)-1-[2-(4-fluorophenyl)ethyl]-4-piperidinemethanol (3) to be crystallized, producing a saturated solution of (R)-α-(2,3-dimethoxyphenyl)-1-[2-(4-fluorophenyl)ethyl]-4-piperidinemethanol (3) containing seed crystals of (R)-α-(2,3-dimethoxyphenyl)-1-[2-(4-fluorophenyl)ethyl]-4-piperidinemethanol (3) as seed crystals and; b) in another vessel, producing a solution of the remaining (R)-α-(2,3-dimethoxyphenyl)-1-[2-(4-fluorophenyl)ethyl]-4-piperidinemethanol (3) by dissolving the (R)-α-(2,3-dimethoxyphenyl)-1-[2-(4-fluorophenyl)ethyl]-4-piperidinemethanol (3) in a solvent wherein the (R)-α-(2,3-dimethoxyphenyl)-1-[2-(4-fluorophenyl)ethyl]-4-piperidinemethanol (3) exhibits a high degree of solubility at moderate temperature (i.e., temperatures from about 35° C. to about 75° C.) such that the solvent will produce a supersaturated solution when combined with the seed crystals present in the solution formed in step a; c) adding the solution formed in step b) to the solution formed in step a) while adjusting the solvent composition by the addition of a suitable antisolvent to maintain an acceptable yield by minimizing solubility at the isolation temperature; and d) allowing the (R)-α-(2,3-dimethoxyphenyl)-1-[2-(4-fluorophenyl)ethyl]-4-piperidinemethanol (3) in solution to crystallize on the seed crystals.

Also encompassed by the present invention are certain novel intermediates useful in the preparation of (R)-α-(2,3-dimethoxyphenyl)-1-[2-(4-fluorophenyl)ethyl]-4-piperidinemethanol (3), which are: (R)-α-(2,3-dimethoxyphenyl)-4-piperidinemethanol (1); 4-[1-oxo-1-(2,3-dimethoxyphenyl)methyl]-N-2-(4-fluorophen-1-oxo-ethyl) piperidine (4); 3)(R) -α-(2,3-dimethoxyphenyl)-1-[2-(4-fluorophenyl)ethyl]-4-piperidinemethanol, (2S,3S)-(+)-di -(p-anisoyl)tartaric acid salt (3a); 4) 4-[1-hydroxy-1-(2,3-dimethoxyphenyl)methyl]pyridine (10); 5) 4-(2,3-dimethoxybenzoyl)pyridine (12); and 6) 4-[1-hydroxy-1-(2, 3-dimethoxyphenyl)methyl]-N-2-(4-fluorophen-1-oxo-ethyl)piperidine (20).

Also provided in the present invention are certain novel processes to prepare various intermediates useful in the preparation of (R)-α-(2,3-dimethoxyphenyl)-1-[2-(4-fluorophenyl)ethyl]-4-piperidinemethanol (3). For example, there is provided a process for preparing 4-[1-hydroxy-1-(2,3-dimethoxyphenyl)methyl]piperidine (11) comprising subjecting 4-[1-hydroxy-1-(2,3-dimethoxyphenyl)methyl] pyridine (10) to catalytic hydrogenation using a suitable catalyst, such as rhodium on carbon. There is provided a process for preparing (R)-4-(1-hydroxy-1-(2,3-dimethoxyphenyl)-1-piperidinecarboxylic acid, 1,1-dimethylethyl ester (8) comprising reacting 4-(2,3-dimethoxybenzoyl)-1-piperidinecarboxylic acid, 1-1-dimethyl ethyl ester (7) with a suitable chiral reducing agent, such as (+)-β-chlorodiisopinocamphenylborane or potassium 9-O-(1,2-isopropylidine-5-deoxy-α-D-xylofuranosyl-9-borabicyclo[3.3.1] nonane. Also provided is a process for preparing (R)-α-(2, 3-dimethoxyphenyl)-4-piperidinemethanol (1) comprising the steps of: a) reacting 4-[1-hydroxy-1-(2,3-dimethoxyphenyl)methyl]piperidine (11) with a suitable chiral acid, such as (2R,3R) -(–)-di-(p-toluoyl)tartaric acid or (2R,3R)-(–)-di-(p-anisoyl)tartaric acid, to give a racemic mixture of (R)-4-[1-hydroxy-1-(2,3-dimethoxyphenyl)methyl]piperidine, chiral acid salt and (S)-4-[1-hydroxy-1-(2,3-dimethoxyphenyl)methyl]piperidine, chiral acid salt; b) separating the (R)-4-[1-hydroxy-1-(2,3-dimethoxyphenyl)methyl]piperidine, chiral acid salt from the (S)-4-[1-hydroxy-1-(2,3-dimethoxyphenyl)methyl]piperidine, chiral acid salt; and c) reacting the (R)-4-[1-hydroxy-1-(2,3-dimethoxyphenyl)methyl]piperidine, chiral acid salt with a suitable base to give the (R)-α-(2,3-dimethoxyphenyl)-4-piperidinemethanol (1). Also provided is a process for preparing 4-[1-hydroxy-1-(2, 3-dimethoxyphenyl)methyl]piperidine (11) comprising reacting 4-(2,3-dimethoxybenzoyl)pyridine (12) with a suitable reducing agent, such as catalytic hydrogenation with rhodium/alumina or rhodium/carbon as catalysts. In addition, there is provided a process for preparing 4-[1-hydroxy-1-(2,3-dimethoxyphenyl)methyl]-N-2-(4-fluorophen-1-oxo-ethyl)piperidine (20) comprising reacting 4-[1-oxo-1-(2,3-dimethoxyphenyl)methyl]-N-2-(4-fluorophen-1-oxo-ethyl) piperidine (4) with a suitable reducing agent.

In another embodiment, there are provided methods of treating schizophrenia, anxiety, variant angina, anorexia nervosa, Raynaud's phenomenon, intermittent claudication, coronary or peripheral vasospasms, fibromyalgia, cardiac arrhythmia's, thrombotic illness and in controlling the extrapyramidal symptoms associated with neuroleptic therapy comprising administering an effective amount of (R)-α-(2,3-dimethoxyphenyl)-1-[2-(4-fluorophenyl)ethyl]-4-piperidinemethanol wherein the (R)-α-(2,3-dimethoxyphenyl)-1-[2-(4-fluorophenyl)ethyl]-4-piperidinemethanol has a particle size range of approximately 25 μm to approximately 250 μm.

In a further embodiment, there are provided pharmaceutical compositions containing effective amounts of (R)-α-(2,3-dimethoxyphenyl)-1-[2-(4-fluorophenyl)ethyl]-4-piperidinemethanol, including compositions wherein the (R)-α-(2,3-dimethoxyphenyl)-1-[2-(4-fluorophenyl)ethyl]-4-piperidinemethanol has a particle size range of approximately 25 μm to approximately 250 μm.

In yet a further embodiment, there are provided processes for preparing pharmaceutical compositions containing effective amounts of (R)-α-(2,3-dimethoxyphenyl)-1-[2-(4-fluorophenyl)ethyl]-4-piperidinemethanol.

DETAILED DESCRIPTION OF THE INVENTION

Scheme A, depicts the various processes of the present invention for the preparation of (R)-α-(2,3-dimethoxyphenyl)-1-[2-(4-fluorophenyl)ethyl]-4-piperidinemethanol (3).

In Scheme A, step a, the piperidine functionality of (R)-α-(2,3-dimethoxyphenyl)-4-piperidinemethanol (1) is reacted with a 4-fluorophenylethyl alkylating agent of structure (2) to give (R)-α-(2,3-dimethoxyphenyl)-1-[2-(4-fluorophenyl)ethyl]-4-piperidinemethanol (3) using techniques and procedures well known to one of ordinary skill in the art.

For example, (R)-α-(2,3-dimethoxyphenyl)-4-piperidinemethanol (1) with an enantiomeric excess (ee) of between about 80% to >99% can be reacted with the 4-fluorophenylethyl alkylating agent of structure (2), wherein X is a suitable leaving group such as halide, methanesulfonate, and the like, in the presence of a suitable base, such as potassium carbonate, optionally in the presence of a suitable catalyst such as sodium iodide, in a suitable organic solvent, such as acetonitrile or aqueous tetrahydrofuran. The reactants are typically stirred together at a temperature of from about room temperature to 100° C. for a period of time ranging from about 2 hours to about 25 hours. The resulting (R)-α-(2,3-dimethoxyphenyl)-1-[2-(4-fluorophenyl)ethyl]-4-piperidinemethanol (3) may be recovered from the reaction zone by extractive methods as are

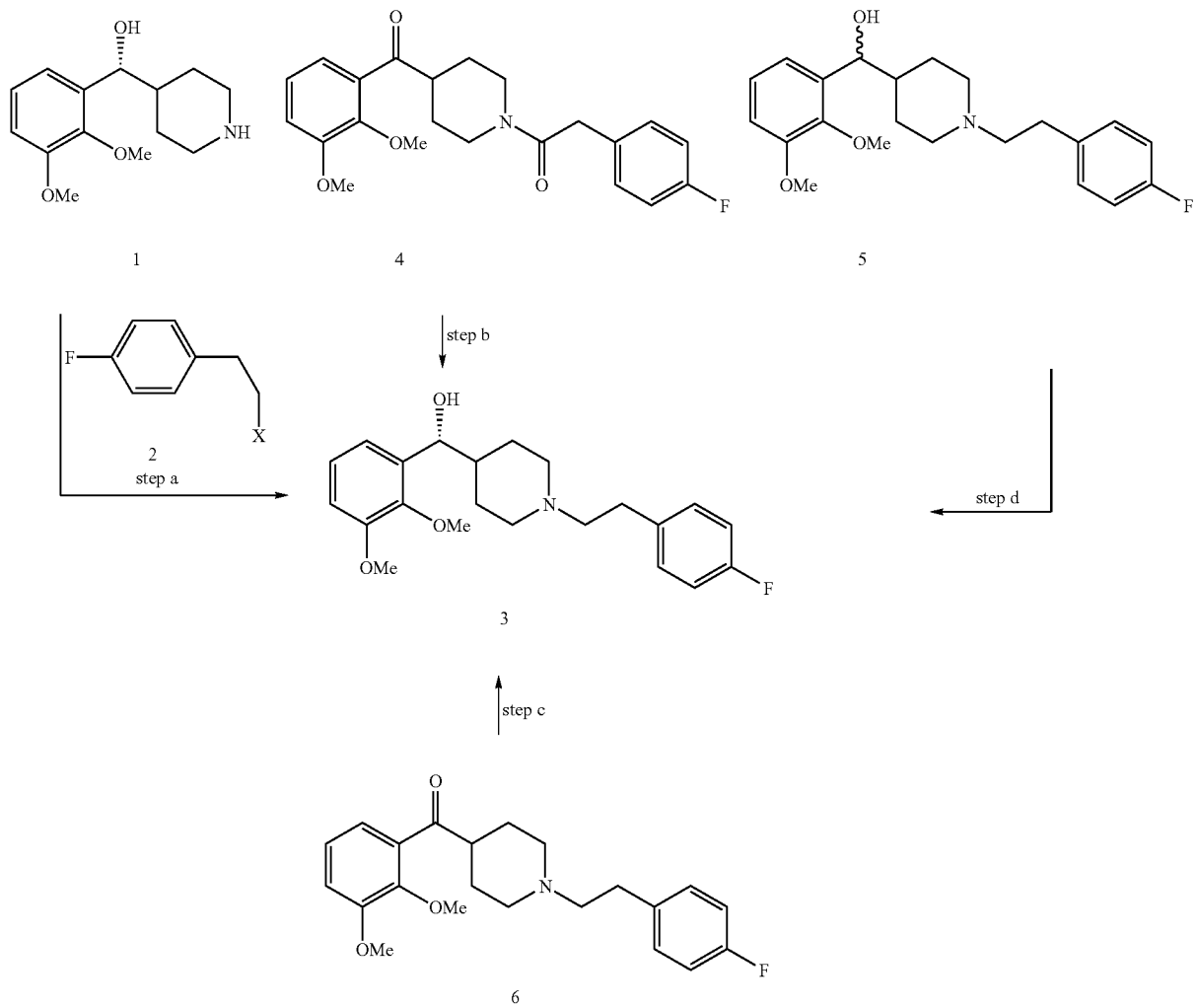

Scheme A known in the art and will typically have an ee of from about 85% to >99%. The resulting (R)-α-(2,3-dimethoxyphenyl)-1-[2-(4-fluorophenyl)ethyl]-4-piperidinemethanol (3) may be purified by removal of solvent and either 1) dissolution in a suitable solvent or solvent mixture, such as ethanol/toluene, and stirring with silica gel at a temperature range of from about 5° C. to about 30° C. for a period of time ranging from about 30 minutes to 5 hours; or 2) washing the organic extracts from the extractive work-up with an aqueous solution of sodium metabisulfite to give material having an ee of from about 90 to >99%. The resulting material may be further purified by crystallization from a suitable solvent, such as isopropanol.

The ee of (R)-α-(2,3-dimethoxyphenyl)-1-[2-(4-fluorophenyl)ethyl]-4-piperidinemethanol (3) prepared by Scheme A, step a, may be increased by selective enzymatic ester hydrolysis techniques as hereinafter described in Scheme E or by diastereomeric salt separation techniques using (2S,3S)-(+)-di-(p-anisoyl)tartaric acid as described hereinafter in Schemes B, C, and D or as described in Scheme A, step c, Table 1.

In Scheme A, step b, 4-[1-hydroxy-1-(2,3-dimethoxyphenyl)methyl]-N-2-(4-fluorophen-1-oxo-ethyl)piperidine (4) is converted to (R)-α-(2,3-dimethoxyphenyl)-1-[2-(4-fluorophenyl)ethyl]-4-piperidinemethanol (3).

For example, 4-[1-oxo-1-(2,3-dimethoxyphenyl)methyl-N-2-(4-fluorophen-1-oxo-ethyl)piperidine (4) is contacted with a suitable chiral reducing agent, such as (+)-β-chlorodiisopinocamphenylborane, in a suitable solvent, such as tetrahydrofuran. The reactants are typically stirred together at a temperature range of from about 5° C. to about 30° C. for a period of time ranging from about 2 hours to 100 hours. The reaction is typically quenched with acetaldehyde, and the to (R)-α-(2,3-dimethoxyphenyl)-1-[2-(4-fluorophenyl)ethyl]-4-piperidinemethanol (3) recovered from the reaction zone by extractive methods as are known in the art and may be purified by chromatography to typically give (R)-α-(2,3-dimethoxyphenyl)-1-[2-(4-fluorophenyl)ethyl]-4-piperidinemethanol (3) in approximately 60% ee to approximately 85% ee.

The ee of (R)-α-(2,3-Dimethoxyphenyl)-1-[2-(4-fluorophenyl)ethyl]-4-piperidinemethanol (3) prepared by Scheme A, step b, may be increased by selective enzymatic ester hydrolysis techniques as hereinafter described in Scheme E or by diastereomeric salt separation techniques using (2S,3S)-(+)-di-(p-anisoyl)tartaric acid as described hereinafter in Schemes B, C, and D or as described in Scheme A, step c, Table 1.

In scheme A, step c, 4-[1-oxo-1-(2,3-dimethoxyphenyl)methyl-N-2-(4-fluorophenylethyl)-piperidine (6) is converted to (R)-α-(2,3-dimethoxyphenyl)-1-[2-(4-fluorophenyl)ethyl]-4-piperidinemethanol (3).

For example, 4-[1-oxo-1-(2,3-dimethoxyphenyl)methyl-N-2-(4-fluorophenylethyl)-piperidine (6) is contacted with a suitable chiral reducing agent, such as (+)-β-chlorodiisopinocamphenylborane, in a suitable solvent, such as tetrahydrofuran. The reactants are typically stirred together at a temperature range of from about 5° C. to about 30° C. for a period of time ranging from about 20 minutes to 10 hours. The reaction is typically treated with a suitable oxidizing agent, such as hydrogen peroxide, and the (R)-α-(2,3-dimethoxyphenyl)-1-[2-(4-fluorophenyl)ethyl]-4-piperidinemethanol (3) recovered from the reaction zone by extractive methods as are known in the art and may be purified by chromatography to typically give >75% ee material.

The ee of (R)-α-(2,3-Dimethoxyphenyl)-1-[2-(4-fluorophenyl)ethyl]-4-piperidinemethanol (3) prepared by Scheme A, step c, may be increased by selective enzymatic ester hydrolysis techniques as hereinafter described in Scheme E or by diastereomeric salt separation techniques using (2S,3S)-(+)-di-(p-anisoyl)tartaric acid as described hereinafter in Schemes B, C, and D. Alternatively, various other chiral acids may be utilized as shown in Table 1:

TABLE 1

| Chiral Acid Used | m.p. of Salt Formed[a] | % Diastereomeric Excess[c] |
|---|---|---|
| (2R,3R)-(−)-Di-(p-toluoyl)-tartaric acid | 108-113° C. | 95 |
| (2S,3S)-(+)-Di-(p-toluoyl)-tartaric acid | 100-112° C. | 92 |
| (+)-Dibenzoyl-D-tartaric acid | 100-110° C. | 90 |
| (−)-Dibenzoyl-L-tartaric acid | 100-110° C. | 90 |
| (−)-1,1'-Binaphthyl-2,2'-diyl hydrogen phosphate[b] | 152-155° C. | 92 |

[a]Equal molar amounts of (R)-α-(2,3-Dimethoxyphenyl)-1-[2-(4-fluorophenyl)ethyl]-4-piperidinemethanol (3) and the chiral acid were dissolved in acetone; the resulting solution was slowly evaporated at room temperature to dryness to provide the salt.
[b]MeOH was used to dissolve the chiral acid.
[c]% Diastereomeric excess was determined by the conversion of the salt to (R)-α-(2,3-dimethoxyphenyl)-1-[2-(4-fluorophenyl)ethyl]-4-piperidinemethanol (3) with 1 M NaOH in H$_2$O/EtOAc followed by HPLC analysis.

In Scheme A, step d, α-(2,3-dimethoxyphenyl)-1-[2-(4-fluorophenyl)ethyl]-4-piperidinemethanol (5) is optically purified to give (R)-α-(2,3-dimethoxyphenyl)-1-[2-(4-fluorophenyl)ethyl]-4-piperidinemethanol (3) by either diastereomeric salt separation techniques or selective enzymatic hydrolysis. Diastereomeric salt separation techniques to convert α-(2,3-dimethoxyphenyl)-1-[2-(4-fluorophenyl)ethyl]-4-piperidinemethanol (5) to (R)-α-(2,3-dimethoxyphenyl)-1-[2-(4-fluorophenyl)ethyl]-4-piperidinemethanol (3) are described in Schemes B, C, and D. Selective enzymatic hydrolysis techniques are described in Scheme E. As used herein, the term "α-(2,3-dimethoxyphenyl)-1-[2-(4-fluorophenyl)ethyl]-4-piperidinemethanol (5)" refers to material which has an enantiomeric purity of approximately 0% to approximately 5%.

In Scheme B and Scheme C, samples of varying optical purity of α-(2,3-dimethoxyphenyl)-1-[2-(4-fluorophenyl)ethyl]-4-piperidinemethanol (5) are improved in terms of optical purity to give (R)-α-(2,3-dimethoxyphenyl)-1-[2-(4-fluorophenyl)ethyl]-4-piperidinemethanol (3) by diastereomeric salt separation techniques utilizing (2S,3S)-(+)-di-(p-anisoyl)tartaric acid.

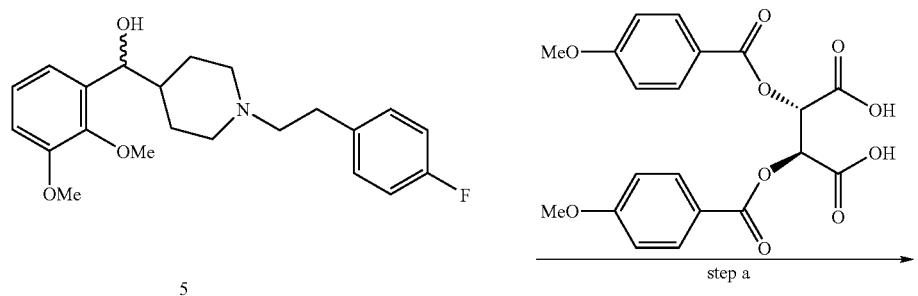
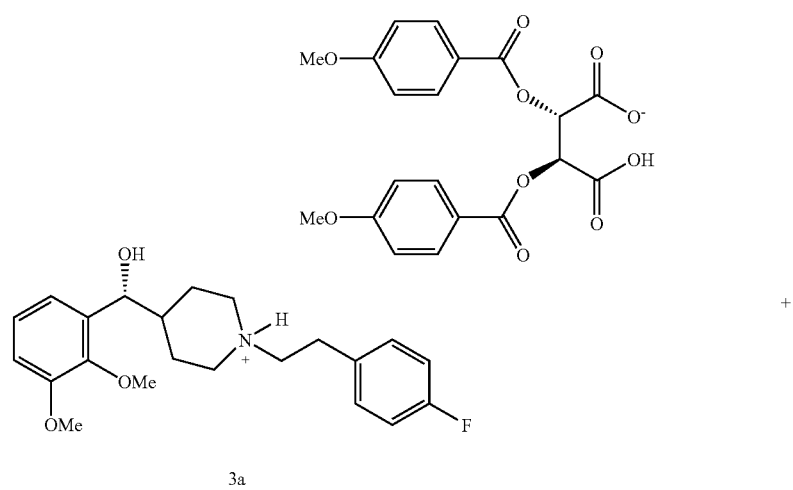
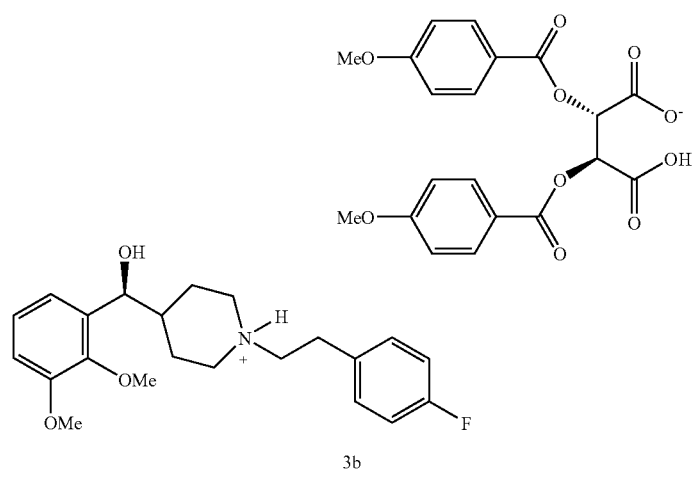

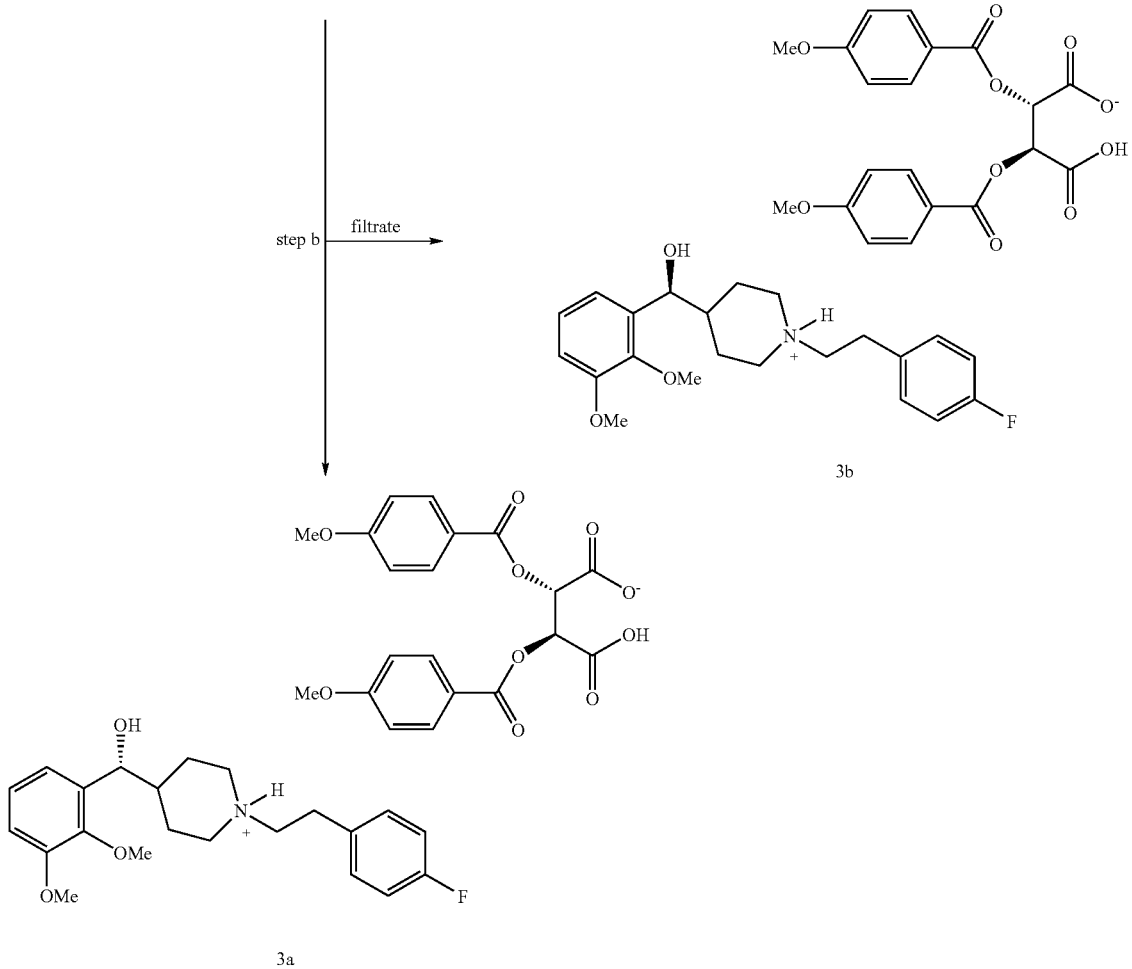

In Scheme B, step a, α-(2,3-dimethoxyphenyl)-1-[2-(4-fluorophenyl)ethyl]-4-piperidinemethanol (5) is reacted with (2S,3S)-(+)-di-(p-anisoyl)tartaric acid to give a mixture of (R)-α-(2,3-dimethoxyphenyl)-1-[2-(4-fluorophenyl)ethyl]-4-piperidinemethanol, (2S,3S) -(+)-di-(p-anisoyl)tartaric acid salt (3a) and (S)-α-(2,3-dimethoxyphenyl)-1-[2-(4-fluorophenyl)ethyl]-4-piperidinemethanol, (2S,3S)-(+)-di-(p-anisoyl)tartaric acid salt (3b). In Scheme B, step b, the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) is separated from the mixture of (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) and (S)-α-(2,3-dimethoxyphenyl)-1-[2-(4-fluorophenyl)ethyl]-4-piperidinemethanol, (2S,3S)-(+)-di-(p-anisoyl) tartaric acid salt (3b) by filtration.

For example, α-(2,3-dimethoxyphenyl)-1-[2-(4-fluorophenyl)ethyl]-4-piperidinemethanol (5) is contacted with (2S,3S)-(+)-di-(p-anisoyl)tartaric acid in a suitable organic solvent or solvent mixture, such as 2-butanone, methanol, methanol/water, methyl ethyl ketone, ethanol, acetic acid acetic acid/methyl ethyl ketone, acetic acid/water, or acetic acid/methanol, with methanol being preferred, at a temperature of 50° C. to reflux temperature of the chosen solvent or solvent mixture for a period of time ranging from the time necessary to form a homogenous solution to about 24 hours. The reaction mixture is then typically cooled to a temperature range of from 0° C. to 40° C. over a period of time ranging from 20 minutes to 20 hours, optionally seeding with (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) which has a high enantiomeric excess (>95%). In addition, when crystallization appears complete, a few drops of concentrated sulfuric acid may optionally be added and the mixture held at a temperature range of from room temperature to about 50° C. for a period of time ranging from 10 minutes to 5 hours. When acetic acid/water is used in Scheme B, step a, the melting point of the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) is 170° C.-172° C., whereas when methanol is used in Scheme B, step a, the melting point of the (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a) is 110° C.-115° C. In addition, the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) formed in acetic acid/acid water is less soluble in acetone, requiring the addition of water for solution. These findings indicate that (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) recovered from acetic acid/water and (R)-α-

(2,3-dimethoxyphenyl)-1-[2-(4-fluorophenyl)ethyl]-4-piperidinemethanol, (2S,3S)-(+)-di-(p-anisoyl)tartaric acid salt (3a) recovered from methanol are different crystalline forms, with the (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a) recovered from acetic acid/water being a more stable form. (R)-α-(2,3-dimethoxyphenyl)-1-[2-(4-fluorophenyl)ethyl]-4-piperidinemethanol, (2S,3S)-(+)-di -(p-anisoyl)tartaric acid salt (3a) typically precipitates from the reaction mixture and is typically recovered from the reaction zone by filtration (3a), leaving the majority of (S)-α-(2,3-dimethoxyphenyl)-1-[2-(4-fluorophenyl)ethyl]-4-piperidinemethanol, (2S,3S)-(+)-di-(p -anisoyl)tartaric acid salt (3b) in the filtrate. Typically, the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) recovered from the reaction zone has an enantiomeric excess (ee) of between about 75% to about 95%.

In Scheme C, the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) is converted to (R)-α-(2,3-dimethoxyphenyl)-1-[2-(4-fluorophenyl)ethyl]-4-piperidinemethanol (3).

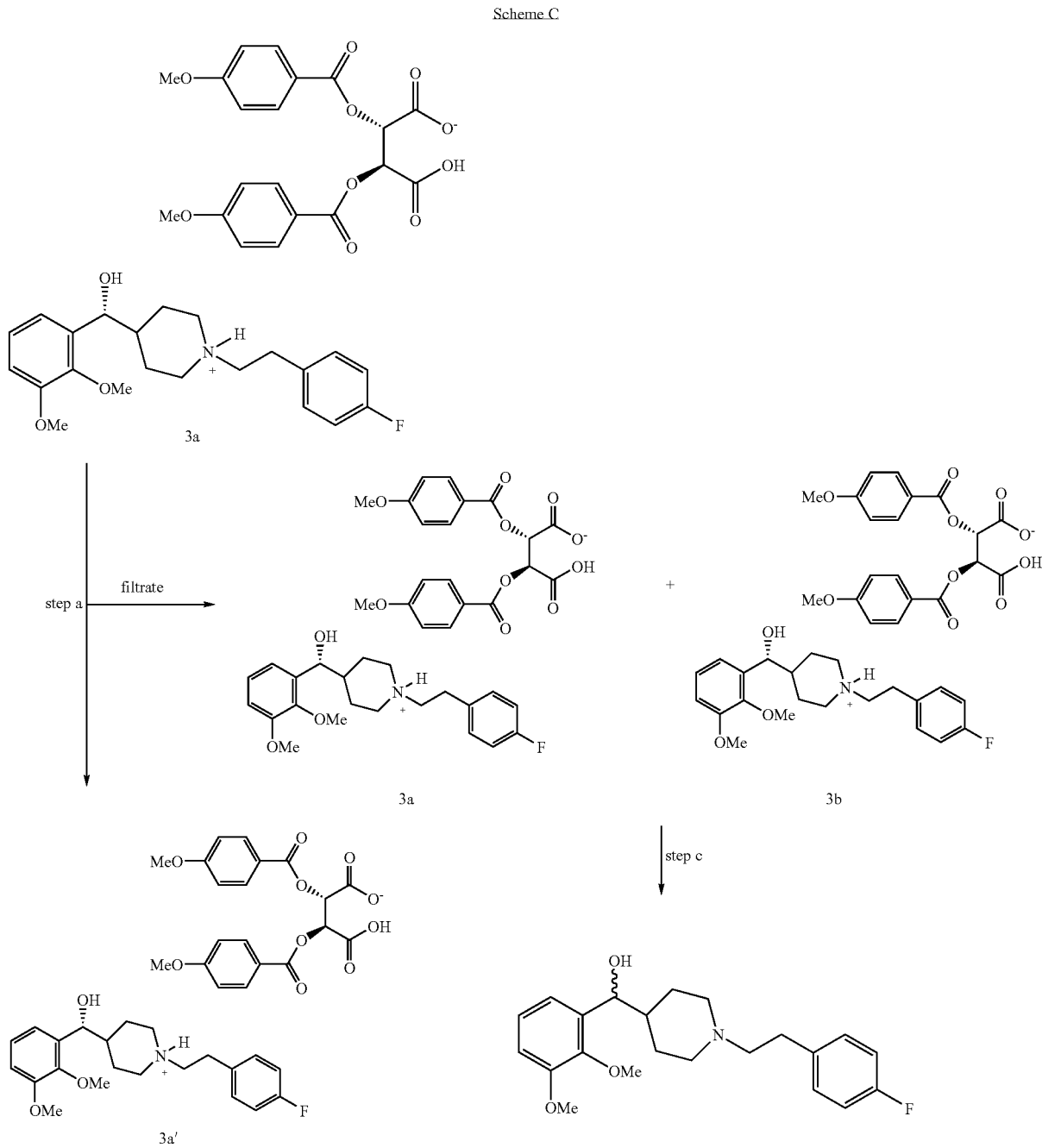

step b ↓

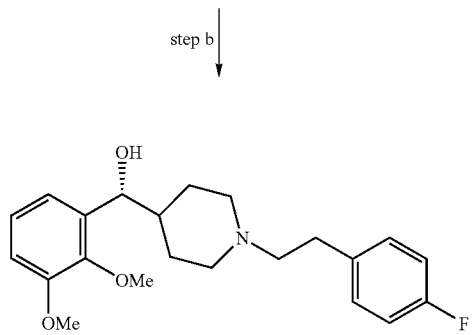

3

In Scheme C, step a, the ee of (R)-α-(2,3-dimethoxyphenyl)-1-[2-(4-fluorophenyl)ethyl]-4-piperidinemethanol, (2S, 3S)-(+)-di-(p-anisoyl)tartaric acid salt (3a) may optionally be improved by recrystallization one or more times, typically using acetic acid, acetic acid/water, acetone, acetone/water, methanol, methyl ethyl ketone, methanol/water, or ethanol as a crystallization solvent. After the recrystallization mixture becomes homogeneous upon heating, it is then typically cooled to a temperature range of from 0° C. to 40° C. over a period of time ranging from 20 minutes to 20 hours, optionally seeding with (R)-α-(2,3-dimethoxyphenyl)-1-[2-(4-fluorophenyl)ethyl]-4-piperidinemethanol, (2S, 3S)-(+)-di-(p-anisoyl)tartaric acid salt (3a) which has a high enantiomeric excess (>95%). Such recrystallization typically gives (R)-α-(2,3-dimethoxyphenyl)-1-[2-(4-fluorophenyl)ethyl]-4-piperidinemethanol, (2S,3S)-(+)-di-(p-anisoyl)tartaric acid salt with ee's of from about 85% to 100%. As used herein, the designation of (R)-α-(2,3-dimethoxyphenyl)-1-[2-(4-fluorophenyl)ethyl]-4-piperidinemethanol, (2S,3S)-(+)-di-(p-anisoyl)tartaric acid salt as (3a') refers to material which has been recrystallized once, the designation of (R)-α-(2,3-dimethoxyphenyl)-1-[2-(4-fluorophenyl)ethyl]-4-piperidinemethanol, (2S,3S)-(+)-di-(p-anisoyl)tartaric acid salt as (3a'') refers to material which has been recrystallized twice; and the designation of (R)-α-(2,3-dimethoxyphenyl)-1-[2-(4-fluorophenyl)ethyl]-4-piperidinemethanol, (2S,3S)-(+)-di-(p-anisoyl)tartaric acid salt as (3a''') refers to material which has been recrystallized thrice. As one of ordinary skill of the art will readily appreciate, the ee of (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a', 3a'', or 3a''') will typically vary with the ee of the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) as isolated from the reaction zone as well as the number of recrystallizations utilized.

In Scheme C, step b, the (R)-α-(2,3-dimethoxyphenyl)-1-[2-(4-fluorophenyl)ethyl]-4-piperidinemethanol, (2S,3S)-(+)-di-(p-anisoyl)tartaric acid salt as (3a, 3a', 3a'', or 3a''') is converted to (R)-α-(2,3-dimethoxyphenyl)-1-[2-(4-fluorophenyl)ethyl]-4-piperidinemethanol (3) by treatment with a suitable base.

For example, the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a, 3a', 3a'', or 3a''') having an enantiomeric excess typically in the range of from about 95% to >99% is typically contacted with a suitable base, such as aqueous bases (i.e., aqueous ammonia, aqueous sodium hydroxide, aqueous potassium carbonate, and the like), or such as organic bases (i.e., triethylamine and the like), in a suitable organic solvent, such as toluene, aqueous toluene, methanol/toluene, aqueous methanol/toluene, aqueous methanol/tetrahydrofuran, tetrahydrofuran or aqueous tetrahydrofuran at a temperature of between 0° C. to 75° C. for a period of time ranging from about 15 minutes to about 5 hours. The (R)-α-(2,3-dimethoxyphenyl)-1-[2-(4-fluorophenyl)ethyl]-4-piperidinemethanol (3) is typically recovered from the reaction zone by extractive methods as are known in the art and may be purified by recrystallization one or more times, with for example, 2-propanol, methanol, methanol/water, or a mixture of 2-propanol/methanol/water to typically give (R)-α-(2,3-dimethoxyphenyl)-1-[2-(4-fluorophenyl)ethyl]-4-piperidinemethanol (3) with an enantiomeric excess of between about 97% and >99%.

In Scheme C, step b, (2S,3S)-(+)-di-(p-anisoyl)tartaric acid may be recovered from the basic aqueous phase by treatment of the basic aqueous phase with an appropriate acid, such as hydrochloric acid. The recovered (2S,3S)-(+)-di-(p-anisoyl)tartaric acid is typically recovered from the reaction zone by filtration and may be recycled for use in Scheme B, step a.

In Scheme C, step c, the mother liquor(s) or filtrate(s) from the recrystallization(s) of the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (Scheme C, step a) contain an essentially racemic mixture of (R)-α-(2,3-dimethoxyphenyl)-1-[2-(4-fluorophenyl)ethyl]-4-piperidinemethanol, (2S,3S)-(+)-di-(p-anisoyl)tartaric acid salt as (3a) and (S)-α-(2,3-dimethoxyphenyl)-1-[2-(4-fluorophenyl)ethyl]-4-piperidinemethanol, (2S,3S)-(+)-di-(p-anisoyl)tartaric acid salt as (3b) and may be treated with a suitable aqueous base to give α-(2,3-dimethoxyphenyl)-1-[2-(4-fluorophenyl)ethyl]-4-piperidinemethanol (5) which may be recycled for use in Scheme B, step a.

For example, the mother liquor(s) or filtrate(s) from the recrystallization(s) of the (R)-α-(2,3-dimethoxyphenyl)-1-[2-(4-fluorophenyl)ethyl]-4-piperidinemethanol, (2S,3S)-(+)-di -(p-anisoyl)tartaric acid salt (3a) (Scheme C, step a) containing an essentially racemic mixture of (R)-α-(2,3-dimethoxyphenyl)-1-[2-(4-fluorophenyl)ethyl]-4-piperidinemethanol, (2S,3S) -(+)-di-(p-anisoyl)tartaric acid salt as (3a) and (S)-α-(2,3-dimethoxyphenyl)-1-[2-(4-fluorophenyl)ethyl]-4-piperidinemethanol, (2S,3S)-(+)-di-(p-anisoyl) tartaric acid salt as (3b) is typically contacted with a suitable aqueous base, such as ammonia, sodium hydroxide, potassium carbonate, and the like, in a suitable organic solvent, such as toluene, aqueous toluene, methanol/toluene, aqueous methanol, tetrahydrofuran or aqueous tetrahydrofuran at a temperature of between 0° C. to 75° C. for a period of time ranging from about 15 minutes to about 5 hours. The essentially racemic mixture, α-(2,3-dimethoxyphenyl)-1-[2-(4-fluorophenyl)ethyl]-4-piperidinemethanol (5), is typically recovered from the reaction zone by extractive methods as are known in the art and may be purified by recrystallization one or more times prior to use in Scheme B, step a.

In Scheme C, step c, (2S,3S)-(+)-di-(p-anisoyl)tartaric acid may be recovered from the basic aqueous phase by treatment of the basic aqueous phase with an appropriate acid, such as hydrochloric acid. The recovered (2S,3S)-(+)-di-(p-anisoyl)tartaric acid is typically recovered from the reaction zone by filtration and may be recycled for use in Scheme B, step a.

In Scheme D, the mother liquor or filtrate resulting from the resolution of (R)-α-(2,3-dimethoxyphenyl)-1-[2-(4-fluorophenyl)ethyl]-4-piperidinemethanol, (2S,3S)-(+)-di-(p-anisoyl)tartaric acid salt in Scheme B, step b, contains (S)-α-(2,3-dimethoxyphenyl)-1-[2-(4-fluorophenyl)ethyl]-4-piperidinemethanol, (2S,3S)-(+)-di-(p-anisoyl)tartaric acid salt (3b) as its major component which may be converted to α-(2,3-dimethoxyphenyl)-1-[2-(4-fluorophenyl)ethyl]-4-piperidinemethanol (5) and recycled for use in Scheme B, step a.

Scheme D

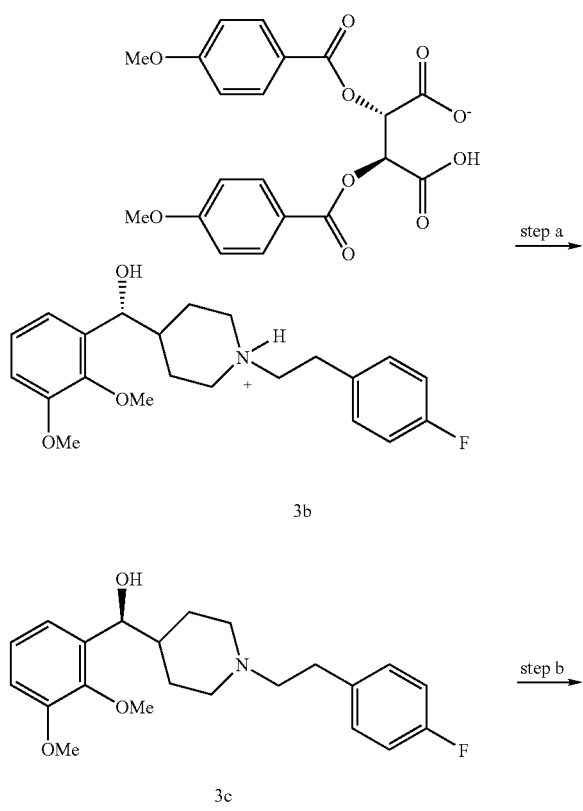

3b

3c

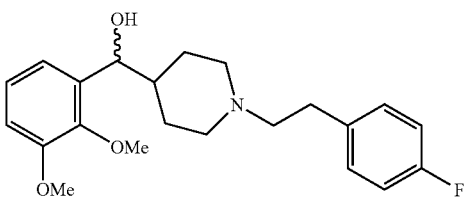

5

In Scheme D, step a, the mother liquor or filtrate resulting from the resolution of (R)-α-(2,3-dimethoxyphenyl)-1-[2-(4-fluorophenyl)ethyl]-4-piperidinemethanol, (2S,3S)-(+)-di -(p-anisoyl)tartaric acid salt in Scheme B, step b, containing (S)-α-(2,3-dimethoxyphenyl)-1-[2-(4-fluorophenyl) ethyl]-4-piperidinemethanol, (2S,3S)-(+)-di-(p-anisoyl) tartaric acid salt (3b) as its major component is converted to (S)-α-(2,3-dimethoxyphenyl)-1-[2-(4-fluorophenyl)ethyl]-4-piperidinemethanol (3c) by treatment with a suitable base. Alternatively, the (S)-α-(2,3-dimethoxyphenyl)-1-[2-(4-fluorophenyl)ethyl]-4-piperidinemethanol, (2S,3S)-(+)-di-(p-anisoyl)tartaric acid salt (3b) may be isolated from the mother liquor or filtrate resulting from Scheme B, step b, prior to treatment with a suitable base as described above.

For example, the mother liquor or filtrate resulting from the resolution of (R)-α-(2,3-dimethoxyphenyl)-1-[2-(4-fluorophenyl)ethyl]-4-piperidinemethanol, (2S,3S)-(+)-di-(p -anisoyl)tartaric acid salt in Scheme B, step b, containing (S)-α-(2,3-dimethoxyphenyl)-1-[2-(4-fluorophenyl)ethyl]-4-piperidinemethanol, (2S,3S)-(+)-di-(p-anisoyl)tartaric acid salt (3b) as its major component is typically treated with a suitable base, such as ammonia, sodium hydroxide, potassium carbonate, and the like, in a suitable organic solvent, such as toluene, aqueous toluene, methanol/toluene, aqueous methanol, tetrahydrofuran or aqueous tetrahydrofuran at a temperature of between 0° C. to 75° C. for a period of time ranging from about 15 minutes to about 5 hours. The (S)-α-(2,3-dimethoxyphenyl)-1-[2-(4-fluorophenyl)ethyl]-4-piperidinemethanol (3c) may be recovered from the reaction zone by filtration or extractive methods as are known in the art and may be purified by recrystallization.

In Scheme D, step a, the (2S,3S)-(+)-di-(p-anisoyl)tartaric acid may be recovered from the basic aqueous phase by treatment of the basic aqueous phase with an appropriate acid, such as hydrochloric acid. The recovered (2S,3S)-(+)-di-(p-anisoyl)tartaric acid is typically recovered from the reaction zone by filtration and may be recycled for use in Scheme B, step a.

In Scheme D, step b, the (S)-α-(2,3-dimethoxyphenyl)-1-[2-(4-fluorophenyl)ethyl]-4-piperidinemethanol (3c) is racemized to give α-(2,3-dimethoxyphenyl)-1-[2-(4-fluorophenyl)ethyl]-4-piperidinemethanol (5) by treatment with a suitable acid.

For example, (S)-α-(2,3-dimethoxyphenyl)-1-[2-(4-fluorophenyl)ethyl]-4-piperidinemethanol (3c) is contacted with a suitable acid, such as hydrochloric acid or sulfuric acid in a suitable solvent such as tetrahydrofuran, aqueous tetrahydrofuran, methanol, isopropanol/water, aqueous glyme, typically at the reflux temperature of the solvent chosen for a period of time ranging from about 2 hours to about 40 hours. The α-(2,3-dimethoxyphenyl)-1-[2-(4-fluorophenyl) ethyl]-4-piperidinemethanol (5) is typically recovered from the reaction zone by filtration or extractive methods as are known in the art and may be purified by recrystallization prior to use in Scheme B, step a.

As stated previously, Scheme A, step d, encompasses the optical purification of α-(2,3-dimethoxyphenyl)-1-[2-(4-fluorophenyl)ethyl]-4-piperidinemethanol (5) to (R)-α-(2,3-dimethoxyphenyl)-1-[2-(4-fluorophenyl)ethyl]-4-piperidinemethanol (3) by either diastereomeric salt separation techniques or selective enzymatic hydrolysis. Schemes B, C, and D described diastereomeric salt separation techniques to convert α-(2,3-dimethoxyphenyl)-1-[2-(4-fluorophenyl) ethyl]-4-piperidinemethanol (5) to (R)-α-(2,3-dimethoxyphenyl)-1-[2-(4-fluorophenyl)ethyl]-4-piperidinemethanol (3), while Scheme E describes selective enzymatic ester hydrolysis techniques to convert α-(2,3-dimethoxyphenyl)-1-[2-(4-fluorophenyl)ethyl]-4-piperidinemethanol (5), via its butyrate ester, to (R)-α-(2,3-dimethoxyphenyl)-1-[2-(4-fluorophenyl)ethyl]-4-piperidinemethanol (3).

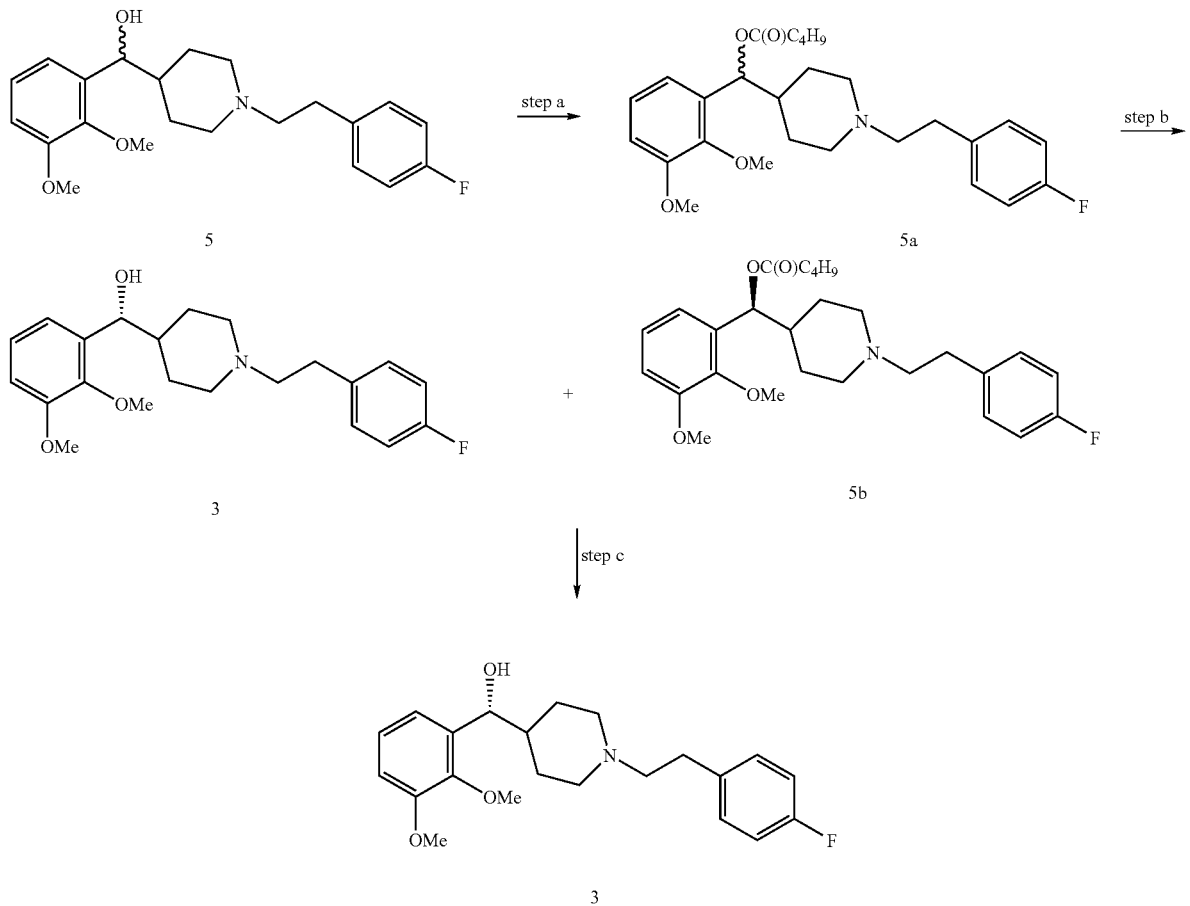

In Scheme E, step a, α-(2,3-dimethoxyphenyl)-1-[2-(4-fluorophenyl)ethyl]-4-piperidinemethanol (5) is converted to its butyrate ester using techniques and procedures well known to one of ordinary skill in the art.

For example, α-(2,3-dimethoxyphenyl)-1-[2-(4-fluorophenyl)ethyl]-4-piperidinemethanol (5) is contacted with butyryl chloride, preferably in the presence of a suitable acid scavenger, such as triethylamine, and a suitable catalyst, such as dimethylaminopyridine, in a suitable solvent, such as chloroform at reflux temperatures for a period of time ranging from 2 hours to 24 hours. The α-(2,3-dimethoxyphenyl)-1-[2-(4-fluorophenyl)ethyl]-4-piperidinemethanol, butyrate ester (5a) is typically recovered from the reaction zone by extractive methods as are known in the art and may be purified by chromatography.

In Scheme E, step b, the α-(2,3-dimethoxyphenyl)-1-[2-(4-fluorophenyl)ethyl]-4-piperidinemethanol, butyrate ester (5a) is subjected to enzymatic hydrolysis using, for example, lipase of *Candida cylindracea*, in a suitable medium, such as 0.1M phosphate buffer (pH 7.0) at a temperature range of from about 35° C. to about 50° C. for a period of time ranging from about 5 hours to 5 days. The enzyme selectively hydrolyzes the (R)-butyrate ester giving a mixture of (R)-α-(2,3-dimethoxyphenyl)-1-[2-(4-fluorophenyl)ethyl]-4-piperidinemethanol (3) and (S)-α-(2,3-dimethoxyphenyl)-1-[2-(4-fluorophenyl)ethyl]-4-piperidinemethanol, butyrate ester (5b).

In Scheme E, step c, the (R)-α-(2,3-dimethoxyphenyl)-1-[2-(4-fluorophenyl)ethyl]-4-piperidinemethanol (3) is separated from the (S)-α-(2,3-dimethoxyphenyl)-1-[2-(4-fluorophenyl)ethyl]-4-piperidinemethanol, butyrate ester (5b), for example, by chromatography.

Starting materials for use in Scheme A may be prepared by a variety of methods. For example, (R)-α-(2,3-Dimethoxyphenyl)-4-piperidinemethanol (1) for use in Scheme A, step a, may be prepared by a variety of methods as shown in Scheme F. 4-[1-Oxo-1-(2,3-dimethoxyphenyl)methyl]-N-2-(4-fluorophen-1-oxo-ethyl)piperidine (4) for use in Scheme A, step b, may be prepared as in Scheme J. α-(2,3-Dimethoxyphenyl)-1-[2-(4-fluorophenyl)ethyl]-4-piperidinemethanol (5) for use in Scheme A, step c, may be prepared as described in U.S. Pat. No. 5,169,096, as described in Scheme C, Scheme D or Scheme I As stated above, (R)-α-(2,3-dimethoxyphenyl)-4-piperidinemethanol (1) for use in Scheme A, step a, may be prepared as described in Scheme F.

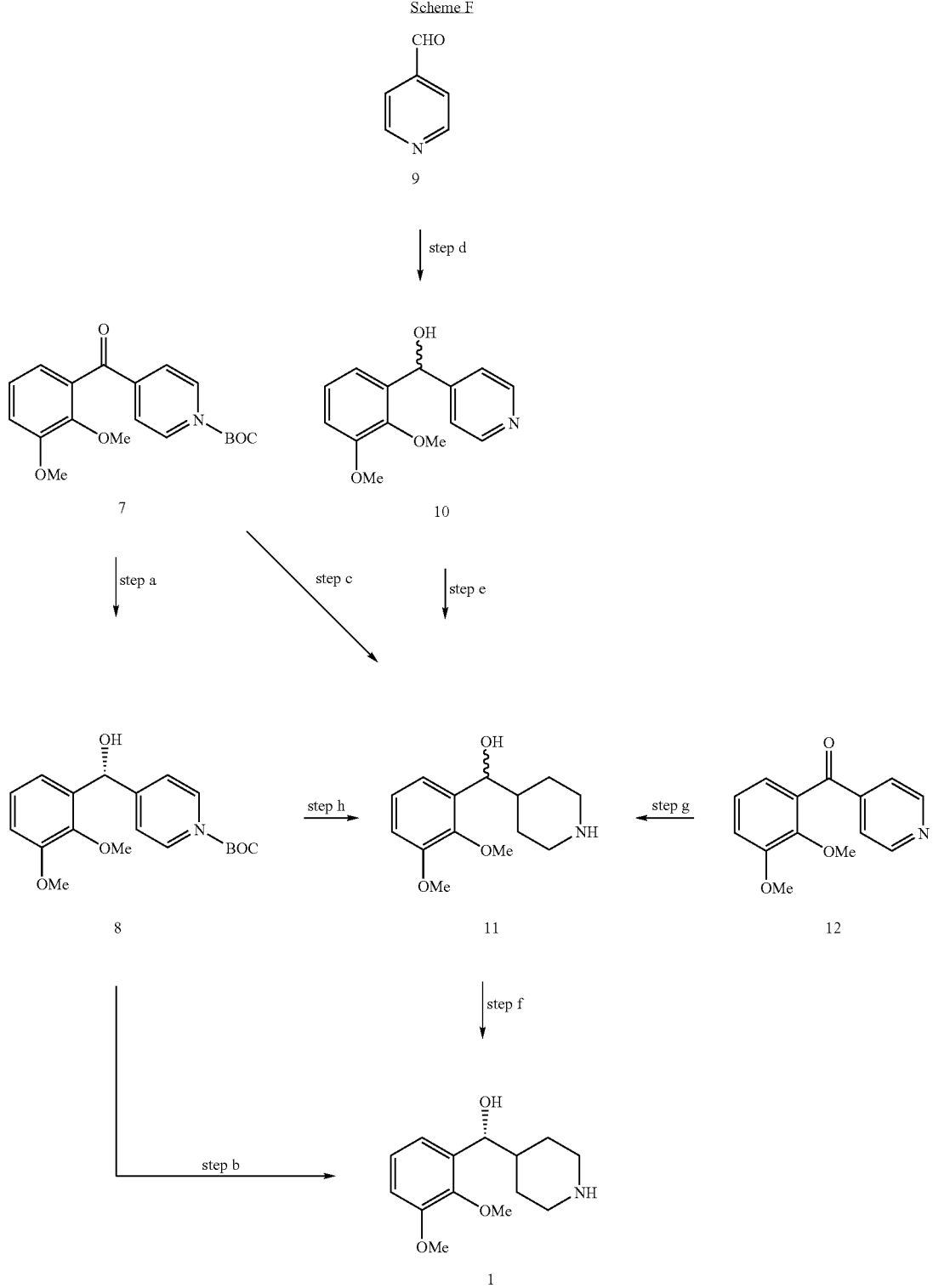

In Scheme F, step a, the ketone functionality of 4-(2,3-dimethoxybenzoyl)-1-piperidinecarboxylic acid, 1,1-dimethylethyl ester (7) is selectively reduced to give (R)-4-(1-hydroxy-1-(2,3-dimethoxyphenyl)-1-piperidinecarboxylic acid, 1,1-dimethylethyl ester (8).

For example, 4-(2,3-dimethoxybenzoyl)-1-piperidinecarboxylic acid, 1,1-dimethylethyl ester (7) is contacted with a suitable chiral reducing agent, such as (+)-β-chlorodiisopinocamphenylborane or potassium 9-O-(1,2-isopropylidine-5-deoxy-α-D-xylofuranosyl)-9-borabicyclo[3.3.1]nonane. Typically, the reagents are contacted in a suitable solvent, such as tetrahydrofuran, at a temperature of about −50° C. to room temperature for a period of time ranging from 10 hours to about 10 days. (R)-4-(1-Hydroxy-1-(2,3-dimethoxyphenyl)-1-piperidinecarboxylic acid, 1,1-dimethylethyl ester (8) may be recovered from the reaction zone by extractive methods as are well known in the art, typically (R)-4-(1-hydroxy-1-(2,3-dimethoxyphenyl)-1-piperidinecarboxylic acid, 1,1-dimethylethyl ester (8) with an enantiomeric excess of about 80% to >99%.

In Scheme F, step b, the 1,1-dimethylethyl ester protecting group of (R)-4-(1-hydroxy-1-(2,3-dimethoxyphenyl)-1-piperidinecarboxylic acid, 1,1-dimethylethyl ester (8) is removed to give (R)-α-(2,3-dimethoxyphenyl)-4-piperidinemethanol (1).

For example, (R)-4-( 1-hydroxy-1-(2,3-dimethoxyphenyl)-1-piperidinecarboxylic acid, 1,1-dimethylethyl ester (8) is contacted with a suitable acid, such as aqueous hydrochloric acid or trifluoroacetic acid, at a temperature range of from about 5° C. to about room temperature for a period of time ranging from about 5 minutes to 5 hours. The (R)-α-(2,3-dimethoxyphenyl)-4-piperidinemethanol (1) is recovered from the reaction zone by filtration or extractive methods as are known in the art and may be purified by recrystallization.

In Scheme F, step c, the ketone functionality of 4-(2,3-dimethoxybenzoyl)-1-piperidinecarboxylic acid, 1,1-dimethylethyl ester (7) is reduced and the 1,1-dimethylester protecting group is removed to give 4-[1-hydroxy-1-(2,3-dimethoxyphenyl)methyl]piperidine (11).

For example 4-(2,3-dimethoxybenzoyl)-1-piperidinecarboxylic acid, 1,1-dimethylethyl ester (7) is contacted with sodium borohydride in a suitable solvent, such as tetrahydrofuran at a temperature of about 0° C. to room temperature for a period of time ranging from about 30 minutes to 10 days. The intermediate 4-[1-hydroxy-1-(2,3-dimethoxyphenyl)methyl]piperidine, 1,1-dimethylethyl ester (not shown) may be recovered from the reaction zone by extractive methods as are known in the art and may be purified by chromatography. The 1,1-dimethyl ester protecting group on the intermediate 4-[1-hydroxy-1-(2,3-dimethoxyphenyl)methyl]piperidine, 1,1-dimethylethyl ester may be removed and the 4-[1-hydroxy-1-(2,3-dimethoxyphenyl)-methyl]piperidine (11) may be recovered from the reaction zone essentially as described above in Scheme F, step b. Alternatively, the 1,1-dimethylethyl ester functionality of the 4-(2,3-dimethoxybenzoyl)-1-piperidinecarboxylic acid, 1,1-dimethylethyl ester (7) may be removed first by treatment with acid as described above to give 4-(2,3-dimethoxybenzoyl)-1-piperidine, which is then reduced as described above to give the 4-[1-hydroxy-1-(2,3-dimethoxyphenyl)-methyl]piperidine (11).

In Scheme F, step d, 4-pyridinecarboxaldehyde (9) is reacted with lithiated veratrole to give 4-[1-hydroxy-1-(2,3-dimethoxyphenyl)methyl]pyridine (10).

For example, 4-pyridinecarboxaldehyde (9) is reacted with lithiated veratrole in the presence of a suitable aprotic solvent, such as hexane, tetrahydrofuran, toluene, mixtures of hexane and tetrahydrofuran, mixtures of hexane and toluene, mixtures of tetrahydrofuran and toluene, or mixtures of hexane, tetrahydrofuran and toluene, at a temperature of from about −25° C. to over 30° C. for a period of time ranging from about 30 minutes to 10 hours. 4-[1-Hydroxy-1-(2,3-dimethoxyphenyl)methyl]pyridine (10) is recovered from the reaction zone by extractive methods as are known in the art and may be purified by recrystallization.

In Scheme F, step e, the pyridine functionality of 4-[1-hydroxy-1-(2,3-dimethoxyphenyl)methyl]pyridine (10) is reduced to give 4-[1-hydroxy-1-(2,3-dimethoxyphenyl)methyl]piperidine (11).

For example, 4-[1-hydroxy-1-(2,3-dimethoxyphenyl)methyl]pyridine (10) is subjected to catalytic hydrogenation, using 5% rhodium on carbon or rhodium on alumina as catalyst in a suitable solvent, such as methanol, toluene, acetic acid, or mixtures thereof. The reaction is typically conducted at about 55 to about 150 psig at a temperature of about room temperature to 80° C. for a period of time ranging from about 2 hours to about 20 hours. The 4-[1-hydroxy-1-(2,3-dimethoxyphenyl)methyl]piperidine (11) may be recovered from the reaction zone by filtration of the catalyst followed by concentration.

In Scheme F, step f, (R)-α-(2,3-dimethoxyphenyl)-4-piperidinemethanol (1) is separated from racemic 4-[1-hydroxy-1-(2,3-dimethoxyphenyl)methyl]piperidine (11) using. diastereomeric salt separation techniques.

For example, 4-[1-hydroxy-1-(2,3-dimethoxyphenyl)methyl]piperidine (11) is contacted with a suitable chiral acid, such as (2R,3R)-(−)-di-(p-toluoyl)tartaric acid or (2R,3R)-(−)-di-(p-anisoyl)tartaric acid, in the presence of a suitable solvent, such as isopropanol, at reflux temperatures. After cooling, (R)-α-(2,3-dimethoxyphenyl)-4-piperidinemethanol, acid salt selectively crystallizes and may be separated from the (S)-α-(2,3-dimethoxyphenyl)-4-piperidinemethanol, acid salt by filtration as generally described previously in Scheme B. The enantiomeric excess of (R)-α-(2,3-dimethoxyphenyl)-4-piperidinemethanol, acid salt may be further increased by recrystallization as described previously in Scheme C, step a for (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a). Treatment with a suitable base as described previously in Scheme C, step b, for (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) yields (R)-α-(2,3-dimethoxyphenyl)-4-piperidinemethanol (1) typically having an enantiomeric excess in the range of from about 85% to >99%. The enantiomeric excess of (R)-α-(2,3-dimethoxyphenyl)-4-piperidinemethanol (1) may be further increased by selective enzymatic hydrolysis techniques as described previously in Scheme E for (R)-α-(2,3-dimethoxyphenyl)-1-[2-(4-fluorophenyl)ethyl]-4-piperidinemethanol (3). In addition, similar techniques as described previously in Schemes B, C and D may be used for recovery of resolving agent and recovery of racemic 4-[1-hydroxy-1-(2,3-dimethoxyphenyl)methyl]piperidine (11) from recrystallization and salt-forming mother liquors.

In Scheme F, step g, the pyridine and ketone functionality's of 4-(2,3-dimethoxybenzoyl)pyridine (12) are reduced to give 4-[1-hydroxy-1-(2,3-dimethoxyphenyl)methyl]piperidine (11).

For example, 4-(2,3-dimethoxybenzoyl)pyridine (12) is subjected to catalytic hydrogenation using a suitable catalyst, such as rhodium on carbon or rhodium on alumina in a suitable solvent, such as methanol. The hydrogenation is typically carried out at approximately 55 psig at room temperature for a period of time ranging from about 10 hours to 48 hours. The 4-[1-hydroxy-1-(2,3-dimethoxyphenyl)methyl]piperidine (11) is typically recovered from the reaction zone by filtration of the catalyst and concentration.

In Scheme F, step h, the (R)-4-(1-hydroxy-1-(2,3-dimethoxyphenyl)-1-piperidinecarboxylic acid, 1,1-dimethylethyl ester (8) may be racemized to 4-(1-hydroxy-1-(2,3-dimethoxyphenyl)-1-piperidinecarboxylic acid, 1,1-dimethylethyl ester (11) by treatment with a suitable acid, such as hydrochloric acid or trifluoroacetic acid, with heating at a temperature range of from about 35° C. to about 100° C. for a period of time ranging from about 15 minutes to 15 hours. The 4-(1-hydroxy-1-(2,3-dimethoxyphenyl)-1-piperidinecarboxylic acid, 1,1-dimethylethyl ester (11) may be recovered from the reaction zone by extractive methods as are known in the art.

4-(2,3-Dimethoxybenzoyl)-1-piperidinecarboxylic acid, 1,1-dimethylethyl ester (7) for use in Scheme F, steps a and c, may be prepared as described in Scheme G. 4-(2,3-Dimethoxybenzoyl)pyridine (12) for use in Scheme F, step g, may be prepared as described in Scheme H.

As stated above, 4-(2,3-dimethoxybenzoyl)-1-piperidinecarboxylic acid, 1,1-dimethylethyl ester (7) for use in Scheme F, steps a and c, may be prepared as described in Scheme G.

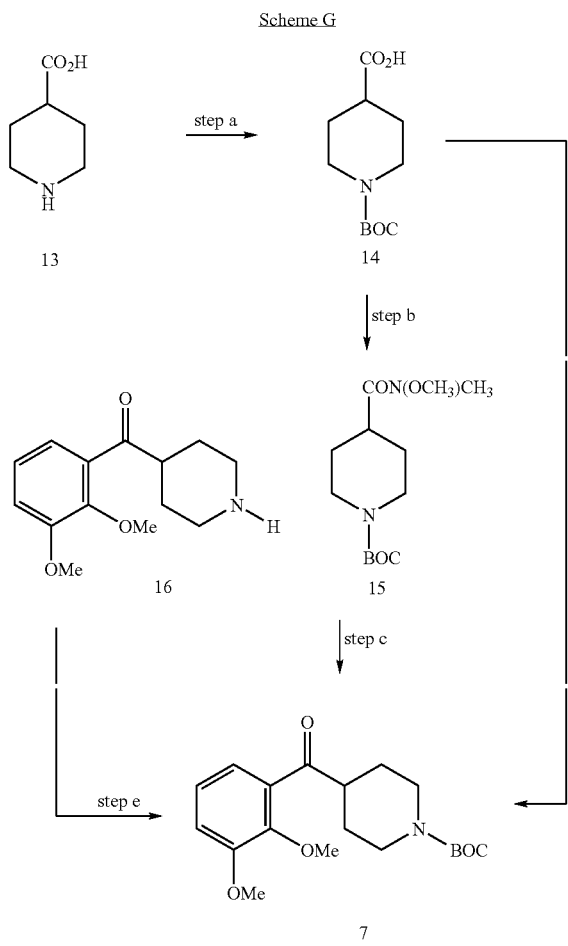

In Scheme G, step a, the piperidine functionality of 4-piperidinecarboxylic acid (13) is protected to give 1,4-piperidinedicarboxylic acid, 1-(1,1-dimethylethyl)ester (14).

For example, 4-piperidinecarboxylic acid (13) is contacted with di-tert-butyldicarbonate in the presence of a suitable base, such as sodium hydroxide, in a suitable solvent such as t-butanol, aqueous ethanol, or ethanol, at a temperature range of from about 0° C. to about 50° C. for a period of time ranging from about 30 minutes to 24 hours. After carefully quenching with a suitable acid, such as hydrochloric acid, the 1,4-piperidinedicarboxylic acid, 1-(1,1-dimethylethyl)ester (14) is typically recovered from the reaction zone by extractive methods as are known in the art.

In Scheme G, step b, the 4-carboxylic acid functionality of 1,4-piperidinedicarboxylic acid, 1-(1,1-dimethylethyl)ester (14) is reacted with N,O-dimethylhydroxylamine hydrochloride to give 4-[(methoxymethylamino)carbonyl]-1-piperidinecarboxylic acid, 1,1-dimethylethyl ester (15).

For example, 1,4-piperidinedicarboxylic acid, 1-(1,1-dimethylethyl)ester (14) is first contacted with a reagent suitable for forming an activated form of 1,4-piperidinedicarboxylic acid, 1-(1,1-dimethylethyl)ester (14), such as 1,1'-carbonyldiimidazole or oxalyl chloride. When 1,1'-carbonyldiimidazole is utilized, suitable solvents are methylene chloride and the like and the reactants are typically contacted at room temperature for a period of time ranging from about 30 minutes to 5 hours. When oxalyl chloride is utilized, suitable solvents are toluene and the like, and are preferably contacted in the presence of a suitable catalyst, such as N,N-dimethylformamide. The reactants are typically contacted at a temperature range of from about 15° C. to about 50° C. for a period of time ranging from about 10 minutes to 2 hours. The activated form of 1,4-piperidinedicarboxylic acid, 1-(1,1-dimethylethyl) ester is then contacted with N,O-dimethylhydroxylamine at room temperature for a period of time ranging from about 3 hours to 15 hours. Regardless of the reagent used, the 4-[(methoxymethylamino)carbonyl]-1-piperidinecarboxylic acid, 1,1-dimethylethyl ester (15) may be recovered from the reaction zone by extractive methods as are known in the art and may be crystallized from a suitable solvent, such as heptane or a mixture of heptanes.

In Scheme G, step c, 4-[(methoxymethylamino)carbonyl]-1-piperidinecarboxylic acid, 1,1-dimethylethyl ester (15) is reacted with lithiated veratrole to give 4-(2,3-dimethoxybenzoyl)-1-piperidinecarboxylic acid, 1,1-dimethylethyl ester (7).

For example, 4-[(methoxymethylamino)carbonyl]-1-piperidinecarboxylic acid, 1,1-dimethylethyl ester (15) is typically contacted with a solution of lithiated veratrole in tetrahydrofuran at a temperature range of from about −78° C. to about room temperature for a period of time ranging from about 6 hours to 24 hours. The 4-(2,3-dimethoxybenzoyl)-1-piperidinecarboxylic acid, 1,1-dimethylethyl ester (7) may be recovered from the reaction zone by extractive methods as are known in the art and may be purified by chromatography.

In Scheme G, step d, 1,4-piperidinedicarboxylic acid, 1-(1,1-dimethylethyl)ester (14) is reacted with lithiated veratrole to give 4-(2,3-dimethoxybenzoyl)-1-piperidinecarboxylic acid, 1,1-dimethylethyl ester (7).

For example, 1,4-piperidinedicarboxylic acid, 1-(1,1-dimethylethyl)ester (14) is first contacted with a solution of n-butyl lithium in a suitable solvent, such as tetrahydrofuran, at a temperature range of from about −78° to 0° C. for a period of time ranging from about 15 minutes to 2 hours.

The reaction mixture is then treated with lithiated veratrole, typically as a tetrahydrofuran solution, at a temperature range of from about −5° C. to about room temperature for a period of time ranging from about 2 hours to 24 hours. The 4-(2,3-dimethoxybenzoyl)-1-piperidinecarboxylic acid, 1,1-dimethylethyl ester (7) may be recovered from the reaction by extractive methods as are known in the art and may be purified by chromatography.

In Scheme G, step e, 4-(2,3-dimethoxybenzoyl)piperidine (16) is protected to give 4-(2,3-dimethoxybenzoyl)-1-piperidinecarboxylic acid, 1,1-dimethylethyl ester (7).

For example, 4-(2,3-dimethoxybenzoyl)piperidine (16) is contacted with di-tert-butyldicarbonate in the presence of a suitable base, such as sodium hydroxide, and a suitable solvent, such as aqueous ethanol, at room temperature for a period of time ranging from about 30 minutes to 10 hours. The 4-(2,3-dimethoxybenzoyl)-1-piperidinecarboxylic acid, 1,1-dimethylethyl ester (7) may be recovered from the reaction zone by extractive methods as are known in the art.

4-(2,3-Dimethoxybenzoyl)piperidine (16) for use in Scheme G, step e, may be prepared as described in U.S. Pat. No. 5,169,096 or as described in Scheme L.

As stated previously, 4-(2,3-dimethoxybenzoyl)pyridine (12) for use in Scheme F, step g, may be prepared as described in Scheme H.

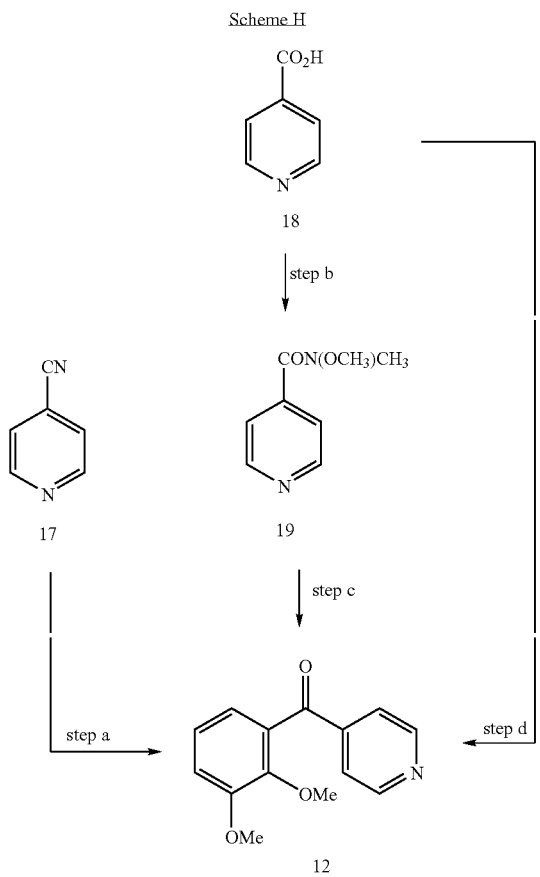

In Scheme H, step a, 4-cyanopyridine (17) is reacted with lithiated veratrole to give 4-(2,3-dimethoxybenzoyl)pyridine (13).

For example, 4-cyanopyridine (17) is contacted with lithiated veratrole in a suitable solvent, such as tetrahydrofuran, diethyl ether, hexane, toluene, or mixtures thereof, at a temperature range of below 6° C. to room temperature for a period of time ranging from 30 minutes to 5 hours. After quenching with a suitable acid, such as hydrochloric acid, the 4-(2,3-dimethoxybenzoyl)pyridine (13) is recovered from the reaction zone by extractive methods as are known in the art.

In Scheme H, step b, 4-pyridinecarboxylic acid (18) is reacted with N,O-dimethylhydroxylamine hydrochloride to give 4-[(methoxymethylamino)carbonyl]pyridine (19).

For example, 4-pyridinecarboxylic acid (18) is first contacted with a reagent suitable for forming an activated form of 4-pyridinecarboxylic acid (18), such as 1,1'-carbonyldiimidazole or oxalyl chloride. When 1,1'-carbonyldiimidazole is utilized, suitable solvents are methylene chloride and the like and the reactants are typically contacted at room temperature for a period of time ranging from about 30 minutes to 5 hours. When oxalyl chloride is utilized, suitable solvents are toluene and the like, and are preferably contacted in the presence of a suitable catalyst, such as N,N-dimethylformamide. The reactants are typically contacted at a temperature range of from about 15° C. to about 50° C. for a period of time ranging from about 10 minutes to 12 hours. The activated form of 4-pyridinecarboxylic acid is then contacted with N,O-dimethylhydroxylamine at room temperature for a period of time ranging from about 3 hours to 15 hours. Regardless of the reagent used, the 4-[(methoxymethylamino)carbonyl]pyridine (19) may be recovered from the reaction zone by extractive methods as are known in the art and may be purified by distillation.

In Scheme H, step c, 4-[(methoxymethylamino)carbonyl]pyridine (19) is reacted with lithiated veratrole to give 4-(2,3-dimethoxybenzoyl)pyridine (12).

For example, 4-[(methoxymethylamino)carbonyl]pyridine (19) is contacted with lithiated veratrole in a suitable solvent, such as tetrahydrofuran, at a temperature range of from about −78° C. to room temperature for a period of time ranging from about 1 hour to 24 hours. After quenching with a suitable acid, such as acetic acid or hydrochloric acid, the 4-(2,3-dimethoxybenzoyl)pyridine (12) is recovered from the reaction zone by extractive methods as are known in the art.

In Scheme H, step d, 4-pyridinecarboxylic acid (18) is reacted with lithiated veratrole to give 4-(2,3-dimethoxybenzoyl)pyridine (12).

For example, 4-pyridinecarboxylic acid (18) is contacted with lithiated veratrole in a suitable solvent, such as tetrahydrofuran, at a temperature range of from about −78° C. to room temperature for a period of time ranging from about 6 hours to 24 hours. After quenching with a suitable acid, such as acetic acid or hydrochloric acid, the 4-(2,3-dimethoxybenzoyl)pyridine (12) is recovered from the reaction zone by extractive methods as are known in the art.

As stated previously, α-(2,3-dimethoxyphenyl)-1-[2-(4-fluorophenyl)ethyl]-4-piperidinemethanol (5) for use in Scheme A, step c, is described in U.S. Pat. No. 5,169,096 or may be prepared as described in Scheme C, Scheme D or Scheme I.

As stated above, α-(2,3-dimethoxyphenyl)-1-[2-(4-fluorophenyl)ethyl]-4-piperidinemethanol (5) for use in Scheme A, step c, may be prepared as described in Scheme I.

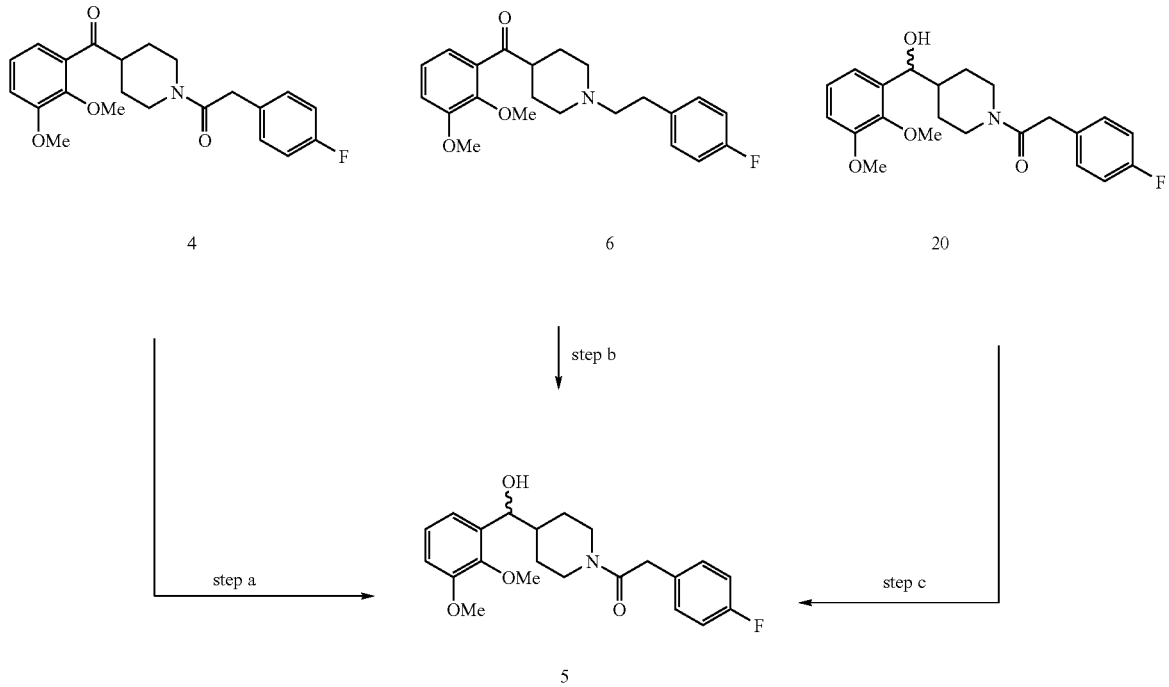

Scheme I

In Scheme I, step a, 4-[1-oxo-1-(2,3-dimethoxyphenyl) methyl]-N-2-(4-fluorophen-1-oxo-ethyl)-piperidine (4) is reduced to give α-(2,3-dimethoxyphenyl)-1-[2-(4-fluorophenyl)ethyl]-4-piperidinemethanol (5).

For example, 4-[1-oxo-1-(2,3-dimethoxyphenyl)methyl]-N-2-(4-fluorophenyl-1-oxo-ethyl)-piperidine (4) is contacted with a suitable reducing agent, such as sodium bis(2-methoxyethoxy)aluminum hydride or borane, in a suitable solvent, such as toluene, tetrahydrofuran, or mixtures of toluene/tetrahydrofuran, at a temperature range of from about −15° C. to about 60° C. for a period of time ranging from about 30 minutes to about 10 hours. After quenching with a suitable base, such as sodium hydroxide or diethylenetriamine, the α-(2,3-dimethoxyphenyl)-1-[2-(4-fluorophenyl) ethyl]-4-piperidinemethanol (5) may be recovered from the reaction zone by extractive methods as are known in the art and may be purified by recrystallization.

In Scheme I, step b, 4-[1-oxo-1-(2,3-dimethoxyphenyl) methyl]-N-2-(4-fluorophenylethyl)-piperidine (6) is reduced to give α-(2,3-dimethoxyphenyl)-1-[2-(4-fluorophenyl) ethyl]-4-piperidinemethanol (5).

For example, 4-[1-oxo-1-(2,3-dimethoxyphenyl)methyl]-N-2-(4-fluorophenylethyl)-piperidine (6) is contacted with a suitable reducing agent, such as sodium borohydride or lithium aluminum hydride, in a suitable solvent, such as ethanol for sodium borohydride and tetrahydrofuran for lithium aluminum hydride, at a temperature range of from about 0° C. to room temperature, for a period of time ranging from about 2 hours to 24 hours. The α-(2,3-dimethoxyphenyl)-1-[2-(4-fluorophenyl)ethyl]-4-piperidinemethanol (5) may be recovered from the reaction zone by extractive methods as are known in the art and may be purified by recrystallization.

In Scheme I, step c, 4-[1-hydroxy-1-(2,3-dimethoxyphenyl)methyl]-N-2-(4-fluorophen-1-oxo-ethyl)piperidine (20) is reduced to give α-(2,3-dimethoxyphenyl)-1-[2-(4-fluorophenyl)ethyl]-4-piperidinemethanol (5).

For example, 4-[1-hydroxy-1-(2,3-dimethoxyphenyl)methyl]-N-2-(4-fluorophen-1-oxo-ethyl)piperidine (20) is contacted with a suitable reducing agent, such as borane or borane-dimethylsulfide complex, in a suitable solvent, such as toluene, tetrahydrofuran, and the like, at a temperature range of from about −20° C. to about 60° C. for a period of time ranging from about 1 hour to 5 hours. After quenching with a suitable base, such as diethylenetriamine, the α-(2,3-dimethoxyphenyl)-1-[2-(4-fluorophenyl)ethyl]-4-piperidinemethanol (5) may be recovered from the reaction zone by extractive methods as are known in the art or by filtration.

4-[1-Oxo-1-(2,3-dimethoxyphenyl)methyl]-N-2-(4-fluorophen-1-oxo-ethyl)piperidine (4) for use in Scheme I, step a, may be prepared as described in Scheme J. 4-[1-Oxo-1-(2,3-dimethoxyphenyl)methyl]-N-2-(4-fluorophenylethyl) piperidine (6) for use in Scheme I, step b, may be prepared as described in U.S. Pat. No. 5,169,096 or as described in Scheme K. 4-[1-Hydroxy-1-(2,3-dimethoxyphenyl)methyl]-N-2-(4-fluorophen-1-oxo-ethyl)piperidine (20) for use in Scheme I, step c, may be prepared as described in Scheme M.

As stated above, 4-[1-oxo-1-(2,3-dimethoxyphenyl)methyl]-N-2-(4-fluorophen-1-oxo -ethyl)piperidine (4) for use in Scheme I, step a, may be prepared as described in Scheme J.

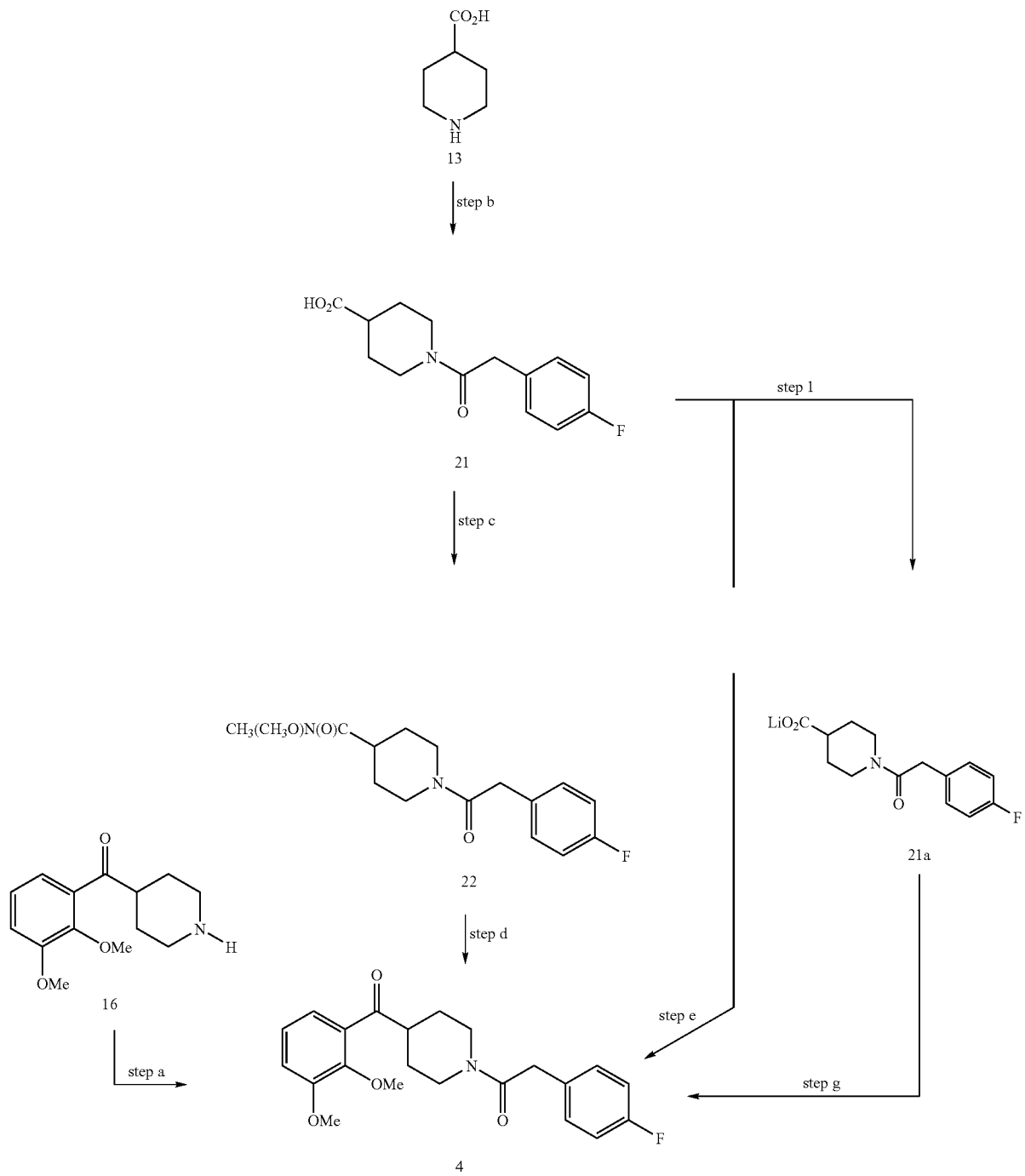

In Scheme J, step a, 4-(2,3-dimethoxybenzoyl)piperidine (16) is reacted with an appropriate 4-fluorophenylacetylating reagent to give 4-[1-oxo-1-(2,3-dimethoxyphenyl)methyl]-N-2-(4-fluorophen-1-oxo-ethyl)piperidine (4).

For example, 4-(2,3-dimethoxybenzoyl)piperidine (16) is contacted with an appropriate 4-fluorophenylacetylating reagent, such as 4-fluorophenylacetyl chloride, in a suitable solvent, such as toluene or aqueous toluene, in the presence of a suitable basic scavenging agent, such as hydroxides (e.g., sodium hydroxide, potassium hydroxide) and organic amine bases (e.g., diethylamine and) diisopropylethylamine), at a temperature range of from about −15° C. to about room temperature for a period of time ranging from about 30 minutes to 5 hours. The 4-[1-oxo-1-(2,3-dimethoxyphenyl)methyl]-N-2-(4-fluorophen-1-oxo-ethyl)piperidine (4) may be recovered from the reaction zone by extractive methods as are known in the art.

In Scheme J, step b, 4-piperidinecarboxylic acid (13) is reacted with an appropriate 4-fluorophenylacetylating reagent to give N-(4-fluorophenylacetyl)-4-carboxylpiperidine (21).

For example, 4-piperidinecarboxylic acid (13) is contacted with an appropriate 4-fluorophenylacetylating reagent, such as 4-fluorophenylacetyl chloride, in the presence of a suitable basic scavenger, such as hydroxides (e.g., sodium hydroxide or potassium hydroxide) and carbonates (e.g., potassium carbonate and sodium carbonate), in a suitable aqueous medium, such as water or mixtures of water and acetone, at a temperature range of from about 0° C. to 50° C. for a period of time ranging from about 10 minutes to 5 hours. The N-4-fluorophenylacetyl)-4-carboxylpiperidine (21) may be recovered from the reaction zone by extractive methods as are known in the art.

In Scheme J, step c, N-(4-fluorophenylacetyl)-4-carboxylpiperidine (21) is reacted with N,O-dimethylhydroxylamino to give N-(4-fluorophenylacetyl)-4-(N,O-dimethylhydroxyaminocarboxy)piperidine (22).

For example, N-(4-fluorophenylacetyl)-4-carboxylpiperidine (21) is first contacted with a reagent suitable for forming an activated form of N-(4-fluorophenylacetyl)-4-carboxylpiperidine (21), such as 1,1'-carbonyldiimidazole or oxalyl chloride. When 1,1'-carbonyldiimidazole is utilized, suitable solvents are methylene chloride and the like and the reactants are typically contacted at room temperature for a period of time ranging from about 30 minutes to 5 hours. When oxalyl chloride is utilized, suitable solvents are toluene and the like, and are preferably contacted in the presence of a suitable catalyst, such as N,N-dimethylformamide. The reactants are typically contacted at a temperature range of from about 15° C. to about 50° C. for a period of time ranging from about 10 minutes to 12 hours. The activated form of N-(4-fluorophenylacetyl)-4-carboxylpiperidine is then contacted with N,O-dimethylhydroxylamine at room temperature for a period of time ranging from about 3 hours to 15 hours. Regardless of the reagent used, the N-(4-fluorophenylacetyl)-4-(N,O-dimethylhydroxyaminocarboxy)piperidine (22) may be recovered from the reaction zone by extractive methods as are known in the art and may be purified by distillation.

In Scheme J, step d, N-(4-fluorophenylacetyl)-4-(N,O-dimethylhydroxyaminocarboxy)piperidine (22) is reacted with lithiated veratrole to give 4-[1-oxo-1-(2,3-dimethoxyphenyl)methyl]-N-2-(4-fluorophen-1-oxo-ethyl)piperidine (4).

For example, N-(4-fluorophenylacetyl)-4-(N,O-dimethylhydroxyaminocarboxy)piperidine (22) is contacted with lithiated veratrole in a suitable solvent, such as tetrahydrofuran, at a temperature range of from about −78° C. to room temperature for a period of time ranging from 2 hours to 12 hours. The 4-[1-oxo-1-(2,3-dimethoxyphenyl)methyl]-N-2-(4-fluorophen-1-oxo-ethyl)piperidine (4) may be recovered from the reaction zone by extractive methods as are known in the art and may be purified by chromatography.

In Scheme J, step e, N-(4-fluorophenylacetyl)-4-carboxylpiperidine (21) is reacted with lithiated veratrole to give 4-[1-oxo-1-(2,3-dimethoxyphenyl)methyl]-N-2-(4-fluorophen-1-oxo-ethyl)piperidine (4).

For example, N-(4-fluorophenylacetyl)-4-carboxylpiperidine (21) is contacted with lithiated veratrole in a suitable solvent, such as tetrahydrofuran, at a temperature range of from about −78° C. to room temperature for a period of time ranging from about 2 hours to 12 hours. The 4-[1-oxo-1-(2,3-dimethoxyphenyl)methyl]-N-2-(4-fluorophen-1-oxo-ethyl)piperidine (4) may be recovered from the reaction zone by extractive methods as are known in the art and may be purified by chromatography.

In Scheme J, step f, N-(4-fluorophenylacetyl)-4-carboxylpiperidine (21) is reacted with lithium hydroxide to give N-(4-fluorophenylacetyl)-4-carboxylpiperidine, lithium salt (21a).

For example, N-(4-fluorophenylacetyl)-4-carboxylpiperidine (21) is contacted with lithium hydroxide monohydrate in a suitable aqueous solvent system, such as aqueous tetrahydrofuran, at a temperature range of from about 0° C. to about 50° C. for a period of time ranging from about 5 minutes to about 5 hours. The N-(4-fluorophenylacetyl)-4-carboxylpiperidine, lithium salt (21a) may be recovered from the reaction zone by methods as are known in the art, such as azeotropic distillation with toluene.

In Scheme J, step g, N-(4-fluorophenylacetyl)-4-carboxylpiperidine, lithium salt (21a) is reacted with lithiated veratrole to give 4-[1-oxo-1-(2,3-dimethoxyphenyl)methyl]-N-2-(4-fluorophen-1-oxo-ethyl)piperidine (4).

For example, N-(4-fluorophenylacetyl)-4-carboxylpiperidine, lithium salt (21a) is contacted with lithiated veratrole in a suitable solvent, such as tetrahydrofuran, at a temperature range of from about −25° C. to about room temperature for a period of time ranging from about 15 minutes to about 12 hours. The 4-[1-oxo-1-(2,3-dimethoxyphenyl)methyl]-N-2-(4-fluorophen-1-oxo-ethyl)piperidine (4) may be recovered from the reaction zone by extractive methods as are known in the art and may be purified by chromatography.

4-(2,3-Dimethoxybenzoyl)piperidine (16) for use in Scheme J, step a, may be prepared as described in U.S. Pat. No. 5,169,096 or as described in Scheme L.

As stated previously, 4-[1-oxo-1-(2,3-dimethoxyphenyl)methyl]-N-2-(4-fluorophenylethyl)piperidine (6) for use in Scheme I, step b, may be prepared as described in U.S. Pat. No. 5,169,096 or as described in Scheme K.

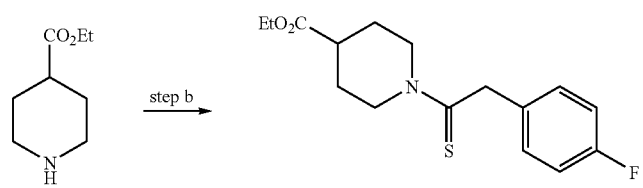

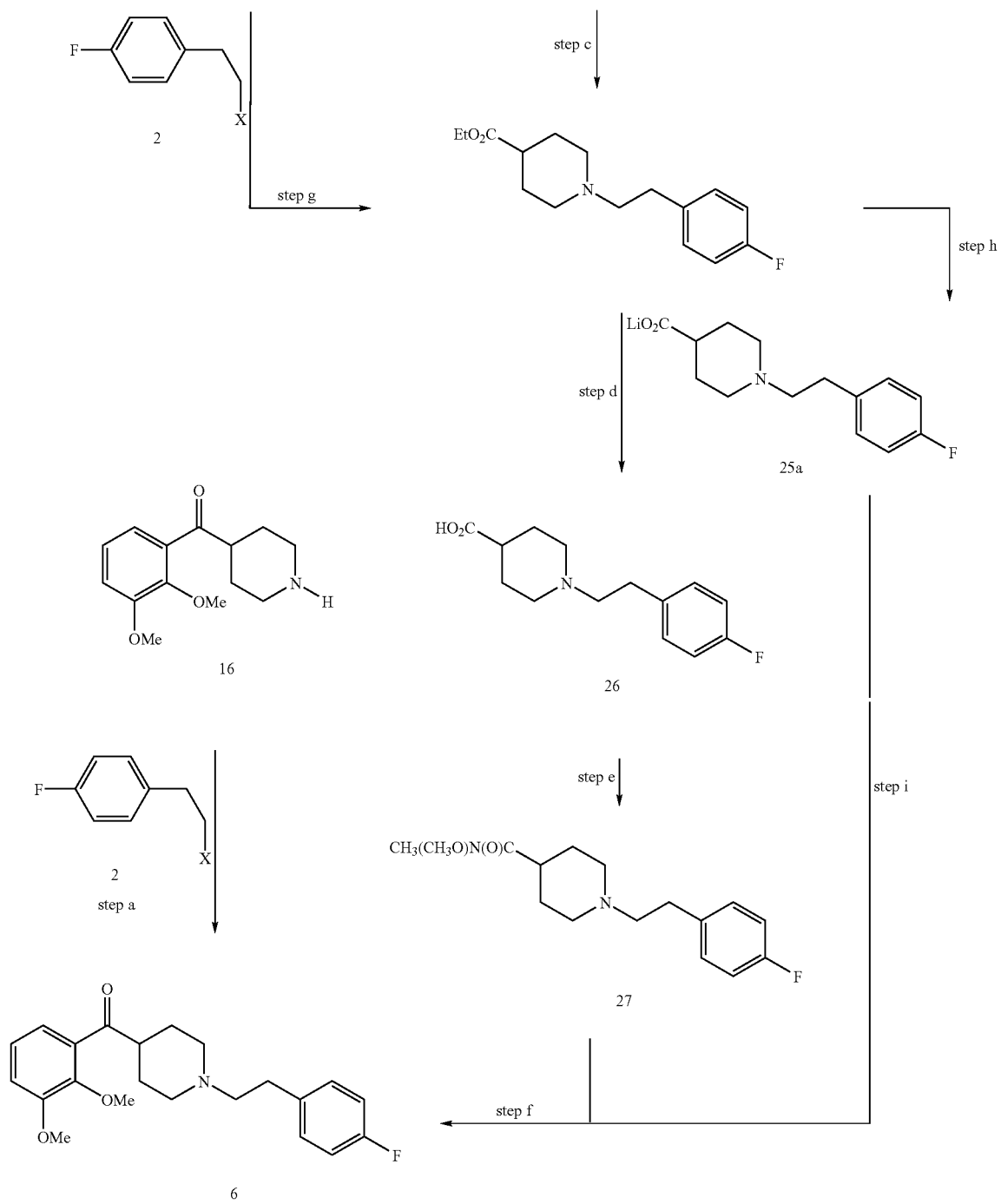

In Scheme K, step a, 4-(2,3-dimethoxybenzoyl)piperidine (16) is reacted with a 4-fluorophenylethyl alkylating agent of structure (2) to give 4-[1-oxo-1-(2,3-dimethoxyphenyl)methyl]-N-2-(4-fluorophenylethyl)piperidine (6) using techniques and procedures well known to one of ordinary skill in the art.

For example, 4-(2,3-dimethoxybenzoyl)piperidine (16) can be reacted with the 4-fluorophenylethyl alkylating agent of structure (2), wherein X is a suitable leaving group such as halide, methanesulfonate, and the like, in the presence of a suitable base, such as potassium carbonate, optionally in the presence of a suitable catalyst such as sodium iodide or potassium iodide, in a suitable organic solvent, such as acetonitrile or aqueous tetrahydrofuran. The reactants are typically stirred together at a temperature of from about room temperature to reflux temperature of the solvent chosen for a period of time ranging from about 2 hours to about 25 hours. The resulting 4-[1-oxo-1-(2,3-dimethoxyphenyl)

methyl]-N-2-(4-fluorophenylethyl)piperidine (6) may be recovered from the reaction zone by extractive methods as are known in the art.

In Scheme K, step b, 4-piperidinecarboxylic acid, ethyl ester (23) is reacted with p-fluoroacetophenone and sulfur to give ethyl N-(4-fluorophenylthioacetyl)-4-carboxylpiperidine (24).

For example, 4-piperidinecarboxylic acid, ethyl ester (23) is contacted with p-fluoroacetophenone and sulfur, in the presence of a catalytic amount of p-toluenesulfonic acid, in a suitable solvent, such as toluene, at a temperature sufficient to azeotropically remove water. Water is removed over a period of time ranging from about 3 hours to 7 hours. The ethyl N-(4-fluorophenylthioacetyl)-4-carboxylpiperidine (24) may be recovered from the reaction zone by extractive methods as are known in the art and may be purified by distillation or chromatography.

In Scheme K, step c, ethyl N-(4-fluorophenylthioacetyl)-4-carboxylpiperidine (24) is reduced to give 1-(4-carboethoxypiperidine)-2-(4-fluorophenyl)ethane (25).

For example, ethyl N-(4-fluorophenylthioacetyl)-4-carboxylpiperidine (24) is contacted with a suitable reducing agent, such as borane·dimethylsulfide complex, in a suitable solvent, such as tetrahydrofuran at room temperature for a period of time ranging from about 15 minutes to 3 hours. After a methanol quench, the 1-(4-carboethoxypiperidine)-2-(4-fluorophenyl)ethane (25) is recovered from the reaction zone by concentration of the solvent and may be purified by distillation.

In Scheme K, step d, 1-(4-carboethoxypiperidine)-2-(4-fluorophenyl)ethane (25) is hydrolyzed to give 1-(4-carboxypiperidine)-2-(4-fluorophenyl)ethane (26).

For example, 1-(4-carboethoxypiperidine)-2-(4-fluorophenyl)ethane (25) is contacted with a suitable hydrolyzing agent, such as aqueous hydrochloric acid and/or aqueous acetic acid at reflux temperature for a period of time ranging from 30 minutes to 5 hours. The 1-(4-carboxypiperidine)-2-(4-fluorophenyl)ethane (26) may be recovered from the reaction zone by concentration of the solvent and may be purified by crystallization.

In Scheme K, step e, 1-(4-carboxypiperidine)-2-(4-fluorophenyl)ethane (26) is reacted with N,O-dimethylhydroxylamine to give 1-(4'-(N,O-dimethylhydroxylaminocarboxy)piperidino)-2-(4'-fluorophenyl)ethane (27).

For example, 1-(4-carboxypiperidine)-2-(4-fluorophenyl)ethane (26) is first contacted with a reagent suitable for forming an activated form of 1-(4-carboxypiperidine)-2-(4-fluorophenyl)ethane (26), such as 1,1'-carbonyldiimidazole or oxalyl chloride. When 1,1'-carbonyldiimidazole is utilized, suitable solvents are chloroform, methylene chloride and the like and the reactants are typically contacted at room temperature for a period of time ranging from about 30 minutes to 5 hours. When oxalyl chloride is utilized, suitable solvents are toluene and the like, and are preferably contacted in the presence of a suitable catalyst, such as N,N-dimethylformamide. The reactants are typically contacted at a temperature range of from about 15° C. to about 50° C. for a period of time ranging from about 10 minutes to 12 hours. The activated form of 1-(4-carboxypiperidine)-2-(4-fluorophenyl)ethane is then contacted with N,O-dimethylhydroxylamine at room temperature for a period of time ranging from about 3 hours to 15 hours. Regardless of the reagent used, the 1-(4'-(N,O-dimethylhydroxylaminocarboxy)piperidino)-2-(4'-fluorophenyl)ethane (27) may be recovered from the reaction zone by extractive methods as are known in the art and may be purified by distillation.

In Scheme K, step f, 1-(4'-(N,O-dimethylhydroxylaminocarboxy)piperidino)-2-(4'-fluorophenyl)ethane (27) is reacted with lithiated veratrole to give 4-[1-oxo-1-(2,3-dimethoxyphenyl)methyl]-N-2-(4-fluorophenylethyl)-piperidine (6).

For example, 1-(4'-(N,O-dimethylhydroxylaminocarboxy)piperidino)-2-(4'-fluorophenyl)ethane (27) is contacted with lithiated veratrole in a suitable solvent, such as tetrahydrofuran, at a temperature range of from –20° C. to room temperature for a period of time ranging from 30 minutes to 8 hours. The 4-[1-oxo-1-(2,3-dimethoxyphenyl)methyl]-N-2-(4-fluorophenylethyl)-piperidine (6) may be recovered from the reaction zone by extractive methods as are known in the art.

In Scheme K, step g, 4-piperidinecarboxylic acid, ethyl ester (23) is reacted with a 4-fluorophenylethyl alkylating agent of structure (2) to give 1-(4-carboethoxypiperidine)-2-(4-fluorophenyl)ethane (25) using techniques and procedures well known to one of ordinary skill in the art.

For example, 4-piperidinecarboxylic acid, ethyl ester (23) can be reacted with the 4-fluorophenylethyl alkylating agent of structure (2), wherein X is a suitable leaving group such as halide, methanesulfonate, and the like, with methanesulfonate being preferred, in the presence of a suitable base, such as potassium carbonate, optionally in the presence of a suitable catalyst such as sodium iodide or potassium iodide, in a suitable organic solvent, such as acetonitrile or aqueous tetrahydrofuran. The reactants are typically stirred together at a temperature of from about room temperature to reflux temperature of the solvent chosen for a period of time ranging from about 2 hours to about 25 hours. The resulting 1-(4-carboethoxypiperidine)-2-(4-fluorophenyl)ethane (25) may be recovered from the reaction zone by extractive methods as are known in the art.

In Scheme K, step h, 1-(4-carboethoxypiperidine)-2-(4-fluorophenyl)ethane (25) is reacted with lithium hydroxide to give 1-(4-carboxypiperidine)-2-(4-fluorophenyl)ethane, lithium salt (25a).

For example, 1-(4-carboethoxypiperidine)-2-(4-fluorophenyl)ethane (25) is contacted with lithium hydroxide monohydrate in a suitable aqueous solvent system, such as aqueous tetrahydrofuran, at a temperature range of from about room temperature to about 80° C. for a period of time ranging from about 1 hours to about 24 hours. The 1-(4-carboxypiperidine)-2-(4-fluorophenyl)ethane, lithium salt (25a) may be recovered from the reaction zone by methods as is known in the art, such as azeotropic distillation.

In Scheme K, step i, 1-(4-carboxypiperidine)-2-(4-fluorophenyl)ethane, lithium salt (25a) is reacted with lithiated veratrole to give 4-[1-oxo-1-(2,3-dimethoxyphenyl)methyl]-N-2-(4-fluorophenylethyl)-piperidine (6).

For example, 1-(4-carboxypiperidine)-2-(4-fluorophenyl)ethane, lithium salt (25a) is contacted with lithiated veratrole in a suitable solvent, such as tetrahydrofuran, at a temperature range of from about –20° C. to about 20° C. for a period of time ranging from about 30 minutes to about 24 hours. The 4-[1-oxo-1-(2,3-dimethoxyphenyl)methyl]-N-2-(4-fluorophenylethyl)-piperidine (6) may be recovered from the reaction zone by extractive methods as are known in the art.

As stated previously, 4-(2,3-dimethoxybenzoyl)piperidine (16) for use in Scheme J, step a, and for use in Scheme K, step a, may be prepared as described in U.S. Pat. No. 5,169,096 or as described in Scheme L.

Scheme L

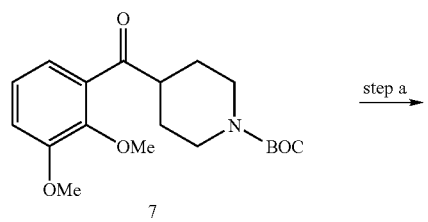

step a

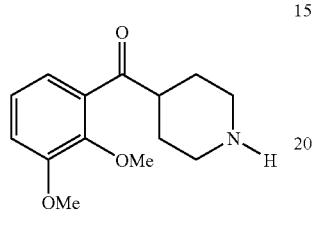

In Scheme L, step a, 4-(2,3-dimethoxybenzoyl)-1-piperidinecarboxylic acid, 1,1-dimethylethyl ester (7) is deprotected to give 4-(2,3-dimethoxybenzoyl)piperidine (16).

For example, 4-(2,3-dimethoxybenzoyl)-1-piperidinecarboxylic acid, 1,1-dimethylethyl ester (7) is contacted with a suitable acid, such as trifluoroacetic acid or aqueous hydrochloric acid, optionally in the presence of a suitable solvent, such as tetrahydrofuran at a temperature range of from room temperature to 60° C. for a period of time ranging from about 30 minutes to 24 hours. The 4-(2,3-dimethoxybenzoyl)piperidine (16) may be recovered from the reaction zone by treatment with a suitable base, such as sodium hydroxide, followed by extractive methods as are well known in the art.

4-(2,3-Dimethoxybenzoyl)-1-piperidinecarboxylic acid, 1,1-dimethylethyl ester (7) for use in Scheme L, step a may be prepared as described in Scheme G. 4-[(Methoxymethylamino)-carbonyl]-1-piperidinecarboxylic acid, 1,1-dimethylethyl ester (15) for use in Scheme L, step b, may be prepared as described in Scheme G, step b.

As stated previously, 4-[1-hydroxy-1-(2,3-dimethoxyphenyl)methyl]-N-2-(4-fluorophen-1-oxo-ethyl)piperidine (20) for use in Scheme I, step c, may be prepared as described in Scheme M.

Scheme M

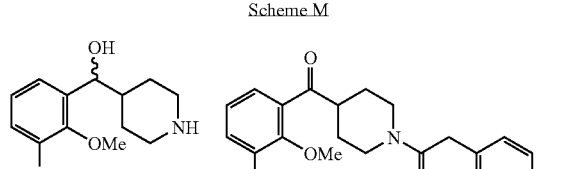

-continued step b

In Scheme M, step a, 4-[1-hydroxy-1-(2,3-dimethoxyphenyl)methyl]piperidine (11) is reacted with a suitable 4-fluorophenylacetylating reagent to give 4-[1-hydroxy-1-(2,3-dimethoxyphenyl)methyl]-N-2-(4-fluorophen-1-oxo-ethyl)piperidine (20).

For example, 4-[1-hydroxy-1-(2,3-dimethoxyphenyl)methyl]piperidine (11) is contacted with a suitable 4-fluorophenylacetylating reagent, such as 4-fluorophenylacetyl chloride, in the presence of a suitable base, such as sodium hydroxide, in a suitable solvent, such as methanol, toluene, toluene/methanol, aqueous toluene, methanol/acetic acid, methanol/acetic acid/toluene, or toluene/acetic acid at a temperature range of from 0° C. to 50° C. for a period of time ranging from 15 minutes to 5 hours. The 4-[1-hydroxy-1-(2,3-dimethoxyphenyl)methyl]-N-2-(4-fluorophen-1-oxo-ethyl)piperidine (20) may be recovered from the reaction zone by extractive methods as are known in the art and may be purified by distillation.

In Scheme M, step b, 4-[1-oxo-1-(2,3-dimethoxyphenyl)methyl]-N-2-(4-flurophen-1-oxo-ethyl)piperidine (4) is reduced to give 4-[1-hydroxy-1-(2,3-dimethoxyphenyl)methyl]-N-2-(4-fluorophen-1-oxo-ethyl)piperidine (20).

For example, 4-[1-oxo-1-(2,3-dimethoxyphenyl)methyl]-N-2-(4-flurophen-1-oxo -ethyl)piperidine (4) is contacted with a suitable reducing agent, such as sodium borohydride, optionally in the presence of a suitable catalyst, such as sodium hydroxide, in a suitable solvent, such as ethanol at room temperature for a period of time ranging from about 2 hours to 24 hours. The 4-[1-hydroxy-1-(2,3-dimethoxyphenyl)methyl]-N-2-(4-fluorophen-1-oxo -ethyl)piperidine (20) is recovered from the reaction zone by extractive methods as are known in the art and may be purified by chromatography.

4-[1-Hydroxy-1-(2,3-dimethoxyphenyl)methyl]piperidine (11) for use in Scheme M, step a, may be prepared as described in Scheme F, steps c, e, and f. 4-[1-Oxo-1-(2,3-dimethoxyphenyl)methyl]-N-2-(4-fluorophen-1-oxo-ethyl)piperidine (4) for use in Scheme M, step b, may be prepared as described previously in Scheme J.

A preferred process for preparing (R)-α-(2,3-dimethoxyphenyl)-1-[2-(4-fluorophenyl)ethyl]-4-piperidinemethanol is shown in Scheme N.

Scheme N

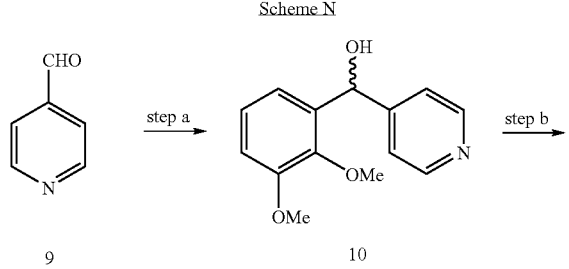

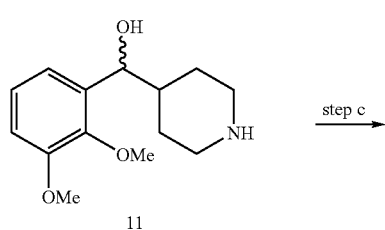

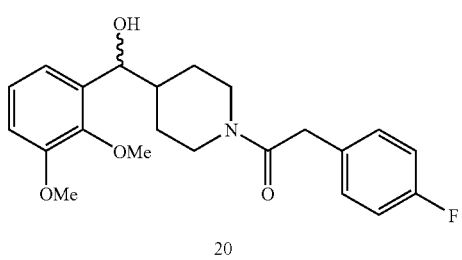

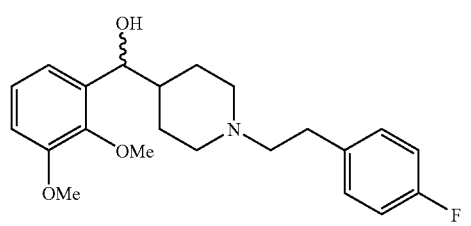

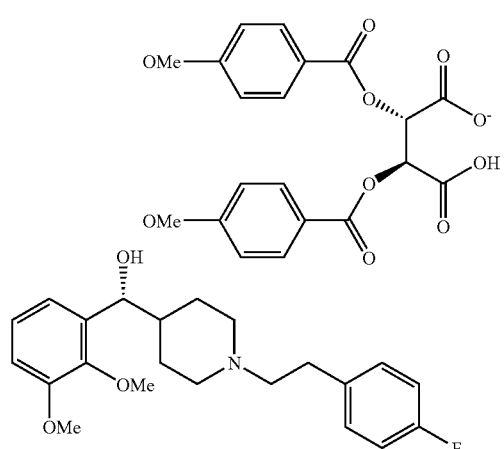

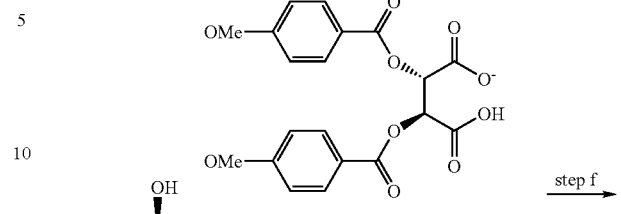

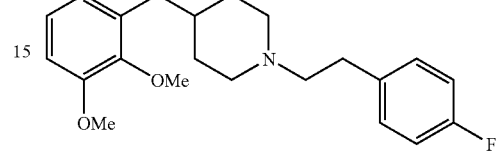

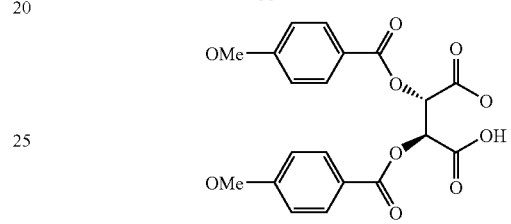

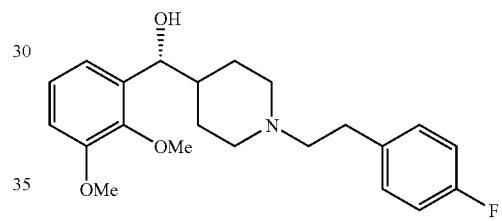

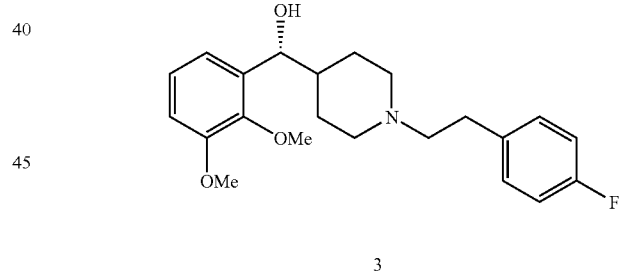

In Scheme N, step a, 4-pyridinecarboxaldehyde (9) is reacted with lithiated veratrole to give 4-[1-hydroxy-1-(2,3-dimethoxyphenyl)methyl]pyridine (10) as described previously in Scheme F, step d.

In Scheme N, step b, the pyridine functionality of 4-[1-hydroxy-1-(2,3-dimethoxyphenyl)methyl]pyridine (10) is reduced to give 4-[1-hydroxy-1-(2,3-dimethoxyphenyl)methyl]piperidine (11) as described previously in Scheme F, step e.

In Scheme N, step c, 4-[1-hydroxy-1-(2,3-dimethoxyphenyl)methyl]piperidine (11) is reacted with a suitable 4-fluorophenylacetylating reagent to give 4-[1-hydroxy-1-(2,3-dimethoxyphenyl)methyl]-N-2-(4-fluorophen-1-oxo-ethyl)piperidine (20) as described previously in Scheme M, step a.

In Scheme N, step d, 4-[1-hydroxy-1-(2,3-dimethoxyphenyl)methyl]-N-2-(4-fluorophen-1-oxo-ethyl)piperidine (20) is reduced to give α-(2,3-dimethoxyphenyl)-1-[2-(4-fluorophenyl)ethyl]-4-piperidinemethanol (5) as described previously in Scheme I, step c.

In Scheme N, step e, α-(2,3-dimethoxyphenyl)-1-[2-(4-fluorophenyl)ethyl]-4-piperidinemethanol (5) is reacted with (2S,3S)-(+)-di-(p-anisoyl)tartaric acid to give a mixture of (R)-α-(2,3-dimethoxyphenyl)-1-[2-(4-fluorophenyl)ethyl]-4-piperidinemethanol, (2S,3S) -(+)-di-(p-anisoyl)tartaric acid salt (3a) and (S)-α-(2,3-dimethoxyphenyl)-1-[2-(4-fluorophenyl)ethyl]-4-piperidinemethanol, (2S,3S)-(+)-di-(p-anisoyl)tartaric acid salt (3b) as described previously in Scheme B, step a.

In Scheme N, step f, the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) is separated from the mixture of (R)-α-(2,3-dimethoxyphenyl)-1-[2-(4-fluorophenyl)ethyl]-4-piperidinemethanol, (2S,3S)-(+)-di-(p-anisoyl) tartaric acid salt (3a) and (S)-α-(2,3-dimethoxyphenyl)-1-[2-(4-fluorophenyl)ethyl]-4-piperidinemethanol, (2S,3S)-(+)-di-(p-anisoyl)tartaric acid salt (3b) by filtration as described previously in Scheme B, step b.

In Scheme N, step g, the (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) is converted to (R)-α-(2,3-dimethoxyphenyl)-1-[2-(4-fluorophenyl)ethyl]-4-piperidinemethanol (3) by treatment with a suitable base as described previously in Scheme C, step b. The ee of (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a) may optionally be improved by recrystallization as described previously in Scheme C, step a prior to conversion to (R)-α-(2,3-dimethoxyphenyl)-1-[2-(4-fluorophenyl)ethyl]-4-piperidinemethanol (3).

The following examples present typical syntheses as described in Schemes A through M. These examples are illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; ° C. refers to degrees Celsius; "mm Hg" refers to millimeters of mercury; "µL" refers to microliters; "µg" refers to micrograms; "nm" refers to nanomolar; "µM" refers to micromolar; "HPLC" refers to High Performance Liquid Chromatography; and "ee" refers to enantiomeric excess.

EXAMPLE 1

Scheme A, step a: (R)-α-(2,3-Dimethoxyphenyl)-1-[2-(4-fluorophenyl)ethyl]-4-piperidinemethanol (3)

A suitable reactor maintained under nitrogen was charged with 4-fluorophenethyl alcohol (2.6 kg, 18.6 mol) and 18 L of methylene chloride. The stirred solution was cooled to and maintained at 0-5° C. while triethylamine 2.85 kg (28.2 mol) was added fairly rapidly. The reaction temperature was maintained at 0-5° C. while adding methanesulfonyl chloride (2.5 kg, 21.8 mol) over 1 hour. The stirred reaction mixture was maintained at 0-5° C. for 1 hour, then it was warmed to room temperature within approximately 2 hours. The reaction mixture was diluted with a solution of 0.5 kg of 33% hydrochloric acid in 10 L of water. The organic phase was separated and washed with a solution of 0.2 kg of 33% hydrochloric acid in 5 L of water. Both acidic extracts were combined and extracted with 5 L of methylene chloride. Both organic phases were combined, washed with 2×15 L of water, then dried with sodium sulfate (2 kg). Drying agent was filtered off and washed with 2×5 L of methylene chloride. The majority of the solvent was boiled off at atmospheric pressure, with the final amount distilled off at 35° C./500 torr to give 4-fluorophenethyl alcohol methanesulfonate (4.17 kg.)

A suitable reactor maintained under nitrogen was charged with (R)-α-(2,3-dimethoxyphenyl)-4-piperidinemethanol (1) from Scheme F, steps a and b, Example 45 (3.7 kg, 14.7 mol, 95.5% ee), potassium carbonate (2.65 kg, 19.2 mol), sodium iodide (0.25 kg, 1.67 mol) and 60 L of acetonitrile were then added. The stirred reaction mixture was slowly heated to 75° C. over 15 hours. After cooling the reaction mixture to 50° C., it was diluted with 15 L of water. Solvent was distilled off below 50° C. at 500 to 200 torr. The residue was cooled to 25° C. and 25 L of water was added. The mixture was extracted with 2×35 L of methylene chloride. Organic extracts were combined, washed with 2×35 L of water, then sodium sulfate (5 kg) and activated carbon (0.3 kg) were added. After stirring for 30 minutes, the drying agent and activated carbon were filtered off and washed with 2×10 L of methylene chloride. Solvent was distilled off below 40° C. at 500 torr. The residue obtained was diluted with 30 L of isopropanol, then the stirred mixture was heated to 52° C. to obtain complete solution. The stirred mixture was slowly cooled to room temperature over 17 hours, then cooled to 17° C. Solid which crystallized was filtered off, washed with 2×3 L of cold isopropanol, then air dried to give the title compound (R)-α-(2,3-dimethoxyphenyl)-1-[2-(4-fluorophenyl)ethyl]-4-piperidinemethanol (3) (3.25 kg, 59% yield, 98.5% ee).

A suitable reactor maintained under nitrogen is charged with (R)-α-(2,3-dimethoxyphenyl)-1-[2-(4-fluorophenyl)ethyl]-4-piperidinemethanol (3) (3.25 kg), 6.8 L of ethanol and 34 L of toluene. The mixture was stirred until solution was obtained, then silica gel (5 kg) was added. The mixture was stirred at 18° C. for 2 hours. The silica gel was filtered off and washed twice with a mixture of 2 L of ethanol/10 L of toluene. The filtrate was concentrated to a residue below 50° C. at 500 to 200 torr. The residue was diluted with 5 L of isopropanol and solvent was distilled off below 50° C. at 200 torr. The residue obtained was diluted with 8.5 L of isopropanol. The stirred mixture was heated to 70-75° C. until complete solution was obtained. The stirred mixture was cooled to 60° C., then seeded with laboratory material having an optical purity of 99% ee. The stirred mixture was slowly cooled to 20° C. over 20 hours. (R) -α-(2,3-Dimethoxyphenyl)-1-[2-(4-fluorophenyl)ethyl]-4-piperidinemethanol (3) which crystallized was filtered off, washed with 2×1 L of cold isopropanol, then dried in a circulating oven below 40° C. to give the title compound (R)-α-(2,3-dimethoxyphenyl)-1-[2-(4-fluorophenyl)ethyl]-4-piperidinemethanol (3) (2.75 kg, 85% recovery, ee >99%).

The following procedure can be used as an alternative to the silica gel purification. A solution of approximately 1 g of crude (R)-α-(2,3-dimethoxyphenyl)-1-[2-(4-fluorophenyl)ethyl]-4-piperidinemethanol (3)/5 mL of toluene is washed successively with a solution of 0.125 g of sodium metabisulfite/5 mL of water, a solution of 0.04 g of sodium metabisulfite/1.8 mL of water, and 2.0×2.5 mL of saturated sodium chloride solution.

EXAMPLE 2

Scheme A, step b: (R)-α-(2,3-Dimethoxyphenyl)-1-[2-(4-fluorophenyl)ethyl]-4-piperidinemethanol (3)

A solution of 4-[1-oxo-1-(2,3-dimethoxyphenyl)methyl]-N-2-(4-fluorophen-1-oxo-ethyl)piperidine (4) (1.5 g, 3.8 mmol) in tetrahydrofuran (10 mL) is treated with (+)-β-chlorodiisopinocamphenylborane (6.0 g, 18 mmol). The resulting solution is stirred for 60 hours at ambient temperature. The reaction mixture is treated with acetaldehyde (1 mL) and stirred overnight. The mixture is treated with NaOH (2 N) and extracted into toluene. The organic extract is washed with $H_2O$, dried, filtered and concentrated at reduced pressure to leave an oil. Flash chromatography ($SiO_2$, 3:1 EtOAc/toluene) gives the title compound (R)-α-(2,3-dimethoxyphenyl)-1-[2-(4-fluorophenyl)ethyl]-4-piperidinemethanol (3) (0.6 g, 40% yield, 90:10 (R:S).

EXAMPLE 3

Scheme A, step c: (R)-α-(2,3-Dimethoxyphenyl)-1-[2-(4-fluorophenyl)ethyl]-4-piperidinemethanol (3)

A mixture of 4-[1-oxo-1-(2,3-dimethoxyphenyl)methyl]-N-2-(4-fluorophenylethyl)-piperidine (6) hydrochloride salt (212 g, 0.52 mol), aqueous NaOH (1N, 1 L) and methylene chloride (2 L) was stirred at room temperature for 30 minutes. Phases were separated and the aqueous layer was extracted with methylene chloride (1 L). The combined organic solutions were washed with brine (1.5 L) and dried ($MgSO_4$). The mixture was filtered and the filtrate was concentrated (30° C./20 torr) to a residue which was dissolved in anhydrous tetrahydrofuran (400 mL). The resulting solution was added to a solution of 4-[1-hydroxy-1-(2,3-dimethoxyphenyl)methyl]-N-2-(4-fluorophen-1-oxo-ethyl)piperidine-β-chlorodiisopinocamphenylborane ((+)-$Ipc_2BCl$, 500 g, 1.56 mol) in tetrahydrofuran (860 mL) and the mixture was stirred at room temperature for 3 days. Water (210 mL) followed by 30% $H_2O_2$ (260 mL) were added to the solution over 1.5 hours at 10° C. The resulting mixture was extracted with methylene chloride (2 L). The organic layer was washed with 10% $NaHSO_3$ (1 L), 5% NaOH (1 L) and brine (1 L) and dried ($MgSO_4$). The mixture was filtered and the filtrate was concentrated (30° C./20 torr) to a residue which was divided into two portions. Each portion was purified by flash chromatography ($SiO_2$, 10 cm×15 cm, eluted with 2 L of hexane, 3 L of 1:4 EtOAc:hexane, 4 L of 1:1 EtOAc:hexane and 4 L of 1:19 MeOH:EtOAc). The desired fractions (TLC, $R_f$ 0.28, 1:19 MeOH:EtOAc) were combined and concentrated (35° C./20 torr) to give the title compound (5) as a white solid [(R)-enriched, 130 g, 67% yield, 82% ee]; m.p.=105-108° C.

IR (KBr) 3558, 3422, 3141, 2962, 2942, 2833, 2804, 1600, 1584, 1510, 1478, 1430, 1302, 1266, 1222, 1081, 1041, 1006., 836, 792, 755 $cm^{-1}$;

$^1$H NMR ($CDCl_3$) δ 6.7-7.2 (m, 7H, aryl), 4.63 (d, 1H, J=8.5 Hz, CHO), 3.87 (s, 6H, $OCH_3$'s), 3.1 (m, 1H), 2.9 (m, 1H), 2.7 (m, 2H), 2.5 (m, 3H), 1.8-2.1 (m, 3H), 1.7 (m, 1H), 1.2-1.6 (m, 3H);

$^{13}$C NMR ($CDCl_3$) δ 161.3 (d, $J_{F-C}$=242.3 Hz), 152.4, 146.5, 136.4, 136.0, 130.0, 123.9, 119.3, 115.0 (d, $J_{F-C}$=10.5 Hz), 111.4, 74.5, 60.9, 55.7, 53.7, 42.8, 32.9, 28.8, 28.7;

$^{19}$F NMR ($CDCl_3$) δ-118.1;

MS (CI, $CH_4$) m/z (rel. Intensity) 374 ($MH^+$, 65%), 356 (68), 364 (27), 342 (6), 322 (8), 264 (100), 236 (7);

$[α]_D^{20}$+10.30 (c 1.04, $CHCl_3$);

Anal. Calc'd for $C_{22}H_{28}FNO_3$ (373.5): C, 70.75; H, 7.56; N, 3.75. Found: C, 70.53; H, 7.73; N, 3.63.

EXAMPLE 4

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

To a stirred suspension of α-(2,3-dimethoxyphenyl)-1-[2-(4-fluorophenyl)ethyl]-4-piperidinemethanol (5) (16.5 g, 44 mmol) in 2-butanone (100 mL) was added (2S,3S)-(+)-di-(p-anisoyl)tartaric acid (19.3 g, 44 mmol). The mixture was heated to reflux and another 50 mL 2-butanone added. The resulting clear solution was allowed to cool to room temperature while stirring and after the addition of seed crystals [obtained from tetrahydrofuran, using equimolar amounts of α-(2,3-dimethoxyphenyl)-1-[2-(4-fluorophenyl)ethyl]-4-piperidinemethanol (5) and (2S,3S)-(+)-di-(p-anisoyl)tartaric acid (3a', 3a'', or 3a''')] a precipitate formed. After three hours the precipitate was collected, rinsed with 2-butanone and dried to give material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (13.2 g, 37%, 87% ee).

Recrystallization of material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) from 270 mL 2-butanone gave diastereomerically pure (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (10.1 g, 28% yield).

EXAMPLE 5

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

A 100 mL glass round bottom flask was charged with α-(2,3-dimethoxyphenyl)-1-[2-(4-fluorophenyl)ethyl]-4-piperidinemethanol (5) (3.41 g, 9.1 mmol), (2S,3S)-(+)-di-(p-anisoyl)tartaric acid (3.98 g, 9.5 mmol) and methyl ethyl ketone (31 mL). The slurry was heated to reflux until the solution became homogeneous. The resulting yellow solution was cooled to room temperature over a 1-1.5 hour period and allowed to crystallize. Nucleation of the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) occurred at approximately 30-35° C. The slurry was then cooled to 0-5° C. and held at that temperature for 2.5 hours. The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was isolated by filtration on a coarse sintered glass funnel and washed with 9-mL of chilled methyl ethyl ketone. The wet cake was dried in a vacuum oven at 65° C. to a constant weight to give 3.27 g of material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) in a 41.3% yield of 90.7% ee product. In a 100 mL glass round bottom flask the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (3.1 g, 3.9 mmol) was suspended in methyl ethyl ketone (62 mL). The slurry was heated to reflux (78.8° C.) and the resulting homogeneous solution was cooled to room temperature over a 10-15 minute period. Following crystallization of the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a'), the slurry was cooled to 0-5° C. and held at that temperature for 1-1.5 hours. The purified (R) -α-(2,3-dimethoxyphenyl)-1-[2-(4-fluorophenyl)ethyl]-4-piperidinemethanol, (2S,3S)-(+)-di -(p-anisoyl) tartaric acid salt (3a') was then isolated by filtration on a sintered glass funnel and washed with 10-mL of methyl ethyl ketone. The wet cake was dried in a vacuum oven at 65° C. to a constant weight to give the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (2.62 g, 35.9% yield, 97.1% ee).

EXAMPLE 6

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

A three necked round bottomed flask was charged with α-(2,3-dimethoxyphenyl)-1-[2-(4-fluorophenyl)ethyl]-4-piperidinemethanol (5) (36.6 g, 98 mmol), (2S,3S)-(+)-di-(p-anisoyl)tartaric acid (42.9 g, 103 mmol) and methyl ethyl ketone (330 mL). The mixture was heated to reflux over about 20 minutes. When the internal temperature was 45° C. the nearly homogeneous solution began to crystallize. When reflux was achieved the solution was almost homogeneous. The flask was insulated to allow for a slow cool down. After two hours the solution had cooled to 50° C. and was again homogeneous. Seeds of purified (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a, 3a', 3a", or 3a''') were added and the resulting mixture was allowed to cool to ambient temperatures. Prior to isolation the slurry was cooled in an ice bath. The product was isolated by filtration through a coarse sintered glass funnel. The filter cake was washed with cold methyl ethyl ketone (50 mL) and dried by suction. The mass yield of material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was 26.8 g with 92.5% ee. The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was suspended in methyl ethyl ketone (520 mL) and the mixture was heated to reflux over approximately 15 minutes. The homogeneous solution was allowed to cool to ambient temperatures. After stirring overnight, seed crystals of purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a40, 3a", or 3a''') were added and the mixture was stirred at ambient temperatures for 24 hours. The purified (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a') was isolated by filtration through a sintered glass funnel. The filter cake was washed with cold methyl ethyl ketone (50 mL) and dried in a vacuum oven to give the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') as a white solid (14.8 g, 99% ee).

EXAMPLE 7

Scheme B, step a and step b, and Scheme C, step a: (R)-α-(2,3-Dimethoxyphenyl)-1-[2-(4-fluorophenyl)ethyl]-4-piperidinemethanol (2S,3S)-(+)-di-(p-anisoyl)tartaric acid salt (3a")

A 1 L jacketed reactor was charged with (α-(2,3-dimethoxyphenyl)-1-[2-(4-fluorophenyl)ethyl]-4-piperidinemethanol (5) (41.8 g, 0.11 mol), (2S,3S)-(+)-di-(p-anisoyl)tartaric acid (49.9 g, 0.12 mol) and methyl ethyl ketone (375 mL). The mixture was stirred for one hour at 30° C. during which time the solution initially became homogeneous and then crystallized. The slurry was heated to 58-60° C. over about one hour and digested at these temperatures overnight. The slurry was cooled to 5° C. over about 11 hours and the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was isolated by filtration on a sintered glass funnel. The filter cake was washed with cold methyl ethyl ketone (100 mL) to give material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (34.5 g, 86% ee). The material enriched in (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a) (33.8 g, 43 mmol) was suspended in methyl ethyl ketone (675 mL) and digested at 51° C. for about two hours. The slurry was then cooled to 4° C. over about 7.5 hours. The purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') was isolated by filtration on a coarse sintered glass funnel, washed with cold methyl ethyl ketone (100 mL) and suction dried to give the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (30.8 g, 87% ee). The purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (29.5 g, 37 mmol) and methyl ethyl ketone (590 mL) were charged to a 1 L jacketed reactor and the mixture was heated to reflux. A homogeneous yellow solution was obtained which was cooled over about one hour to 51° C. After one hour at 51° C., seed crystals of purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a', 3a", or 3a''') were added to induce crystallization. After an additional 1.5 hours at 51° C. the slurry was cooled to 6° C. overnight. The purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a") was isolated by filtration on a sintered glass funnel, washed with cold methyl ethyl ketone (70 mL), suction dried, and dried overnight in a vacuum oven to give the purified (R)-α-(2,3-dimethoxyphenyl)-1-[2-(4-fluorophenyl)ethyl]-4-piperidinemethanol, (2S,3S)-(+)-di-(p -anisoyl) tartaric acid salt (3a") (15.6 g, 99% ee).

EXAMPLE 8

Scheme B, step a and step b: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a)

α-(2,3-Dimethoxyphenyl)-1-[2-(4-fluorophenyl)ethyl]-4-piperidinemethanol (5) (39.6 g, 106 mmol) was dissolved in methyl ethyl ketone (300 mL) at 45° C. in a Camile® controlled 1 L jacketed reactor. The solution was cooled to 30° C. and (2S,3S)-(+)-di-(p-anisoyl)tartaric acid (46.6 g, 111 mmol) was added. An additional rinse of methyl ethyl ketone (60 mL) was added with the (2S,3S)-(+)-di-(p-anisoyl)tartaric acid. The (2S,3S)-(+)-di-(p-anisoyl)tartaric acid was immediately soluble at 30° C. and the jacket temperature was stepped to 20° C. When the internal temperature reached 24° C. very rapid nucleation and crystallization occurred. The mixture was then cooled to 0° C. over 5 hours and then held at 0° C. prior to isolation. The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was isolated by filtration on a sintered glass funnel. The filter cake was washed with cold methyl ethyl ketone (75 mL) to give the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) after drying in a vacuum oven overnight (48 g, 79% ee).

EXAMPLE 9

Scheme B, step a and step b, and Scheme C, step) a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

A 100 mL glass round bottom flask was charged with (α-(2,3-dimethoxyphenyl)-1-[2-(4-fluorophenyl)ethyl]-4-piperidinemethanol (5) (2.06 g, 5.5 mmol) and (2S,3S)-(+)-di-(p-anisoyl)tartaric acid (2.4 g, 5.7 mmol) and methanol (17 mL). The slurry was heated to reflux and dissolved. The clear homogeneous solution was then cooled to room temperature with crystallization of material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) occurring very rapidly. The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was then isolated by filtration on a coarse sintered glass funnel and the wet cake was washed with cold methanol (10 mL) to give the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (2.21 g, 88.4% ee). The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (2.10 g, 2.7 mmol) was recrystallized from methanol (21 mL) at reflux. The refluxing solution was cooled to room temperature and then chilled in an ice-bath to 0-5° C. Isolation of the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') by filtration on a coarse sintered glass funnel gave 1.86 g, 44% yield, >99% ee.

EXAMPLE 10

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

A 100 mL glass round bottom flask was charged with α-(2,3-dimethoxyphenyl)-1-[2-(4-fluorophenyl)ethyl]-4-piperidinemethanol (5) (2.14 g, 5.7 mmol), (2S,3S)-(+)-di-(p-anisoyl)tartaric acid (2.5 g, 6.0 mmol) and 90% methanol, 10% water (9.5 mL). The slurry was heated to reflux and dissolved. The clear homogeneous solution was then cooled to room temperature with crystallization of the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) occurring very rapidly. The slurry was heated to dissolve some of the diastereomeric salt until the slurry was thin. The mixture was allowed to slowly cool to ambient temperatures. The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was isolated by filtration on a coarse sintered glass funnel and the wet cake washed with cold 90% methanol, 10% water (8 mL) to give the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (2.4g, 52% yield, 90% ee). The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (2.26 g, 2.9 mmol) was recrystallized from 90% methanol, 10% water (23 mL) at reflux. The solution was cooled to room temperature and then chilled in an ice-bath to 0-5° C. Nucleation and crystallization began at 45° C. Isolation by filtration on a coarse sintered glass funnel gave the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (1.93 g, 44.0% yield, >99% ee).

EXAMPLE 11

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

A 100 mL glass round bottom flask was charged with α-(2,3-dimethoxyphenyl)-1-[2-(4-fluorophenyl)ethyl]-4-piperidinemethanol (5) (2.3 g, 6.2 mmol), (2S,3S)-(+)-di-(p-anisoyl)tartaric acid (2.69 g, 6.4 mmol) and ethanol (10 mL). The slurry was heated to reflux and dissolved. The clear homogeneous solution was then cooled to room temperature with crystallization of the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) occurring very rapidly. The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was then isolated by filtration on a coarse sintered glass funnel and the wet cake was washed with cold ethanol (11 mL) to give material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (2.65 g, 53% yield, 89% ee). The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (2.36 g, 3.0 mmol) was recrystallized from ethanol (108 mL) at reflux. The refluxing solution was cooled to room temperature and then chilled in an ice-bath to 0-5° C. Isolation by filtration on a coarse sintered glass funnel gave the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (1.68 g, 38% yield, 96% ee).

EXAMPLE 12

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

A 100 mL glass round bottom flask was charged with α-(2,3-dimethoxyphenyl)-1-[2-(4-fluorophenyl)ethyl]-4-piperidinemethanol (5) (2.02 g, 5.4 mmol), (2S,3S)-(+)-di-(p-anisoyl)tartaric acid (2.5 g, 6 mmol) and ethanol (13 mL). The slurry was heated to reflux and dissolved. The clear homogeneous solution was then cooled to room temperature with crystallization of the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) occurring very rapidly. The thick slurry was heated to dissolve most of the crystals and then allowed to cool slowly to ambient temperature. Filtration on a coarse sintered glass funnel and washing the wet cake with cold ethanol (10 mL) gave the material enriched in (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a)(2.13 g, 49% yield, 92% ee). The material enriched in (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a) (1.96 g, 2.4 mmol) was recrystallized from ethanol (58 mL). The refluxing solution was cooled to room temperature and then chilled in an ice-bath to 0-5° C. Isolation by filtration on a coarse sintered glass funnel gave the purified (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a') (1.73 g, 43% yield, >99% ee).

EXAMPLE 13

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

α-(2,3-Dimethoxyphenyl)-1-[2-(4-fluorophenyl)ethyl]-4-piperidinemethanol (5) (53.9 g, 144 mmol), (2S,3S)-(+)-di-(p-anisoyl)tartaric acid (63.0 g, 150 mmol) and methanol (563 mL) were charged to a 1L Camile® controlled jacketed reactor. The mixture was heated to reflux to prepare a homogeneous solution. The mixture was refluxed for approximately one hour before cooling to 25° C. over 3.5 hours. On the way to 25° C., when the internal temperature was 48° C., very rapid crystallization occurred (monitored with a fibre optic probe). When the internal temperature reached ambient temperature, there was a crust on the surface which was not being agitated. The mixture was heated to 62° C. to thin the slurry. The thin slurry was digested at 62° C. for 3 hours and then cooled at 4° C./hour for 4 hours then at 8° C./hour to 0° C. The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was isolated by filtration on a coarse sintered glass funnel to give 58.6 g, 94% ee after drying. The material enriched in (R)-α-(2,3-dimethoxyphenyl)-1-[2-(4-fluorophenyl)ethyl]-4-piperidinemethanol, (2S,3S)-(+) -di-(p-anisoyl)tartaric acid salt (3a) (45.5 g) was dissolved at reflux into methanol (500 mL). The mixture was held at reflux for thirty minutes and then cooled at 4° C./hour for 5 hours and finally 8° C./hour to 0° C. The slurry was held at 0° C. overnight before isolating the purified (R)-α-(2,3-dimethoxyphenyl)-1-[2-(4-fluorophenyl)ethyl]-4-piperidinemethanol, (2S,3S)-(+) -di-(p-anisoyl)tartaric acid salt (3a') by filtration through a coarse sintered glass funnel. The filter cake was washed with cold methanol (75 mL) and dried in a vacuum oven to give the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (37.8 g, >99% ee).

EXAMPLE 14

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

In a 100 mL glass round bottom flask, α-(2,3-dimethoxyphenyl)-1-[2-(4-fluorophenyl)ethyl]-4-piperidinemethanol (5) (3.21 g, 8.6 mmol), (2S,3S)-(+)-di-(p-anisoyl)tartaric acid (2.17 g, 5.2 mmol), and acetic acid (0.35 g, 5.8 mmol) were slurried in methyl ethyl ketone (29 mL). The slurry became homogeneous upon heating to 50° C. The solution was then cooled to room temperature and seeded with crystals of purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a). After 5 days, the slurry was cooled in an ice bath and isolated by filtration on a coarse sintered glass funnel to give the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (2.76 g, 39.6% yield, 92% ee). The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (2.62 g, 3.3 mmol) was charged to a 100 mL glass round bottom flask with methyl ethyl ketone (52 mL). The slurry was heated to reflux. The diastereomeric salt did not go into solution and additional methyl ethyl ketone (600 mL) was added at reflux until the crystals dissolved completely. Once dissolved, the solution was concentrated by evaporating 350 mL of the methyl ethyl ketone on the rotary evaporator. The yellow solution was seeded with purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') and then chilled in an ice bath. Crystallization occurred after approximately 2 hours of cooling. The slurry was filtered on a coarse sintered glass funnel, and washed with 10 mL of methyl ethyl ketone to give the purified (R)-α-(2,3-dimethoxyphenyl)-1-[2-(4-fluorophenyl)ethyl]-4-piperidinemethanol, (2S,3S)-(+)-di-(p -anisoyl)tartaric acid salt (3a') (0.98 g, 15% yield, >99% ee).

EXAMPLE 15

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

A 100 mL round bottom flask was charged with α-(2,3-dimethoxyphenyl)-1-[2-(4-fluorophenyl)ethyl]-4-piperidinemethanol (5) (3.0 g, 8 mmol), (2S,3S)-(+)-di-(p-anisoyl)tartaric acid (1.71 g, 4.1 mmol), acetic acid (0.29 g, 4.8 mmol) and methanol (12 mL). The slurry was heated to reflux (65° C.) and the resulting homogeneous solution was cooled to room temperature over about 2.5 hours. Nucleation occurred followed by rapid crystallization. The slurry was digested at 45° C. and then cooled to room temperature.

Prior to isolation, the slurry was cooled in an ice bath and then filtered on a coarse sintered glass funnel. The wet cake was washed with cold methanol (6 mL) and dried to give the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) as white needles (1.64 g, 25.4% yield, 95% ee). The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (1.53 g, 2 mmol) was recrystallized from methanol (18 mL) in a 100 mL glass round bottom flask. After cooling, the slurry was heated to 40° C. to crystal digest for 1 hour, then cooled to room temperature. The mixture was cooled in an ice bath prior to filtration on a coarse sintered glass funnel to give the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (1.45 g, 24.1% yield, >99% ee).

EXAMPLE 16

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

A 100 mL round bottom flask was charged with α-(2,3-dimethoxyphenyl)-1-[2-(4-fluorophenyl)ethyl]-4-piperidinemethanol (5) (2.87 g, 7.7 mmol), (2S,3S)-(+)-di-(p-anisoyl)tartaric acid (3.35 g, 8 mmol) and methanol (31 mL). The mixture was heated to reflux providing a homogeneous solution which was cooled to 50° C. and allowed to crystallize. Once crystallization appeared complete, concentrated sulphuric acid (5 drops) was added and the mixture was digested at 50° C. for approximately 2 hours. The slurry was cooled to ambient temperatures, then chilled in an ice water bath prior to isolation of the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a). The product was isolated as a white solid by filtration on a coarse sintered glass funnel. The filter cake was washed with cold methanol (10 mL) to give the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (3.1 g, 89% ee). The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (3.0 g) was dissolved in methanol (35 mL) at reflux. The mixture was allowed to cool slowly to ambient temperature. Nucleation and crystallization occurred at 48° C. The slurry was chilled in an ice bath prior to isolating by filtration on a coarse sintered glass funnel to give the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') as a white solid (2.8 g, 97.6% ee).

EXAMPLE 17

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a)

A 1L Camile®-controlled bottom-drain straight-walled jacketed reactor was fitted with a glass head containing a stainless steel thermocouple, a nitrogen bubbler, a fiber optic probe, an agitator, and a water addition tube. The water addition tube was inserted above the liquid level and allowed water to run down the wall in a dropwise fashion. A piston pump provided slow, constant flow. The agitator was a 4-bladed impeller, pitched 45° for down-flow pumping. The vessel was charged with α-(2,3-dimethoxyphenyl)-1-[2-(4-fluorophenyl)ethyl]-4-piperidinemethanol (5) (72.8 g), (2S,3S)-(+)-di-(p-anisoyl)tartaric acid (45.1 g) and 50% acetic acid (300 g). The mixture was stirred at 350 rpm at a jacket set point of 57° C. The contents were heated to complete dissolution at 53° C. in 10 minutes. After 0.5 hours, the solution at 55° C. was seeded with 94% ee (R)-α-(2,3-dimethoxyphenyl)-1-[2-(4-fluorophenyl)ethyl]-4-piperidinemethanol,(2S,3S)-(+)-di-(p-anisoyl)tartaric acid salt (3a' or 3a"). One hour later, the addition of 75 g of deionized water was started at a rate of 0.14 mL/min. After addition of about ⅔ of the water, the addition rate was increased to 0.23 mL/min. The addition required 7.9 hours. After 1.5 hours, the slurry was cooled from 57° C. to 35° C. at 0.15° C./minute. The slurry was stirred at 35° C. for 11 hours before isolation. The contents were drained to a beaker and immediately separated on a warm 350-mL M (10-15 μm) fritted glass funnel by suction filtration. The 283 g mother liquor was a clear pale yellow. The wet cake was rinsed on the funnel with 112 g 40% HOAc (20° C.). The combined mother liquor and rinse weighed 437 g. The wet cake, 153.5 g, was transferred to a pan and dried in a fume hood to 72.22 g of white crystals. Correcting for the added seed crystal, the gravimetric yield of material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) was 91.7%. By HPLC, the crystal product contained 50.4 wt % (2S,3S)-(+)-di-(p-anisoyl)tartaric acid and 47.1 wt % α-(2,3-dimethoxyphenyl)-1-[2-(4-fluorophenyl)ethyl]-4-piperidinemethanol. By chiral HPLC, the area % ratio of (R)-α-(2,3-dimethoxyphenyl)-1-[2-(4-fluorophenyl)ethyl]-4-piperidinemethanol (3) to (S)-α-(2,3-dimethoxyphenyl)-1-[2-(4-fluorophenyl)ethyl]-4-piperidinemethanol (3c) was 94.3%: 5.7% or 88.6% ee. The combined mother liquor plus rinse solution contained 1.56 wt % (2S,3S)-(+)-di-(p-anisoyl)tartaric acid and 8.82 wt % α-(2,3-dimethoxyphenyl)-1-[2-(4-fluorophenyl)ethyl]-4-piperidinemethanol. By chiral HPLC, the ratio of (R)-α-(2,3-dimethoxyphenyl)-1-[2-(4-fluorophenyl)ethyl]-4-piperidinemethanol (3) to (S)-α-(2,3-dimethoxyphenyl)-1-[2-(4-fluorophenyl)ethyl]-4-piperidinemethanol (3c) was 11.1%:88.9%. The mass accountability was 94% for (2S,3S)-(+)-di-(p-anisoyl)tartaric acid, and was 96% for α-(2,3-dimethoxyphenyl)-1-[2-(4-fluorophenyl)ethyl]-4-piperidinemethanol (5) (assuming 100% assay of raw materials). The normalized molar accountability of (R)-α-(2,3-dimethoxyphenyl)-1-[2-(4-fluorophenyl)ethyl]-4-piperidinemethanol (3):(S)-α-(2,3-dimethoxyphenyl)-1-[2-(4-fluorophenyl)ethyl]-4-piperidinemethanol (3c) was 50.7: 49.3.

EXAMPLE 18

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

α-(2,3-Dimethoxyphenyl)-1-[2-(4-fluorophenyl)ethyl]-4-piperidinemethanol (5) recovered from the racemization of the mother liquors of Example 38 (39.5 g, 0.1 mol) and (2S,3S)-(+)-di-(p-anisoyl)tartaric acid (46.46 g, 0.1 mol)

were dissolved in methanol (400 mL) at reflux in a 1 L round bottomed flask. The clear solution was suction filtered to remove any insoluble sodium sulfate and allowed to slowly cool to ambient temperatures. At 40° C. crystallization occurred. The slurry was chilled in an ice bath and then isolated by filtration, washed with chilled methanol (50 mL) and dried to a constant weight (46.5 g, 55%, 87.5% ee). The material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (45.38 g) was dissolved in methanol (460 mL) at reflux, allowed to cool and was isolated by filtration. The white solid was washed with chilled methanol (50 mL) then dried to constant weight to give purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (40.58 g, 49.6% yield, 98.6% ee).

EXAMPLE 19

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a")

In a 500 mL glass round bottom flask equipped with a cold water condenser, heating mantle, magnetic stirrer and a nitrogen line, α-(2,3-dimethoxyphenyl)-1-[2-(4-fluorophenyl)ethyl]-4-piperidinemethanol (5) (17.68 g, 47 mmol; recovered from the racemization of the mother liquors of Example 37), (2S,3S)-(+)-di-(p-anisoyl)tartaric acid (20.79 g, 50 mmol) and methanol (197 mL) were combined and heated to reflux. The solution crystallized at 55° C. while cooling to room temperature. The slurry was chilled in an ice bath to 0° C. The crystals were suction filtered and washed with methanol (25 mL) before being dried to a constant weight in a vacuum oven. Isolation of the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (15.22 g) was done in a 40.6% yield (maximum yield is 50%) and had an optical purity of 79.9%.

The dried crystals were then re-crystallized. In a 500 mL glass round bottom flask, the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (15.0 g) was combined with methanol (195 mL). The slurry was heated to reflux and cooled slowly to room temperature, crystallization occurred at approximately 50° C. The slurry was chilled in an ice bath for 30 minutes and then suction filtered. The crystals were washed with methanol (20-25 mL) before being dried in a vacuum oven to a constant weight. Isolation of the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (12.94 g) was in a 35% yield (based on the yield from the first crystallization) and had an optical purity of 96.5%. The purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') was still less than the desired purity of >99% so a second recrystallization was done.

The 96.5% ee purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (12.75 g) was combined with methanol (200 mL) and heated to reflux. The solution was cooled to room temperature and crystallized. The slurry was chilled in an ice bath for 30 minutes and then suction filtered through a coarse sintered glass funnel. The isolation of the twice recrystallized purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a") (10.53 g) was in a 28.9% yield (based on yield of the second crystallization) having an optical purity of 98.9%.

EXAMPLE 20

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

In a suitable reactor, maintained under an argon atmosphere, is slurried p-anisic acid (39.5 kg, 260 mol) with about 51 kg of xylenes.[1] Oxalyl chloride (27.7 kg) is added while maintaining the temperature below about 60° C. The mixture is heated between 50-60° C. for about 1 hour until a homogeneous solution is formed. The mixture is heated to about 100° C. and any remaining oxalyl chloride is removed by distillation. The mixture is then cooled to 60-70° C.

In a second suitable reactor, (2S,3S)-(−)-tartaric acid (12.7 kg, 85 mol) is slurried with about 45 kg of xylenes[2]. The warm (above 70° C.) solution of p-anisoyl chloride is added and the mixture is heated to about 135° C. for about 3 hours. The mixture is then cooled to about 60° C. About 13 kg of oxalyl chloride is added and the mixture is heated to about 65° C. for at least 1 hour. The reaction mixture may be heated to about 70° C. to partially dissolve the anhydride[3]. The mixture is then maintained at this temperature for about 1 hour. The crystallization is completed by cooling the mixture to about −10° C. for approximately 1 hour prior to isolating the anhydride by filtration. The wet cake is washed with about 38 kg of cold xylenes to typically afford 22-36 kg (13-20% xylenes) of anhydride (70-91% yield)[4].

A suitable reactor is charged with anhydride (28 kg, 60 mol) as a xylenes wet cake, acetone (78 kg) and 26 kg of water. The mixture is heated at reflux (60° C.) for about 2 hours. To the mixture (at about 60° C.) is added about 190 kg of water, causing precipitation of (2S,3S)-(+)-di-(p-anisoyl)tartaric acid. Acetone is removed by distillation until the temperature of the mixture reaches about 80° C. The mixture is cooled to about 5° C. and the product is isolated by filtration. The reactor and transfer lines are rinsed with about 38 kg of water. The wet cake is washed with about 170 kg of water to typically afford 23-33 kg (with 5-30% solvent) of (2S,3S)-(+)-di-(p-anisoyl)tartaric acid (64-104% yield).[5] The product is dried at about 70-80° C. (under vacuum).[6]

A suitable reactor is charged with α-(2,3-dimethoxyphenyl)-1-[2-(4-fluorophenyl)ethyl]-4-piperidinemethanol (5) (40.0 kg, 107 mol) as an isopropanol wet cake and (2S,3S)-(+)-di-(p-anisolyl)tartaric acid (46.8 kg, 112 mol). About 285 kg of methanol is added and the mixture is heated to about 65° C. The mixture is cooled to below 5° C. for at least 1 hour and material enriched in (R)-α-(2,3-dimethoxyphenyl)-1-[2-(4-fluorophenyl)ethyl]-4-piperidinemethanol, (2S,3S)-(+)-di-(p-anisolyl)tartaric acid salt (3a) (85-90% ee) is recovered by filtration. The wet cake is washed with about 28 kg of methanol to typically afford 48-49 kg of material enriched in (R)-α-(2,3-dimethoxyphenyl)-1-[2-(4-fluorophenyl)ethyl]-4-piperidinemethanol, (2S,3S)-(+)-di-(p-anisolyl)tartaric acid salt (3a) (45-50% yield)[7].

Into a suitable reactor is charged the material enriched in (R)-α-(2,3-dimethoxyphenyl)-1-[2-(4-fluorophenyl)ethyl]-4-piperidinemethanol, (2S,3S)-(+)-di-(p-anisolyl)tartaric acid salt (3a) and about 383 kg of methanol.[8] The mixture is heated at about 65° C. The mixture is cooled to below 5° C. for at least 1 hour and the purified (R)-α-(2,3-dimethoxyphenyl)-1-[2-(4-fluorophenyl)ethyl]-4-piperidinemethanol, (2S,3S)-(+)-di-(p-anisolyl)tartaric acid salt (3a') (98-100% ee) is isolated by filtration.[9] The filter cake is washed with about 43 kg of cold methanol to typically afford 37.4 to 39.3 kg of purified (R)-α-(2,3-dimethoxyphenyl)-1-[2-(4-fluorophenyl)ethyl]-4-piperidinemethanol, (2S,3S)-(+)-di-(p-anisolyl)tartaric acid salt (3a') (90-95% yield) as a methanol wet cake.[9]

[1]The mother liquors from the filtration of anhydride of previous batches contain p-anisoyl chloride and anhydride and can be recycled. The exact amount of p-anisic acid used for each bath is determined following an assay of the mother liquors.
[2]The amount of xylenes used to slurry the tartaric acid is reduced when a batch using mother liquor from the filtration of anhydride of previous batches according to footnote 1 is used. The amount of xylenes added is adjusted to maintain the concentration of anhydride in the crystallization step.
[3]The mixture may be seeded with anhydride to aid the crystallization.
[4]The yields are determined by HPLC assay and loss on drying.
[5]The yields are determined in combination with loss on drying and HPLC assay.
[6]The product from other batches may be combined to dry.
[7]The weights of the material enriched in (R)-α-(2,3-dimethoxyphenyl)-1-[2-(4-fluorophenyl)ethyl]-4-piperidinemethanol, (2S,3S)-(+)-di-(p-anisolyl)tartaric acid salt (3a) are based on HPLC assay. The % ee is determined by chiral HPLC analysis.
[8]The dry weight of material enriched in (R)-α-(2,3-dimethoxyphenyl)-1-[2-(4-fluorophenyl)ethyl]-4-piperidinemethanol, (2S,3S)-(+)-di-(p-anisolyl)tartaric acid salt (3a) is used as the basis amount of methanol to be added.
[9]The yields are determined by HPLC assay. The % ee is determined by a chiral HPLC procedure.

EXAMPLE 21

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

In a suitable reactor, maintained under an inert atmosphere, p-anisic acid (361 kg, 2376 mol) is slurried with about 385 kg of xylenes.[1] Oxalyl chloride (about 329 kg) is added maintaining the temperature below about 60° C. The mixture is heated between 50-60° C. for about 1 hour until a homogeneous solution is formed. The mixture is heated to about 100° C. and any remaining oxalyl chloride is removed by distillation. The mixture is then cooled to 60-70° C. In a second suitable reactor, (2S,3S)-(−)-tartaric acid (117 kg, 783 mol) is slurried with about 340 kg of xylenes.2 The warm (above 70° C.) solution of p-anisoyl chloride is added and the mixture is heated to about 135° C. for about 3 hours or until hydrogen chloride evolution stops. The mixture is slowly cooled to about 60° C. About 155 kg of oxalyl chloride is added and the mixture is heated to about 65° C. for at least 1 hour. The reaction mixture is heated to about 70° C. to partially dissolve the anhydride[3]. The mixture is then maintained at this temperature for about 1 hour. The crystallization is completed by cooling the mixture to about −10° C. The slurry is held at about −10° C. for approximately 1 hour prior to isolating the anhydride by filtration. The wet cake is washed with about 290 kg of cold xylenes to typically afford 200-330 kg of anhydride as a wet cake containing about 13-20% xylenes (70-96% yield)[4].

A suitable reactor is charged with anhydride (256 kg, 549 mol) as a xylenes wet cake, acetone (710 kg) and about 240 kg of water. The mixture is heated at reflux (60° C.) for about 2 hours. About 1740 kg of water is added to the mixture at about 60° C., causing precipitation of (2S,3S)-(+)-di-(p-anisoyl)tartaric acid. Acetone is removed by distillation until the temperature of the mixture reaches about 80° C. The mixture is cooled to about 5° C. and the product is isolated by filtration. The reactor and transfer lines are rinsed with about 350 kg of water. The wet cake is washed with about 1550 kg of water to typically afford 210-302 kg of (2S,3S)-(+)-di-(p-anisoyl)tartaric acid as a wet cake containing 5-30% of solvent (64-104% yield)[5]. The product from six batches were combined and dried at 70-80° C. (under vacuum).

A suitable reactor is charged with α-(2,3-dimethoxyphenyl)-1-[2-(4-fluorophenyl)ethyl]-4-piperidinemethanol (5) (40.0 kg, 107 mol) as an isopropanol wet cake and (2S,3S)-(+)-di-(p-anisoyl)tartaric acid (46.8 kg, 112 mol). About 285 kg of methanol is added and the mixture is heated to about 65° C. The mixture is cooled to below 5° C. and material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (85-90% ee) is recovered by filtration. The wet cake is washed with about 10 kg of methanol to typically afford 48-49 kg of material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (45-50% yield).[6] Into a suitable reactor is charged the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) and about 380 kg of methanol.[7] The mixture is heated at about 65° C. The mixture is cooled to below 5° C. and the purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') is isolated by filtration.[5] The filter cake is washed with about 40 kg of cold methanol to typically afford 37.4 to 39.3 kg of purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (90-95% yield, 98-100% ee) as a methanol wet cake.[9]

[1]The mother liquors from the from the filtration of anhydride of previous batches contain p-anisoyl chloride and anhydride and can be recycled. The exact amount of p-anisic acid used for each bath is determined following an assay of the mother liquors.
[2]The amount of xylenes used to slurry the tartaric acid is reduced when a batch using mother liquor from the filtration of anhydride of previous batches according to footnote 1 is used. The amount of xylenes added is adjusted to maintain the concentration of anhydride in the crystallization step.
[3]The mixture may be seeded with anhydride to aid the crystallization.
[4]The yields are determined by HPLC assay and loss on drying.
[5]The yields are determined in combination with loss on drying and HPLC assay.
[6]The weights of the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) are based on HPLC assay. The % ee is determined by a chiral HPLC procedure.
[7](R)-α-(2,3-dimethoxyphenyl)-1-[2-(4-fluorophenyl)ethyl]-4-piperidinemethanol recovered from the filtrates which result from the conversion of (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) to (R)-α-(2,3-dimethoxyphenyl)-1-[2-(4-fluorophenyl)ethyl]-4-piperidinemethanol in Scheme B, step c and (R)-α-(2,3-dimethoxyphenyl)-1-[2-(4-fluorophenyl)ethyl]-4-piperidinemethanol recovered from the filtrates which result from the recrystallization of (R)-α-(2,3-dimethoxyphenyl)-1-[2-(4-fluorophenyl)ethyl]-4-piperidinemethanol in Scheme B, step c, as an isopropanol wet cake may also be charged to the reactor with (2S,3S)-(+)-di-(p-anisoyl)tartaric acid in a 1 to 1 molar ratio. The recovered (R)-α-(2,3-dimethoxyphenyl)-1-[2-(4-fluorophenyl)ethyl]-4-piperidinemethanol typically has an enantiomeric excess of 95% in (R)-α-(2,3-dimethoxyphenyl)-1-[2-(4-fluorophenyl)ethyl]-4-piperidinemethanol. The dry weight of (R)-α-(2,3-dimethoxyphenyl)-1-[2-(4-fluorophenyl)ethyl]-4-piperidinemethanol, (2S,3S)-(+)-di-(p-anisoyl)tartaric acid salt (or equivalent, adjusted for recovered (R)-α-(2,3-dimethoxyphenyl)-1-[2-(4-fluorophenyl)ethyl]-4-piperidinemethanol) is used as the basis amount of methanol to be added.
[8]Methanol may be recovered from the filtrates of both resolution crystallization by distillation for reuse in this reaction step.
[9]The yields are determined by HPLC assay. The % ee is determined by a chiral HPLC procedure.

EXAMPLE 22

Scheme B, step a and step b, and Scheme C, step a: (R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a')

In a suitable reactor maintained under an inert atmosphere, p-anisic acid (361 kg, 2.37 kmol) is slurried with about 385 kg of xylenes.[1] Oxalyl chloride (about 330 kg) is added while maintaining the temperature at about 60° C. The mixture is held at about 60° C. for about 1 hour until a solution is formed. The mixture is heated to about 100° C. and any remaining oxalyl chloride is removed by atmospheric distillation. The mixture is then cooled to about 70° C. In a second suitable reactor, (2S,3S)-(−)-tartaric acid (117 kg, 0.78 kmol) is slurried with about 340 kg of xylenes[2]. The solution of p-anisoyl chloride is added to the slurry and the mixture is heated to about 135° C. for about 3 hours or until hydrogen chloride evolution stops. The mixture is cooled to about 60° C. About 155 kg of oxalyl chloride is added and the mixture is heated to about 65° C. for at least 1 hour. The mixture is heated to about 70° C. to partially dissolve the anhydride. The mixture is then maintained at this temperature for at least 1 hour[3]. The crystallization is completed by cooling the mixture to about −10° C. The mixture is then filtered and the wet cake is washed with about 290 kg of cold xylenes to typically afford about 280 kg (about 17% xylenes) of anhydride (about 80% yield)[4].

A suitable reactor is charged with anhydride (256 kg, 639 mol) as a xylene wet cake, acetone (710 kg) and 240 kg of water. The mixture is heated at reflux (about 60° C.) for at least 2 hours. About 1740 kg of water is added to the mixture at about 60° C. Acetone is removed by atmospheric distillation until the temperature of the mixture reaches about 80° C. The mixture is cooled to about 5° C. The mixture is filtered using about 350 kg of water to rinse the reactor. The wet cake is washed with about 1550 kg of water to typically afford about 250 kg (with about 5-30% of solvent) of (2S,3S)-(+)-di-(p-anisoyl)tartaric acid (about 80% yield).[5] The (2S,3S)-(+)-di-(p-anisoyl)tartaric acid from 6 batches were combined and dried under vacuum at about 70° C.

A suitable reactor is charged with α-(2,3-dimethoxyphenyl)-1-[2-(4-fluorophenyl)ethyl]-4-piperidinemethanol (5) (40.0 kg, 107 mol) as an isopropanol wet cake and (2S,3S)-(+)-di-(p-anisoyl)tartaric acid (46.8 kg, 112 mol). About 285 kg of methanol is added and the mixture is heated to about 65° C.[6] The mixture is cooled to about 5° C. and the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (about 85-90% ee) is recovered by filtration. The wet cake is washed with about 10 kg of methanol (about 5° C.) to typically afford about 40 kg of material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (about 47% yield).[7,8] The filtrate contains mainly enriched (S)-α-(2,3-dimethoxyphenyl)-1-[2-(4-fluorophenyl)ethyl]-4-piperidinemethanol, (2S,3S)-(+)-di-(p-anisoyl)tartaric acid salt (3b).[7] Into a suitable reactor is charged the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) and about 380 kg of methanol.[6,9] The mixture is heated at about 65° C. The mixture is cooled to about 5° C. The mixture is filtered and the filter cake is washed with about 40 kg of cold methanol to typically afford about 38 kg of purified (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (about 90-95% yield, about 98-100% ee) as a methanol wet cake.[10] The filtrate contains mainly α-(2,3-dimethoxyphenyl)-1-[2-(4-fluorophenyl)ethyl]-4-piperidinemethanol, (2S,3S)-(+)-di-(p-anisoyl)tartaric acid salt (essentially racemic mixture of 3a and 3b)[7]

[1] The mother liquors from the final filtration of previous batches contain p-anisoyl chloride and (2S,3S)-(+)-di-(p-anisoyl)tartaric acid and can be recycled. The exact amount of p-anisic acid used for each batch is determined following an assay of the mother liquors by HPLC analysis.
[2] The amount of xylenes used to slurry the tartaric acid is reduced if a batch using mother liquors from previous batches of the final filtration is used (see footnote 1). The amount of xylenes added is adjusted to maintain the concentration of anhydride in the crystallization step.
[3] The mixture may be seeded with anhydride to aid the crystallization.
[4] The yields are determined by HPLC assay and loss on drying.
[5] The yields are determined in combination with loss on drying and HPLC assay.
[6] Methanol recovered by distillation from the filtrates of both resolution crystallization (Scheme B, step b) may be used in this process step.
[7] The filtrates are stored at about 5° C. for use in Scheme C, step a.
[8] The weights of the material enriched in (R)-α-(2,3-dimethoxyphenyl)-1-[2-(4-fluorophenyl)ethyl]-4-piperidinemethanol, (2S,3S)-(+)-di-(p-anisoyl)tartaric acid salt are based on HPLC assay. The % ee is determined by a chiral HPLC procedure.
[9] (R)-α-(2,3-Dimethoxyphenyl)-1-[2-(4-fluorophenyl)ethyl]-4-piperidinemethanol (3) which is recovered by distillation to approximately 14 to 30 wt. % solution followed by crystallization and filtration from the filtrates of Scheme B, step c and the final recrystallization of (R)-α-(2,3-dimethoxyphenyl)-1-[2-(4-fluorophenyl)ethyl]-4-piperidinemethanol (3) as an isopropanol wet cake, may also be charged to the reactor with (2S,3S)-(+)-di-(p-anisoyl)tartaric acid in a 1 to 1 molar ratio. The recovered (R)-α-(2,3-dimethoxyphenyl)-1-[2-(4-fluorophenyl)ethyl]-4-piperidinemethanol (3) typically has an enantiomeric excess of about 95%. The dry weight of (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a) (or equivalent, adjusted for recovered (R)-α-(2,3-dimethoxyphenyl)-1-[2-(4-fluorophenyl)ethyl]-4-piperidinemethanol (3)) is used as the basis for the amount of methanol to be added.
[10] The yields are determined by HPLC assay. The % ee is determined by a chiral HPLC procedure.

EXAMPLE 23

Scheme C, step b: (R)-α-(2,3-Dimethoxyphenyl)-1-[2-(4-fluorophenyl)ethyl]-4-piperidinemethanol (3)

(R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a') (10.1 g) was stirred with 100 mL 6.5N ammonia and 100 mL toluene for 2 hours at room temperature. The toluene layer was separated and the water layer was extracted twice with 50 mL toluene. The combined toluene layers were washed with 30 mL 10% KOH solution and 30 mL brine, dried on sodium sulphate, filtered, and evaporated to give the title compound (R)-α-(2,3-dimethoxyphenyl)-1-[2-(4-fluorophenyl)ethyl]-4-piperidinemethanol (3) as a white solid (>99% ee); $[\alpha]_{578}$ +23.8° (c=0.5, MeOH).

EXAMPLE 24

Scheme C, step b: (R)-α-(2,3-Dimethoxyphenyl)-1-[2-(4-fluorophenyl)ethyl]-4-piperidinemethanol (3)

(R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a' or 3a") (9.1 kg, 8.0 kg dry weight) was suspended in toluene (20.1 kg) with stirring in a 50 L round bottom reactor. Aqueous potassium carbonate (13.7 kg of a 12.8 wt % solution) was added over about 60 minutes between 18-38° C. The mixture was heated within the range of 40-45° C. with stirring for about 30 minutes. The agitation was stopped and the phases were allowed to separate. The temperature was maintained in the range of 40-45° C. for the decant. The phases were decanted and the aqueous phase (about 18.5 kg) was allowed to cool in preparation for the recovery of (2S,3S)-(+)-di-(p-anisoyl)tartaric acid[1]. The toluene solution was extracted with additional aqueous potassium carbonate (4 kg of 12.5 wt % solution). Agitation was continued for about 1 hour in the range 40-45° C. The phases were allowed to settle and the aqueous phase was decanted within the temperature range of 40-45° C. The aqueous phase (about 4.4 kg) was discarded. If required to remove residual (2S,3S)-(+)-di-(p-anisoyl)tartaric acid, the toluene solution can be extracted with additional aqueous potassium carbonate (4 kg of a 12.5 wt % solution). Agitation was continued for about 1 hour within the temperature range 40-45° C. The phases were allowed to settle and the aqueous phase was decanted within the temperature range 40-45° C. The aqueous phase was discarded. The toluene phase (about 23.6 kg) was analyzed for wt % (R)-α-(2,3-dimethoxyphenyl)-1-[2-(4-fluorophenyl)ethyl]-4-piperidinemethanol (3) (typical range 12-16 wt %) and wt % (2S,3S)-(+)-di-(p-anisoyl)tartaric acid (typical range 0.2 wt % to not detectable at 0.04 wt %) prior to further processing. The toluene phase (23.6 kg, containing about 3.5 kg of (R)-α-(2,3-dimethoxyphenyl)-1-[2-(4-fluorophenyl)ethyl]-4-piperidinemethanol) (3)) was either shot-added or continuously added to a 20 L rotary evaporator to keep a proper working volume. Solvent was removed at <40° C. and 35-65 mm Hg, until the feed was gone and the amount of solvent taken overhead diminished. 2-Propanol (10.5 kg) was added and the solvent was removed overhead at <40° C. and about 35 mm Hg to azeotropically remove the remaining toluene. 2-Propanol (7.5 kg) was added and the 20 L pot was heated under nitrogen to about 75° C. to dissolve the (R)-α-(2,3-dimethoxyphenyl)-1-[2-(4-fluorophenyl)ethyl]-4-piperidinemethanol (3). The solution was polish filtered through a 0.2 μm filter while transferring to a 50 L crystallizer. The crystallizer was stirred under a nitrogen blanket while cooling at <0.2° C./m to ambient temperature. Three batches from the 20 L rotary evaporation were combined for one 50 L crystallizer batch. (R)-α-(2,3-Dimethoxyphenyl)-1-[2-(4-fluorophenyl)ethyl]-4-piperidinemethanol (3) was recrystallized by heating the 50 L flask to a thin slurry at about 62° C. and cooling to <10° C. in >6 hours. The (R)-α-(2,3-dimethoxyphenyl)-1-[2-(4-fluorophenyl)ethyl]-4-piperidinemethanol (3) crystals were isolated by vacuum filtration on a 14-inch diameter ceramic funnel with a polypropylene filter cloth, 0.5 μm particle retention. The wet cake was washed with about 2.6 kg of cold, filtered (0.2 μm) 2-propanol, transferred to a drying dish, and dried in a vacuum oven at 32-36° C. and 35-65 mm Hg to constant weight. The dry crystals (loss on drying=8-13%) of (R)-α-(2,3-dimethoxyphenyl)-1-[2-(4-fluorophenyl)ethyl]-4-piperidinemethanol (3) were large, white, and triangular-shaped, weighing about 9.5 kg (90% isolated yield).

[1] The aqueous phase from the initial agitation was diluted with 2-propanol (6.9 kg). Hydrochloric acid (5 wt %, 19.9 kg) was added to the well agitated aqueous solution of the potassium salt of (2S,3S)-(+)-di-(p-anisoyl)tartaric acid over about 1.5 hours. The temperature of the mixture was maintained below about 30° C. during this addition. The precipitated (2S,3S)-(+)-di-(p-anisoyl)tartaric acid was isolated by filtration. The filter cake was washed with about 16 kg of water and suction dried. The recovered (2S,3S)-(+)-di-(p-anisoyl)tartaric acid (6-16 kg) was analyzed for residual anisic acid (typically not detected) and a loss on drying was obtained (35-82%).

EXAMPLE 25

Scheme C, step b: (R)-α-(2,3-Dimethoxyphenyl)-1-[2-(4-fluorophenyl)ethyl]-4-piperidinemethanol (3)

(R)-α-(2,3-Dimethoxyphenyl)-1-[2-(4-fluorophenyl)ethyl]-4-piperidinemethanol, (2S,3S)-(+)-di-(p-anisoyl)tartaric acid salt (3a') from Example 18 (40.58 g, 98.6% ee) was suspended in toluene (206 mL) and neutralized with 12.8% aqueous potassium carbonate (61 g). The phases were stirred at 60° C. for about 30 minutes. The phases were separated and the organic phase was extracted twice with 12.8% potassium carbonate (30 g and 14 g). The toluene was removed on the rotary evaporator. The residual solid was dissolved in 2-propanol, concentrated on the rotary evaporation and then dissolved in 2-propanol (28 mL) and crystallized. The slurry was cooled in an ice bath prior to filtration. The (R)-α-(2,3-dimethoxyphenyl)-1-[2-(4-fluorophenyl)ethyl]-4-piperidinemethanol (3) was isolated in 16.2 g yield (99.8% ee, 102% assay). The yield of (R)-α-(2,3-dimethoxyphenyl)-1-[2-(4-fluorophenyl)ethyl]-4-piperidinemethanol (3) from (S)-α-(2,3-dimethoxyphenyl)-1-[2-(4-fluorophenyl)ethyl]-4-piperidinemethanol (3c) in Example 38 in the initial toluene was 32.5%.

EXAMPLE 26

Scheme C, step b: (R)-α-(2,3-Dimethoxyphenyl)-1-[2-(4-fluorophenyl)ethyl]-4-piperidinemethanol (3)

In a 500 mL glass round bottom flask equipped with a heating mantle, cold water condenser, magnetic stirrer and a nitrogen line, 98.8% ee (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a") from Example 19 (10.41 g, 13.2 mmol) was suspended in toluene (54 mL). To the suspension an aqueous solution of 12.8 wt % potassium carbonate (15.6 g) was added. The phases were agitated at 60° C. for 45 minutes and then separated. The top organic phase was extracted a second time with more of the carbonate solution (4.2 g). Again the phases were agitated at 60° C. for 30 minutes before being separated. The top organic phase was assayed and was found to contain 9.5 wt % (4.57 g, 12.2 mmol) (R)-α-(2,3-dimethoxyphenyl)-1-[2-(4-fluorophenyl)ethyl]-4-piperidinemethanol (3). The solution was stripped to an oil and then dissolved in 2-propanol. The solution was then concentrated to a white residue. The residue was dissolved in 2-propanol (10.6 g) to give a 30 wt % solution of (R)-α-(2,3-dimethoxyphenyl)-1-[2-(4-fluorophenyl)ethyl]-4-piperidinemethanol (3). The solution was heated to reflux, cooled to room temperature and allowed to crystallize. The crystals were digested at 60° C. for 45 minutes. The slurry was then cooled to room temperature, chilled in an ice bath and suction filtered. The wet cake was washed with 4-6 mL of chilled 2-propanol. Assay of the mother liquors showed 2.2 wt % (0.26 g) (R)-α-(2,3-dimethoxyphenyl)-1-[2-(4-fluorophenyl)ethyl]-4-piperidinemethanol (3). Isolation of the crystals gave an 83.1% yield (based on weight of (R)-diastereomeric salt used) and the product had an optical purity of 99.9%.

EXAMPLE 27

Scheme C, step b: (R)-α-(2,3-Dimethoxyphenyl)-1-[2-(4-fluorophenyl)ethyl]-4-piperidinemethanol (3)

A mixture of (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (as a methanol wet cake, 98-100% ee) from Example 20 (8.9 kg, 11.2 mol) in toluene (20 kg) is prepared in a suitable reactor at about 25° C. The salt is neutralized by the addition of about 14 kg of a 13% aqueous potassium carbonate solution.[1] The mixture is heated to about 40° C. and the phases are separated. The aqueous phase is transferred to a separate reactor and the (2S,3S)-(+)-di-(p-anisoyl)tartaric acid is recovered from the phase.[2] The toluene solution containing (R)-α-(2,3-dimethoxyphenyl)-1-[2-(4-fluorophenyl)ethyl]-4-piperidinemethanol (3) is extracted with about 4 kg of a 13% aqueous potassium carbonate solution, and the aqueous phase is discarded. The toluene solution[3] is concentrated by vacuum distillation.[4] About 11 kg of isopropanol is added and the mixture is warmed to about 40° C. and the isopropanol and residual toluene are removed by vacuum distillation.[4] The residue is dissolved in about 8 kg of isopropanol at about 70° C. and the solution is clarification filtered, using about 0.2 kg of isopropanol as a rinse. The filtered solution is heated to about 62° C., then cooled to about 10° C. and (R)-α-(2,3-dimethoxyphenyl)-1-[2-(4-fluorophenyl)ethyl]-4-piperidinemethanol (3) is isolated by filtration.[5] The filter cake is washed with about 3 kg of isopropanol and the (R)-α-(2,3-dimethoxyphenyl)-1-[2-(4-fluorophenyl)ethyl]-4-piperidinemethanol (3) is dried at about 30° C. under vacuum. The yield of (R)-α-(2,3-dimethoxyphenyl)-1-[2-(4-fluorophenyl)ethyl]-4-piperidinemethanol (3) is typically 10 kg (91% yield) as determined by HPLC assay.

[1]The 13% aqueous potassium carbonate solution is prepared by dissolving about 2.3 kg of anhydrous potassium carbonate in 15.7 kg of water.
[2]The aqueous solution is diluted with about 10 kg of isopropanol and then made acidic by adding about 19 kg of an approximately 5% hydrochloric acid solution (prepared by diluting about 3.4 kg of 32% aqueous hydrochloric acid with about 15.6 kg of water). The precipitated (2S,3S)-(+)-di-(p-anisoyl) tartaric acid is isolated by filtration. The wet cake is washed with about 19 kg of water. The recovered solid typically weighs 10 kg, with a typical loss on drying of 35-82%. This mixture is analyzed for the presence of p-anisic acid by HPLC.
[3]The range of concentrations of (R)-α-(2,3-dimethoxyphenyl)-1-[2-(4-fluorophenyl)ethyl]-4-piperidinemethanol (3) in toluene that were obtained were 11.6-16 wt % as determined by HPLC assay. The (2S,3S)-(+)-di-(p-anisoyl) tartaric acid varied from none detectable-0.2% as determined by HPLC assay, and the enantiomeric excess varied from 98-99% as determined by chiral HPLC assay.
[4]Distillation is continued until no further solvent is being condensed.
[5]The isopropanol organic phases from 3 runs are combined in a suitable reactor and processed as a single batch.

EXAMPLE 28

Scheme C, step b: (R)-α-(2,3-Dimethoxyphenyl)-1-[2-(4-fluorophenyl)ethyl]-4-piperidinemethanol (3)

A mixture of (R)-α-(2,3-dimethoxyphenyl)-1-[2-(4-fluorophenyl)ethyl]-4-piperidinemethanol, (2S,3S)-(+)-di-(p-anisoyl)tartaric acid salt (3a') (as a methanol wet cake, 98-100% ee) from Example 21 (29.5 kg, 37.2 mol) in toluene (74 kg) is prepared in a suitable reactor at about 50° C. The salt is neutralized by the addition of about 59 kg of a 13% aqueous potassium carbonate solution.[1] The mixture is maintained at about 50° C. and the phases are separated. The aqueous phase is transferred to a separate reactor and the (2S,3S)-(+)-di-(p-anisoyl)tartaric acid is recovered from the phase.[2] The toluene solution containing (R)-α-(2,3-dimethoxyphenyl)-1-[2-(4-fluorophenyl)ethyl]-4-piperidinemethanol (3) is mixed at about 50° C. with about 13 kg of a 13% aqueous potassium carbonate solution, and the aqueous phase discarded. The toluene solution containing (R)-α-(2,3-dimethoxyphenyl)-1-[2-(4-fluorophenyl)ethyl]-4-piperidinemethanol (3) is mixed at about 50° C. with about 30 kg of water and the aqueous phase discarded. The toluene solution is filtered, using about 35.4 kg of isopropanol mixed with 8.9 kg of water as a rinse. The solvent is exchanged from toluene to isopropanol and water by distillation removing about 245 kg of solvent. After each of the first four 49 kg increments of distillate, another 35.4 kg of isopropanol and 8.9 kg of water are added to the solution for a total of 141.6 kg of isopropanol and 35.6 kg of water. About 9.3 kg of water is added to the solution while maintaining the temperature at or above 70° C. The solution is then cooled to below 0° C. and (R)-α-(2,3-dimethoxyphenyl)-1-[2-(4-fluorophenyl)ethyl]-4-piperidinemethanol (3) is isolated by filtration. The filter cake is washed with about 9.1 kg of isopropanol. The yield of (R)-α-(2,3-dimethoxyphenyl)-1-[2-(4-fluorophenyl)ethyl]-4-piperidinemethanol (3) is typically 12.3 kg (89% yield as determined by HPLC assay). The (R)-α-(2,3-dimethoxyphenyl)-1-[2-(4-fluorophenyl) ethyl]-4-piperidinemethanol (3) remaining in the filtrate[3] may be recovered and returned to Scheme B, step a, to improve its enantiomeric excess.[4]

A suitable vessel is charged with about 0.6 kg (dry basis) of (R)-α-(2,3-dimethoxyphenyl)-1-[2-(4-fluorophenyl)ethyl]-4-piperidinemethanol (3) (as an isopropanol/water wet cake). About 3.6 kg of methanol is added to dissolve the (R)-α-(2,3-dimethoxyphenyl)-1-[2-(4-fluorophenyl) ethyl]-4-piperidinemethanol (3).[5] The solution is filtered. A slurry of seed crystals is formed by merging with rapid mixing the continuous additions of the methanol solution and about 57 kg of water at a constant ratio into a suitable inerted vessel. About 0.2 kg of isopropanol is used to flush the methanol solution addition and about 33 kg of water is used to flush the seed crystals into the vessel.[6] The slurry is held at 15 to 20° C. In a separate inerted vessel, about 0.9 kg (dry basis) of (R)-α-(2,3-dimethoxyphenyl)-1-[2-(4-fluorophenyl)ethyl]-4-piperidinemethanol (3) (as an isopropanol/water wet cake) is dissolved into about 54 kg of isopropanol. The solution is agitated and heated to dissolve the (R)-α-(2,3-dimethoxyphenyl)-1-[2-(4-fluorophenyl) ethyl]-4-piperidinemethanol (3) and then maintained at 15 to 20° C. The isopropanol solution is filtered into the seed crystal slurry. In a separate inerted vessel, about 10.8 kg (dry basis) of (R)-α-(2,3-dimethoxyphenyl)-1-[2-(4-fluorophenyl)ethyl]-4-piperidinemethanol (3) is dissolved into about 39.1 kg of isopropanol and about 9.7 kg of water. The solution is agitated and heated to dissolve the (R)-α-(2,3-dimethoxyphenyl)-1-[2-(4-fluorophenyl)ethyl]-4-piperidinemethanol (3) and then it is held at about 65° C. The isopropanol solution is filtered into the seed crystal slurry while the slurry is maintained at 15 to 25° C. About 6.5 kg of isopropanol is used as a rinse. About 58.2 kg of water is added to the slurry while maintaining the temperature at 15 to 25° C. The slurry is cooled to 0° C. and the (R)-α-(2,3-dimethoxyphenyl)-1-[2-(4-fluorophenyl)ethyl]-4-piperidinemethanol (3) is isolated by filtration. The filter cake is washed with about 18 kg of water and the (R)-α-(2,3-dimethoxyphenyl)-1-[2-(4-fluorophenyl)ethyl]-4-piperidinemethanol (3) is dried at about 70° C. under vacuum. The yield of (R)-α-(2,3-dimethoxyphenyl)-1-[2-(4-fluorophenyl)ethyl]-4-piperidinemethanol (3) is typically about 11.4 kg (93% yield as determined by HPLC assay). The (R)-α-(2,3-dimethoxyphenyl)-1-[2-(4-fluorophenyl)ethyl]-4-piperidinemethanol (3) remaining in the filtrate[7] may be recovered and returned to Scheme B, step a, to improve its enantiomeric purity.[8]

[1]The 13% aqueous potassium carbonate solution is prepared by dissolving about 9.2 kg of anhydrous potassium carbonate in 62.8 kg of water.
[2]About 21 kg of the aqueous solution is diluted with about 10 kg of isopropanol and then made acidic by adding about 19 kg of an approximately 5% hydrochloric acid solution (prepared by diluting about 3.4 kg of 32% aqueous hydrochloric acid with about 15.6 kg of water). The precipitated (2S,3S)-(+)-di-(p-anisoyl)tartaric acid is isolated by filtration. The wet cake is washed with about 19 kg of water. The recovered solid typically weighs 10 kg, with a typical loss on drying of 35-82%. This mixture is analyzed for the presence of p-anisic acid by HPLC assay.
[3]This filtrate may be combined with the filtrate from the final recrystallization of (R)-α-(2,3-dimethoxyphenyl)-1-[2-(4-fluorophenyl)ethyl]-4-piperidinemethanol (3) to recover the (R)-α-(2,3-dimethoxyphenyl)-1-[2-(4-fluorophenyl)ethyl]-4-piperidinemethanol (3) for recycle.
[4]The (R)-α-(2,3-dimethoxyphenyl)-1-[2-(4-fluorophenyl)ethyl]-4-piperidinemethanol (3) remaining in the filtrate may be recovered by concentrating the solution while adding isopropanol (as necessary) to keep the boiling point below 90° C. and then cooling to about 0° C. and isolating by filtration. The filter cake is washed with isopropanol. The yield of (R)-α-(2, 3-dimethoxyphenyl)-1-[2-(4-fluorophenyl)ethyl]-4-piperidinemethanol (3) is typically about 1.0 kg when the filtrates from this process step, Scheme B, step c, and the filtrate from the final recrystallization of (R)-α-(2,3-dimethoxyphenyl)-1-[2-(4-fluorophenyl)ethyl]-4-piperidinemethanol (3) are combined (41% yield as determined by HPLC assay with an enantiomeric excess of 95% (R)-α-(2,3-dimethoxyphenyl)-1-[2-(4-fluorophenyl)ethyl]-4-piperidinemethanol (3) as determined by chiral HPLC assay.

[5] A portion of the methanol may be reserved and used as a flush following the filtration.

[6] If more water is mixed with the methanol solution, the flush amount is reduced so that the total water mixed with the methanol solution is not changed.

[7] The isopropanol filtrate from the isolation of (R)-α-(2,3-Dimethoxyphenyl)-1-[2-(4-fluorophenyl)ethyl]-4-piperidinemethanol (3), from the basic hydrolysis of the diastereomeric salt, may be combined with the filtrate from the final recrystallization to recover (R)-α-(2,3-dimethoxyphenyl)-1-[2-(4-fluorophenyl)ethyl]-4-piperidinemethanol (3) for recycle.

[8] The (R)-α-(2,3-dimethoxyphenyl)-1-[2-(4-fluorophenyl)ethyl]-4-piperidinemethanol (3) remaining in the filtrate may be recovered by concentrating the solution while adding isopropanol (as necessary) to keep the boiling point below 90° C. and then cooling to about 0° C. and isolating by filtration. The filter cake is washed with isopropanol. The yield of (R)-α-(2, 3-dimethoxyphenyl)-1-[2-(4-fluorophenyl)ethyl]-4-piperidinemethanol (3) is typically about 1.0 kg when the isopropanol filtrate from the isolation of (R)-α-(2,3-Dimethoxyphenyl)-1-[2-(4-fluorophenyl)ethyl]-4-piperidinemethanol (3) from the basic hydrolysis of the diastereomeric salt is combined with the filtrate from the final recrystallization (41% yield as determined by HPLC assay with an enantiomeric excess of 95% (R)-α-(2, 3-dimethoxyphenyl)-1-[2-(4-fluorophenyl)ethyl]-4-piperidinemethanol (3) as determined by HPLC assay).

EXAMPLE 29

Scheme C, step b: (R)-α-(2,3-Dimethoxyphenyl)-1-[2-(4-fluorophenyl)ethyl]-4-piperidinemethanol (3)

(R)-α-(2,3-dimethoxyphenyl)-1-[2-(4-fluorophenyl) ethyl]-4-piperidinemethanol, (2S,3S)-(+)-di-(p-anisoyl)tartaric acid salt (3a') (100 kg, 126 mol) as a methanol wet cake (98-100% ee, from Example 22) and toluene (250 kg) are charged to a suitable reactor and the mixture is warmed to about 50° C. About 195 kg of a, 13% aqueous potassium carbonate solution[1] is added and the phases are separated.[2] The toluene solution containing (R)-α-(2,3-dimethoxyphenyl)-1-[2-(4-fluorophenyl)ethyl]-4-piperidinemethanol) (3) is extracted at about 50° C. with about 50 kg of a 13% aqueous potassium carbonate solution[1], and the aqueous phase is discarded. The toluene solution is extracted at about 50° C. with about 100 kg of water and the aqueous phase is discarded. The organic phase is filtered. A mixture of about 120 kg of isopropanol and about 30 kg of water is used as a filter rinse. The solvent is exchanged from toluene to isopropanol and water by portion-wise addition of isopropanol and water for a total of 480 kg of isopropanol and 120 kg of water. About 30 kg of water is added to the mixture while maintaining the temperature at about 65° C. The solution is cooled to about 0° C. and (R)-α-(2,3-dimethoxyphenyl)-1-[2-(4-fluorophenyl)ethyl]-4-piperidinemethanol) (3) is isolated by filtration. The filter cake is washed with about 30 kg of cold isopropanol. The yield of (R)-α-(2,3-dimethoxyphenyl)-1-[2-(4-fluorophenyl)ethyl]-4-piperidinemethanol) (3) is typically about 42 g (89% yield as determined by HPLC assay).[3]

A suitable vessel is charged with about 2.0 kg (dry basis ) of (R)-α-(2,3-dimethoxyphenyl)-1-[2-(4-fluorophenyl)ethyl]-4-piperidinemethanol (3) (as an isopropanol/water wet cake). About 12.2 kg of methanol is added[6] and the solution is filtered. A slurry of seed crystals is formed by continuously feeding at a constant rate both the (R)-α-(2,3-dimethoxyphenyl)-1-[2-(4-fluorophenyl)ethyl]-4-piperidinemethanol (3) solution and about 300 kg of water to a suitable vessel[7]. The seed crystal slurry is held at about 15° C. (solution A). About 3.1 kg (dry basis) of (R)-α-(2,3-dimethoxyphenyl)-1-[2-(4-fluorophenyl)ethyl]-4-piperidinemethanol (3) (as an isopropanol/water wet cake) and about 180 kg of isopropanol are charged to a separate vessel (solution B). The solution is heated to above about 25° C. and maintained at about 20° C. Solution B is filtered into the seed crystal slurry (solution A), forming solution C. About 35.6 kg (dry basis) of (R)-α-(2,3-dimethoxyphenyl)-1-[2-(4-fluorophenyl)ethyl]-4-piperidinemethanol (3) (as an isopropanol/water wet cake), about 85 kg of isopropanol and about 22 kg water are charged to a separate vessel (solution D). The mixture is heated to about 65° C. This solution (solution D) is filtered into solution C while maintaining the temperature at about 25° C. About 22 kg of isopropanol is used as a rinse. About 138 kg of water is added to the slurry while maintaining the temperature at about 15 to 25° C. The mixture is cooled to about 0° C. and the (R)-α-(2,3-dimethoxyphenyl)-1-[2-(4-fluorophenyl)ethyl]-4-piperidinemethanol (3) isolated by filtration. The filter cake is washed with about 80 kg of water. The (R)-α-(2,3-dimethoxyphenyl)-1-[2-(4-fluorophenyl)ethyl]-4-piperidinemethanol (3) is dried at about 70° C. under vacuum. The yield of (R)-α-(2,3-dimethoxyphenyl)-1-[2-(4-fluorophenyl)ethyl]-4-piperidinemethanol (3) is typically about 38.7 kg (95% yield as determined by HPLC assay).[8]

[1] The 13% aqueous potassium carbonate solution is prepared by dissolving about 32 kg of anhydrous potassium carbonate in 214 kg of water.

[2] A suitable reactor is charged with the initial aqueous potassium carbonate solution containing (2S,3S)-(+)-di-(p-anisoyl)tartaric acid, potassium salt (61.8 kg) (see footnote 4). About 186 kg of water and hydrochloric acid (106 kg, 32%) are then added and the addition line is flushed with about 9 kg of water. The mixture is allowed to degas for at least 1 hour and the pH of the solution is measured to confirm that the pH # 2 (see footnote 5). Acetone (62 kg) is added to the slurry and the mixture is warmed to about 70° C. The pH is then measured again to ensure a pH of # 2 (see footnote 5). The mixture is then cooled to about 70° C. and held there for approximately 2 hours before cooling to about 15° C. The recovered (2S,3S)-(+)-di-(p-anisoyl)tartaric acid is collected by filtration. The wet cake is washed with about 185 kg of water to afford about 45 kg of recovered (2S,3S)-(+)-di-(p-anisoyl)tartaric acid (80% yield as determined by HPLC assay).

[3] The filtrate from this step may be combined with that from the final crystallization of (R)-α-(2,3-dimethoxyphenyl)-1-[2-(4-fluorophenyl)ethyl]-4-piperidinemethanol (3) to recover the (R)-α-(2,3-dimethoxyphenyl)-1-[2-(4-fluorophenyl)ethyl]-4-piperidinemethanol (3) for recycle to Scheme B, step a.

[4] Aqueous solutions from multiple batches can be combined for processing. The wt % of (2S,3S)-(+)-di-(p-anisoyl)tartaric acid in solution is typically about 12 wt %, as determined by HPLC assay.

[5] Additional hydrochloric acid can be added as needed to achieve the desired pH.

[6] A portion of the methanol may be reserved and used as a flush following the filtration.

[7] A portion of the water (typically 30 kg) is reserved and used to flush the seed crystals to the vessel.

[8] The (R)-α-(2,3-dimethoxyphenyl)-1-[2-(4-fluorophenyl)ethyl]-4-piperidinemethanol (3) remaining in the filtrate from this step and the filtrate from the isolation of (R)-α-(2,3-dimethoxyphenyl)-1-[2-(4-fluorophenyl) ethyl]-4-piperidinemethanol (3) from the basic hydrolysis of the diastereomeric salt may be recovered by concentrating the solution while adding isopropanol (as necessary) to maintain the boiling point to about 90° C., followed by cooling to about 0° C. and isolating by filtration. The filter cake is washed with isopropanol. The yield of (R)-α-(2,3-dimethoxyphenyl)-1-[2-(4-fluorophenyl)ethyl]-4-piperidinemethanol (3) is typically about 1.0 kg when the filtrates from this step and the filtrate from the isolation of (R)-α-(2,3-dimethoxyphenyl)-1-[2-(4-fluorophenyl)ethyl]-4-piperidinemethanol (3) from the basic hydrolysis of the diastereomeric salt (41% yield as determined by HPLC assay with an enantiomeric excess of 95% (R)-α-(2,3-dimethoxyphenyl)-1-[2-(4-fluorophenyl)ethyl]-4-piperidinemethanol (3) as determined by chiral HPLC assay).

EXAMPLE 30

Scheme C, step c: α-(2,3-Dimethoxyphenyl)-1-[2-(4-fluorophenyl)ethyl]-4-piperidinemethanol (5)

The mother liquors (filtrates) from a second recrystallization of material enriched in (R)-α-(2,3-dimethoxyphenyl)-1-[2-(4-fluorophenyl)ethyl]-4-piperidinemethanol, (2S,3S)-

(+)-di-(p-anisoyl)tartaric acid (3a) in Scheme C, step a, were concentrated to a foam on the rotary evaporator. The residue (3.6 g, 4.6 mmol) was slurried in methanol (4.25 g) and water (5.4 g). To this slurry was added dropwise a solution of potassium carbonate (0.8 g, 4 mmol) in water (5.4 mL). The slurry was stirred for about 30 minutes, a white crystalline slurry was obtained which was digested at 50° C. for 1 hour prior to cooling and isolating the white solid by filtration. The solid filter cake was washed with chilled 2-propanol (1.6 mL). The isolated product was dried to a constant weight to give 1.4 g, 98% assay and 83% yield. Chiral HPLC confirmed this to be the α-(2,3-dimethoxyphenyl)-1-[2-(4-fluorophenyl)ethyl]-4-piperidinemethanol (5).

The aqueous methanol filtrate was added to a solution of 32% HCl (1 mL) in water (7.2 mL) and the (2S,3S)-(+)-di-(p-anisoyl)tartaric acid was isolated by filtration and dried to constant weight, 1.5 g, 92% assay, 79% recovery.

EXAMPLE 31

Scheme D, steps a and b: α-(2,3-Dimethoxyphenyl)-1-[2-(4-fluorophenyl)ethyl]-4-piperidinemethanol (5)

A 287.18 g sample of resolution mother liquor and wash solutions from Scheme B, step b,[1] was loaded to a 1-L jacketed bottom-drain reactor with 46 g of tetrahydrofuran and 125 g of 50% sodium hydroxide, and the mixture was warmed to 40° C. The basic 391.7 g aqueous phase was removed. The organic phase was washed with 30 g of brine, and the 45.86 g aqueous phase was removed. The 45.66 g organic phase[2] was loaded to a 100-mL jacketed bottom-drain reactor with 22.5 g of water and 14.76 g of sulfuric acid. The mixture was heated at reflux overnight. Analysis by chiral HPLC indicated that the mixture was racemic.

The mixture was cooled to 20° C. and diluted with 44 g of toluene, 24 g of 50% sodium hydroxide, and 10 g of water. The 68.8 g aqueous phase was removed. The organic phase was washed with 15 g of water, and the 16 g aqueous phase was removed. The organic phase was heated to remove 32.2 g of distillate to an internal temperature of 115° C., then cooled to 70° C., seeded, and cooled to 0° C. The solid was collected by filtration and washed with 3 g of 2-propanol to give 9.35 g of α-(2,3-dimethoxyphenyl)-1-[2-(4-fluorophenyl)ethyl]-4-piperidinemethanol (5) (62% yield). The mother liquor was evaporated to a residue of 4.15 g (28% of theoretical).

[1] From crystallization using 30.0 g of α-(2,3-dimethoxyphenyl)-1-[2-(4-fluorophenyl)ethyl]-4-piperidinemethanol (5), 18.0 g of (2S,3S)-(+)-di-(p-anisoyl)tartaric acid, 81 g of acetic acid, 189 g of water, and 47 g of 30% aqueous acetic acid as wash; 5.14 wt % (15 g) α-(2,3-dimethoxyphenyl)-1-[2-(4-fluorophenyl)ethyl]-4-piperidinemethanol isomers by HPLC assay.
[2] Containing 13.7 g of α-(2,3-dimethoxyphenyl)-1-[2-(4-fluorophenyl)ethyl]-4-piperidinemethanol isomers by HPLC assay

EXAMPLE 32

Scheme D, step a: (S)-α-(2,3-Dimethoxyphenyl)-1-[2-(4-fluorophenyl)ethyl]-4-piperidinemethanol (3c)

A portion of the resolution methanol mother liquor (filtrate) from Scheme B, step b, (465.44 g) was concentrated to 0.67 g/mL.[1] The concentrated solution was added dropwise, over 1-1.5 hours, to an agitated suspension of toluene (590 mL), water (304 mL) and solid potassium carbonate (44.34 g, 0.32 mol). The phases were agitated for 15 minutes at 50-60° C. Two phases formed and were separated by use of a 2-L separatory funnel. The bottom aqueous phase was decanted and assayed for residual (S)-α-(2,3-dimethoxyphenyl)-1-[2-(4-fluorophenyl)ethyl]-4-piperidinemethanol (3c). HPLC analysis showed 1.3 wt % (S)-α-(2,3-dimethoxyphenyl)-1-[2-(4-fluorophenyl)ethyl]-4-piperidinemethanol (3c) in solution (8.7 g). The aqueous phase was extracted a second time with toluene (290 mL). The phases were agitated at 60° C. for a half an hour and then separated. Analysis of the twice extracted aqueous phase showed 0.42 wt % (2.76 g) (S)-α-(2,3-dimethoxyphenyl)-1-[2-(4-fluorophenyl)ethyl]-4-piperidinemethanol (3c) and 8.65 wt % (56.6 g) (2S,3S)-(+)-di-(p-anisoyl)tartaric acid in solution.

The two top organic phases were combined and assayed for (S)-α-(2,3-dimethoxyphenyl)-1-[2-(4-fluorophenyl) ethyl]-4-piperidinemethanol (3c)[3]. The organic phase was concentrated to an oil by evaporating the toluene under vacuum. The residual oil was dissolved with 2-propanol and evaporated a second time to remove the residual toluene. Assuming 84.7 g of (S)-α-(2,3-dimethoxyphenyl)-1-[2-(4-fluorophenyl)ethyl]-4-piperidinemethanol (3c) were in the organic phase, the concentrated oil was dissolved in 2-propanol (350mL) until a 30 wt % solution was achieved. The solution was then heated to reflux and then slowly cooled and allowed to crystallize. The slurry was chilled to 0-5° C. in an ice bath before suction filtration through a coarse sintered glass funnel. The wet cake was washed with chilled 2-propanol (100 mL) and then dried to a constant weight. Isolation of the slurry gave 55.6 g of white crystals of (S)-α-(2,3-dimethoxyphenyl)-1-[2-(4-fluorophenyl)ethyl]-4-piperidinemethanol (3c) in a 66.8% yield. The mother liquors from the filtration showed 9.0 wt % (24.2 g) of (S)-α-(2,3-dimethoxyphenyl)-1-[2-(4-fluorophenyl)ethyl]-4-piperidinemethanol (3c) in solution. A second crop of crystals obtained from the mother liquors gave 8.7 g of (S)-α-(2,3-dimethoxyphenyl)-1-[2-(4-fluorophenyl)ethyl]-4-piperidinemethanol (3c). The overall yield of recovered (S)-α-(2,3-dimethoxyphenyl)-1-[2-(4-fluorophenyl)ethyl]-4-piperidinemethanol (3c) was 68.7%.

[1] Assay of the solution showed approximately 44 wt % of (S)-α-(2,3-dimethoxyphenyl)-1-[2-(4-fluorophenyl)ethyl]-4-piperidinemethanol (3b) in solution. All unit ratios are based on the calculated weight of (S)-α-(2,3-dimethoxyphenyl)-1-[2-(4-fluorophenyl)ethyl]-4-piperidinemethanol (3c) in solution (201 g, 0.25 mol).
[2] The aqueous phase from the recovery of (S)-α-(2,3-dimethoxyphenyl)-1-[2-(4-fluorophenyl)ethyl]-4-piperidinemethanol was added dropwise to a dilute acid solution consisting of 32% HCl (73.13 g, 0.64 mol) and water (400 mL). The addition was initially slow to avoid the precipitation of the (2S,3S)-(+)-di-(p-anisoyl)tartaric acid as a taffy like substance. Once crystals formed the addition rate could be increased. White crystals formed and were digested at 50-60° C. for an hour. The crystals were suction filtered through a coarse sintered glass funnel and washed with water (200 mL). The isolated crystals were dried in a vacuum oven at 60° C. until a constant weight was achieved (73.58 g). Isolation of the (2S,3S)-(+)-di-(p-anisoyl)tartaric acid was in 69% yield.
[3] HPLC analysis showed 9.5 wt % (84.7 g) of (S)-α-(2,3-dimethoxyphenyl)-1-[2-(4-fluorophenyl)ethyl]-4-piperidinemethanol (3c) in solution.

EXAMPLE 33

Scheme D, step b: α-(2,3-Dimethoxyphenyl)-1-[2-(4-fluorophenyl)ethyl]-4-piperidinemethanol (5)

In a 100-mL glass round bottom flask equipped with a cold water condenser, magnetic stirrer and a nitrogen line, (S)-α-(2,3-dimethoxyphenyl)-1-[2-(4-fluorophenyl)ethyl]-4-piperidinemethanol (3c) (4.82 g, 13 mmol), methanol (18 mL), water (6 mL) and 37% HCl (5.46 g, 55 mmol) were combined and heated to reflux (76° C.). The reaction solution was sampled periodically to check for the conversion of (S)-α-(2,3-dimethoxyphenyl)-1-[2-(4-fluorophenyl)ethyl]-4-piperidinemethanol (3c) to α-(2,3-dimethoxyphenyl)-1-[2-(4-fluorophenyl)ethyl]-4-piperidinemethanol (5). After 24 hours at reflux the reaction was complete. The solution was cooled to room temperature and then neutralized with 50% NaOH (4.2 g). After agitation of the phases for 10 minutes the methanol was removed by rotary evaporation. Toluene (29 mL) was added to the residue with mixing, the phases were allowed to separate and the organic phase was decanted and stripped to a solid. The phase cut was not very good due to the formation of an emulsion. The white residue obtained from concentration of the toluene phase was assayed. Analysis showed only 10.4 wt % α-(2,3-dimethoxyphenyl)-1-[2-(4-fluorophenyl)ethyl]-4-piperidinemethanol (5).

EXAMPLE 34

Scheme D, steps a and b: α-(2,3-Dimethoxyphenyl)-1-[2-(4-fluorophenyl)ethyl]-4-piperidinemethanol (5)

A portion of the resolution methanol mother liquors from Scheme B, step b, is concentrated to a solid (185.6 g of salt). The residue was dissolved in methanol to a concentration of 0.67 g/mL. The methanol solution was then added dropwise to an agitated suspension of toluene (464 g), water (280 g) and potassium carbonate (40.86 g, 0.3 mol). The phases were agitated for a half hour at 50° C. and then allowed to separate. The bottom aqueous phases were extracted a second time with toluene (250 mL). The two organic phases were combined and concentrated on the rotary evaporation to a solid. The solid (82 g, 0.22 mol of (S)-α-(2,3-dimethoxyphenyl)-1-[2-(4-fluorophenyl)ethyl]-4-piperidinemethanol (3c) by assay) was then dissolved in isopropanol (382 mL) and water (127 mL). To the solution, 37% HCl (138 g, 1.4 mol) was added. The solution was heated to reflux for a total of 17 hours. The solution was cooled to room temperature and neutralized with 50% NaOH (112.8 g, 1.41 mol). The addition was done slowly to control exotherm. The phases were agitated for 10 minutes before removing the isopropanol on the rotary evaporator. Toluene (500 mL) was added to the residue. The phases were agitated for 10 minutes before being separated. The bottom aqueous phase was extracted a second time with toluene (200 mL). The organic phases were then combined and concentrated on the rotary evaporation until an approximately 30 wt % of α-(2,3-dimethoxyphenyl)-1-[2-(4-fluorophenyl)ethyl]-4-piperidinemethanol (5) was reached. The slurry was heated to reflux and then slowly cooled to 40° C. where it was seeded. The solution crystallized and was cooled to room, temperature. The slurry was chilled in an ice bath for a half an hour before being suction filtered through a coarse sintered glass funnel. The wet cake was washed with 50 mL of chilled isopropanol and then dried to a constant weight. Isolation of the slurry gave 19.96 g of α-(2,3-dimethoxyphenyl)-1-[2-(4-fluorophenyl)ethyl]-4-piperidinemethanol (5) (23.6% yield, 95% assay). The mother liquor contained 3.3% (4.22 g) α-(2,3-dimethoxyphenyl)-1-[2-(4-fluorophenyl)ethyl]-4-piperidinemethanol (5).

EXAMPLE 35

Scheme D, step b: α-(2,3-Dimethoxyphenyl)-1-[2-(4-fluorophenyl)ethyl]-4-piperidinemethanol (5)

In a 250 mL glass round bottom flask equipped with a magnetic stirrer, cold water condenser and a nitrogen line, 97.5% pure (S)-α-(2,3-dimethoxyphenyl)-1-[2-(4-fluorophenyl)ethyl]-4-piperidinemethanol (3c) (10.49 g, 28 mmol), water (13 mL), glyme (40 mL) and 37% HCl (13.86 g, 140 mmol) were combined and heated to reflux. The solution was assayed initially and showed 14.4 wt % (10.39 g) (S)-α-(2,3-dimethoxyphenyl)-1-[2-(4-fluorophenyl)ethyl]-4-piperidinemethanol (3c) in solution. The clear homogeneous solution was heated for 4-5 hours. Analysis of the reaction solution at the end of racemization showed an optical purity of 1.1% of (S)-α-(2,3-dimethoxyphenyl)-1-[2-(4-fluorophenyl)ethyl]-4-piperidinemethanol (3c). The solution was cooled to room temperature and neutralized with 50% NaOH (11.25 g, 140 mmol). The solution was cooled before the base was added to help control the exotherm produced during the addition. The reaction mixture was stirred for 5-10 minutes. The glyme was removed by rotary evaporation. To the residue, toluene (53 mL) was added. The phases were agitated and heated to 70° C. The phases were separated at 60° C. The bottom aqueous phase was removed and extracted a second time with toluene (27 mL). The phases were heated and stirred for 15 minutes before being separated. The organic phases were combined and assayed at 9.5 wt % (8.2 g) α-(2,3-dimethoxyphenyl)-1-[2-(4-fluorophenyl)ethyl]-4-piperidinemethanol (5) in solution. There was essentially no product left in the aqueous phase. The organic solution was stripped to a solid on the rotary evaporator. The residue was dissolved in 2-propanol (15 g) to give a 35 wt % solution of α-(2,3-dimethoxyphenyl)-1-[2-(4-fluorophenyl)ethyl]-4-piperidinemethanol (5). The solution was heated to reflux and cooled to room temperature. The solution crystallized, the slurry was warmed and the crystals were digested at 45-50° C. for 30 minutes. The slurry was then cooled to room temperature and then chilled in an ice bath for 30 minutes. The crystals were suction filtered through a coarse sintered glass funnel. The wet cake was washed with 17 mL of 2-propanol before being dried in a vacuum oven at 60° C. The mother liquor showed 2.6 wt % (0.66 g) α-(2,3-dimethoxyphenyl)-1-[2-(4-fluorophenyl)ethyl]-4-piperidinemethanol (5) in solution. Isolation of the α-(2,3-dimethoxyphenyl)-1-[2-(4-fluorophenyl)ethyl]-4-piperidinemethanol (5) crystals were done in a 69.7% yield based on the initial amount of (S)-α-(2,3-dimethoxyphenyl)-1-[2-(4-fluorophenyl)ethyl]-4-piperidinemethanol (3c) used. Assay of the crystals was >100% and showed an optical purity of 1.2% (S)-α-(2,3-dimethoxyphenyl)-1-[2-(4-fluorophenyl)ethyl]-4-piperidinemethanol (3c).

EXAMPLE 36

Scheme D, step b: α-(2,3-Dimethoxyphenyl)-1-[2-(4-fluorophenyl)ethyl]-4-piperidinemethanol (5)

In a 1-neck 250 mL glass round bottom flask equipped with a cold water condenser, magnetic stirrer, and a nitrogen line, 97.5% (S)-α-(2,3-dimethoxyphenyl)-1-[2-(4-fluorophenyl)ethyl]-4-piperidinemethanol (3c) (10.4 g, 28 mmol), water (16 mL), glyme (37 mL), and 98% $H_2SO_4$ (9.75 g, 97 mmol) were combined and heated to reflux. The clear homogeneous solution was assayed initially. The assay showed 15.5 wt % (10.38 g) (S)-α-(2,3-dimethoxyphenyl)-1-[2-(4-fluorophenyl)ethyl]-4-piperidinemethanol (3c) in solution. After 5 hours at reflux, an assay of the solution showed 13.9 wt % (8.97 g) α-(2,3-dimethoxyphenyl)-1-[2-(4-fluorophenyl)ethyl]-4-piperidinemethanol (5). The reaction mixture was cooled to room temperature and neutralized with 50% NaOH (15.59 g). Additional water (15 mL) was needed to dissolve the sodium sulfate salt formed. The glyme was removed from the reaction mixture by rotary evaporation. Toluene (53 mL) was added to the residue. Two phases formed and were agitated while being heated at 70° C. The phases were cooled to 60° C. and separated. The bottom aqueous phase was extracted a second time with toluene (26 mL). The two organic extractions were combined and assayed. There was 11.1 wt % (8.84 g) α-(2,3-dimethoxyphenyl)-1-[2-(4-fluorophenyl)ethyl]-4-piperidinemethanol (5) in solution. The solution was stripped to a solid and then dissolved in 2-propanol (20 g) to a 30 wt % solution of α-(2,3-dimethoxyphenyl)-1-[2-(4-fluorophenyl)ethyl]-4-piperidinemethanol (5). The solution was heated to reflux, cooled, and allowed to crystallize. The crystals were digested at 50° C. for 30 minutes before being chilled to approximately 0° C. in an ice bath. The crystals were isolated through a coarse sintered glass funnel and washed with 10 mL of 2-propanol. The wet cake was dried in a vacuum oven to a constant weight. Analysis of the mother liquors showed 4.4 wt % (1.13 g) α-(2,3-dimethoxyphenyl)-1-[2-(4-fluorophenyl)ethyl]-4-piperidinemethanol (5) in solution. Isolation of the α-(2,3-dimethoxyphenyl)-1-[2-(4-fluorophenyl)ethyl]-4-piperidinemethanol (5) was done in a 76.6% yield giving 98.7% pure white crystals.

EXAMPLE 37

Scheme D, step b: α-(2,3-Dimethoxyphenyl)-1-[2-(4-fluorophenyl)ethyl]-4-piperidinemethanol (5)

In a 1-neck 500 mL glass round bottom flask equipped with a cold water condenser, magnetic stirrer and a nitrogen line, 97.5% pure (S)-α-(2,3-dimethoxyphenyl)-1-[2-(4-fluorophenyl)ethyl]-4-piperidinemethanol (3c) (20.43 g, 55 mmol), tetrahydrofuran (71.5 mL), water (35 mL) and sulphuric acid (19.27 g, 196 mmol) were combined. The solution was assayed initially and showed 14.7 wt % (20.4 g) (S)-α-(2,3-dimethoxyphenyl)-1-[2-(4-fluorophenyl)ethyl]-4-piperidinemethanol (3c) in solution. The solution was heated to reflux for 12 hours. The solution was cooled to room temperature and chilled in an ice bath for the neutralization. To the reaction solution, 50% NaOH (30.1 g, 0.38 mol) was added slowly. The addition was exothermic. The tetrahydrofuran was then removed by rotary evaporation. The residue was dissolved in toluene (72 mL). Excess water (30 mL) was added to the mixture to help keep the sodium salt dissolved. The phases were agitated and heated to 70° C. for 30 minutes. The phases were separated and the bottom aqueous phase was extracted a second time with toluene (37 mL). The organic phases were combined and assayed. The phase cut must be done warm to ensure that the α-(2,3-dimethoxyphenyl)-1-[2-(4-fluorophenyl)ethyl]-4-piperidinemethanol (5) stays in solution and the sodium sulfate salt remains dissolved in the aqueous phase. The assay of the top organic phases showed 16.8 wt % (19.6 g) α-(2,3-dimethoxyphenyl)-1-[2-(4-fluorophenyl)ethyl]-4-piperidinemethanol (5) in solution. There was no residual product left in the aqueous phase following the second extraction. The toluene solution was stripped to a white solid by rotary evaporation. The solid residue was dissolved in 2-propanol (25.5 g) to give a 30 wt % solution of α-(2,3-dimethoxyphenyl)-1-[2-(4-fluorophenyl)ethyl]-4-piperidinemethanol (5). The solution was heated to reflux and slowly cooled to room temperature. The solution crystallized and was chilled in an ice bath for 30 minutes. Isolation of the slurry was done by suction filtration. The wet cake was washed with 15 mL of chilled 2-propanol and then dried to a constant weight. Analysis of the mother liquors showed 9.0 wt % (5.71 g) α-(2,3-dimethoxyphenyl)-1-[2-(4-fluorophenyl)ethyl]-4-piperidinemethanol (5). The solution was then concentrated on the roto-vap to half its original weight and crystallized. The crystals were chilled in an ice bath and suction filtered through a coarse sintered glass funnel. The assay of the mother liquors from the second crop showed 4.0 wt % (1.11 g) α-(2,3-dimethoxyphenyl)-1-[2-(4-fluorophenyl)ethyl]-4-piperidinemethanol (5) in solution. The two crops of crystals were combined and dried to a constant weight. Isolation of the slurry gave 100% pure α-(2,3-dimethoxyphenyl)-1-[2-(4-fluorophenyl)ethyl]-4-piperidinemethanol (5) crystals in a 87.4% yield having an optical purity of 16.3% (S)-α-(2,3-dimethoxyphenyl)-1-[2-(4-fluorophenyl)ethyl]-4-piperidinemethanol (3c). Accounting for the weight left in the mother liquor, the yield was raised to 92.8%.

EXAMPLE 38

Scheme D, steps a and b: α-(2,3-Dimethoxyphenyl)-1-[2-(4-fluorophenyl)ethyl]-4-piperidinemethanol (5)

The concentrated resolution mother liquors from Scheme B, step b, (302.3 g, assayed 38.5 wt % diastereomeric salt (116 g, 147 mmol of salt)) were concentrated on the rotary evaporator to a solution which was approximately 0.67 g/mL. This solution was added dropwise to a suspension of toluene (250 mL), water (175 mL) and potassium carbonate (25.58 g, 0.185 mol). The mixture was stirred for about 30 minutes at 40° C. (The organic phase contained 14.1 wt %, 49.8 g (S)-α-(2,3-dimethoxyphenyl)-1-[2-(4-fluorophenyl)ethyl]-4-piperidinemethanol (3c) by assay. The aqueous phase contained 1.3 wt %, 5 g of (S)-α-(2,3-dimethoxyphenyl)-1-[2-(4-fluorophenyl)ethyl]-4-piperidinemethanol (3c) by assay). The toluene was removed by evaporation to give a white solid (60 g). This residue was dissolved in tetrahydrofuran (174 mL), water (75 mL) and sulphuric acid (47.6 g, 0.48 mol). (The pale yellow solution was assayed, 14.8 wt %, 50.3 g of (S)-α-(2,3-dimethoxyphenyl)-1-[2-(4-fluorophenyl)ethyl]-4-piperidinemethanol (3c)). The mixture was heated at reflux for 32 hours. After 16 hours, an additional portion (6.5 g, 66 mmol) of sulphuric acid was added. The reaction mixture was cooled to ambient temperature and carefully neutralized with 50% aqueous sodium hydroxide (87.92 g, 1.1 mol). The tetrahydrofuran was removed by vacuum distillation on the rotary evaporator, toluene (175 mL) and water (55 mL) were added and the mixture was stirred at 60-70° C. for about 30 minutes. The phases were decanted at 60° C. and the aqueous phase was extracted a second time with toluene (80 mL). The toluene phases were combined and concentrated on the rotary evaporator to remove water. The solution was assayed (29.7%, 43.2 g α-(2,3-dimethoxyphenyl)-1-[2-(4-fluorophenyl)ethyl]-4-piperidinemethanol) (5), heated to reflux and slowly cooled. Seeding at 50° C. was required. The slurry was digested at 50° C. prior to cooling to 0-5° C. prior to isolation by filtration. The filter cake was washed with chilled toluene (30 mL) and dried to a constant weight to obtain α-(2,3-dimethoxyphenyl)-1-[2-(4-fluorophenyl)ethyl]-4-piperidinemethanol (5) (40.25 g, 81%, 97.5% assay).

[1] The aqueous phase which contained the (2S,3S)-(+)-di-(p-anisoyl)tartaric acid was added dropwise to a solution of 32% HCl (42.57 g, 0.37 mol) and water (234 mL) at 40° C. The (2S,3S)-(+)-di-(p-anisoyl)tartaric acid precipitated as a white solid. The solution was cooled to room temperature overnight and in an ice bath for 45 minutes prior to isolation by filtration. The recovered solid was washed with cold water, suction filtered, and finally dried to a constant weight in a vacuum oven to give 47.55 g of product (77% recovery).

EXAMPLE 39

Scheme D, steps a and b: α-(2,3-Dimethoxyphenyl)-1-[2-(4-fluorophenyl)ethyl]-4-piperidinemethanol (5)

A suitable reactor is charged with the resolution filtrates from Scheme B, step b, Example 21 containing about 88.7 kg of diastereomeric salts. The mixture is concentrated to about 46% by distillation as determined by HPLC assay. About 220 kg of toluene and 150 kg of 13% aqueous potassium carbonate[1] are added to the concentrated filtrates. The solution temperature is controlled at about 50° C. and the phases are separated. The organic phase is retained and the aqueous phase is discarded.[2] The organic solution is concentrated by distillation until no more distillate is collected. About 130 kg of tetrahydrofuran is added to the reactor to dissolve the distillation residue. About 60 kg of water and about 39 kg of sulfuric acid (98%) are added to the reactor. The solution is heated to reflux (about 75° C.) for about 18 hours or until the enantiomeric excess of the mixture is less than 4% as determined by chiral HPLC assay. The solution is cooled to below 40° C. while about 62 kg of 50% sodium hydroxide is added to neutralize the sulfuric acid. The pH of the solution is checked to assure that it is #7. About 113 kg of solvent is removed by distillation before about 125 kg of toluene is added. Then about 170 kg of solvent is distilled and about 65 kg of toluene is added to complete the solvent exchange to toluene, resulting in an α-(2,3-dimethoxyphenyl)-1-[2-(4-fluorophenyl)ethyl]-4-piperidinemethanol (5) concentration of 20-30 wt % as determined by HPLC assay. The solution is then held at about 70° C. The salts are dissolved by adding about 355 kg of water and then separating the phases[3]. The aqueous phase is discarded. The solution is cooled below −10° C. and the α-(2,3-dimethoxyphenyl)-1-[2-(4-fluorophenyl)ethyl]-4-piperidinemethanol (5) is collected by filtration[4]. The wet cake is washed with about 5 kg of cold isopropanol to typically afford about 31 kg of α-(2,3-dimethoxyphenyl)-1-[2-(4-fluorophenyl)ethyl]-4-piperidinemethanol (5) (74% yield as determined by HPLC assay).

[1] The 13% potassium carbonate solution is prepared by dissolving about 20 kg of potassium carbonate in 130 kg of water.
[2] The aqueous phase may be extracted twice more with about 65 kg of toluene each to improve the recovery. All of the organic phases are combined and the aqueous phase is discarded.
[3] The organic phase may be dried by azeotropic [toluene, isopropanol, and water] distillation following the phase separation.
[4] α-(2,3-Dimethoxyphenyl)-1-[2-(4-fluorophenyl)ethyl]-4-piperidinemethanol (5) may be recovered from the filtrates (228 kg) by concentrating them under vacuum to about 11 wt % (see footnote 1) and then acidifying at about 25° C. with about 3.4 equivalents of 1N HCl (50 kg). The organic phase is discarded and the aqueous phase is neutralized with NaOH. The α-(2,3-dimethoxyphenyl)-1-[2-(4-fluorophenyl)ethyl]-4-piperidinemethanol (5) is extracted into toluene (85 kg) and the aqueous phase is discarded. The toluene solution is concentrated by distillation to about 25-30 wt % as determined by HPLC assay. The solution is cooled below −10° C. and the α-(2,3-dimethoxyphenyl)-1-[2-(4-fluorophenyl)ethyl]-4-piperidinemethanol (5) is collected by filtration. The wet cake is washed with about 5 kg of cold isopropanol to typically afford about 2.3 kg of α-(2,3-dimethoxyphenyl)-1-[2-(4-fluorophenyl)ethyl]-4-piperidinemethanol (5) as determined by chiral HPLC assay.

EXAMPLE 40

Scheme D, steps a and b: α-(2,3-Dimethoxyphenyl)-1-[2-(4-fluorophenyl)ethyl]-4-piperidinemethanol (5)

A suitable reactor is charged with the resolution filtrates from Scheme B, step b, and the recrystallization filtrates from Scheme C, step a, from Example 22 containing about 277 kg of diastereomeric salts (0.35 kmol). The mixture is concentrated under vacuum at about 25° C. About 1600 kg of toluene[1] and 1110 kg of 13 wt % aqueous potassium carbonate[1] are added. The mixture is maintained at about 50° C. and the phases are separated. The aqueous phase is retained[2] and contains (2S,3S)-(+)-di-(p-anisoyl)tartaric acid. The organic solution is concentrated by distillation.

Tetrahydrofuran (940 kg) is added followed by the addition of about 450 kg of water and sulfuric acid (98%, 274 kg, 2.74 kmol). The mixture is heated to reflux (about 75° C.) for about 18 hours or until the enantiomeric excess of the mixture is less than 4% as determined by chiral HPLC assay. The solution is cooled to about 25° C. while a 50% sodium hydroxide solution (444 kg, 5.56 kmol) and about 1080 kg of toluene are added. The mixture is then warmed to about 50° C. The phases are separated and the aqueous phase is discarded. Solvent is removed by atmospheric distillation until the temperature reaches about 105° C. The mixture is then cooled to about 70° C. About 276 kg of water is added and the phases are separated. The aqueous phase is discarded. Toluene is removed by atmospheric distillation until the temperature reaches about 110° C.[3]. The solution is cooled to about −10° C. and α-(2,3-dimethoxyphenyl)-1-[2-(4-fluorophenyl)ethyl]-4-piperidinemethanol (5) is collected by filtration.[4] The wet cake is washed with about 220 kg of cold toluene to typically afford about 100 kg of α-(2,3-dimethoxyphenyl)-1-[2-(4-fluorophenyl)ethyl]-4-piperidinemethanol (5) (77% yield as determined by HPLC assay).

[1] The 13 wt % potassium carbonate solution is prepared by dissolving about 144 kg of potassium carbonate in about 966 kg of water.
[2] The aqueous phase may be extracted twice more with about 65 kg of toluene each to improve the recovery. All of the organic phases are combined for recovery of (2S,3S)-(+)-di-(p-anisoyl)tartaric acid.
[3] The concentration of α-(2,3-dimethoxyphenyl)-1-[2-(4-fluorophenyl)ethyl]-4-piperidinemethanol (5) is estimated by mass balance. Toluene can be back added to obtain a concentration of α-(2,3-dimethoxyphenyl)-1-[2-(4-fluorophenyl)ethyl]-4-piperidinemethanol (5) between 15-30% if necessary (determined by HPLC assay).
[4] α-(2,3-Dimethoxyphenyl)-1-[2-(4-fluorophenyl)ethyl]-4-piperidinemethanol (5) may be recovered from the filtrates by concentrating them under vacuum to about 11 wt % (determined by HPLC assay) and then acidifying at about 25° C. with 1N hydrochloric acid. The organic phase is discarded and the aqueous phase is neutralized with sodium hydroxide solution. The α-(2,3-dimethoxyphenyl)-1-[2-(4-fluorophenyl)ethyl]-4-piperidinemethanol (5) is extracted into toluene and the aqueous phase is discarded. The toluene solution is concentrated by atmospheric distillation to about 25-30 wt % (determined by HPLC assay). The solution is cooled to about −10° C. and the α-(2,3-dimethoxyphenyl)-1-[2-(4-fluorophenyl)ethyl]-4-piperidinemethanol (5) is collected by filtration. The wet cake is washed with cold isopropanol to afford additional α-(2,3-dimethoxyphenyl)-1-[2-(4-fluorophenyl)ethyl]-4-piperidinemethanol (5) (determined by HPLC assay).

EXAMPLE 41

Scheme E, step a: α-(2,3-dimethoxyphenyl)-1-[2-(4-fluorophenyl)ethyl]-4-piperidinemethanol, butyrate ester (5a)

Add butyryl chloride (140 mL, 1.34 mol) to a solution of α-(2,3-dimethoxyphenyl)-1-[2-(4-fluorophenyl)ethyl]-4-piperidinemethanol (5) (100 g, 0.27 mol), triethylamine (75 mL, 54 g, 0.54 mol), and dimethylaminopyridine (1.64 g, 0.01 mol) in chloroform (1.8 L) over 10 min under nitrogen. Stir the resulting solution under reflux for 16 hours. Cool to room temperature and wash with 5% aqueous sodium carbonate (3×2 L), saturated sodium bicarbonate (2 L), brine (2 L) and dry (MgSO$_4$). Filter the mixture and concentrate the filtrate (35° C./20 torr), and purify the residue by flash chromatography (SiO$_2$, 10 cm×15 cm, eluted with hexane (2 L), 1:4 EtOAc:hexane (4 L), and 1:2 EtOAc:hexane (4 L)). Combine the desired fractions and concentrate (35° C./20 torr) to give α-(2,3-dimethoxyphenyl)-1-[2-(4-fluorophenyl)ethyl]-4-piperidinemethanol, butyrate ester (5a).

EXAMPLE 42

Scheme E, step b and step c: (R)-α-(2,3-dimethoxyphenyl)-1-[2-(4-fluorophenyl)ethyl]-4-piperidinemethanol (3)

A suspension of 20 g of lipase from *Candida cylindracea* (Sigma; 665 units/mg solid; 4780 units/mg protein) in 400 mL of distilled water was stirred at room temperature for 30 minutes. The solution was centrifuged at 12000 g for 20 minutes. The supernatant was collected and $(NH_4)_2SO_4$ (140 g) was added in portions with stirring. The mixture was stirred for 2 hours and then centrifuged (12000 g; 20 minutes). The supernatant was discarded and a solution of the precipitate in 30 mL of distilled water was dialyzed against distilled water overnight. The dialyzed solution was used in further experiments.

To a solution of α-(2,3-dimethoxyphenyl)-1-[2-(4-fluorophenyl)ethyl]-4-piperidinemethanol, butyrate ester (5a) (2.77 g, 6.2 mmol) in t-BuOMe (10 mL), Baker silica (8.3 g, 40 μ) was added. After evaporation of the ether, the silica was transferred to 180 mL of 0.1M phosphate buffer (pH 7.0) and then 25 mL of the partially purified lipase (100 g crude=230 mL of a solution) was added. The suspension was stirred at 45° C. for 4 days. The reaction was stopped by filtering the reaction mixture. Both filtrate and silica were extracted with ethyl acetate (300 mL). The organic layer was dried over $MgSO_4$, evaporated under vacuum to give a residue, which was purified by column chromatography (60 g Baker silica (40 μ); EtOAc/heptane=3:1). ($R_f$0.45 for (S)-α-(2,3-dimethoxyphenyl)-1-[2-(4-fluorophenyl)ethyl]-4-piperidinemethanol, butyrate ester (5b) and 0.06 for (R)-α-(2,3-dimethoxyphenyl)-1-[2-(4-fluorophenyl)ethyl]-4-piperidinemethanol (3)). After the ester was eluted, the eluant was changed to MeOH/EtOAc=3:7 to recover (R)-α-(2,3-dimethoxyphenyl)-1-[2-(4-fluorophenyl)ethyl]-4-piperidinemethanol (3) as a yellow oil (1.08 g, 46%, 98% ee). Recrystallization twice from EtOAc/heptane gave (R)-α-(2,3-dimethoxyphenyl)-1-[2-(4-fluorophenyl)ethyl]-4-piperidinemethanol (3) as a white crystalline compound (770 mg, 33%, 99% ee); m.p.=114-116° C.; $[\alpha]_D$=14.3 (c=1; $CHCl_3$).

$^1$H NMR ($CDCl_3$) δ 1.2-1.6 (m, 3H), 1.7 (m, 1H), 1.9-2.0 (m, 3H), 2.35 (brd, 1H), 2.5 (m, 2H), 2.8 (m, 2H), 2.93 (brd, 1H), 3.07 (brd, 1H), 3.88 (s, 6H), 4.63 (d, 1H), 6.34 (dd, 1H, J=1.5, 8.1 Hz), 6.89 (dd, 1H, J=1.5, 7.8 Hz), 6.94 (dd, 2H; J=8.8, J=8.8 Hz), 7.05 (dd, 1H, J=9, 7.9 Hz); 7.13 (dd, 2H; J=5.4; 8.7 Hz).

$^{19}$F NMR ($CDCl_3$, 282.2 MHz) δ 118.5 (brs; proton coupling is unresolved);

IR (KBr) 3150, 1430, 1222 cm$^{-1}$;

MS: m/e (relative intensity): 402 (23), 374 (100), 356 (62), 264 (60);

Anal. Calcd for $C_{22}H_{28}FNO_3$ (MW 373.5): C, 70.75; H, 7.56; N, 3.75; Found: C, 70.47; H, 7.84; N, 3.86.

EXAMPLE 43

Scheme E, step a: α-(2,3-dimethoxyphenyl)-1-[2-(4-fluorophenyl)ethyl]-4-piperidinemethanol, butyrate ester (5a)

Butyryl chloride (140 mL, 1.34 mol) was added to a solution of (R)-enriched α-(2,3-dimethoxyphenyl)-1-[2-(4-fluorophenyl)ethyl]-4-piperidinemethanol (5) (100 g, 0.27 mol), triethylamine (75 mL, 54 g, 0.54 mol), and dimethylaminopyridine (1.64 g, 0.01 mol) in chloroform (1.8 L) over 10 minutes under nitrogen atmosphere. The resulting solution was stirred under reflux for 16 hours. After cooling to room temperature, the solution was washed with 5% aqueous sodium carbonate (3×2 L), saturated sodium bicarbonate (2 L), brine (2 L) and dried ($MgSO_4$). The mixture was filtered and the filtrate was concentrated (35° C./20 torr) to a residue which was purified by flash chromatography ($SiO_2$, 10 cm×15 cm, eluted with hexane (2 L), 1:4 of EtOAc:hexane ((4 L), and 1:2 EtOAc: hexane (4 L)). The desired fractions (TLC, $R_f$0.45, 1.1 EtOAc:hexane) were combined and concentrated (35° C./20 torr) to give (R)-enriched α-(2,3-dimethoxyphenyl)-1-[2-(4-fluorophenyl)ethyl]-4-piperidinemethanol, butyrate ester (5a) as an oil (116 g, 82% ee, 98% yield).

IR (neat) 3069, 3040, 2941, 2877, 2803, 1735, 1643, 1601, 1588, 1510, 1482, 1374, 1268, 1221, 1180, 1089, 1005, 827, 752 cm$^{-1}$;

$^1$H NMR ($CDCl_3$) δ 6.8-7.2 (m, 7H, aryl), 5.85 (d, 1H, J=7.5 Hz, CHO), 3.91 (s, 3H, $OCH_3$), 3.85 (s, 3H, $OCH_3$), 3.0 (m, 2H), 2.8 (m, 2H), 2.5 (m, 2H), 2.30 (t, 2H, J=7.5 Hz, $CH_2CO$), 1.9 (m, 1H), 1.8 (m, 2H), 1.6 (m, 2H), 1.5 (m, 4), 0.90 (t, 3H, J=7.5 Hz, $CH_3$);

$^{13}$C NMR ($CDCl_3$) δ 172, 161.3 (d, $J_{F-C}$=243.0 Hz), 152.4, 146.4, 133.6, 130.0 (d, $J_{F-C}$=8.0 Hz), 123.9, 118.6, 115.1 (d, $J_{F-C}$=21.3 Hz), 111.3, 73.6, 60.4, 55.6, 53.4, 40.9, 36.4, 32.7, 27.8, 18.4, 13.7;

$^{19}$F NMR ($CDCl_3$) δ-117.9;

MS (CI, $CH_4$) m/z (rel. Intensity) 444 (MH$^+$, 57%), 424 (35), 356 (100), 334 (98);

$[\alpha]_D^{20}$+4.8° (c 1.03, $CHCl_3$);

Anal. Calc'd for $C_{26}H_{34}FNO_4$0.3 $H_2O$ (448.9): C, 69.55; H, 7.77; N, 3.12. Found: C, 69.49; H, 7.90; N, 2.94.

EXAMPLE 44

Scheme E, step b and step c: (R)-α-(2,3-dimethoxyphenyl)-1-[2-(4-fluorophenyl)ethyl]-4-piperidinemethanol (3)

Silica gel (EM Sciences, 230-400 mesh, 215 g) was added to a solution of (R)-enriched α-(2,3-dimethoxyphenyl)-1-[2-(4-fluorophenyl)ethyl]-4-piperidinemethanol, butyrate ester (5a) (72 g, 0.16 mol, 82% ee) in t-BuOMe (320 mL). The resulting slurry was concentrated (35° C./20 torr) to give a light yellow powder. A mixture of the powder, partially purified *Candida cylindracea* lipase (17.1 g, equivalent to 522 g of crude enzyme from Sigma) in phosphate buffer (0.1 M, pH 7, 5.2 L) was stirred at 45° C. for 4 days. EtOAc (4 L) was added and the mixture was stirred at room temperature for 1 hour. Solid material was removed by filtration, and the two phases in the filtrate were separated. Both the solid and aqueous layer were extracted with EtOAc (2 L). The combined organic solutions were concentrated (35° C./20 torr) to a residue which was purified by flash chromatography ($SiO_2$, 10 cm×15 cm, eluted with 1:1 EtOAc; hexane (8 L) and 1:19 EtOAc: MeOH (8 L)). The desired fractions (TLC, $R_f$ 0.16, acetone) were combined and concentrated (35° C./20 torr) to a residue which was dissolved in methylene chloride (800 mL). The solution was washed with 0.5N NaOH (2×600 mL), brine (600 mL) and dried ($MgSO_4$). The mixture was filtered and the filtrate was concentrated (30° C./20 torr) to give a solid which was recrystallized from cyclohexane (2 L) to give (R)-α-(2,3-dimethoxyphenyl)-1-[2-(4-fluorophenyl)ethyl]-4-piperidinemethanol (3) as a white solid (31 g, 52% yield, 99.9% ee); m.p. 113-114° C., $[\alpha]_D^{20}$+14.0° (c 0.49, $CHCl_3$).

Anal. Calc'd. For $C_{22}H_{28}FNO_3$ (373.5): C, 70.75; H, 7.56; N, 3.75. Found: C, 70.62; H, 7.60; N, 3.61.

EXAMPLE 45

Scheme F, steps a and b:
(R)-α-(2,3-dimethoxyphenyl)methyl]piperidine (1)

A suitable reactor maintained under argon was charged with (+)-β-chlorodiisopinocamphenylborane (18.2 kg, 56.7 mol) and 4 L of tetrahydrofuran. This stirred mixture was cooled to and maintained below −10° C. while adding a solution of 4-(2,3-dimethoxybenzoyl)-1-piperidinecarboxylic acid, 1,1-dimethylethyl ester (7) (15.05 kg, 39.8 mol, 13.03 kg theory) in 4 L of tetrahydrofuran over a period of 2 hours. The stirred mixture was maintained below −10° C. for 20 hours, then below −5° C. for 20 hours, then below +5° C. for 30 hours, and finally it was maintained at 15° C. for 4 days. The reaction mixture was diluted with 11 L of tetrahydrofuran, followed by the addition of a solution of diethanolamine (6 kg, 57.1 mol) in 18 L of tetrahydrofuran while maintaining the reaction temperature below 20° C. The reaction mixture was transferred to a larger reactor and 19 L of tetrahydrofuran was distilled off at atmospheric pressure. The mixture was diluted with 30 L of water and the remaining tetrahydrofuran was distilled off below 45° C. at 300 torr. A solution of 5 kg of 33% hydrochloric acid in 40 L of water was added over 5 minutes while maintaining a reaction temperature of 15° C. The reaction mixture was extracted with 75 L of heptane. The organic phase was separated and extracted successively with a solution of 2.2 kg of 33% hydrochloric acid in 20 L of water, followed by a solution of 0.55 kg of 33% hydrochloric acid in 5 L of water. The acid extracts were combined and diluted with a mixture of 20% sodium hydroxide (23.9 kg, 119.5 mol) and 5 L of water. The aqueous basic solution was stirred for 17 hours at room temperature while the product crystallized. The stirred mixture was cooled and maintained at 5° C. for 1 hour, then product was filtered off and washed with 3 L of water. After drying at ambient temperature, the quantity obtained was 6.45 kg (72.9% ee). The 6.45 kg was added to a solution of 43 L of acetone and 86 L of water. The stirred mixture was heated at reflux for 30 minutes, then was slowly cooled to room temperature over 20 hours. After cooling to 3° C., product was filtered off, washed with 2×3 L of water, then air dried at 40° C. to give 4.6 kg (93% ee). The 4.6 kg was added to a solution of 11 L of acetone and 22 L of water. The stirred mixture was heated at reflux for 30 minutes, then was slowly cooled to room temperature over 20 hours. After cooling to 3° C., product was filtered off, washed with 2×2 L of water, then air dried at 40° C. to give (R)-α-(2,3-dimethoxyphenyl)methyl]piperidine (1) (34% yield, 95.5% ee).

EXAMPLE 46

Scheme F, step a: (R)-4-(1-hydroxy-1-(2,3-dimethoxyphenyl)-1-piperidinecarboxylic acid, 1,1-dimethylethyl ester (8)

1,2:3,5-Di-O-isopropylidene-D-xylofuranose (70.66 g, 0.30 mol) is treated with $H_2SO_4$ (0.1 M, 300 mL). Upon stirring, the xylose slowly dissolves. After 30 minutes, the reaction is quenched with $NH_4OH$ (pH 9.0) and half of the water removed at reduced pressure. The aqueous layer is diluted with brine (100 mL) and extracted with ethyl acetate (3×200 mL). A normal work-up provides an oil. Kugelrohr distillation provides 1,2-O-isopropylidene-D-xylofuranose (40 g, 68.5%); b.p. 120-135° C./0.4 mm Hg.

1,2-O-Isopropylidene-D-xylofuranose (8.35 g, 43.9 mmol) is dissolved in pyridine (50 mL); the resulting solution is cooled to 0° C. and treated with tosyl chloride (10.0 g, 52.5 mmol) and dimethylaminopyridine (0.5 g). After reacting for 16 hours at 0° C., the solution is quenched with water (50 mL) and diluted with toluene (50 mL). The organic phase is separated, dried, filtered and concentrated at reduced pressure <40° C. (pyridine is still present in the organic phase). The oil is dissolved in ethyl acetate (100 mL), extracted with 10% acetic acid, washed with water, then extracted with $NaHCO_3$ (saturated). The organic phase is dried, filtered and concentrated at reduced pressure to leave a white solid. The solid is dissolved in ethyl acetate (50 mL) with heating, diluted with hexane (50 mL), filtered through Celite7 filter aid and cooled to 0° C. to provide 1,2-O-isopropylidene-5-(p-toluenesulfonyl)-D-xylofuranose as white crystals (10.1 g, 67% yield); m.p. 137-8° C.

1,2-O-Isopropylidene-5-(p-toluenesulfonyl)-D-xylofuranose (10.0 g, 29 mmol) is added to a solution of NaOMe at 0° C. (prepared from 1.3 g, 56 mmol, Na added to 50 mL MeOH). The reaction mixture is permitted to warm to room temperature overnight. The reaction is quenched with ammonium chloride (saturated, 20 mL), then concentrated at reduced pressure to remove MeOH. The slurry is diluted with water (30 mL), and extracted with ethyl acetate (4×50 mL). The combined organic extracts are extracted with brine, dried, filtered, and concentrated at reduced pressure to leave an oil. Kugelrohr distillation provides 3,5-anhydro-1,2-O-isopropylidenexylofuranose as a clear oil (4.1 g, 82% yield); b.p. 55-70° C./0.5 mm Hg.

3,5-Anhydro-1,2-O-isopropylidenexylofuranose (4.0 g, 23 mmol) is dissolved in ether and treated portionwise with solid $LiAlH_4$ (1.76 g, 46 mmol). Upon completion of the addition, the reaction mixture is heated at reflux for 16 hours. The reaction is quenched by slow addition of acetone (4 mL), followed by 10% acetic acid/water (35 mL). The mixture is diluted with ethyl acetate (50 mL) and treated with filter aid. After stirring for 30 minutes, the suspension is centrifuged; the supernatant is filtered through filter-aid and the phases are separated. The aqueous phase is neutralized with $NaHCO_3$, then saturated NaCl. The mixture is extracted with EtOAc (2×50 mL). Pellets from the centrifuge tubes are resuspended in 50% $H_2O$/EtOAc mixture (100 mL). After stirring for 30 minutes, the mixture is re-centrifuged. The supernatant is filtered and the phases separated. The aqueous phase is combined with the original aqueous phase and extracted with ethyl acetate (50 mL). The combined organic phases are washed with brine, dried, filtered and concentrated at reduced pressure to leave an oil. Kugelrohr distillation provides 5-deoxy-1,2-O-isopropylidene-D-xylofuranose as a solid (3.05 g, 76% yield); m.p. 70-72° C.

A tetrahydrofuran solution of 9-BBN (0.5 M, 45 mL, 22.5 mmol) is treated with a solution of 5-deoxy-1,2-O-isopropylidenne-D-xylofuranose (3.90 g, 22.4 mmol, 15 mL tetrahydrofuran) and stirred at ambient temperature for 2 hours, then at reflux for 1 hour to complete the formation of 9-O-(1,2-isopropylidene-5-deoxy-α-D-xylofuranosyl)-9-borabicyclo[3.3.1]nonane. The solution is cooled to ambient temperature and transferred, via cannula, into a flask containing solid KH (2.0 g, 49 mmol). The reaction mixture warms upon mixing. After stirring for 4 hours, the reaction mixture is permitted to stand under argon overnight. The clear solution (0.35 mM in borohydride reagent) is used as is for the reduction of 4-(2,3-dimethoxybenzoyl)-1-piperidinecarboxylic acid, 1,1-dimethylethyl ester (7).

A solution of 4-(2,3-dimethoxybenzoyl)-1-piperidinecarboxylic acid, 1,1-dimethylethyl ester (7) (1.0 g, 2.9 mmol) in tetrahydrofuran (5 mL) is cooled to −40° C. and treated with a −40° C. solution of the borohydride reagent (10 mL, 0.35 M, 3.5 mmol). The reaction mixture is warmed to −15° C. and allowed to react at this temperature for 18 hours. The reaction is quenched with MeOH, followed by NH$_4$Cl (saturated). The product is extracted into toluene. After a normal work-up, the residue is flash chromatographed to provide (R)-4-(1-hydroxy-1-(2,3-dimethoxyphenyl)-1-piperidinecarboxylic acid, 1,1-dimethylethyl ester (8) (0.64 g, 63%, 80% ee).

EXAMPLE 47

Scheme F, step c: 4-[1-Hydroxy-1-(2,3-dimethoxyphenyl)methyl]piperidine (11)

To a 50 mL flask equipped with nitrogen bubbler was added 0.19 g (0.54 mmol) 4-(2,3-dimethoxybenzoyl)-1-piperidinecarboxylic acid, 1,1-dimethylethyl ester (7) and 10 mL of tetrahydrofuran. The solution was cooled to 0° C., then 0.10 g ((2.6 mmol) of small sodium borohydride pellets were added. The reaction mixture was stirred one hour at 0° C. and then for 5 days at room temperature. The reaction mixture was poured into 50 mL of tetrahydrofuran and 10 mL of water in a separatory funnel. The tetrahydrofuran solution was then washed with brine (3×15 mL) and dried over magnesium sulfate. The solution was filtered and then evaporated to leave 0.22 g of a colorless oil. The crude intermediate 4-[1-hydroxy-1-(2,3-dimethoxyphenyl)methyl]piperidine, 1,1-dimethylethyl ester was purified by column chromatography (silica gel, 20% ethyl acetate in toluene as eluant) to give the title compound (11) as a colorless oil after solvent removal (0.15 g, 79%).

Cool the intermediate 4-[1-hydroxy-1-(2,3-dimethoxyphenyl)methyl]piperidine, 1,1-dimethylethyl ester to 0° C., treat with trifluoroacetic acid (~10 mL), and stir at ambient temperature for 1 hour. Concentrate in vacuo, dissolve the residue in water (~30mL), wash with hexane (~2×10 mL) and treat with solid sodium hydroxide (~1.8 g). Extract the resulting aqueous solution with methylene chloride (3×20 mL). Combine the organic extracts, wash with brine (~20 mL), dry (MgSO$_4$) and concentrate in vacuo. Dissolve the resulting residue in ethanol (~10 mL), cool to 0° C., treat with anhydrous hydrogen chloride gas until acidic, dilute with ether (~10 mL) and stir for 1 hour. Collect the resulting solid by filtration to give 4-[1-hydroxy-1-(2,3-dimethoxyphenyl)-methyl]piperidine (11).

EXAMPLE 48

Scheme F, step d: 4-[1-Hydroxy-1-(2,3-dimethoxyphenyl)methyl]pyridine (10)

A 2-L, three-necked, round-bottomed flask, equipped with a mechanical stirrer, nitrogen bubbler, addition funnel, and thermocouple, was charged with 58.52 g (0.42 mol) of veratrole and 350 mL of tetrahydrofuran. The resulting solution was cooled to −14° C. The addition funnel was charged with 160 mL of a 2.5 M solution of n-butyllithium (400 mmol) in hexanes. The butyllithium was added to the reaction vessel over 15 minutes while maintaining the temperature of the reaction mixture between −10 and −15° C. A white solid began to precipitate in the reaction vessel near the end of the butyllithium addition. The reaction mixture was warmed to room temperature. The lithiated veratrole slurry was difficult to stir, so it was diluted with 100 mL of additional tetrahydrofuran. The reaction mixture was allowed to stir at room temperature for 2 hours under nitrogen before cooling to 2° C. with an ice bath.

The addition funnel was charged with a solution of 40.45 g (0.38 mol) of 4-pyridinecarboxaldehyde (9) in 200 mL of tetrahydrofuran. The solution of 4-pyridinecarboxaldehyde was added to the reaction vessel over 1 hour, while maintaining the temperature of the reaction mixture less than 10° C. The reaction mixture was allowed to warm to room temperature and stir for 3.5 hours.

The reaction mixture was cooled to 1° C. and quenched with 285.78 g of 20% aqueous sodium chloride over 7 minutes. The temperature of the reaction mixture increased to 8° C. during the quench. The quenched solution was allowed to stir for 5 minutes. The mixture was transferred to a separatory funnel and the phases were separated. The aqueous phase weighed 277.54 g. The organic phase was washed with 286.73 g of 20% aqueous sodium chloride. The aqueous phase weighed 296.98 g; the organic phase weighed 853.65 g and contained 9.2% of the title compound (10) (85% yield).

In a separate experiment, it was found that the title compound (10) can be isolated as a solid. After the extractions, the organic phase was dried over anhydrous magnesium sulfate, filtered through a medium sintered glass funnel, and evaporated to dryness using a rotary evaporator and vacuum oven overnight at room temperature. The crude yellow solid, 14.77 g, was slurried in 200 mL of mixed heptanes and heated to 70° C. Ethyl acetate was added in 25 mL increments until the solid nearly dissolved; 200 mL of ethyl acetate was required. The solution was cooled to room temperature while agitating with a magnetic stir bar. The solution was stored in a freezer at −5° C. overnight. The solid was isolated by vacuum filtration of the reaction mixture through a medium sintered glass funnel. The solid was washed with 50 mL of mixed heptanes and dried overnight in a vacuum oven at room temperature to give the title compound (10) as a pale yellow solid (10.90 g); m.p. 126-128° C.

$^1$H NMR (CDCl$_3$) δ 8.42 (d, 2H, J=5.5 Hz, aromatic), 7.32 (d, 2H, J=5.5 Hz, aromatic); 7.08-6.86 (m, 3H, aromatic), 5.97 (d, 1H, J=5.5 Hz, ArCH), 4.41 (d, 1H, J=5.5 Hz, OH), 3.85 (s, 3H, OCH$_3$), 3.62 (s, 3H, OCH$_3$);

$^{13}$C NMR (CDCl$_3$) δ 153.5, 152.7, 149.5, 146.4, 136.4, 124.3, 121.3, 119.9, 112.6, 70.9, 60.5, 55.8.

EXAMPLE 48a

Scheme F, step d: 4-[1-Hydroxy-1-(2,3-dimethoxyphenyl)methyl]pyridine (10)

In a 2 L flask, 72 g of veratrole was dissolved in 300 g of toluene and 155.3 g of butyl lithium in toluene were added at temperatures from −10° C. to over 30° C. The mixture was stirred from 1-4 hours at ambient temperature. Then 40 g of 4-pyridinecarboxaldehyde (9) in 180 mL of toluene was added at around ambient temperature. The reaction mixture was stirred from 30 minutes to 5 hours. The solution was then cooled to around 5° C. and quenched with 200 mL of water. The solution was then heated to 40-85° C. and subsequently cooled to −5° C. The product was collected by filtration and washed with 60 g of water and 60 g of toluene. The yield was about 80 g of 4-[1-hydroxy-1-(2,3-dimethoxyphenyl)methyl]pyridine (10).

EXAMPLE 48b

Scheme F, step d: 4-[1-Hydroxy-1-(2,3-dimethoxyphenyl)methyl]pyridine (10)

In a 2 L flask, 72 g of veratrole was dissolved in 300 g of tetrahydrofuran and 155.3 g of butyllithium in toluene was added at temperatures from −10° C. to over 30° C. The mixture was stirred from 1-4 hours at ambient temperature. Then 40 g of 4-pyridinecarboxaldehyde (9) in 180 mL of toluene was added around ambient temperature. The reaction mixture was stirred from 30 minutes to 5 hours. The solution was then cooled to around 5° C. and quenched with 200 mL of water. The phases were separated and the organic phase was distilled to remove the tetrahydrofuran. The residue was taken up in toluene at −5° C. The 4-[1-hydroxy-1-(2,3-dimethoxyphenyl)methyl]pyridine (10) was collected by filtration and washed with 60 g of toluene.

EXAMPLE 48c

Scheme F, step d: 4-[1-Hydroxy-1-(2,3-dimethoxyphenyl)methyl]pyridine (10)

In a 2 L flask, 48 g of veratrole was dissolved in 200 g of toluene and 138 g of butyl lithium solution (15% in hexane) were added at temperatures from 4° C. to 6° C. The mixture was stirred for one hour at about 5° C. and 3 hours at ambient temperature. Then 26.7 g of 4-pyridinecarboxaldehyde (9) in 120 g of toluene was added at around ambient temperature. The reaction mixture was stirred for about 4.5 hours. The mixture was then cooled to around 5° C. and quenched with 133 mL of water. The mixture was then heated to around 80° C. The organic layer was separated, washed with 67 mL of water and separated. The residual water was removed by azeotropic distillation. The solution was then cooled to −15° C. to −5° C. The product was collected by filtration and washed with 27 g of cold toluene. The yield was 50 g of 4-[1-hydroxy-1-(2,3-dimethoxyphenyl)methyl]pyridine (10) (81% yield).

EXAMPLE 48d

Scheme F, step d: 4-[1-Hydroxy-1-(2,3-dimethoxyphenyl)methyl]pyridine (10)

A 2-L, three-necked, round-bottomed flask, equipped with a mechanical stir paddle, thermocouple, nitrogen bubbler, and addition funnel, was charged with 70.51 g (0.51 mol) of veratrole and 469.64 g of tetrahydrofuran. The resulting solution was cooled to −14° C. The addition funnel was charged with 125.50 g (0.48 mol) of a 24.6 wt % solution of butyllithium in hexanes. The solution of butyllithium was added to the reaction vessel over 7 min. while maintaining the temperature of the reaction mixture between −13 and −16° C. The reaction mixture was warmed to 0° C. for 1 h and then warmed to room temperature for 3.3 h.

The reaction mixture was cooled to −13° C. The addition funnel was charged with a solution of 39.59 g (0.37 mol) of 4-pyridinecarboxaldehyde in 177.15 g of tetrahydrofuran. The aldehyde solution was added to the reaction vessel over 1.3 h while maintaining the temperature of the reaction mixture between −9 and −14° C. The reaction mixture was allowed to stir for 1 h at −10° C. and was then warmed to 0° C. over the course of an hour. The reaction mixture was quenched with 201.58 g of city water. The temperature of the reaction mixture was maintained at less than 10° C. during the water addition. After stirring for 10 min., the quenched solution was diluted with 322.51 g of toluene. The aqueous phase was removed. The organic phase was washed with 100.83 g of city water. The organic layer was concentrated by atmospheric distillation. When the temperature of the distillate reached 87° C., an additional 86.06 g of toluene was added. The distillation was stopped when the distillate temperature reached 101° C.; the distillate collected weighed 812.36 g. The reaction mixture was cooled slowly to −15° C. The product was isolated by vacuum filtration, washed with 44.32 g of cold toluene, and dried in a vacuum oven at room temperature overnight to afford 66.94 g (74% yield) of the title compound as a pale yellow solid; $^1$H NMR (CDCl$_3$) δ 8.42 (d, 2H, J=5.5 Hz, aromatic), 7.32 (d, 2H, J=5.5 Hz, aromatic), 7.08-6.86 (m, 3H, aromatic), 5.97 (d, 1H, J=5.5 Hz), 4.41 (d, 1H, J=5.5 Hz), 3.85 (s, 3H, OCH$_3$), 3.62 (s, 3H, OCH$_3$); $^{13}$C NMR δ 153.5, 152.7, 149.5, 146.4, 136.4, 124.3, 121.3, 119.9, 112.6, 70.9, 60.5, 55.8.

EXAMPLE 49

Scheme F, step d: 4-[1-Hydroxy-1-(2,3-dimethoxyphenyl)methyl]pyridine (10)

A suitable reactor, maintained under an inert atmosphere is charged with veratrole (36 kg, 261 mol) and about 240 kg tetrahydrofuran. n-Butyllithium (63 kg, 242 mol, 24.6% in n-hexane) is added maintaining the temperature at about 0° C. The addition line is flushed with about 5 kg tetrahydrofuran. The reaction mixture is held at about 0° C. for at least 1 hour, then heated to about 25° C. and maintained there for about 3 hours. In a second suitable vessel, 4-pyridinecarboxaldehyde (9) (20 kg, 187 mol) is mixed with about 90 kg of tetrahydrofuran. The 4-pyridinecarboxaldehyde/tetrahydrofuran solution is added to the lithiated veratrole slurry at a rate to maintain the temperature at about −10° C. The reaction mixture is maintained at about −15° C. for at least 1 hour, then warmed to about 0° C. over about a 1 hour period. Water (about 100 kg) is added to the reaction mixture while maintaining the temperature at about 10° C. Toluene (about 160 kg) is added and the phases are separated. The organic phase is washed with about 50 kg of water and the phases are separated. The concentration of product in the organic phase is adjusted to about 20 wt % by atmospheric distillation. The optimum tetrahydrofuran range is about 10 to 20 wt % as determined by GC analysis. The solution is cooled to less than about −15° C., and 4-[1-hydroxy-1-(2,3-dimethoxyphenyl)methyl]pyridine is collected by filtration. The wet cake is washed with about 20 kg of cold toluene to give the title compound (10) (30 kg, 70% yield).

EXAMPLE 50a

Scheme F, step e: 4-[1-Hydroxy-1-(2,3-dimethoxyphenyl)methyl]piperidine (11)

4-[1-Hydroxy-1-(2,3-dimethoxyphenyl)methyl]pyridine (10) (10.1 g, 41 mmol) was dissolved in 100 mL of methanol and hydrogenated using a 5% rhodium on carbon catalyst. At the conclusion of the reaction, the catalyst was removed by filtration. The filtrate weighed 111.51 g. The reactor and catalyst cake were washed with methanol. The combined washes weighed 170.27 g and contained 7.6% of the title compound (11).

EXAMPLE 50b

Scheme F, step e: 4-[1-Hydroxy-1-(2,3-dimethoxyphenyl)methyl]piperidine (11)

A 1-L Parr reactor was charged with 12.43 g (0.051 mol) of 4-[1-hydroxy-1-(2,3-dimethoxyphenyl)methyl]pyridine (10), 5.74 g of a 5% Rhodium on Carbon catalyst, and 237 g of methanol. The solution was warmed to 40° C. and treated with 100 psi of hydrogen for 5.5 h. When the reaction was complete, the solution was filtered and the catalyst washed with 108 g of methanol which was added to the filtrate. The weight of the filtered solution was 310.45 g. The methanol solution was assayed for the title compound using high pressure liquid chromatography. The methanol solution was found to contain 3.7% title compound by weight. This corresponds to 11.5 g (90% yield) of title compound.

A sample of a methanol solution of the title compound was evaporated to dryness using a rotary evaporator and vacuum oven at room temperature. The title compound was isolated as a white solid: $^1$H NMR (CDCl$_3$) δ 7.06-6.82 (m, 3H, aromatic), 4.61 (d, 1H, J=7.8 Hz), 3.86 (s, 3H, OCH$_3$), 3.85 (s, 3H, OCH$_3$), 3.09 (d, 1H, J=12.2 Hz), 2.97 (d, 1H, J=12.2 Hz), 2.58-2.41 (m, 4H), 2.01-1.97 (m, 1H), 1.75-1.72 (m, 1H), 1.30-1.17 (m, 3H); $^{13}$C NMR δ 152.5, 146.6, 136.6, 123.9, 119.7, 111.4, 74.3, 60.9, 55.7, 46.4, 43.3, 29.9, 29.7.

EXAMPLE 51a

Scheme F, step e: 4-[1-Hydroxy-1-(2,3-dimethoxyphenyl)methyl]piperidine (11)

A suitable inert reactor is charged with 4-[1-hydroxy-1-(2,3-dimethoxyphenyl)methyl]pyridine (10) (13.6 kg, 55.5 mol) as a toluene wet cake and 5% rhodium on carbon catalyst (2.7 kg, 50% wet with water) as a water wet cake at about 25° C. About 190 kg of methanol is added and the reactor is pressured to about 100 psig with hydrogen for about 4-12 hours at about 50° C. The catalyst is removed by filtration and the reactor and catalyst are rinsed with about 7 kg of methanol. Deionized water is used as a final wash of the catalyst wet cake. The reactor rinse filtrate and the reaction mixture filtrate are combined. The concentration of 4-[1-hydroxy-1-(2,3-dimethoxyphenyl)methyl]piperidine (11) is about 7 wt %, affording about 13 kg (90% average yield) of the title compound (11).

EXAMPLE 51b

Scheme F, step e: 4-[1-Hydroxy-1-(2,3-dimethoxyphenyl)methyl]piperidine (11)

Into a suitable inerted reactor was charged 118 kg (481 mol) of 4-[1-hydroxy-1-(2,3-dimethoxyphenyl)methyl]pyridine (10) as a toluene wet cake and 23.6 kg of 5% rhodium on carbon catalyst at 25° C. To the slurry was then added 850 kg of methanol and 29 kg of glacial acetic acid. The reactor was then pressurized to about 100 psi with hydrogen for about 4-12 hours[1] at 40° C. The catalyst was removed by filtration and the reactor and the catalyst were rinsed with 150 kg of methanol.[2] The reactor rinse filtrate and the reaction mixture filtrate were combined. The concentration of 4-[1-hydroxy-1-(2,3-dimethoxyphenyl)methyl]piperidine (11) is typically about 10 wt %, affording about 116 kg of 4-[1-hydroxy-1-(2,3-dimethoxyphenyl)methyl]piperidine (11) (96% yield)[3].

[1] A HPLC analysis of the reaction mixture is used to determine that the reaction conversion is at least 98%.
[2] For increase safety, deionized water may be used as a final wash of the catalyst wet cake.
[3] The weight percent of 4-[1-hydroxy-1-(2,3-dimethoxyphenyl)methyl]piperidine (11) and yield are based upon HPLC assay.

EXAMPLE 52

Scheme F, step f: (R)-α-(2,3-Dimethoxyphenyl)-4-piperidinemethanol (1)

Add p-toluic acid (0.55 mol) to 100 mL SOCl$_2$ and stir overnight at room temperature. Evaporate the excess SOCl$_2$ to give p-toluoyl chloride. Add (2R,3R)-(+)-tartaric acid (25 g, 166 mmol) and stir the mixture and heat at 170° C. for an hour. Allow the mixture to cool to 100° C. and add 200 mL toluene. Cool the mixture to room temperature and add another 100 mL toluene. Collect the precipitate, rinse with toluene and dry. Reflux the crude product in a mixture of 300 mL acetone and 20 mL water for two hours. Then add 200 mL water and evaporate the acetone. Add another 200 mL water and collect the precipitate, rinse with water and dry. Reflux the product in 200 mL toluene for 15 minutes and collect the precipitate while the mixture is hot. Rinse the precipitate with 50 mL warm toluene and dry to give (2R,3R)-(−)-di-(p-toluoyl)tartaric acid.

Dissolve 4-[1-hydroxy-1-(2,3-dimethoxyphenyl)methyl]piperidine (11) (11.0 g, 43.8 mmol) and 17.0 g (40.1 mmol) (2R,3R)-(−)-di-(p-toluoyl)tartaric acid in 400 mL refluxing isopropanol. Allow the mixture to cool to room temperature. Collect the precipitate, rinse with isopropanol and dry to give the (R)-α-(2,3-dimethoxyphenyl)-4-piperidinemethanol, (2R,3R)-(−)-di-(p-toluoyl)tartaric acid salt. Recrystallize the (R)-α-(2,3-dimethoxyphenyl)-4-piperidinemethanol, (2R,3R)-(−)-di-(p-toluoyl)tartaric acid salt from 250 mL isopropanol.

Stir the (R)-α-(2,3-dimethoxyphenyl)-4-piperidinemethanol, (2R,3R)-(−)-di-(p-toluoyl)tartaric acid salt (7 g) with 10 mL concentrated ammonia and 20 mL MeOH. After 2 hours, add 30 mL H$_2$O and evaporate the MeOH/ammonia. After adding another 30 mL H$_2$O, collect the precipitate, rinse with water and dry to give the (R)-α-(2,3-dimethoxyphenyl)-4-piperidinemethanol (1) which will typically have an ee of 85%.

Acidify the aqueous layer with 1N HCl and collect the precipitate and dry to recover the (2R,3R)-(−)-di-(p-toluoyl)tartaric acid.

EXAMPLE 53

Scheme F, step f: (R)-α-(2,3-Dimethoxyphenyl)-4-piperidinemethanol (1)

Add p-anisic acid (77 g, 0.55 mol) to 100 mL SOCl$_2$ and stir overnight at room temperature. Evaporate the excess SOCl$_2$ to give p-anisoyl chloride. Add (2R,3R)-(+)-tartaric acid (25 g, 166 mmol) and stir the mixture and heat at 170° C. for an hour. Allow the mixture to cool to 100° C. and add 200 mL toluene. Cool the mixture to room temperature and add another 100 mL toluene. Collect the precipitate, rinse with toluene and dry. Reflux the crude product in a mixture of 300 mL acetone and 20 mL water for two hours. Then add 200 mL water and evaporate the acetone. Add another 200 mL water and collect the precipitate, rinse with water and dry. Reflux the product in 200 mL toluene for 15 minutes and collect the precipitate while the mixture is hot. Rinse the precipitate with 50 mL warm toluene and dry to give (2R,3R)-(−)-di-(p-anisoyl)tartaric acid.

Dissolve 4-[1-hydroxy-1-(2,3-dimethoxyphenyl)methyl]piperidine (11) (11.0 g, 43.8 mmol) and 17.0 g (40.1 mmol) (2R,3R)-(−)-di-(p-anisoyl)tartaric acid in 400 mL refluxing isopropanol. Allow the mixture to cool to room temperature. Collect the precipitate, rinse with isopropanol and dry to give the (R)-α-(2,3-dimethoxyphenyl)-4-piperidinemethanol, (2R,3R)-(−)-di-(p-anisoyl)tartaric acid. Recrystallize the (R)-α-(2,3-dimethoxyphenyl)-4-piperidinemethanol, (2R,3R)-(−)-di-(p-anisoyl)tartaric acid salt from 250 mL isopropanol.

Stir the (R)-α-(2,3-dimethoxyphenyl)-4-piperidinemethanol, (2R,3R)-(−)-di-(p-anisoyl)tartaric acid (7 g) with 10 mL concentrated ammonia and 20 mL MeOH. After 2 hours, add 30 mL $H_2O$ and evaporate the MeOH/ammonia. After adding another 30 mL $H_2O$, collect the precipitate, rinse with water and dry to give the (R)-α-(2,3-dimethoxyphenyl)-4-piperidinemethanol (1) (1.8 g, >99% ee).

Acidify the aqueous layer with 1N HCl and collect the precipitate and dry to recover the (2R,3R)-(−)-di-(p-anisoyl)tartaric acid.

EXAMPLE 54

Scheme F, step g: 4-[1-Hydroxy-1-(2,3-dimethoxyphenyl)methyl]piperidine (11)

A solution of 4-(2,3-dimethoxybenzoyl)pyridine (12) (2.10 g, 8.6 mmol) in MeOH (10 mL) is treated with 5% Rh/alumina (0.72 g). The mixture is hydrogenated in a Parr shaker at 55 psig for 22 hours. After filtration through Celite 7 filter aid, the filtrate is concentrated at reduced pressure to give the title compound (11) as a solid (2.0 g, 92% yield).

EXAMPLE 55

Scheme F, step g: 4-[1-Hydroxy-1-(2,3-dimethoxyphenyl)methyl]piperidine (11)

4-(2,3-Dimethoxybenzoyl)pyridine (12) (10.09 g, 42 mmol) was dissolved in 100 mL of methanol and hydrogenated using a 5% rhodium on carbon catalyst. At the conclusion of the reaction, the catalyst was removed by filtration. The filtrate weighed 113.90 g. The reactor and catalyst cake were washed with methanol. The combined washes weighed 165.26 g.

A sample of the methanol solution was evaporated to dryness using a rotary evaporator and vacuum oven at room temperature. The title product (11) was isolated as a white solid; m.p. 171-173° C.

$^1$H NMR (CDCl$_3$) δ 7.06-6.82 (m, 3H, aromatic), 4.61 (d, 1H, J=7.8 Hz, ArCH), 3.86 (s, 3H, OCH$_3$), 3.85 (s, 3H, OCH$_3$), 3.09 (d, 1H, J=12.2 Hz), 2.97 (d, 1H, J=12.2 Hz), 258-2.41 (m, 4H), 2.01-1.97 (m, 1H), 1.75-1.72 (m, 1H), 1.30-1.17 (m, 3H);

$^{13}$C NMR (CDCl$_3$) δ 152.5, 146.6, 136.6, 123.9, 119.7, 111.4, 74.3, 60.9, 55.7, 46.4, 43.3, 29.9, 29.7.

EXAMPLE 56

Scheme G, step a: 1,4-Piperidinedicarboxylic acid, 1-(1,1-dimethylethyl)ester (14)

Into a 500-mL jacketed-bottom-drain resin pot fitted with a four-joint head equipped with a mechanical stirrer, reflux condenser topped with a nitrogen bubbler, a thermowell with a thermocouple, and a septum with a needle connected to a nitrogen source was placed 4-piperidinecarboxylic acid (13) (15.0 g, 0.12 mol), aqueous 50% solution of sodium hydroxide (10.4 g, 0.13 mol), water (90 g), and ethanol 2B (79.5 g). The reaction mixture was warmed to 50° C. and di-tert-butyl dicarbonate (26.7 g, 0.122 mol) was added via syringe in one portion (6° C. exotherm) and the reaction stirred for 1.25 hours. The reaction was cooled to 5° C. and aqueous hydrochloric acid (15.0 g of 37%) was added, causing the product to precipitate. To the thick slurry was added water (130 g) and the product was collected by suction filtration and dried under vacuum (28 Hg, 58° C.) for 72 hours to give the title compound (14) as a white crystalline material (23.9 g, 91%); m.p. 150-151° C.

$^1$H NMR (CDCl$_3$) δ 4.10 (m, 2H), 2.84 (t, 2H, J=11.7 Hz), 2.47 (m, 1H), 1.90 (m, 2H), 1.62 (m, 2H), 1.45 (s, 9H, (CH$_3$)Si));

$^{13}$C NMR (CDCl$_3$) δ 180.0, 154.8, 79.8, 43.1; 40.9; 28.5; 27.5.

EXAMPLE 57

Scheme G, step a: 1,4-Piperidinedicarboxylic acid, 1-(1,1-dimethylethyl)ester (14)

To a solution of 4-piperidinecarboxylic acid (13) (16.2 g, 0.125 mol) in aqueous sodium hydroxide (1M, 150 mL), and t-butanol (100 mL) at 0° C. was added a solution of di-t-butyldicarbonate (30.0 g, 0.137 mol) in t-butanol (50 mL). The resulting mixture was stirred overnight at ambient temperature. The reaction was quenched by addition of hydrochloric acid (3M, 75 mL) at 0° C. and extracted with ether (3×200 mL). The combined organic extracts were dried (MgSO$_4$) and concentrated in vacuo to afford the title compound (14) as a fluffy white solid (28.4 g, 99%); mp 149-150° C.

EXAMPLE 58

Scheme G, step a: 1,4-Piperidinedicarboxylic acid, 1-(1,1-dimethylethyl)ester (14)

A 3-L three-neck flask containing 1.0 L (1 mol) of 1N NaOH was cooled to 0° C. 4-Piperidinecarboxylic acid (13) (108 g, 0.84 mol) and 500 mL of t-butanol were then added to the aqueous solution which was maintained at 0° C. A solution of 200 g (0.92 mol) of di-t-butyldicarbonate in 500 mL of t-butanol was placed in a pressure equalizing addition funnel and added to the reaction mixture over a 45 minute period while maintaining the temperature below 5° C. After completion of the addition, the reaction was allowed to warm to room temperature and then stirred an additional 22 hours. The cloudy reaction mixture was reduced to one half of its original volume using a rotary evaporator at 40° C. The resulting solution was cooled to 5° C. in a 3 L flask, then 500 mL (1.5 mol) of 3N HCl was added to the cooled solution over a 30 minute period. The resulting thick slurry was extracted with tetrahydrofuran (3×500 mL) and the combined extracts were dried over sodium sulfate. The drying agent was removed by filtration and the solvent was then evaporated (20 mm Hg, 40° C.) to give the title compound (14) as a white solid (189.5 g, 99% yield).

EXAMPLE 59

Scheme G, step a: 1,4-Piperidinedicarboxylic acid, 1-(1,1-dimethylethyl)ester (14)

Solid di-t-butyldicarbonate (300 g, 1.37 mol) was added to a solution of 4-piperidinecarboxylic acid (13) (162 g, 1.25 mol) in aqueous NaOH (1N, 1.5 L) and t-BuOH (1.5 L) at 4° C. over 30 minutes. The reaction mixture was stirred at room temperature for 18 hours. The resulting solution was concentrated (40° C./20 torr) to half of its volume. Aqueous HCl (3N, 750 mL) was added to the concentrated solution at 4° C. over 30 minutes. The resulting slurry was extracted with ethyl ether (3×2 L). The combined ethereal solutions were dried (MgSO$_4$). The mixture was filtered and the filtrate was concentrated (30° C./20 torr) to give the title compound (14) after air drying (277 g, 97%); m.p. 145-147° C.

$^1$H NMR (CDCl$_3$) δ 4.01 (d, 2H, J=12.0 Hz, CHN's), 2.83 (dd, 2H, J=12.0 Hz, CHN's), 2.5 (m, 1H, CH), 1.9 (m, 2H), 1.6 (m, 2H), 1.46 (s, 9H);

$^{13}$C NMR (CDCl$_3$) δ180.2, 154.7, 79.8, 43.0, 40.8, 28.4, 27.7;

MS (CI, CH$_4$) m/z (rel. Intensity) 230 (MH$^+$, 32%), 174 (100), 156 (71), 130 (25);

IR (KBr) 3451, 3208, 3002, 2974, 2932, 1734, 1661, 1452, 1431, 1393, 1369, 1283, 1170, 1159, 1035, 924, 862 cm$^{-1}$;

Anal. Calc'd for C$_{11}$H$_{19}$NO$_4$ (229.3): C, 57.62; H, 8.35; N, 6.11. Found: C, 57.68; H, 8.62; N, 6.00.

EXAMPLE 60

Scheme G, step a: 1,4-Piperidinedicarboxylic acid, 1-(1,1-dimethylethyl)ester (14)

To a solution of 4-piperidinecarboxylic acid (13) (700 g, 5.42 mol) in aqueous NaOH (1N, 6.5 L) and t-butanol (6.5 L) at 0° C. was added di-t-butyldicarbonate (1295.8 g, 5.94 mol) slowly over 30 minutes. The reaction mixture was stirred overnight at ambient temperature. The resulting solution was concentrated (48° C./20 torr) to half of its volume and quenched by the addition of HCl (10%, 2.6 L). The white solid which precipitated was filtered off, washed with water (1L) and air-dried to give the title compound (14) (1178 g, 100% yield); m.p. 144-146° C.

$^1$H NMR (CDCl$_3$) δ 4.1 (d, 2H, J=12.0 Hz), 2.91 (t, 2H, J=12.0 Hz), 2.5 (m, 1H), 2.0 (m, 2H), 1.7 (m, 2H), 1.52 (s, 9H).

EXAMPLE 61

Scheme G, step a: 1,4-Piperidinedicarboxylic acid, 1-(1,1-dimethylethyl)ester (14)

4-Piperidinecarboxylic acid (10 kg, 77.4 mol) and 50 L of water were charged to a suitable vessel maintained under nitrogen. The stirred mixture was cooled to 5° C. 20% Sodium hydroxide (17 kg, 85 mol) and 70 L of ethanol were charged while maintaining a reaction temperature of 5° C. A solution of di-t-butyl dicarbonate (17.8 kg, 81.6 mol) in 65 L of ethanol was charged to the stirred reaction mixture over a period of 15 minutes. Cooling was discontinued and the reaction mixture was stirred for a total of 22 hours. A total of 150 L of solvent was distilled from the reaction mixture below 50° C. at 150 torr. The residue was diluted with 110 L of water and the stirred mixture was cooled to 5° C. The stirred mixture was diluted with 22 L of water and 33% hydrochloric acid (10 kg). After stirring at 5° C. for 2 hours, product was filtered off, washed with 2×5 L, then dried below 40° C. at 150 torr to give 16.5 kg, 93% yield.

EXAMPLE 62

Scheme G, step b: 4-[(Methoxymethylamino)carbonyl]-1-piperidinecarboxylic acid, 1,1-dimethylethyl ester (15)

A 3L Morton flask equipped with mechanical stirrer and a gas outlet connected to a bubbler was charged with 1 L of methylene chloride and 189 g (0.82 mol) of 1,4-piperidinedicarboxylic acid, 1-(1,1-dimethylethyl)ester (14). The solution was vigorously stirred one hour in order to dissolve all of the solids, resulting in a colorless, slightly cloudy, solution. A slurry of 1,1'-carbonyldiimidazole (147 g, 0.91 mol) in 250 mL of methylene chloride was added portion-wise over a 15 minute period. Caution: a large volume of gas was evolved during the addition. After complete addition, the pale yellow reaction mixture was stirred for 4 hours after which most gas evolution had ceased. N,O-Dimethylhydroxylamine hydrochloride (88.5 g, 0.91 mol) was added to the reaction mixture which was then stirred an additional 24 hours at room temperature. The resulting mixture of yellow solution and cream colored solids was then washed sequentially with 1N HCl (2×1.5 L), saturated sodium bicarbonate solution (1.5 L), and brine (1 L) and then dried over sodium sulfate. The solution was filtered and concentrated to give a pale green oil. The oil was distilled (185° C., 1 mm Hg) to give the title compound (15) which solidified at room temperature (177 g, 84% yield).

EXAMPLE 63

Scheme G, step b: 4-[(Methoxymethylamino)carbonyl]-1-piperidinecarboxylic acid. 1,1-dimethylethyl ester (15)

1,1'-Carbonyldiimidazole (200 g, 1.23 mol) was added portionwise to a solution of 1,4-piperidinedicarboxylic acid, 1-(1,1-dimethylethyl)ester (14) (257 g, 1.12 mol) in methylene chloride under nitrogen at room temperature. After stirring for 2 hours, the solution was treated with N,O-dimethylhydroxylamine hydrochloride (120 g, 1.23 mol). The resulting mixture was stirred at room temperature for 18 hours. The mixture was washed with aqueous hydrochloric acid (1N, 2×2L), saturated sodium bicarbonate (2L) and brine (2L). The organic layer was dried (MgSO$_4$) and filtered. The filtrate was concentrated (30° C./20 torr) to a residue which was distilled (150° C./0.9 torr) to give the title compound (15) (276 g, 91%).

IR (neat) 2973, 2934, 1693, 1663, 1421, 1366, 1289, 1234, 1171, 1132, 1032, 998, 939, 870, 770 cm$^{-1}$;

$^1$H NMR (CDCl$_3$) δ 4.1 (m, 2H, CHN's), 3.70 (s, 3H, OCH$_3$), 3.19 (s, 3H, NCH$_3$), 2.8 (m, 3H), 1.7 (m, 4H, CH$_2$'s), 1.47 (s, 9H, t-Bu);

$^{13}$C NMR (CDCl$_3$) δ 175.6, 154.6, 79.4, 61.5, 43.3, 38.1, 32.2, 28.3, 27.9;

MS (CI, CH$_4$) m/z (rel. Intensity) 273 (MH$^+$, 20%), 217 (100), 199 (52), 173 (23);

Anal. Calc'd for C$_{13}$H$_{24}$N$_2$O$_4$ (272.3): C, 57.33; H, 8.88; N, 10.29. Found: C, 57.19; H, 9.14; N, 10.29.

EXAMPLE 64

Scheme G, step b: 4-[(Methoxymethylamino)carbonyl]-1-piperidinecarboxylic acid, 1,1-dimethylethyl ester (15)

To a solution of 1,4-piperidinedicarboxylic acid, 1-(1,1-dimethylethyl)ester (14) (27.85 g, 0.1206 mol) in methylene chloride (300 mL) under a dry nitrogen atmosphere was added 1,1'-carbonyldiimidazole (21.5 g, 0.133 mol) portionwise, with water cooling. The resulting mixture was stirred for 2 hours at ambient temperature and then treated with N,O-dimethylhydroxylamine hydrochloride (12.9 g, 0.132 mol) portionwise, with water cooling. The reaction mixture was stirred overnight at ambient temperature and then washed with hydrochloric acid (1M, 2×200 mL), saturated aqueous sodium bicarbonate solution (200 mL) and brine (200 mL) and dried (MgSO$_4$). The title compound (15) was isolated as a viscous colorless oil following concentration in vacuo and kugelrohr distillation (31.76 g, 97%); bp 155-160° C. [oven temperature], 1.75 mm Hg.

EXAMPLE 65

Scheme G, step b: 4-[(Methoxymethylamino)carbonyl]-1-piperidinecarboxylic acid, 1,1-dimethylethyl ester (15)

To a solution of 1,4-piperidinedicarboxylic acid, 1-(1,1-dimethylethyl)ester (14) (1177.5 g, 5.42 mol) in methylene chloride (11.5 L) under nitrogen was added carbonyldiimidazole (922.8 g, 5.69 mol) portionwise. The resulting mixture was at room temperature for 2 hours, then N,O-dimethylhydroxylamine hydrochloride (550 g, 5.64 mol) was added in one portion. The reaction mixture was stirred at room temperature for 18 hours then washed with aqueous HCl (5%, 2×4L), saturated NaHCO$_3$ (2×4L), and brine solution (2×4L). The organic layer was dried (MgSO$_4$) and filtered. The filtrate was concentrated (35° C./50 torr) to give the title compound (15) as a thick oil which later crystallized to a waxy white solid (1289.5 g, 87.4%); m.p. 68-70° C.

IR (KBr) 3436, 2972, 2934, 1693, 1663, 1420, 1233, 1170, 1132 cm$^{-1}$;

$^1$H NMR (CDCl$_3$) δ 4.1 (m, 2H), 3.70 (s, 3H, OCH$_3$), 3.19 (s, 3H, NCH$_3$), 2.8 (m, 3H), 1.7 (m, 4H), 1.46 (s, 9H, t-Bu);

$^{13}$C NMR (CDCl$_3$) δ 175.6, 154.6, 79.4, 61.5, 43.1, 38.1, 32.2, 28.4, 27.9;

MS (CI/CH$_4$) m/z (rel. Intensity) 273 (MH$^+$, 8%), 217 (100), 199 (50), 171 (30);

EXAMPLE 66

Scheme G, step b: 4-[(Methoxymethylamino)carbonyl]-1-piperidinecarboxylic acid, 1,1-dimethylethyl ester (15)

Into a 250-mL four-neck flask equipped with a mechanical stirrer, a nitrogen bubbler, a 125-mL addition funnel with a stopper, and a thermowell with a thermocouple was placed 1,1'-carbonyldiimidazole (7.2 g, 0.044 mol) and methylene chloride (20 g). The addition funnel was charged with a solution of 1,4-piperidinedicarboxylic acid, 1-(1,1-dimethylethyl)ester (14) (10.0 g, 0.043 mol) and methylene chloride (75 g). The solution was added to the reaction mixture over a 2 minute period, causing rapid CO$_2$ evolution. The reaction mixture was allowed to stir at 28° C. for 2 hours.

Into a 500-mL four-neck flask equipped with a mechanical stirrer, a nitrogen bubbler, a thermowell with a thermocouple, and a 125-mL addition funnel with a septum was placed N,O-dimethylhydroxylamine hydrochloride (4.9 g, 0.049 mol) and methylene chloride (38 g). The imidazole amide intermediate/methylene chloride solution was added to the slurry of N,O-dimethylhydroxylamine hydrochloride and methylene chloride over a 20 minute period. The resulting slurry was allowed to stir at 28° C. for 2 hours. To the reaction mixture was added sodium bicarbonate (4.3 g) and water (75 g). After stirring for 30 minutes at ambient temperature, the phases were allowed to stand and separate for 20 minutes. The phases were separated and to the organic phase was added toluene (100 g). The solution was concentrated and azeotropically dried by rotary evaporation (29 Hg, bath 60° C.) to afford the crude title compound as a thick oil. The oil and heptane (25 g) were placed into a 100-mL jacketed-bottom-drain resin pot fitted with a four-joint head equipped with a mechanical stirrer, a thermowell with a thermocouple, a nitrogen bubbler, and a stopper. The slurry was warmed to 60° C. before allowing it to slowly cool to 10° C. over a 2 hour period. The solution was maintained at 10° C. for 1 hour (nucleation temperature) before cooling to 3° C. and stirring overnight. The title compound was collected by suction filtration and washed with cold heptane (7 g, ~0° C.). The wet cake was allowed to air dry for 24 hours to afford the title compound (15) as a white crystalline material (10.5 g, 89%); m.p. 69-71° C.

$^1$H NMR (CDCl$_3$) δ 4.08 (m, 2H, CHN's), 3.66 (s, 3H, —OCH$_3$), 3.13 (s, 3H, —NCH$_3$), 2.76 (m, 3H), 1.51 (m, 4H, CH$_2$'s), 1.40 (s, 9H, t-Bu);

$^{13}$C NMR (CDCl$_3$) δ 175.5, 154.7, 121.6, 79.5, 61.6, 43.3, 36.1, 28.5, 28.0;

IR (KBr) 2973, 2935, 1694, 1663, 1421, 1367, 1289, 1133, 998, 870, 770 cm$^{-1}$.

Into a 250-mL three-neck flask equipped with a mechanical stirrer, a nitrogen bubbler, and a septum was placed 4-[(methoxymethylamino)carbonyl]-1-piperidinecarboxylic acid, 1,1-dimethylethyl ester (15) (10.0 g, 0.037 mol) and n-heptane (40 g). The mixture was brought to reflux, before the solution was polish filtered through a medium sintered glass funnel containing Celite 7. filter aid. The solution was then placed into another 250-mL three-neck flask equipped with a mechanical stirrer, a nitrogen bubbler, and a stopper. The solution was slowly cooled to ambient temperature (23° C.) over a 2 hour period (nucleated near 38° C.). The slurry was cooled to 0° C. and the title compound was collected by suction filtration and washed with cold n-heptane (6 g, 0° C.). The wet cake was allowed to air dry for 24 hours to give (15) as a white crystalline material (9.4 g, 94%); m.p. 69-71° C.

$^1$H NMR (CDCl$_3$) δ 4.14 (m, 2H, CHN's), 3.72 (s, 3H, —OCH$_3$), 3.19 (s, 3H, —NCH$_3$), 2.82 (m, 3H), 1.66 (m, 4H, CH$_2$'s), 1.46 (s, 9H, t-Bu);

$^{13}$C NMR (CDCl$_3$) δ 175.5, 154.6, 121.5, 79.4, 61.5, 43.2, 36.0, 28.4, 27.9.

Into a 250-mL three-neck flask equipped with a stir bar, a nitrogen bubbler, a thermowell with a thermocouple and a stopper was placed 4-[(methoxymethylamino)carbonyl]-1-piperidinecarboxylic acid, 1,1-dimethylethyl ester (15) (10.0 g, 0.037 mol) and heptanes (30 g). The solution was warmed to 65° C. and polish filtered through a medium sintered glass funnel containing Celite 7 filter aid. The solution was allowed to slowly cool, nucleation began at ~35° C. The slurry was allowed to stir at ambient temperature (23° C.) overnight, then cooled to 0° C. for 1 hour. The title compound was collected by suction filtration and dried under vacuum (29 Hg, 40° C.) for 6 hours to give (15) as a white crystalline material (9.2 g, 92%); mp 69.5-71° C.

EXAMPLE 67

Scheme G, step b: 4-[(Methoxymethylamino)carbonyl]-1-piperidinecarboxylic acid, 1,1-dimethylethyl ester (15)

A suitable reactor maintained under nitrogen was charged with 7.6 kg of 1,1'-carbonyldiimidazole and 15 L of methylene chloride. A solution of 1,4-piperidinedicarboxylic acid, 1-(1,1-dimethylethyl)ester (14) (10.5 kg, 45.8 mol) in 62 L of methylene chloride was added over 30 minutes while maintaining a reaction temperature of 20° C. After stirring the reaction mixture at ambient temperature for 2 hours, 0.1 kg of 1,1'-carbonyldiimidazole was added. A solution of 4.55 kg of N,O-dimethylhydroxylamine hydrochloride in 32 L of methylene chloride was added to the mixture with stirring. The reaction mixture was stirred at 28° C. for 24 hours, followed by the addition of 0.52 kg of N,O-dimethylhydroxylamine hydrochloride and 0.7 kg of 1,1'-carbonyldiimidazole. Stirring was continued at 28° C. for 48 hours. The stirred reaction mixture was diluted with a solution of sodium bicarbonate (4.5 kg, 53.6 mol) in 50 L of water. The organic phase was separated and washed with a solution of sodium chloride (7 kg) in 46 L of water. The organic phase was separated and dried with sodium sulfate (4 kg). Drying agent was filtered off and washed with 2×5 L of methylene chloride. Solvent was removed below 50° C. at 500 torr. The residue was diluted with 5 L of heptane and solvent was removed below 50° C. at 500 torr. A total of 40 L of heptane was added and the stirred solution was heated to 70° C. to obtain solution. The stirred solution was cooled to ambient temperature over 18 hours, then cooled to and maintained at 10° C. for 12 hours, then cooled to 0° C. Solid which crystallized was filtered off, then dried at ambient temperature to give 11.1 kg (89% yield).

EXAMPLE 68

Scheme G, step b: 4-[(Methoxymethylamino)carbonyl]-1-piperidinecarboxylic acid, 1,1-dimethylethyl ester (15)

A suitable reactor maintained under nitrogen is charged with 1,4-piperidinedicarboxylic acid, 1-(1,1-dimethylethyl) ester (14) (24.9 kg, 109 mol) and 1,1'-carbonyldiimidazole (19.6 kg, 121 mol). About 206 kg of methylene chloride is gradually added and the solution is stirred for at least 1 hour at about 25° C.[1] The mixture is added to a second stirred reactor containing a slurry of N,O-dimethylhydroxylamine hydrochloride (12.0 kg, 123 mol) and about 112 kg of methylene chloride. The reaction mixture is stirred above 28° C. for at least 4 hours.[2] The methylene chloride is removed by distillation, then the toluene is added. The toluene slurry is extracted with about 198 kg of an aqueous 5.5 wt % sodium bicarbonate solution and the mixture is stirred for at least 15 minutes.[3] The organic and aqueous phases are separated and the aqueous phase is discarded. The toluene is removed by vacuum distillation leaving an oil. Then about 63 kg of heptanes is added. The mixture is heated above 60° C. and filtered. The filter is flushed with about 10 kg of heptanes. The filtrate is cooled −15° C. The solid is isolated by filtration and washed with about 25 kg of cold heptanes to afford typically 26.6 kg to 28.1 kg (dry weight basis) of 4-[(methoxymethylamino)carbonyl]-1-piperidinecarboxylic acid, 1,1-dimethylethyl ester (15) (90-95% yield). This material may be used as a wet cake in Scheme C, step c.[4]

[1] A sample can be removed and analyzed by GC to determine the state of conversion. The reaction is complete if less than 3 area % of 1,4-piperidinedicarboxylic acid, 1-(1,1-dimethylethyl)ester (14) is detected. If necessary, the reaction time may be extended or additional 1,1'-carbonyldiimidazole may be added to complete the reaction.
[2] The slurry can be sampled and analyzed by GC for 4-[(methoxymethylamino)carbonyl]-1-piperidinecarboxylic acid, 1,1-dimethylethyl ester to determine conversion. If necessary, the reaction time may be extended or more N,O-dimethylhydroxylamine hydrochloride may be added to complete the reaction. The reaction is complete if less than 5 area % of the imidazole ester is detected.
[3] The 5.5 wt % aqueous sodium bicarbonate solution is prepared by dissolving 11 kg of sodium bicarbonate in 187 kg of water.
[4] The mother liquors can be concentrated by vacuum distillation to obtain a second crop. Recrystallization is as described above for the first crop.

EXAMPLE 69

Scheme G, step b: 4-[(Methoxymethylamino)carbonyl]-1-piperidinecarboxylic acid, 1,1-dimethylethyl ester (15)

Into a 100-mL three-neck flask equipped with a mechanical stirrer, a 60-mL addition funnel topped with a nitrogen bubbler, and a thermowell with a thermocouple was placed 1,4-piperidinedicarboxylic acid, 1-(1,1-dimethylethyl)ester (14) (3.0 g, 0.013 mol), N,N-dimethylformamide (~106 mL, 0.13 mmol), and toluene (45 g). The addition funnel was charged with a solution of oxalyl chloride (1.26 mL, 0.014 mol) and toluene (5 g). The oxalyl chloride/toluene solution was added at such a rate as to maintain mild gas evolution (~10 min.). The internal reaction temperature reached 38° C. during the addition. The reaction was stirred at ambient temperature for 40 minutes. Into a 250-mL four-neck flask equipped with a mechanical stirrer, a thermometer, a 125-mL addition funnel topped with a nitrogen bubbler, and a stopper was placed N,O-dimethylhydroxylamine hydrochloride (1.45 g, 0.015 mol), water (25 g) and aqueous 50 wt % sodium hydroxide solution (2.32 g, 0.029 mol), resulting in the formation of a clear solution. The addition funnel was charged with the acid chloride/toluene solution and the solution was added over a 5 minute period at ambient temperature. The reaction was allowed to proceed overnight before agitation was stopped and the phases separated. The organic phase was concentrated by rotary evaporation (28 Hg, bath 58° C.) to give the crude title compound as a thick clear liquid. Further drying under vacuum (0.05 mm Hg, 25° C.) gave the crude title compound (2.4 g, 67%). The crude material was recrystallized from heptane (20 g) to give the title compound as a white crystalline material (2.3 g, 65%); m.p. 69-71° C.

EXAMPLE 70

Scheme G, step c: 4-(2,3-Dimethoxybenzoyl)-1-piperidinecarboxylic acid, 1,1-dimethylethyl ester (7)

A solution of n-BuLi (2.5M, 452 mL) in hexane was added to a solution of veratrole (149 g, 1.08 mol) in anhydrous tetrahydrofuran (1.2 L) over 10 minutes at −78° C. under nitrogen. The resulting solution was stirred at 0° C. for 1 hour and room temperature for 4 hours. A solution of 4-[(methoxymethylamino)carbonyl]-1-piperidinecarboxylic acid, 1,1-dimethylethyl ester (15) (275 g, 1.01 mol) in tetrahydrofuran (800 mL) was added to the reaction slurry at −65° C. over 20 minutes. The mixture was warmed to room temperature, stirred for 18 hours and quenched with saturated ammonium chloride (1 L). After stirring for 1 hour, the phases were separated and the aqueous layer was extracted with ethyl ether (1 L). The combined organic solutions were washed with brine (2 L) and dried (MgSO$_4$). The mixture was filtered and the filtrate was concentrated (30° C./20 torr) to a residue (413 g). The solution may be used directly in Scheme L, step a, Example 108.

EXAMPLE 71

Scheme G, step c:
4-(2,3-Dimethoxybenzoyl)-1-piperidinecarboxylic acid, 1,1-dimethylethyl ester (7)

Into a 250-mL four-neck flask equipped with a mechanical stirrer, a septum, a thermowell with a thermocouple, and a nitrogen bubbler was placed veratrole (17.8 g, 0.129 mol) and 125 g of tetrahydrofuran. The solution was cooled to −20° C. before 33.8 g (0.125 mol) of a 23.3 wt % hexane solution of n-butyllithium was added via syringe. The n-butyllithium/hexane solution was added at such a rate as to maintain the internal reaction temperature below −10° C. during the addition. The solution was then warmed to 0° C. and maintained there for 1 hour, during which time a white precipitate formed. The solution was then warmed to 25° C. and stirred for 2 hours, before cooling to −20° C.

Into a 500-mL jacketed-bottom-drain resin pot fitted with a five-joint head equipped with a mechanical stirrer, a thermocouple, a reflux condenser topped with a nitrogen bubbler, a septum, and a stopper was placed 28.9 g (0.092 mol) of 4-[(methoxymethylamino)carbonyl]-1-piperidinecarboxylic acid, 1,1-dimethylethyl ester (15) (28.9 g, 0.092 mol, 87% pure) and 80 g of tetrahydrofuran. The solution was cooled to −17° C. and the cold lithiated veratrole/tetrahydrofuran slurry was added via cannula while maintaining the internal reaction temperature below −10° C. (15 minutes addition). The reaction mixture was then warmed to 10° C. and stirred for 3 hours. The solution may be used directly in Scheme L, step a, Example 109.

EXAMPLE 72

Scheme G, step c:
4-(2,3-Dimethoxybenzoyl)-1-piperidinecarboxylic acid, 1,1-dimethylethyl ester (7)

To a solution of veratrole (16.6 g, 0.120 mol) in tetrahydrofuran (130 mL) at −78° C. was added n-butyllithium (50.5 mL, of a 2.5 M solution in hexane, 0.126 mmol). The resulting mixture was allowed to warm to ambient temperature over 1 hour and then stirred at this temperature for 4 hours before recooling to −78° C. and treating the resulting slurry with a solution of 4-[(methoxymethylamino)carbonyl]-1-piperidinecarboxylic acid, 1,1-dimethylethyl ester (15) (30.71 g, 0.1128 mol) in tetrahydrofuran (180 mL). The reaction mixture was allowed to warm slowly to ambient temperature overnight and then recooled to 0° C. and quenched by the addition of saturated aqueous ammonium chloride solution (110 mL). The aqueous layer was extracted with ether (110 mL) and the combined organic extracts were washed with brine (220 mL), dried (MgSO$_4$) and concentrated in vacuo to give the title compound (7).

EXAMPLE 73

Scheme G, step c:
4-(2,3-Dimethoxybenzoyl)-1-piperidinecarboxylic acid. 1,1-dimethylethyl ester (7)

Into a 500-mL four-neck flask equipped with a mechanical stirrer, a thermowell with a thermocouple, a nitrogen bubbler, and a septum was placed 17.8 g (0.129 mol) of veratrole and 125 g of tetrahydrofuran. The solution was cooled to −20° C. before 48.9 mL (0.122 mol) of a 2.5 N n-butyllithium/hexane solution was added via syringe, at such a rate, as to maintain the internal reaction temperature below −10° C. The solution was then warmed to 0° C. and maintained there for 1 hour, during which time a white precipitate formed. The solution was then warmed to 25° C. and stirred for 2 hours, before cooling to −20° C.

Into a 500-mL bottom-drain-jacketed resin pot equipped with a four-joint head fitted with a mechanical stirrer, a thermowell with a thermocouple, a septum and a nitrogen bubbler was placed 25.0 g (0.092 mol) of 4-[(methoxymethylamino)carbonyl]-1-piperidinecarboxylic acid, 1,1-dimethylethyl ester (15) and 80 g of tetrahydrofuran. The solution was cooled to −17° C. and maintained under a nitrogen atmosphere. The lithiated veratrole/tetrahydrofuran slurry was added via cannula under nitrogen pressure over a 30 minute period, maintaining the internal reaction temperature below −10° C. The resulting clear orange solution was then warmed to 0° C. (2 hours) and finally to 25° C. (16 hours). At ambient temperature the reaction mixture was quenched with 32.5 g (0.61 mol) of ammonium chloride and 110 g of water. After stirring for 20 minutes the phases were allowed to stand for 20 minutes before separating. The organic phase was dried over 7.5 g of magnesium sulfate. Filtration and concentration by rotary evaporation (27 in Hg, bath 35° C.) afforded 62.4 g of a crude solution of the title product (7) in tetrahydrofuran (46.2 wt %, 90% yield).

EXAMPLE 74

Scheme G, step c:
4-(2,3-Dimethoxybenzoyl)-1-piperidinecarboxylic acid, 1,1-dimethylethyl ester (7)

A 1 L flask equipped with mechanical stirrer, thermometer well, and pressure equalizing addition funnel was charged with 500 mL of tetrahydrofuran and 49 ml (0.38 mol) veratrole under a nitrogen atmosphere. The solution was cooled to −15° C. and 160 mL (2.5M, 0.42 mol) of n-butyllithium was placed in the addition funnel. The n-butyllithium solution was added to the reaction mixture over a 25 minute period while maintaining the reaction temperature below −10° C. After complete addition, the pale green solution was held at 0° C. for one hour and then room temperature for 2 hours resulting in a very thick slurry. A 3 L Morton flask containing 82.3 g (0.32 mol) 4-[(methoxymethylamino)carbonyl]-1-piperidinecarboxylic acid, 1,1-dimethylethyl ester (15) in 300 mL of tetrahydrofuran under nitrogen atmosphere was cooled to −15° C. while the lithiated veratrole slurry was cooled to 0° C. The lithiated veratrole slurry was added to the 4-[(methoxymethylamino) carbonyl]-1-piperidinecarboxylic acid, 1,1-dimethylethyl ester solution over a 15 minute period while keeping the temperature below −10° C. The resulting pale green slurry was stirred an additional 15 minutes at −15° C. and then allowed to warm to room temperature, causing the reaction mixture to become clear. The reaction mixture was stirred for 20 hours at room temperature then quenched with 500 mL of saturated ammonium chloride solution. The aqueous phase was extracted with toluene (2×250 mL) which was then combined with the tetrahydrofuran solution. The organic solution was washed with brine (2×25 mL) and dried over sodium sulfate. The solution was filtered and then concentrated by rotary evaporator to give 140 g of an orange oil. The crude oil was quickly run through 350 g of silica gel using 20% ethyl acetate in toluene as eluant. Solvent evaporation then gave 88.9 g of an orange oil. The orange oil was then placed in a kugelrohr for three hours (80° C., 1 mm Hg) to remove most of the veratrole, giving the title compound (7) remaining in the pot as an orange syrup (55.9 g, 50%).

EXAMPLE 75

Scheme G, step c:
4-(2,3-Dimethoxybenzoyl)-1-piperidinecarboxylic acid, 1,1-dimethylethyl ester (7)

A suitable reactor maintained under nitrogen is charged with veratrole (5.53 kg, 39.8 mol) and 55 L of tetrahydrofuran. The stirred solution was cooled to and maintained below −10° C. while adding n-butyl lithium (11.95 kg, 37.3 mol, 20% in hexanes) over 30 minutes. The mixture was allowed to warm to 0° C. for 1 hour, then to 20° C. for 2 hours. In a separate reactor maintained under nitrogen 4-[(methoxymethylamino)carbonyl]-1-piperidinecarboxylic acid, 1,1-dimethylethyl ester (15) (10.9 kg, 40.0 mol) and tetrahydrofuran (45 L) and cool below −10° C. The mixture was stirred and maintained below −10° C. while adding the veratrole solution over 1.5 hours. The stirred mixture was warmed slowly to room temperature over 17 hours. The stirred mixture was diluted with a solution of ammonium chloride (14.5 kg in 40 L water), followed by 10 L of water and 15 L of toluene. The organic phase was separated and the aqueous phase was extracted with 2×20 L of toluene. Organic extracts were combined, washed with a solution of sodium chloride in 10 L of water, then dried with sodium sulfate (5 kg). Drying agent was filtered off and washed with 2×5 L of toluene. The filtrate was evaporated at 45° C./300 torr, then residual solvent was evaporated at 50° C./20 torr to give the title compound (7) (15.05 kg, theory 13.96 kg (4.38% toluene)).

EXAMPLE 76

Scheme G, step c:
4-(2,3-Dimethoxybenzoyl)-1-piperidinecarboxylic acid, 1,1-dimethylethyl ester (7)

A suitable reactor maintained under nitrogen is charged with veratrole (12.5 kg, 90.0 mol) and about 87 kg of tetrahydrofuran. The solution is cooled and maintained below −10° C. while adding n-butyl lithium (22.9 kg, 83.3 mol, 23.3% solution in hexane). The mixture is warmed to about 0° C. for 1 hour, then to about 25° C. for at least 2 hours. In a separate reactor maintained under nitrogen is charged with 4-[(methoxymethylamino)carbonyl]-1-piperidinecarboxylic acid, 1,1-dimethylethyl ester (15) as a heptanes wet cake (15.6 kg, 57.3 mol, dry weight basis) and about 66 kg of tetrahydrofuran. The mixture is cooled below −10° C.[1] and the lithiated veratrole solution is added at such a rate to maintain the temperature below −10° C. The mixture is warmed to about 25° C. for at least 6 hours.[2] When complete, the title compound may be utilized in Scheme H, step a, Example 108 as the reaction solution.

[1]The solution is sampled and analyzed by GC to determine the amount of 4-[(methoxymethylamino)carbonyl]-1-piperidinecarboxylic acid, 1,1-dimethylethyl ester (15) present.
[2]The solution is sampled and analyzed by GC to confirm the complete formation of 4-(2,3-dimethoxybenzoyl)-1-piperidinecarboxylic acid, 1,1-dimethylethyl ester (7). The reaction is complete if less than 3 area % of 4-[(methoxymethylamino)carbonyl]-1-piperidinecarboxylic acid, 1,1-dimethylethyl ester (15) is detected.

EXAMPLE 77

Scheme G, step d:
4-(2,3-Dimethoxybenzoyl)-1-piperidinecarboxylic acid, 1,1-dimethylethyl ester (7)

Lithiated veratrole was prepared by adding 4.0 mL (10 mmol) of n-butyllithium to a solution of 1.2 mL (9.4 mmol) of veratrole in 25 mL of tetrahydrofuran at 0° C. The solution was stirred one hour at 0° C., 3 hours at room temperature, and then it was cooled back to 0° C. A solution of 1,4-piperidinedicarboxylic acid, 1-(1,1-dimethylethyl)ester (14) was dissolved 40 mL of tetrahydrofuran in a 100 mL flask and cooled to −78° C., then 4.0 mL (10 mmol) of n-butyllithium was added. After 45 minutes, the lithiated veratrole solution was added via canula. The white slurry was allowed to warm to room temperature. The reaction mixture was quenched with 25 mL of ammonium chloride solution after 16 hours. The organic phase was washed with brine (2×25 mL) and dried over magnesium sulfate. Filtration, followed by evaporation of solvent gave 1.41 g of a red oil. Purification by column chromatography (silica gel, 20% ethyl acetate in toluene) gave the title compound (7) as an orange oil (0.40 g, 13% yield).

EXAMPLE 78

Scheme G, step e:
4-(2,3-Dimethoxybenzoyl)-1-piperidinecarboxylic acid, 1,1-dimethylethyl ester (7)

Into a 1-L four-neck flask equipped with a mechanical stirrer, a thermowell with a thermocouple, a nitrogen bubbler, and a stopper was placed 33.0 g (0.12 mol) of 4-(2,3-dimethoxybenzoyl)piperidine hydrochloride (16), 21.5 g (0.27 mol) of a 50 wt % solution of aqueous sodium hydroxide, 330 g of 2B ethanol and 99.0 g of water. To the solution was added 29.7 g (0.14 mol) of di-t-butyl dicarbonate in one portion resulting in a 16° C. exotherm. The solution was clear until the di-t-butyl dicarbonate was added. Within minutes a white precipitate formed. The reaction mixture was stirred under a nitrogen atmosphere at ambient temperature for 4 hours. The precipitated salts were removed by suction filtration through a coarse sintered glass funnel containing Celite® filter aid and the solution was concentrated to afford a liquid containing a white residue. The crude material was taken up in 250 g of water and 250 g of toluene and phase separated. The aqueous phase was extracted with 150 g of additional toluene. The combined organic extracts were dried (MgSO$_4$), filtered and concentrated to afford the title compound (7) (28.3 g, 90% yield).

$^1$H NMR (CDCl$_3$) δ 7.09-6.92 (m, 3H, aromatic), 4.04 (d, 1H, J=12.7 Hz), 3.86 (s, 3H, —OCH$_3$), 3.83 (s, 3H, —OCH$_3$), 3.24-3.17 (m, 1H), 2.80 (t, 2H, J=11.9 Hz), 1.82 (dd, 2H, J=12.9, 2.1 Hz), 1.59 (qd, 2H, J=11.7, 4.2 Hz), 1.42 (s, 9H, —Si(CH$_3$)$_3$);

$^{13}$C NMR (CDCl$_3$) δ 205.7, 154.6, 152.7, 147.0, 134.0, 124.2, 120.2, 115.0, 79.3, 61.6, 55.9, 48.0, 43.3, 28.3, 27.8.

EXAMPLE 79

Scheme H, step a:
4-(2,3-dimethoxybenzoyl)pyridine (12)

A 500-mL, four-necked, round-bottomed flask, equipped with a reflux condenser, addition funnel, thermocouple, mechanical stirrer, and nitrogen bubbler, was charged with 23.55 g (171 mmol) of veratrole and 140 mL of tetrahydrofuran. The resulting solution was cooled to −77° C. In the addition funnel was placed 64 mL of a 2.5 M solution of n-butyllithium (160 mmol) in hexanes. The butyllithium was added to the reaction vessel over 11 minutes. The temperature of the reaction mixture at the conclusion of the addition was −70° C. The reaction mixture was allowed to warm to room temperature over 35 minutes. At 7.5° C., a solid precipitated in the flask. The reaction mixture was allowed to stir for 1 hour at room temperature before cooling to 2° C. with an ice bath.

In the addition funnel was placed a solution of 7.76 g (74.6 mmol) of 4-cyanopyridine (17) in 40 mL of tetrahydrofuran. The solution of 4-cyanopyridine was added to the reaction vessel over 16 minutes while maintaining the temperature of the reaction mixture at less than 6° C. The color of the reaction mixture changed from yellow to purplish black as the first few drops of the 4-cyanopyridine solution were added. The reaction mixture was warmed to room temperature and allowed to stir for 3 hours.

The reaction mixture was cooled to 0° C. and the addition funnel was charged with 130 mL of a 2.5 M solution of hydrochloric acid. The hydrochloric acid was added to the reaction vessel over 12 minutes while maintaining the temperature of the reaction mixture less than 30° C. The reaction mixture was allowed to stir at ambient temperatures for 1 hour. The solution was concentrated by rotary evaporation to remove the tetrahydrofuran. The pH of the remaining aqueous solution was 1.1. The pH of the aqueous solution was adjusted to pH ~11.5 by the addition of 50 mL of a 45% aqueous solution of potassium hydroxide. The color of the reaction mixture changed from purple to greenish black. The basic aqueous phase was extracted with 300 mL of toluene. A black insoluble oil formed in the separatory funnel at the interface of the aqueous and organic phases. The organic and aqueous phases were separated. The majority of the insoluble oil remained adhered to the walls of the separatory funnel. The organic phase was dried over anhydrous magnesium sulfate, filtered through a medium sintered glass funnel, and evaporated to dryness using a rotary evaporator and vacuum oven overnight at room temperature. The resulting black oil weighed 24.75 g. The product was dissolved in 100 mL of methanol; the solution weighed 98.35 g containing 9.4% title product (12) (51% yield.)

EXAMPLE 80

Scheme H, step b:
N-Methyl-N-methoxyisonicotinamide (19)

4-pyridinecarboxylic acid (18) (17.0 g, 0.138 mol) is slurried in methylene chloride (200 mL) and treated with 1,1'-carbonyldiimidazole (25 g, 0.154 mol). After a 1 minute induction period, $CO_2$ evolution begins and the solution becomes homogeneous. After stirring at ambient temperature for 2 hours, the solution is treated with N,O-dimethylhydroxylamine hydrochloride (20 g, 0.20 mol) and stirred at room temperature overnight. The reaction mixture is quenched with 1 N NaOH and the phases separated. After a normal work-up, the organic phase is concentrated to leave an oil. Kugelrohr distillation provided the title compound (19) as a clear liquid (14.34 g, 62% yield); b.p. 120-135° C./0.5 mm Hg.

EXAMPLE 81

Scheme H, step b:
N-Methyl-N-methoxyisonicotinamide (19)

A 2-L, round-bottomed flask, equipped with a magnetic stir bar, reflux condenser, and nitrogen bubbler, was charged sequentially with 84.30 g (0.69 mol) of 4-pyridinecarboxylic acid (18), 1000 mL of methylene chloride, and 125.84 g (0.78 mol) of 1,1'-carbonyldiimidazole. Carbon dioxide evolution began after approximately a one minute induction time. Approximately 15 minutes after the 1,1'-carbonyldiimidazole addition, the solids in the reaction vessel had dissolved. The reaction mixture was allowed to stir under nitrogen at room temperature for 2.5 hours.

In a single portion, 100.45 g (1.03 mol) of N,O-dimethylhydroxylamine hydrochloride was added to the reaction vessel. The temperature of the reaction mixture increased to the boiling point of methylene chloride. A white solid immediately precipitated upon addition of the N,O-dimethylhydroxylamine hydrochloride. The reaction mixture was allowed to stir overnight at room temperature.

The reaction was quenched with 500 mL of 1M sodium hydroxide. The solid present in the reaction vessel dissolved. The resulting two-phase system was allowed to stir for five minutes at room temperature. The reaction mixture was transferred to a separatory funnel and the phases were separated. The methylene chloride layer was washed with 500 mL of additional 1 M sodium hydroxide. The methylene chloride layer was dried over anhydrous magnesium sulfate, filtered through a medium sintered glass funnel, and evaporated to dryness using a rotary evaporator and vacuum oven overnight at room temperature. The pale yellow residue weighed 103.83 g and was purified by Kugelrohr distillation. The title product (19) distilled between 100 and 110° C. at 2.5 mm of Hg. The distilled product weighed 96.78 g, which corresponds to an 85% yield.

$^1$H NMR (CDCl$_3$) δ 8.71 (d, 2H, J=6.0 Hz, aromatic), 7.52 (d, 2H, J=6.0 Hz, aromatic), 3.55 (s, 3H, OC$\underline{H}_3$), 3.37 (s, 3H, NC$\underline{H}_3$);

$^{13}$C NMR (CDCl$_3$) δ 167.5, 149.8, 141.5, 121.9, 61.3, 33.0.

EXAMPLE 82

Scheme H, step c:
4-(2,3-Dimethoxybenzoyl)pyridine (12)

A solution of veratrole (8.04 g, 58.2 mmol) in tetrahydrofuran (50 mL) is treated with BuLi (26 mL, 2.5 M in hexane, 65 mmol) at −70° C. After the addition is complete, the reaction mixture is permitted to warm to room temperature and stirred for 2 hours. The mixture is re-cooled to −70° C. and treated with a solution of N-methyl-N-methoxyisonicotinamide (19) (9.15 g, 55.1 mmol) in tetrahydrofuran (30 mL). The resulting slurry is permitted to slowly warm to room temperature over an hour period. When the reaction mixture reaches 0° C. it becomes homogeneous. After 3 hours at room temperature, the reaction is quenched with 10% AcOH (aqueous, 100 mL). After stirring for 45 minutes, the tetrahydrofuran is removed at reduced pressure and the residue is diluted with toluene (150 mL). After neutralization with NHCO₃, the phases are separated and the organic phase is submitted to a normal workup to provide an oil. Kugelrohr distillation provides the title compound (12) as a dark oil (12.77 g, 95% yield); b.p. 130-150° C./0.05 mm Hg.

EXAMPLE 83

Scheme H, step c:
4-(2,3-Dimethoxybenzoyl)pyridine (12)

A 1-L, four-necked, round-bottomed flask, equipped with a reflux condenser, addition funnel, thermocouple, mechanical stirrer, and nitrogen bubbler, was charged with 55.45 g (0.40 mol) of veratrole and 350 mL of tetrahydrofuran. The resulting solution was cooled to −78° C. In the addition funnel was placed 175 mL of a 2.5 M solution of n-butyllithium (0.44 mol) in hexanes. The butyllithium was added to the reaction vessel over 20 minutes. The temperature of the reaction mixture increased to −69° C. during the addition. The reaction mixture was allowed to warm to room temperature over 45 minutes. At 5° C., a white solid began to precipitate. After stirring at room temperature for 2 hours, the reaction mixture was cooled to −79° C. In the addition funnel was placed a solution of 61.74 g (0.37 mol) of N-methyl-N-methoxyisonicotinamide (19) dissolved in 200 mL of tetrahydrofuran. The solution in the addition funnel was added to the reaction vessel over 18 minutes. The temperature of the reaction mixture increased to −68° C. during the addition. The reaction mixture was slowly warmed to room temperature and stirred overnight.

After stirring overnight, nearly all the solids in the reaction vessel had dissolved. The reaction mixture was quenched with 500 mL of 2.5 M hydrochloric acid. The resulting mixture was allowed to stir for 3 hours at room temperature. The reaction mixture was concentrated using a rotary evaporator. The resulting solution was diluted with 500 mL of 2.5 M hydrochloric acid and transferred to a separatory funnel. The aqueous solution was extracted with 3×200 mL of toluene. The toluene extracts were discarded. The pH of the aqueous phase was 0.08. The pH of the aqueous phase was adjusted to 11.0 by the addition of 82 mL of 50% sodium hydroxide. The basic aqueous layer was extracted with 2×500 mL of toluene. The toluene extracts were combined and dried over anhydrous magnesium sulfate. The solution was filtered through a medium sintered glass funnel, and evaporated to dryness using a rotary evaporator and vacuum oven overnight at room temperature. The tan solid residue weighed 71.71 g.

The crude product was slurried in 1000 mL of mixed heptanes and heated to approximately 65° C. The solid was not completely soluble. The solution was cooled and 100 mL of ethyl acetate was added. The resulting slurry was heated to 55° C. to dissolve the solid. The solution was cooled and held at −5° C. for 6 hours. The white solid was isolated by vacuum filtration of the reaction mixture through a medium sintered glass funnel, washed with 100 mL of mixed heptanes, and dried overnight in a vacuum oven at room temperature to give the title compound (12). The dried solid weighed 61.62 g (68% yield).

¹H NMR (CDCl₃) δ 8.77 (d, 2H, J=5.8 Hz, aromatic), 7.58 (d, 2H, J=5.8 Hz, aromatic), 7.59-6.98 (m, 3H, aromatic), 3.91 (s, 3H, OC$\underline{H}_3$), 3.66 (s, 3H, OC$\underline{H}_3$);

¹³C NMR (CDCl₃) δ 195.4, 152.9, 150.5, 147.6, 144.3, 132.6, 124.2, 122.3, 120.9, 115.7, 61.5, 56.1.

EXAMPLE 84

Scheme H, step d:
4-(2,3-Dimethoxybenzoyl)pyridine (12)

A 250-mL, three-necked, round-bottomed flask, equipped with a reflux condenser, addition funnel, mechanical stirrer, and nitrogen bubbler, was charged with 9.0 g (65 mmol) of veratrole, 6.0 g (49 mmol) of 4-pyridinecarboxylic acid (18), and 75 g of tetrahydrofuran. The reaction mixture was cooled to −12° C. In the addition funnel was placed 46 mL of a 2.5 M solution of n-butyllithium (115 mmol) in hexanes. The butyllithium was added to the reaction vessel over 15 minutes. The temperature of the reaction mixture increased to 0° C. during the addition. The reaction mixture was warmed to 29° C. and allowed to stir for 9 hours under nitrogen. The reaction mixture was allowed to stir for an additional 3 hours at 29° C. Analysis by HPLC indicated 39.8% of the title product (12).

EXAMPLE 85

Scheme I, step a: α-(2,3-Dimethoxyphenyl)-1-[2-(4-fluorophenyl)ethyl]-4-piperidinemethanol (5)

Into a 100-mL jacketed-resin pot fitted with a four-joint head equipped with a mechanical stirrer, a thermowell with a thermocouple, a condenser topped with a nitrogen bubbler and a 60-mL pressure equalized addition funnel was placed sodium bis(2-methoxyethoxy)aluminum hydride (10 mL of a 70 wt % solution in toluene) and toluene (15 g). The addition funnel was charged with 4-[1-oxo-1-(2,3-dimethoxyphenyl)methyl]-N-2-(4-fluorophen-1-oxo-ethyl)piperidine (4) (10 g) and toluene (35 g). The 4-[1-oxo-1-(2,3-dimethoxyphenyl)methyl]-N-2-(4-fluorophen-1-oxo-ethyl)piperidine/toluene solution was added slowly to the hydride/toluene solution at 25° C. over a 10 minute period (resulting in a 38° C. exotherm). The reaction was stirred at ambient temperature for 1.5 hours (28° C.). The reaction was quenched by the addition of 5% aqueous solution of sodium hydroxide (6.96 g), causing the precipitation of a white granular solid. An additional 3.0 g of the 5% aqueous solution of sodium hydroxide was added and the slurry was stirred for 10 minutes, before allowing to stand and phase separate for 30 minutes. The phases were separated and the aqueous phase was extracted with toluene (50 g) and the combined toluene phases were washed with a 5% aqueous sodium chloride solution. The phases were separated and the organic phase was concentrated by rotary evaporation (28 in Hg, bath 58° C.) to give the title compound (5) as a reddish-orange solution (30.65 g).

EXAMPLE 86a

Scheme I, step a: α-(2,3-Dimethoxyphenyl)-1-[2-(4-fluorophenyl)ethyl]-4-piperidinemethanol (5)

Into a 5L four-neck Morton flask equipped with a mechanical stirrer, a thermowell with a thermocouple, a 1-L pressure equalized addition funnel with a stopper, and a reflux condenser topped with a nitrogen bubbler was placed 4-[1-oxo-1-(2,3-dimethoxyphenyl)methyl]-N-2-(4-fluorophen-1-oxo-ethyl)piperidine (4) (635 g of a 29.9 wt % solution in toluene, 189.8 g, 0.49 mol). The solution was cooled to −12° C. and the addition funnel was charged with borane/tetrahydrofuran solution (9.88 g of a 9.0 M solution) in two portions. The borane/tetrahydrofuran solution was added to the 4-[1-oxo-1-(2,3-dimethoxyphenyl)methyl]-N-2-(4-fluorophen-1-oxo-ethyl)piperidine/toluene solution over a 20 minute period resulting in an internal reaction temperature of 8° C. The reaction mixture was warmed to 55° C. over a 1 hour period and maintained there for 1.5 hours before the reaction mixture was cooled to 25° C. and methanol (124 g) was added over a 5 minute period (rapid gas evolution was observed at first). After stirring for 20 minutes, diethylenetriamine (133 g) was added in one portion causing a turbid solution. The solution was then warmed to 65° C. and maintained there for 2 hours. The reaction mixture was then allowed to cool to a temperature below 40° C. before water (1216 g) and tetrahydrofuran (900 g) were added. The mixture was stirred for 20 minutes before the phases were allowed to stand and phase separate (20 minutes). The phases were separated and the organic phase stored as a wet solution containing the title compound (2.46 kg).

The solution was concentrated and 14.96 g of the crude α-(2,3-dimethoxyphenyl)-1-[2-(4-fluorophenyl)ethyl]-4-piperidinemethanol (5) was placed into a 250-mL single-neck flask equipped with a stir bar along with isopropanol (35 g). The mixture was warmed to 70° C. and polished filtered through a medium sintered glass funnel. The solution was allowed to slowly cool to ambient temperature, at approximately 40° C., 50 mg of seed crystals of (R)-α-(2,3-dimethoxyphenyl)-1-[2-(4-fluorophenyl)ethyl]-4-piperidinemethanol (3) was added. The solution was then allowed to stir overnight and crystallize. The solution was cooled to 0° C. prior to collected the crystalline product on a coarse sintered glass funnel. The wet cake was washed with cold isopropanol (20 g, −5° C.) and dried under vacuum (26 in Hg) at 50° C. for 18 hours to give the title compound (5) as a white crystalline material (8.57 g, 57%); m.p. 113-114° C.

$^1$H NMR (CDCl$_3$) δ7.15-6.63 (m, 7H, aromatic), 4.66-4.61 (m, 1H), 3.66 (s, 3H, —OC$\underline{H}_3$), 3.65 (s, 3H, —OC$\underline{H}_3$), 3.11 (d, 1H, J=10.3 Hz), 2.96 (d, 1H, J=11.0 Hz), 2.80-2.75 (m, 2H), 2.60-2.50 (m, 3H), 2.11-1.91 (m, 3H), 1.67-1.65 (m, 1H), 1.53-1.20 (m, 3H);

$^{13}$C NMR (CDCl$_3$) δ 163.0, 159.8, 152.5, 146.6, 136.4, 136.1, 130.0, 129.9, 123.7, 119.7, 115.2, 114.9, 111.6, 96.2, 74.5, 60.8, 60.7, 55.8, 53.7, 42.8, 32.8, 28.7.

EXAMPLE 86b

Scheme I, step a: α-(2,3-Dimethoxyphenyl)-1-[2-(4-fluorophenyl)ethyl]-4-piperidinemethanol (5)

Into a 500-mL four-neck flask equipped with a mechanical stirrer, a thermowell with a thermocouple, a 250-mL pressure equalized addition funnel with a stopper, and a reflux condenser topped with a nitrogen bubbler was placed 67.1 g (10.0 g, 0.054 mol) of a 29.8 wt % solution of 4-[1-oxo-1-(2,3-dimethoxyphenyl)methyl]-N-2-(4-fluorophen-1-oxo-ethyl)piperidine (4) in toluene. The solution was cooled to −11° C. and the addition funnel was charged with 104 g of a 1.0 M borane/tetrahydrofuran solution. The borane/THF solution was added to the 4-[1-oxo-1-(2,3-dimethoxyphenyl)methyl]-N-2-(4-fluorophen-1-oxo-ethyl)piperidine (4)/toluene solution over a 5 min. period resulting in an internal reaction temperature of 2° C. The reaction mixture was warmed to 55° C. over a 1 hour period and maintained there for an additional 1.5 hours before the reaction mixture was cooled to 40° C. and 13 g of methanol was added over a 5 minute period (rapid gas evolution was observed at first). After stirring for 20 min., 14 g of diethylenetriamine was added in one portion causing a turbid solution. The solution was then warmed to 65° C. and maintained there for 2 hours. The reaction mixture was then allowed to cool to a temperature below 35° C. before 130 g of water and 130 g of tetrahydrofuran was added. The mixture was stirred for 20 min. before the phases were allowed to stand and the phases separated (20 minutes). The phases were separated and the organic phase stored as a wet solution (250.1 g) HPLC assay indicated that the 250.1 g solution contained 17.9 g (93% yield) of crude α-(2,3-dimethoxyphenyl)-1-[2-(4-fluorophenyl)ethyl]-4-piperidinemethanol (5).

Into a 250-mL, single-neck flask equipped with a stir bar was placed 14.96 g crude α-(2,3-dimethoxyphenyl)-1-[2-(4-fluorophenyl)ethyl]-4-piperidinemethanol (5) and 35 g of isopropanol. The mixture was warmed to 70° C. and polished filtered through a medium sintered glass funnel. The solution was allowed to slowly cool to ambient temperature, at approximately 40° C., 50 mg of seed (R)-α-(2,3-dimethoxyphenyl)-1-[2-(4-fluorophenyl)ethyl]-4-piperidinemethanol (3) was added. The solution was then allowed to stir overnight and crystallize. The solution was cooled to 0° C. prior to collecting the crystalline product on a coarse sintered glass funnel. The wet cake was washed with 20 g of cold isopropanol (−5° C.) and dried under vacuum (26 in Hg) at 50° C. for 18 h to afford 12.9 g (86%) of α-(2,3-dimethoxyphenyl)-1-[2-(4-fluorophenyl)ethyl]-4-piperidinemethanol (5) as a white crystalline material: m.p. 113-114° C.

$^1$H NMR (CDCl$_3$) δ7.15-6.63 (m, 7H, aromatic), 4.66-4.61 (m, 1H), 3.66 (s, 3H, —OC$\underline{H}_3$), 3.65 (s, 3H, —OC$\underline{H}_3$), 3.11 (d, 1H, J=10.3 Hz), 2.96 (d, 1H, J=11.0 Hz), 2.80-2.75 (m, 2H), 2.60-2.50 (m, 3H), 2.11-1.91 (m, 3H), 1.67-1.65 (m, 1H), 1.53-1.20 (m, 3H);

$^{13}$C NMR (CDCl$_3$) δ 163.0, 159.8, 152.5, 146.6, 136.4, 136.1, 130.0, 129.9, 123.7, 119.7, 115.2, 114.9, 111.6, 96.2, 74.5, 60.8, 60.7, 55.8, 53.7, 42.8, 32.8, 28.7.

EXAMPLE 87

Scheme I, step a: α-(2,3-Dimethoxyphenyl)-1-[2-(4-fluorophenyl)ethyl]-4-piperidinemethanol (5)

To the toluene solution of 4-[1-oxo-1-(2,3-dimethoxyphenyl)methyl]-N-2-(4-fluorophen-1-oxo-ethyl)piperidine (4) from Scheme J, step a, Example 94, is added 1M borane solution (165 kg, 184 mol) in tetrahydrofuran maintaining the temperature below 25° C. The borane solution line is flushed with about 16 kg of tetrahydrofuran. The solution is heated to about 60° C. for at least 3 hours. The solution is cooled and methanol (21 kg) is added, maintaining the temperature below 25° C. The solution is then heated to about 40° C. for at least 30 minutes. To the solution at about 25° C. is added diethylenetriamine (22.2 kg) and the solution is heated above 65° C. for at least 3 hours. The solution is cooled to about 25° C. and about 186 kg of tetrahydrofuran and about 204 kg water is added. The phases were separated.[1] The organic phase is concentrated by vacuum distillation.[2] Two phases form when most of the tetrahydrofuran is removed. While maintaining the temperature at about 60° C., toluene (566 kg) is added and the phases are separated. The concentration of α-(2,3-dimethoxyphenyl)-1-[2-(4-fluorophenyl)ethyl]-4-piperidinemethanol (5) in the organic phase is adjusted to 25-30% wt % by vacuum distillation[3]. The solution is cooled below −10° C. and the α-(2,3-dimethoxyphenyl)-1-[2-(4-fluorophenyl)ethyl]-4-piperidinemethanol (5) is collected by filtration. The wet cake is washed with about 14 kg of cold isopropanol to typically afford 25.0 kg of α-(2,3-dimethoxyphenyl)-1-[2-(4-fluorophenyl)ethyl]-4-piperidinemethanol (5).

[1]The wt % of α-(2,3-dimethoxyphenyl)-1-[2-(4-fluorophenyl)ethyl]-4-piperidinemethanol in solution may be determined by HPLC assay.
[2]The organic phases from 3 runs up to the addition of water are combined in a suitable reactor and processed as a single batch.
[3]The wt % of α-(2,3-dimethoxyphenyl)-1-[2-(4-fluorophenyl)ethyl]-4-piperidinemethanol is determined by HPLC assay. Additional toluene can be added as needed to adjust the concentration.

EXAMPLE 88a

Scheme I, step b: α-(2,3-Dimethoxyphenyl)-1-[2-(4-fluorophenyl)ethyl]-4-piperidinemethanol (5)

A solution of 4-[1-oxo-1-(2,3-dimethoxyphenyl)methyl]-N-2-(4-fluorophenylethyl)-piperidine (6) (21.86 g, 58.8 mmol) in ethanol (400 mL) at 0° C. was treated with sodium borohydride (4.45 g, 117.6 mmol). The resulting mixture was stirred overnight at ambient temperature and then recooled to 0° C. and quenched by the addition of a saturated aqueous solution of ammonium chloride (300 mL). The resulting mixture was concentrated in vacuo to remove a majority of the ethanol and then extracted with methylene chloride (4×300 mL). The combined organic extracts were dried (MgSO$_4$) and concentrated in vacuo. The residue was then eluted through a pad of silica (gradient: ethyl acetate to 9:1 ethyl acetate:methanol) to afford a white semisolid foam. The residue was treated with excess acetic anhydride (20 mL) and pyridine (20 mL) and a catalytic quantity of DMAP (~100 mg) in methylene chloride (200 mL). After stirring for 2 days at ambient temperature and heating at reflux overnight, complete consumption of starting material was achieved. The corresponding acetate was isolated by washing the reaction mixture with water (50 mL), saturated aqueous sodium bicarbonate solution (2×50 mL), drying (MgSO$_4$) and chromatography (ethyl acetate:methanol, 19:1). The acetate was recovered by concentration of the reaction mixture in vacuo, dilution with methylene chloride (~500 mL), washing with water (2×50 mL), drying (MgSO$_4$) and concentration in vacuo. A solution of this material in tetrahydrofuran (500 mL) was then treated with excess lithium aluminum hydride (4.5 g) at 0° C. The resulting mixture was then allowed to warm to ambient temperature overnight. The reaction was quenched at 0° C. by addition of water (5 mL), dilute aqueous sodium hydroxide solution (10%, 10 mL) and a further portion of water (10 mL). This mixture was allowed to warm to ambient temperature and stirred for 1 hour, dried (MgSO$_4$), filtered through a plug of silica with tetrahydrofuran (500 mL) and concentrated in vacuo. Purification was realized by recrystallization from cyclohexane to afford the title compound (5) as a white solid (16.6 g, 76%); m.p. 128-129° C.

EXAMPLE 88b

Scheme I, step b: α-(2,3-Dimethoxyphenyl)-1-[2-(4-fluorophenyl)ethyl]-4-piperidinemethanol (5)

Into a 25-mL single-neck flask equipped with a magnetic stir bar and a reflux condenser topped with a nitrogen bubbler was placed 1.0 g (0.003 mol) of 4-[1-oxo-1-(2,3-dimethoxyphenyl)methyl]-N-2-(4-fluorophenylethyl)-piperidine (6), 0.2 g (0.005 mol) of sodium borohydride and 6.0 g of ethanol (2B). The reaction mixture was warmed to reflux and stirred overnight under a nitrogen atmosphere. The reaction mixture was cooled to 25° C. and concentrated by rotary evaporation to afford a white sludge. To the sludge was added 30 g of toluene and 20 g of a 20 wt % aqueous solution of potassium carbonate. The mixture was stirred for 15 min and the phases were separated. The organic phase was azeotropically dried and concentrated by atmospheric distillation to afford a 17 wt % solution. The solution was allowed to slowly cool and the α-(2,3-dimethoxyphenyl)-1-[2-(4-fluorophenyl)ethyl]-4-piperidinemethanol (5) to crystallize. The product was collected by suction filtration, washed with toluene and dried under vacuum (30 in Hg) at 60° C. for 8 hours to afford 0.81 g (81% yield) of α-(2,3-dimethoxyphenyl)-1-[2-(4-fluorophenyl)ethyl]-4-piperidinemethanol (5) as a white crystalline material: m.p. 113-114° C.

$^1$H NMR (CDCl$_3$) δ7.15-6.63 (m, 7H, aromatic), 4.66-4.61 (m, 1H), 3.66 (s, 3H, —OCH$_3$), 3.65 (s, 3H, —OCH$_3$), 3.11 (d, 1H, J=10.3 Hz), 2.96 (d, 1H, J=11.0 Hz), 2.80-2.75 (m, 2H), 2.60-2.50 (m, 3H), 2.11-1.91 (m, 3H), 1.67-1.65 (m, 1H), 1.53-1.20 (m, 3H);

$^{13}$C NMR (CDCl$_3$) δ 163.0, 159.8, 152.5, 146.6, 136.4, 136.1, 130.0, 129.9, 123.7, 119.7, 115.2, 114.9, 111.6, 96.2, 74.5, 60.8, 60.7, 55.8, 53.7, 42.8, 32.8, 28.7.

EXAMPLE 89

Scheme I, step c: α-(2,3-Dimethoxyphenyl)-1-[2-(4-fluorophenyl)ethyl]-4-piperidinemethanol (5)

A 100-mL, four-necked, round-bottomed flask, equipped with a mechanical stirrer, nitrogen bubbler, reflux condenser, addition funnel, and thermocouple, was charged with 5.06 g (13.1 mmol) of 4-[1-hydroxy-1-(2,3-dimethoxyphenyl)methyl]-N-2-(4-fluorophen-1-oxo-ethyl)piperidine (20) and 25 mL of toluene. The resulting solution was cooled to −16° C. The addition funnel was charged with 30 mL of a 1M borane-tetrahydrofuran complex (30 mmol) in tetrahydrofuran. The borane-tetrahydrofuran complex was added to the reaction vessel over 7 minutes while maintaining the temperature of the reaction mixture between −8 and −17° C. The reaction mixture was warmed to 55° C. over a 1.5 hour period and maintained at this temperature for 2 hours.

The reaction mixture was cooled to room temperature. The addition funnel was charged with 3.33 g of methanol, which was added to the reaction vessel over 4 minutes. Rapid gas evolution was detected and the temperature of the reaction mixture increased to 29° C. from 23° C. during the addition. The reaction mixture was allowed to stir at room temperature for 30 minutes. In a single portion, 3.55 g of diethylenetriamine was added to the reaction vessel. The reaction mixture became turbid upon addition of the diethylenetriamine. The reaction mixture was heated to 70° C. and stirred at this temperature for 2 hours.

The reaction mixture was cooled to 40° C. and added to a solution containing 31.97 g of water and 23.93 g of tetrahydrofuran. The solution was transferred to a separatory funnel and the phases were separated. The organic phase weighed 81.83 g and contained 5.14% title compound (5).

The solution was concentrated using a rotary evaporator and drying in a vacuum oven overnight at room temperature to give the title product (5) as a white solid.

EXAMPLE 90

Scheme I, step c: α-(2,3-Dimethoxyphenyl)-1-[2-(4-fluorophenyl)ethyl]-4-piperidinemethanol (5)

Into a 250-mL jacketed-bottom drain resin pot equipped with a thermowell with thermocouple and a four-joint head fitted with a mechanical stirrer, a 60-mL addition funnel, a reflux condenser topped with a nitrogen bubbler, and a stopper was placed 95.1 g (0.041 mol) of a 16.7 wt % solution of 4-[1-hydroxy-1-(2,3-dimethoxyphenyl)methyl]-N-2-(4-fluorophen-1-oxo-ethyl)piperidine (20) in toluene from Example 113, Scheme M, step a. The additional funnel was charged with 8.8 mL (0.09 mol) of borane-dimethyl sulfide. The borane-dimethyl sulfide complex was added dropwise to the 4-[1-hydroxy-1-(2,3-dimethoxyphenyl)methyl]-N-2-(4-fluorophen-1-oxo-ethyl)piperidine (20)/toluene at 25° C. over a 10 minute period. The reaction mixture was warmed to 50° C. (dimethyl sulfide evolution observed) and maintained there under a nitrogen atmosphere for 3 hours. The mixture was then cooled to approximately 30° C. and the addition funnel was charged with 10.7 g of methanol. The first one third of the methanol was added very slowly due to rapid gas evolution. The reaction mixture was then warmed to 50° C. and the addition funnel was charged with 11.5 g (0.11 mol ) of diethylenetriamine (DETA). DETA was added in one portion and the reaction mixture was warmed to 65° C. and stirred for 3 hours, before adding 49.2 g of water. The mixture was cooled to 55° C. and the phases were separated. The reflux condenser was replaced by a distillation-head containing a receiver and the solution was warmed. The solution was azeotropically dried and concentrated. The 34.2 wt % solution of α-(2,3-dimethoxyphenyl)-1-[2-(4-fluorophenyl)ethyl]-4-piperidinemethanol (5) in toluene was allowed to slowly cool to ambient temperature overnight, before cooling to −20° C. The product was collected by suction filtration, washed with 8.2 g of cold isopropanol (5° C.) and dried under vacuum (31 in Hg) at 70° C. for 12 hours to afford 12.5 g (82% ) of α-(2,3-dimethoxyphenyl)-1-[2-(4-fluorophenyl)ethyl]-4-piperidinemethanol (5) as a white crystalline material; m.p. 113-114° C.

$^1$H NMR (CDCl$_3$) δ 7.15-6.63 (m, 7H, aromatic), 4.66-4.61 (m, 1H), 3.66 (s, 3H, —OCH$_3$), 3.65 (s, 3H, —OCH$_3$), 3.11 (d, 1H, J=10.3 Hz), 2.96 (d, 1H, J=11.0 Hz), 2.80-2.75 (m, 2H), 2.60-2.50 (m, 3H), 2.11-1.91 (m, 3H), 1.67-1.65 (m, 1H), 1.53-1.20 (m, 3H);

$^{13}$C NMR (CDCl$_3$) δ 163.0, 159.8, 152.5, 146.6, 136.4, 136.1, 130.0, 129.9, 123.7, 119.7, 115.2, 114.9, 111.6, 96.2, 74.5, 60.8, 60.7, 55.8, 53.7, 42.8, 32.8, 28.7.

EXAMPLE 91

Scheme I, step c: α-(2,3-Dimethoxyphenyl)-1-[2-(4-fluorophenyl)ethyl]-4-piperidinemethanol (5)

A suitable reactor is charged with 4-[1-hydroxy-1-(2,3-dimethoxyphenyl)methyl]-N-2-(4-fluorophen-1-oxo-ethyl)piperidine (20) (63.6 kg, 164 mol, about 18 wt % in toluene) and the concentration is adjusted to about 12 wt % by the addition of toluene. To this solution is added borane methyl sulfide complex, 96.1% (27.2 kg, 344 mol) while maintaining the temperature at about 25° C.[1] The solution is heated to about 50° C. for at least 3 hours. Methanol (41.3 kg) is added to the solution while maintaining the temperature at about 50° C. The solution is then heated to about 65° C. Diethylenetriamine (44.5 kg) is added and the transfer line is flushed with about 9 kg of methanol. The solution is then held at about 65° C. for at least 3 hours. Water (about 190 kg) is added while maintaining a temperature above approximately 55° C. and the phases are separated. The organic phase is washed with about 190 kg of water and the phases are separated at about 60° C. The concentration of α-(2,3-dimethoxyphenyl)-1-[2-(4-fluorophenyl)ethyl]-4-piperidinemethanol (5) in the organic phase is adjusted to about 14 to 30 wt % by atmospheric distillation.[2] The mixture is cooled to about −15° C. and α-(2,3-dimethoxyphenyl)-1-[2-(4-fluorophenyl)ethyl]-4-piperidinemethanol (5) is collected by filtration. The wet cake is washed with about 32 kg of toluene to afford about 49 kg of α-(2,3-dimethoxyphenyl)-1-[2-(4-fluorophenyl)ethyl]-4-piperidinemethanol (5) (80% yield).[3,4]

[1] A portion of the toluene used in the concentration adjustment can be reserved to flush the borane methyl sulfide solution transfer line.
[2] The concentration of α-(2,3-dimethoxyphenyl)-1-[2-(4-fluorophenyl)ethyl]-4-piperidinemethanol (5) is estimated by mass balance. Additional toluene can be added as needed to adjust the concentration.
[3] The yield is determined using the loss on drying and HPLC assay.
[4] α-(2,3-Dimethoxyphenyl)-1-[2-(4-fluorophenyl)ethyl]-4-piperidinemethanol (5) may be recovered from the filtrates by concentrating under vacuum to about 11 wt % (determined by HPLC assay) and then acidifying at about 25° C. with 1 N HCl. The organic phase is discarded and the aqueous phase is neutralized with a sodium hydroxide solution. The α-(2,3-dimethoxyphenyl)-1-[2-(4-fluorophenyl)ethyl]-4-piperidinemethanol (5) is extracted into toluene and the aqueous phase is discarded. The toluene solution is concentrated by atmospheric distillation to about 25-30 wt % (see footnote 2). The solution is cooled to about −10° C. and the α-(2,3-dimethoxyphenyl)-1-[2-(4-fluorophenyl)ethyl]-4-piperidinemethanol (5) is collected by filtration. The wet cake is washed with cold isopropanol to afford additional α-(2,3-dimethoxyphenyl)-1-[2-(4-fluorophenyl)ethyl]-4-piperidinemethanol (5).

EXAMPLE 92

Scheme J, step a: 4-[1-oxo-1-(2,3-dimethoxyphenyl)methyl]-N-2-(4-fluorophen-1-oxo-ethyl)piperidine (4)

Into a 1-L three-neck flask equipped with a mechanical stirrer, a nitrogen bubbler and a 125-mL addition funnel was placed 4-(2,3-dimethoxybenzoyl)piperidine (16) (106.1 g of a 19.24 wt % solution in toluene, 20.4 g, 0.08 mol) and diisopropylethylamine (16.8 g, 0.13 mol). The solution was cooled to −12° C. and the addition funnel was charged with 4-fluorophenylacetyl chloride (71.5 g of a 26.55 wt % solution in toluene, 19.0 g, 0.11 mol). The acid chloride/toluene solution was added over a 17 minute period at a rate as to maintain the internal reaction temperature below 5° C. The reaction mixture was allowed to warm to 25° C. and stir for 1 hour. To the reaction mixture was added concentrated hydrochloric acid (4.7 g) and water (100 g). The mixture was stirred for 5 minutes, phase separated, and the organic phase was concentrated by rotary evaporation (29 Hg, bath 60° C.) to give an orangish-brown solution (128.4 g). This solution of the 4-[1-oxo-1-(2,3-dimethoxyphenyl)methyl]-N-2-(4-fluorophen-1-oxo-ethyl)piperidine (4) may be used in Example 85, Scheme I, step a without further purification.

EXAMPLE 93

Scheme J, step a: 4-[1-oxo-1-(2,3-dimethoxyphenyl)methyl]-N-2-(4-fluorophen-1-oxo-ethyl)piperidine (4)

Into a 500-mL three-neck flask equipped with a mechanical stirrer, a 125-mL addition funnel, and a nitrogen bubbler was placed 4-(2,3-dimethoxybenzoyl)piperidine (16) (85.9 g of a 17.34 wt % solution in toluene, 14.83 g, 0.059 mol), water (15 g), and 50 wt % aqueous sodium hydroxide solution (7.2 g, 0.09 mol). The solution was cooled to 10° C. and the addition funnel was charged with 4-fluorophenylacetyl chloride (64.2 g of a 19.1 wt % solution in toluene, 12.25 g, 0.071 mol). The acid chloride/toluene solution was added over a 5 minute period, resulting in a 12° C. exotherm. The two-phase reaction mixture was allowed to warm to 25° C. and stir for 1 hour. To the reaction mixture was added 20 wt % aqueous solution of sodium chloride (15 g). The phases were separated and the organic phase was concentrated by rotary evaporation (28 Hg, 60° C.) to give a brownish solution (154 g). This solution of the title compound (4) may be used in Scheme E, step a without further purification.

Purification by flash chromatography on silica gel (1:1 heptane/ethyl acetate) gave the title compound as a thick clear oil.

$^1$H NMR (CDCl$_3$) δ 7.24-6.93 (m, 7H, aromatic), 4.42 (br-singlet, 1H), 3.87 (s, 3H, —OC$\underline{H}_3$), 3.83 (s, 3H, —OC$\underline{H}_3$), 3.67 (s, 2H, Ph—C$\underline{H}_2$—CO—), 3.25 (m, 1H), 3.08 (t, 1H, J=5.8 Hz), 3.81 (t, 1H, J=5.7 Hz), 1.84-1.76 (m, 2H), 1.47 (br-singlet, 2H);

$^{13}$C NMR (CDCl$_3$) δ 205.3, 169.2, 163.4, 160.2, 152.8, 147.1, 133.8, 130.7. 130.2, 130.1, 124.2, 120.4, 115.7, 115.4, 115.3, 96.1, 61.7, 56.0, 47.7, 45.6, 41.5, 40.1.

EXAMPLE 94

Scheme J, step a: 4-[1-oxo-1-(2,3-dimethoxyphenyl)methyl]-N-2-(4-fluorophen-1-oxo-ethyl)piperidine (4)

Into a suitable agitated reactor is charged 4-fluorophenylacetic acid (79.4 kg, 515 mol), N,N-dimethylformamide (0.5 kg, 6.8 mol), and toluene (318 kg). Oxalyl chloride (68.3 kg, 538 mol) is added at a rate as to maintain the temperature below 35° C. The solution is stirred for at least 7 hours at about 25° C., typically affording a 22.1 wt % solution of 4-fluorophenylacetyl chloride.[1]

A suitable reactor is charged with 4-(2,3-dimethoxybenzoyl)piperidine (16) (20.4 kg, 86.3 mol, ~20 wt % in toluene), 50 wt % sodium hydroxide solution (11.6 kg, 145 mol) and about 29 kg of water. The mixture is cooled to about 10° C. The 4-fluorophenylacetyl chloride-toluene solution (17.0 kg, 90.2 mol) is added at a rate as to maintain the temperature below 25° C. The addition line is flushed with about 10 kg of toluene and the mixture is held for at least 30 minutes at about 25° C.[2] The phases are separated and the organic phase is washed with 20 wt % sodium chloride solution (29 kg). The organic solution is concentrated by vacuum distillation to approximately ⅓ of its original volume[3] and is used as a toluene solution in Example 87, Scheme I, step a.

[1] The solution is sampled and analyzed by HPLC assay to determine the wt % of 4-fluorophenylacetyl chloride and yield.
[2] The mixture is sampled and analyzed by HPLC assay to confirm the formation of -[1-oxo-1-(2,3-dimethoxyphenyl)methyl]-N-2-(4-fluorophen-1-oxo-ethyl)piperidine (4).
[3] The concentrate is sampled and weighted to determine the amount of 4-[1-oxo-1-(2,3-dimethoxyphenyl)methyl]-N-2-(4-fluorophen-1-oxo-ethyl) piperidine (4) by HPLC analysis. The water content is determined by Karl Fischer analysis if the water content is greater than 300 ppm additional toluene may be added and the distillation continued.

EXAMPLE 95a

Scheme J, step b: N-4-Fluorophenylacetyl)-4-carboxylpiperidine (21)

p-Fluorophenylacetic acid (31.4 g, 0.203 mol) is treated with SOCl$_2$ (45 mL, 0.62 mol) and the resulting solution is heated at reflux for 4 hours. The reaction mixture is diluted with toluene and concentrated by distillation to remove remaining SOCl$_2$. When the temperature of the distillate reaches 114° C., the distillation is discontinued and the reaction mixture cooled to ambient temperature.

A solution of 4-piperidinecarboxylic acid (13) (31.5 g, 0.24 mol) in 100 mL aqueous caustic (10 g, 0.25 mol NaOH), possessing a pH meter, is cooled to 0° C. and treated portionwise with the acid chloride solution; 10 wt % NaOH (aqueous) is added periodically during the acid chloride addition to maintain the reaction mixture pH between 9 and 9.5. After the addition is complete, the mixture is stirred at ambient temperature for 90 minutes to complete the reaction. The mixture is acidified to pH 2.0 with 6 N HCl to precipitate the product. The product is filtered off, washed with H$_2$O, and the filtercake is slurried in ether at reflux for 3 hours. The mixture is filtered, the product dried at 60° C. overnight to provide the title product (21) (42.81 g, 79% yield).

EXAMPLE 95b

Scheme J step b: N-4-Fluorophenylacetyl)-4-carboxylpiperidine (21)

Into a 100-mL three-neck flask equipped with a magnetic stir bar, a 60-mL addition funnel, a stopper and a nitrogen bubbler was placed 5.0 g (0.039 mol) of isonipecotic acid (13), 20 g of acetone, 20 g of water, and 2.7 g (0.02 mol) of potassium carbonate. The mixture was warmed to approximately 32° C. and gas evolution was observed. The addition funnel was charged with 7.3 g (0.039 mol) of 4-fluorophenylacetyl chloride. The 4-fluorophenylacetyl chloride was added to the reaction mixture over a 10 min. period. The reaction mixture was allowed to cool to 25° C. and stir for 1.5 hours. The reaction mixture was transferred to a single-neck flask and concentrated by rotary evaporation to afford a white sludge. The sludge was treated with 39 mL (0.039 mol) of a 1N aqueous hydrogen chloride solution and 50 g of toluene. After stirring for 30 minutes the phases were separated and the organic layer was concentrated. The resulting residue was treated with 50 g of ethyl acetate and 30 g of water. The phases were separated and the volume of the organic phases was reduced by approximately 50% by rotary evaporation. The solution was allowed to stand at 25° C. for 72 h and crystallize. The slurry was cooled to 0° C. and the product was collected by suction filtration and dried under vacuum (30 in Hg) at 50° C. for 8 h to afford 7.3 g (67% yield) of N-4-fluorophenylacetyl)-4-carboxylpiperidine (21) as a white powder.

$^1$H NMR (CDCl$_3$) δ 11.0 (br, 1H, —CO$_2$H), 7.22-7.17 (m, 2H), 7.00 (t, 2H, J=8.6 Hz), 4.39 (d, 1H, J=13.5 Hz), 3.80 (d, 1H, J=13.2 Hz), 3.72 (s, 2H), 3.11 (t, 1H, J=11.0 Hz), 2.90 (t, 1H, J=10.8 Hz), 2.85-2.49 (m, 1H), 1.95 (dd, 1H, $^1$J=9.0, $^2$J=3.2 Hz), 1.82 (dd, 1H, $^1$J=9.1 Hz, $^2$J=2.8 Hz), 1.51 (qt-d, 1H, $^1$J=10.9 Hz, $^2$J=3.8 Hz), 1.43 (qt-d, 1H, $^1$J=11.0, $^2$J=3.8 Hz;

$^{13}$C NMR (CDCl$_3$) δ.178.6, 169.6, 163.4, 160.1, 130.6, 130.2, 115.7, 115.4, 45.3, 41.2, 40.4, 40.0, 28.0, 27.5

EXAMPLE 96

Scheme J, step c: N-(4-Fluorophenylacetyl)-4-(N,O-dimethylhydroxyaminocarboxy)piperidine (22)

N-(4-Fluorophenylacetyl)-4-carboxylpiperidine (21) (10.0 g, 37.7 mmol) is slurried in methylene chloride (100 mL) and treated with solid carbonyldiimidazole (7.33 g, 45 mmol). After stirring for 2 hours, the solution is treated with N,O-dimethylhydroxylamine hydrochloride (5.25 g, 54 mmol) and the reaction is permitted to proceed overnight. The reaction is quenched with 1 N HCl (150 mL) and the phases are separated. The organic phase is washed with H$_2$O (150 mL), extracted with ½-saturated NaHCO$_3$, dried, filtered, and concentrated at reduced pressure. The resulting oil can be distilled via Kugelrohr at 205° C. at 0.05 mm Hg;

however this sample is flash chromatographed (4 cm×16 cm SiO$_2$ column, EtOAc) to provide the title compound (22) as a colorless oil (11.7 g, 98%).

EXAMPLE 97

Scheme J, step d: 4-[1-oxo-1-(2,3-dimethoxyphenyl)methyl]-N-2-(4-fluorophen-1-oxo-ethyl)piperidine (4)

A solution of veratrole (3.80 g, 27.5 mmol) in tetrahydrofuran (30 mL) is cooled to −70° C. and treated with a hexane solution of BuLi (2.5 M, 11 mL, 27.5 mmol). The reaction mixture is allowed to warm to ambient temperature, then stirred for 3 hours. The mixture is cooled to −70° C. and treated, dropwise, with a solution of N-(4-fluorophenylacetyl)-4-(N,O-dimethylhydroxyaminocarboxy)piperidine (22) (4.04 g, 13.1 mmol) in tetrahydrofuran (30 mL). The reaction mixture is allowed to slowly warm to ambient temperature and stirred overnight. The reaction is quenched with NH$_4$Cl (saturated, 40 mL), diluted with toluene (60 mL) and the phases are separated. The organic phase is washed with H$_2$O, dried, filtered, and concentrated at reduced pressure to leave an oil. Flash chromatography (SiO$_2$, 4 cm×15 cm column, 30% EtOAc/toluene, material loaded on column as a toluene solution) provides the title compound (4) (1.86 g, 4.8 mmol).

EXAMPLE 98a

Scheme J, step e: 4-[1-oxo-1-(2,3-dimethoxyphenyl)methyl]-N-2-(4-fluorophen-1-oxo-ethyl)piperidine (4)

A solution of veratrole (5.4 g, 39 mmol) in tetrahydrofuran (100 mL) is cooled to −70° C. and treated with a hexane solution of BuLi (2.5 M, 16 mL, 40 mmol). The reaction mixture is permitted to warm to ambient temperature. After 3 hours, the slurry is cooled to −70° C. and treated with a slurry of N-(4-fluorophenylacetyl)-4-carboxylpiperidine (21) (3.0 g, 11 mmol) in tetrahydrofuran (50 mL). The reaction slurry is permitted to warm to room temperature and is stirred overnight. The dark solution is quenched with NH$_4$Cl, diluted with toluene, and the organic phase separated. The organic phase is extracted with H$_2$O, dried, filtered and concentrated at reduced pressure. The resulting oil is flash chromatographed (SiO$_2$, 30% EtOAc/toluene) to provide the title compound (4) as an oil (1.0 g, 23% yield).

EXAMPLE 98b

Scheme J, step f: N-4-Fluorophenylacetyl)-4-carboxylpiperidine, lithium salt (21a)

Into a 1-L flask equipped with a magnetic stir bar, and nitrogen bubbler was placed 15.0 g (0.053 mol) of N-4-fluorophenylacetyl)-4-carboxylpiperidine (21), 2.24 g (0.053 mol) of lithium hydroxide monohydrate, 175 g of tetrahydrofuran, and 75 g of water. The mixture was stirred at 25° C. for 30 min and the solvent was removed by rotary evaporation. To the resulting residue was added 500 g of toluene and the slurry was azeotropically dried by rotary evaporation. To the resulting white solid was added 200 g of toluene and the product was collected by suction filtration. The wet cake was washed with toluene and dried under vacuum (29 in Hg) at 65° C. for 18 h to afford 15.2 g (99% yield) of the N-4-fluorophenylacetyl)-4-carboxylpiperidine, lithium salt (21a) as a white powder.

$^1$H NMR (D$_2$O) δ 7.28-7.23 (m, 2H), 7.13 (t, 2H, J=8.9 Hz); 4.35 (d, 1H, J=13.5 Hz), 4.01 (d, 1H, J=14.3 Hz), 3.82 (s, 2H), 3.17 (dt, 1H, 1J=12.9, 2J=2.6 Hz), 2.81 (dt, 1H, 1J=12.5, 2J=2.3 Hz, 2.46-2.36 (m, 1H), 1.86 (t, 2H, J=13.4 Hz), 1.44 (qt-d, 2H, 1J=13.3, 2J=3.8 Hz);

$^{13}$C NMR (D$_2$O) δ.186.5, 174.9, 166.1, 162.9, 133.8, 133.3, 118.4, 118.1, 49.1, 46.8, 45.2, 41.7, 31.9, 31.4.

EXAMPLE 98c

Scheme J, step g: 4-[1-Oxo-1-(2,3-dimethoxyphenyl)methyl]-N-2-(4-fluorophen-1-oxo-ethyl)-piperidine (4)

Into a 100-mL three-neck flask equipped with a magnetic stir bar, a septum, 40-mL addition funnel, and a thermometer was placed 4.3 g (0.031 mol) of veratrole and 35 g of tetrahydrofuran. The solution was cooled to −25° C. and the addition funnel was charged with 12.8 mL (0.032 mol) of a 2.5N solution of n-butyllithium in hexanes. The n-butyllithium solution was added at such a rate as to maintain the internal reaction temperature below 0° C. The solution was maintained at 0° C. for 1 h before warming to 25° C. for 1 hour. The resulting slurry was then cooled to −25° C.

Into a 250-mL four-neck flask equipped with a mechanical stirrer, a thermowell with a thermocouple, a septum, and a nitrogen bubbler was placed 7.0 g (0.025 mol) of N-4-fluorophenylacetyl)-4-carboxylpiperidine, lithium salt (21a) and 35 g of tetrahydrofuran. The slurry was cooled to −20° C. and the lithiated veratrole slurry was added via cannula over a 5 min period. The reaction mixture was allowed to warm to 0° C. for 1 h before warming to 25° C. After stirring at 25° C. for 6 hours, the reaction mixture was quenched with 20.0 g of an aqueous saturated ammonium chloride solution. Toluene (20 g) was added and the phases separated. The organic phase was dried over MgSO$_4$ and concentrated to afford a thick oil. Purification by flash chromatography on EM silica gel (230-400 mesh) using heptane and ethyl acetate (1:1) afforded 3.0 g (31% yield) of 4-[1-oxo-1-(2,3-dimethoxyphenyl)methyl]-N-2-(4-fluorophen-1-oxo-ethyl)-piperidine (4) as a thick clear oil.

$^1$H NMR (CDCl$_3$) δ 7.24-6.93 (m, 7H, aromatic), 4.42 (br singlet, 1H), 3.87 (s, 3H, —OCH$_3$), 3.83 (s, 3H, —OCH$_3$), 3.67 (s, 2H, Ph—CH$_2$—CO), 3.25 (m, 1H), 3.08 (t, 1H, J=5.8 Hz), 3.81 (t, 1H, J=5.7 Hz), 1.84-1.76 (m, 2H), 1.47 (br-singlet, 2H);

$^{13}$C NMR (CDCl$_3$) δ. 205.3, 169.2, 163.4, 160.2, 152.8, 147.1, 133.8, 130.7, 130.2, 130.1, 124.2, 120.4, 115.7, 115.4, 115.3, 96.1, 61.7, 56.0, 47.7, 45.6, 41.5, 40.1.

EXAMPLE 99

Scheme K, step a: 4-[1-Oxo-1-(2,3-dimethoxyphenyl)methyl]-N-2-(4-fluorophenylethyl)-piperidine (6)

Solid K$_2$CO$_3$ (184 g, 1.33 mol) and KI (5.5 g, 0.03 mol) were added to a solution of 4-(2,3-dimethoxybenzoyl)piperidine (16) (190 g, 0.67 mol) and 2-(4-fluorophenyl)ethyl bromide (135 g, 0.67 mol) in tetrahydrofuran (3 L) and water (720 mL). The resulting mixture was stirred under reflux for 18 hours. The mixture was concentrated (40° C./20 torr) to remove the majority of tetrahydrofuran. The resulting aqueous solution was extracted with methylene chloride (3×1.2 L) and the combined organic solutions were washed with brine (1.5 L) and dried (MgSO$_4$). The mixture was filtered through a silica gel pad (SiO$_2$ 60, 230-400 mesh, 10 cm×16 cm i.d.) and SiO$_2$ was washed with EtOAc (5 L). The combined filtrates were concentrated (35° C./20 torr) to a residue which was dissolved in EtOAc (2 L). The solution was treated with HCl gas until the solution turned acidic (moist pH paper). The mixture was filtered to afford the title compound (6) as an off-white solid after air-drying (226 g, 84%), m.p. 232-234° C.

IR (KBr) 3431, 2935, 2629, 2548, 1676, 1580, 1512, 1476, 1487, 1317, 1267, 1227, 1161, 1076, 1017, 1001, 954, 836, 764 cm$^{-1}$;

$^1$H NMR (DMSO-d$_6$) δ 11.0 (s, 1H, HCl), 7.0-7.4 (m, 7H, aryl), 3.85 (s, 3H, OCH$_3$), 3.82 (s, 3H, OCH3), 3.6 (m, 1H), 3.4 (m, 2H), 3.2 (m, 2H), 3.0 (m, 4H), 2.0 (m, 4H);

$^{13}$C NMR (DMSO-d$_6$) δ 203.6, 161.1 (d, J$_{F-C}$=241.0 Hz), 152.5, 146.6, 133.4, 133.3, 132.7, 130.6. 124.3, 119.8, 116.1, 115.4 (d, J$_{F-C}$=21.2 Hz), 61.3, 56.5, 56.0, 50.9, 44.9, 28.4, 25.0;

$^{19}$F NMR (DMSO-d$_6$)-116.0;

MS (CI, CH$_4$) m/z (rel. Intensity) 372 (MH$^+$, 100%), 352 (36), 320 (10), 262 (88);

Anal. Calc'd for C$_{22}$H$_{26}$FNO$_3$ HCl (407.9): C, 64.78; H, 6.67; N, 3.43. Found: C, 64.54; H, 6.86; N, 3.30.

EXAMPLE 100

Scheme K, step a: 4-[1-Oxo-1-(2,3-dimethoxyphenyl)methyl]-N-2-(4-fluorophenylethyl)-piperidine (6)

To a solution of 2-(4-fluorophenyl)ethyl alcohol (13.4 mL, 107 mmol) in dry toluene (150 mL) at 0° C. was added phosphorous tribromide (21.1 mL, 224 mmol). The resulting mixture was stirred at ambient temperature for 5 days and then recooled to 0° C. and crushed ice (200 g) added. The aqueous layer was extracted with ether (2×120 mL) and the combined organic extracts were then washed with saturated aqueous sodium bicarbonate solution (2×30 mL), dried (MgSO$_4$) and concentrated in vacuo. Distillation afforded 2-(4-fluorophenyl)ethyl bromide as a colorless oil (14.08 g, 31%); b.p. 103° C. @ 12 mm Hg.

A mixture of 4-(2,3-dimethoxybenzoyl)piperidine (16) (18.5 g, 64.7 mmol), 2-(4-fluorophenyl)ethyl bromide (13.2 g, 65.0 mmol), potassium carbonate (17.92 g, 129.7 mmol) and potassium iodide (0.54 g, 3.25 mmol) in tetrahydrofuran (300 mL) and water (70 mL) was heated at reflux overnight. The resulting mixture was allowed to cool and then concentrated in vacuo to remove the tetrahydrofuran. The residual material was extracted with methylene chloride (3×120 mL) and the combined organic extracts were washed with brine (150 mL), dried (MgSO$_4$), filtered through a plug of silica with ethyl acetate (500 mL) and concentrated in vacuo to afford the title compound (6) as a yellow oil. (22.69 g, 94%).

EXAMPLE 101

Scheme K, step b: Ethyl N-(4-fluorophenylthioacetyl)-4-carboxylpiperidine (24)

A 250 mL flask, equipped with a magnetic stirrer bar, Dean-Stark trap, reflux condenser and CaCl$_2$ drying tube, is charged with 4-piperidinecarboxylic acid, ethyl ester (23) (79.82 g, 0.507 mol), p-fluoroacetophenone (46.75 g, 0.338 mol), sulfur (13 g, 0.406 mol), p-toluenesulfonic acid (1.0 g) and toluene (60 mL). The reaction mixture is heated at reflux with azeotropic removal of H$_2$O for 2.25 hours, then held at reflux for an additional 1.75 hours, then cooled, diluted with toluene (300 mL) and extracted with HCl (2 N, 250 mL). The organic phase is washed with H$_2$O (100 mL) and the aqueous wash is combined with the acid phase and back-extracted with toluene (100 mL). The toluene extract is combined with the original organic phase, washed with H$_2$O (150 mL), extracted with NaHCO$_3$ (250 mL, saturated), dried, filtered and concentrated at reduced pressure. The residue is diluted with 20% aqueous EtOH (500 mL) and treated with filter aid. The filter aid is rinsed with 20% aqueous EtOH (100 mL), the combined filtrate and wash are decanted away from a thick, dark oil. The clear, yellow aqueous EtOH solution is concentrated at reduced pressure and the residual oil is re-dissolved in toluene (500 mL) then re-concentrated to remove remaining water. The oil is passed through a plug of SiO$_2$ (14 cm high×9 cm diameter), eluting with toluene (2 L), then 20% EtOAc in toluene (2 L) to provide the title compound (24) (57.94 g of 88% pure material, 49% yield). A small amount of this material was purified by Kugelrohr distillation; b.p. 180-195° C./0.8 mm Hg.

EXAMPLE 102

Scheme K, step c: 1-(4-carboethoxypiperidine)-2-(4-fluorophenyl)ethane (25)

Neat ethyl N-4-fluorophenylthioacetyl)-4-carboxylpiperidine (24) (20.61 g of 88% purity, 66 mmol) is treated with a solution of BH$_3$XSMe$_2$ (40 mL of 2M in tetrahydrofuran) at ambient temperature. Off-gassing begins after about 30 seconds and the reaction mixture warms. After stirring for 30 minutes at ambient temperature, the reaction is quenched with MeOH (200 mL) and concentrated by atmospheric distillation to remove B(OMe)$_3$. The residue is treated with an additional 200 mL of MeOH and the distillation is continued. The concentrate is diluted with toluene and concentrated at reduced pressure. This toluene-dilution, concentration is repeated to ensure complete removal of B(OMe)$_3$. Kugelrohr distillation (b.p. 148-160° C./0.8 mm Hg) provides the title compound (25) (13.1 g, 73% yield).

EXAMPLE 103

Scheme K, step d: 1-(4-carboxypiperidine)-2-(4-fluorophenyl)ethane (26)

1-(4-carboethoxypiperidine)-2-(4-fluorophenyl)ethane (25) (13.6 g, 48.7 mmol), AcOH (50 mL) and HCl (50 mL of 6 M) are heated at reflux for 3 hours. The mixture is concentrated to half-volume by atmospheric distillation, then remaining solvent is removed at reduced pressure. The residue is crystallized from isopropanol (100 mL) to provide the title compound (26) (9.82 g, 70% yield); m.p. 215-221° C.

EXAMPLE 104

Scheme K, step e: 1-(4'-(N,O-Dimethylhydroxyaminocarboxy)piperidino)-2-(4'-fluorophenyl)ethane (27)

A slurry of 1-(4-carboxypiperidine)-2-(4-fluorophenyl) ethane (26)(4.36 g, 15.2 mmol) in chloroform (30 mL) is treated with 1,1'-carbonyldiimidazole (2.75 g, 17 mmol).

Within 30 seconds of the addition, $CO_2$ evolution begins and the solution becomes clear. After stirring for 45 minutes at ambient temperature, the solution is treated with N,O-dimethylhydroxylamine hydrochloride (2.1 g, 21 mmol) and stirred overnight. The slurry is concentrated at reduced pressure, then re-slurried in toluene and re-concentrated to ensure complete removal of $CHCl_3$. The residue is stirred in 50% toluene/ether (100 mL) and extracted with NaOH (2.5 M, 60 mL). The organic phase is separated, extracted twice with $H_2O$ (60 mL each), dried, filtered, and concentrated. The solid residue is purified by Kugelrohr distillation (b.p. 155-175° C./1 mm Hg) to give the title compound (27) as a white solid (3.80 g, 85% yield).

EXAMPLE 105a

Scheme K, step f: 4-[1-Oxo-1-(2,3-dimethoxyphenyl)methyl]-N-2-(4-fluorophenylethyl)-piperidine (6)

Veratrole (2.0 g, 14.5 mmol) in tetrahydrofuran (12 mL) is treated with BuLi (6 mL of 2.5 M hexane solution) at −60° C. The reaction mixture is permitted to warm to 20° C. over 45 minutes; then the yellow slurry is cooled to −20° C. and treated with a solution of 1-(4'-(N,O-dimethylhydroxylaminocarboxy)piperidino)-2-(4'-fluorophenyl)ethane (27) (3.8 g, 12.9 mmol) in tetrahydrofuran (20 mL). After the addition is complete, the reaction mixture is permitted to warm to ambient temperature and react for 45 minutes, then quenched with $H_2O$ and diluted with toluene. The organic phase is separated, washed with $H_2O$, dried, filtered and concentrated to provide the title compound (6) as an oil.

EXAMPLE 105b

Scheme K, step g: 1-(4-carboethoxypiperidine)-2-(4-fluorophenyl)ethane (25)

Into a 500-mL three-neck flask equipped with a mechanical stirrer, a reflux condenser topped with a nitrogen bubbler and a stopper was placed 13.0 g (0.083 mol) of 4-piperidinecarboxylic acid, ethyl ester (23), 19.9 g (0.091 mol) or 4-fluorophenyethyl mesylate (2), 12.6 g (0.091 mol) of potassium carbonate, 1.37 g (0.0091 mol) of sodium iodide and 208 g of acetonitrile. The reaction mixture was warmed to 75° C. and stirred under a nitrogen atmosphere overnight. The reaction contents after cooling to 25° C. were transferred to a 1-L single-neck flask containing 56 g of water. The mixture was concentrated by rotary evaporation to afford a yellowish aqueous solution. The aqueous solution was extracted with methylene chloride (2×75 g) and the combined extracts were dried over $MgSO_4$. Filtration and concentration by rotary evaporation afforded 23 g (99% yield) of 1-(4-carboethoxypiperidine)-2-(4-fluorophenyl) ethane (25) as a pale-yellow liquid (purity: 97 area %, by GC analysis).

$^1$H NMR ($CDCl_3$) δ 7.13 (t, 2H, J=7.3 Hz), 6.97-6.91 (m, 2H), 4.15-4.08 (m, 2H), 2.90 (t, 2H, J=11.0 Hz), 2.75 (t, 2H, J=7.3 Hz), 2.54 (t, 2H, J=9.1 Hz), 2.31-2.24 (m, 1H), 2.06 (t, 2H, J=11.2 Hz), 1.91 (d, 2H, J=11.5 Hz), 1.83-1.70 (m, 2H), 1.24 (t, 3H, J=7.0 Hz);

$^{13}$C NMR ($CDCl_3$) δ 175.0, 163.0, 159.8, 136.1, 130.1, 130.0, 115.2, 114.9, 60.6, 60.2, 53.0, 41.2, 32.9, 28.4, 14.2.

EXAMPLE 105c

Scheme K, step h: 1-(4-carboethoxypiperidine)-2-(4-fluorophenyl)ethane, lithium salt (25a)

Into a 100-mL two-neck flask equipped with a magnetic stir bar, a reflux condenser topped with a nitrogen bubbler, and a thermowell with a thermocouple was placed 5.0 g (0.018 mol) of 1-(4-carboethoxypiperidine)-2-(4-fluorophenyl)ethane (25), 0.75 g (0.018 mol) of lithium hydroxide monohydrate, 40 g of tetrahydrofuran and 20 g of water. The mixture was warmed to 63° C. and maintained there under a nitrogen atmosphere overnight (18 hours). The reaction mixture was then cooled to 25° C. and concentrated by rotary evaporation to afford a sludge. Toluene (150 g) was added and removed by rotary evaporation to azeotropically dry the product. The resulting solid was dried under vacuum (27 in Hg) at 70° C. for 6 h to afford 4.6 g (>99% yield) of 1-(4-carboethoxypiperidine)-2-(4-fluorophenyl)ethane, lithium salt (25a) as a white powder.

$^1$H NMR ($D_2O$) δ 7.02 (t, 2H, J=6.3 Hz), 6.44 (t, 2H, J=8.4 Hz), 3.00-2.95 (m, 2H), 2.82-2.75 (m, 2H), 2.58-2.48 (m, 2H), 2.30-2.20 (m, 1H), 1.97-1.72 (m, 4H), 1.54-1.42 (m, 2H);

$^{13}$C NMR ($D_2O$) δ 187.6, 165.8, 162.6, 139.1, 133.2, 133.1, 118.3, 118.0, 62.9, 55.6, 47.7, 47.2, 34.3, 31.8, 31.5.

EXAMPLE 105d

Scheme K, step i: 4-[1-Oxo-1-(2,3-dimethoxyphenyl)methyl]-N-2-(4-fluorophenylethyl)-piperidine (6)

Into a 100-mL three-neck flask equipped with a magnetic stir bar, a septum, a thermowell with a thermocouple, and a nitrogen bubbler was placed 1.8 g (0.013 mol) of veratrole and 30 g of tetrahydrofuran. The solution was cooled to −20° C. before 5.1 mL (0.013 mol) of a 23.3 wt % solution of n-butyllithium in hexanes was added via syringe. The n-butyllithium/hexane solution was added at such a rate as to maintain the internal reaction temperature below −10° C. during the addition. The slurry was then warmed to 25° C. and stirred for 2 h before cooling to −20° C.

Into a 100-mL jacketed-bottom-drain resin pot fitted with a four-joint head equipped with a mechanical stirrer, a thermowell with a thermocouple, a reflux condenser topped with a nitrogen bubbler, and a septum was placed 3.0 g (0.012 mol) of 1-(4-carboethoxypiperidine)-2-(4-fluorophenyl)ethane, lithium salt (25a) and 30 g of tetrahydrofuran. The slurry was cooled to −15° C. and the cold lithiated veratrole/tetrahydrofuran slurry was added via cannula while maintaining the internal reaction temperature below −5° C. The reaction mixture was then maintained at 5° C. for 1 h, before warming to 6° C. The reaction mixture was allowed to stir overnight at 6° C. under a nitrogen atmosphere (15 h). The reaction was determined to be complete by GC analysis. To the reaction mixture was added 50 g of water (at 6° C.) and the solution was warmed to 25° C. The phases were separated and the organic phase was dried over $MgSO_4$. Filtration and concentration by rotary evaporation afforded 3.1 g (70% yield) of 4-[1-oxo-1-(2,3-dimethoxyphenyl)methyl]-N-2-(4-fluorophenylethyl)-piperidine (6), 98% pure by GC analysis.

$^1$H NMR ($CDCl_3$) δ 7.24-7.19 (m, 2H), 7.15-7.08 (m, 3H), 7.00 (t, 2H, J=8.5 Hz), 3.90 (s, 3H), 3.85 (s, 3H), 3.70-3.60 (m, 2H), 3.48-3.39 (m, 2H), 3.27-3.10 (m, 2H), 3.01-2.60 (m, 3H), 2.45-2.31 (m, 2H), 2.16 (d, 2H, J=14.1 Hz)

$^{13}$C NMR (CDCl$_3$) δ 203.7, 152.5, 146.6, 133.4, 133.35, 132.7, 130.6, 124.3, 119.8, 115.5, 115,2, 61.3, 56.5, 56.0, 50.1, 48.7, 44.9, 39.5, 28.4, 25.0.

EXAMPLE 106

Scheme L, step a:
4-(2,3-Dimethoxybenzoyl)piperidine (16)

4-(2,3-dimethoxybenzoyl)-1-piperidinecarboxylic acid, 1,1-dimethylethyl ester (7) (~0.1128 mol) was cooled to 0° C., treated with trifluoroacetic acid (85 mL), and stirred at ambient temperature for 1 hour. Following concentration in vacuo, the material was dissolved in water (300 mL), washed with hexane (2×110 mL) and then treated with solid sodium hydroxide (18 g). The resulting aqueous solution was then extracted with methylene chloride (3×170 mL). The combined organic extracts were washed with brine (220 mL), dried (MgSO$_4$) and concentrated in vacuo. The resulting residue was dissolved in ethanol (110 mL), cooled to 0° C., treated with anhydrous hydrogen chloride gas until acidic, diluted with ether (110 mL) and stirred for 1 hour. The resulting solid was collected by filtration, then washed with a mixture of ethanol and ether (1:1, 110 mL) to afford 4-(2,3-dimethoxybenzoyl)piperidine (16) hydrochloride salt as a white solid (19.18 g, 53%).

EXAMPLE 107

Scheme L, step a:
4-(2,3-Dimethoxybenzoyl)piperidine (16)

Into a 25-mL three-neck flask equipped with a thermowell with a thermocouple, a reflux condenser, a stopper, and a magnetic stir bar was placed 4-(2,3-dimethoxybenzoyl)-1-piperidinecarboxylic acid, 1,1-dimethylethyl ester (7) (1.1 g, 3.0 mmol) and 9.7 g of tetrahydrofuran. After 4-(2,3-dimethoxybenzoyl)-1-piperidinecarboxylic acid, 1,1-dimethylethyl ester (7) had dissolved, 6.3 g of 3N aqueous hydrochloric acid was added in one portion. The reaction was stirred to 18 hours at ambient temperature and then heated to 60° C. for 4 hours to give 4-(2,3-dimethoxybenzoyl)piperidine hydrochloride.

Into a 250-mL flask containing a stir bar was placed 4-(2,3-dimethoxybenzoyl)piperidine hydrochloride (13.2 g, 0.046 mol), 66 g of 2-butanol and 6.6 g of water. The mixture was heated to reflux before allowing to slowly cool to ambient temperature. The crystalline slurry was cooled to 0° C. before the product was collected by vacuum filtration. The wet cake was washed with 10 g of 2-butanol (0° C.) and dried under vacuum (25 in Hg) at 90° C. for 72 hours. Drying afforded 4-(2,3-dimethoxybenzoyl)piperidine hydrochloride (10 g, 76%); m.p. 198-200° C.

$^1$H NMR (D$_2$O) δ 7.32-7.24 (m, 2H, aromatic), 7.14 (s, 2H, J=7.4 Hz, aromatic), 4.89 (s, 1H, —NH), 3.94 (s, 3H, —OCH$_3$), 3.85 (s, 3H, —OCH$_3$), 3.62-3.51 (m, 3H), 3.19 (dt, 2H, J=12.5, 2.6 Hz), 2.18 (d, 2H, J=12.1 Hz), 1.95-1.80 (m, 2H);

$^{13}$C NMR (D$_2$O) δ 210.4, 155.6, 149.6, 135.2, 128.3, 120.1, 65.1, 59.3, 47.6, 46.3, 27.4;

IR (KBr) 3433, 2935, 2711, 1670, 1577, 1473, 1420, 1314, 1256, 1003, 992, 750 cm$^{-1}$.

Into a 250-mL single-neck flask equipped with a stir bar and reflux condenser was placed 5.0 g (0.017 mol) of 4-(2,3-dimethoxybenzoyl)piperidine (16) hydrochloride (5.0 g, 0.017 mol), 2.0 g of a 50 wt % aqueous sodium hydroxide solution and 70 g water. The solution was stirred at 25° C. for 1 hour before 75 g of toluene was added. After stirring for 30 minutes the phases were separated and the organic phase was dried over 5 g of magnesium sulfate. Filtration and concentration by rotary evaporation (29 in Hg, bath temperature 60° C.) resulted in a pale-yellow liquid. The liquid was further concentrated under vacuum (0.05 mm Hg) at 25° C. for 20 hours to afford 4-(2,3-dimethoxybenzoyl)piperidine (16) as a pale yellow thick oil (3.97 g, 94%).

$^1$H NMR (D$_2$O) δ 7.12-6.96 (m, 3H, aromatic), 3.89 (s, 3H, —OCH$_3$), 3.87 (s, 3H, —OCH$_3$), 3.27-3.10 (m, 3H), 2.71-2.64 (m, 3H);

$^{13}$C NMR (D$_2$O) δ 206.2, 152.6, 146.9, 134.1, 124.1, 120.2, 114.8, 61.6, 55.8, 48.3, 45.8, 28.8.

EXAMPLE 108

Scheme L, step a:
4-(2,3-Dimethoxybenzoyl)piperidine (16)

To the reaction solution of 4-(2,3-dimethoxybenzoyl)-1-piperidinecarboxylic acid, 1,1-dimethylethyl ester (7) from Example 76, Scheme G, step c, is added about 188 kg of water and 37% hydrochloric acid (39 kg, 395 mol). The solution is heated to about 60° C. for about 18 hours[1]. The mixture is cooled to about 25° C. and about 47 kg of toluene is added. The phases are separated and the organic phase is discarded. To the aqueous phase is added about 78 kg water, 50 wt % sodium hydroxide solution (31 kg, 391 mol), and about 99 kg of toluene. The phases are separated and the aqueous phase is discarded. The organic phase is concentrated by vacuum distillation. The concentration of 4-(2,3-dimethoxybenzoyl)piperidine (16) in solution ranges from 17 to 53 wt %[1], affording 14.6 to 17.9 kg of 4-(2,3-dimethoxybenzoyl)piperidine (16) (65-76% yield).

[1]The solution is sampled and analyzed by HPLC assay to confirm complete deprotection to afford 4-(2,3-dimethoxybenzoyl)piperidine (16). The reaction is complete if less than 5 area % of 4-(2,3-dimethoxybenzoyl)-1-piperidinecarboxylic acid, 1,1-dimethylethyl ester (7) is detected.

EXAMPLE 109

Scheme L, step a:
4-(2,3-Dimethoxybenzoyl)piperidine (16)

Trifluoroacetic acid (1.1 kg, 745 mL) was added to the residue obtained from Scheme G, step c, Example 70 and the mixture was stirred at room temperature for 1 hour. The resulting solution was concentrated (35° C./20 torr) and the residue was dissolved in water (2.5L). The aqueous solution was washed with hexane (2×1 L) and treated with 50% NaOH (300 g). The resulting solution was extracted with methylene chloride (3×1.5 L). The combined organic solutions were washed with brine (2 L) and dried (MgSO$_4$). The mixture was filtered and the filtrate was concentrated (30° C./20 torr). The residue was dissolved in anhydrous EtOH (1 L) and treated with hydrogen chloride (gas) with stirring until the solution turned acidic (moist pH paper). Ethyl ether (1 L) was added to the mixture which was stirred for 1 hour. Solid was collected by filtration and washed with 1:1 of EtOH:Et$_2$O (1L) to give the title product (16) (212 g, 74%) after air-drying; m.p. 198-200° C.

IR 3433, 2934, 2711, 2509, 1670, 1578, 1472, 1420, 1314, 1266, 1224, 1002, 992, 750 cm$^{-1}$;

$^1$H NMR (CDCl$_3$) δ 9.6 (br s, 1H), 9.4 (br s, 1H), 7.0 (m, 3H, aryl), 3.89 (s, 3H, OCH$_3$), 3.87 (s, 3H, OCH$_3$), 3.4 (m, 3H), 3.1 (m, 2H), 2.2 (m, 2H), 2.1 (m, 2H);

$^{13}$C NMR (CDCl$_3$) δ 203.4, 152.6, 147.0, 132.6, 124.6, 120.5, 115.6, 61.7, 55.9, 44.5, 42.8, 24.8;

MS (EI) m/z (rel. Intensity) 249 (M$^+$, 38%), 218 (21), 193 (100), 165 (49), 122 (15), 82 (17), 77 (19), 56 (60);

Anal. Calc'd. For C$_{14}$H$_{19}$NO$_3$ HCl (285.7): C, 58.84; H, 7.05; N, 4.90. Found: C, 58.56; H, 7.14; N, 5.01.

EXAMPLE 110

Scheme L, step a: 4-(2,3-Dimethoxybenzoyl)piperidine (16)

To the reaction mixture from Scheme G, step c, Example 71 at 10° C. was added 187.5 g of water and 62.5 g of 37% aqueous hydrochloric acid. The reaction mixture was then warmed to 60° C. and stirred for 12 hours (mild gas evolution was observed). The reaction mixture was cooled to 40° C. and 75 g of toluene was added. The phases were separated and the organic phase was discarded. The aqueous phase was cooled to 0° C. and 50 g of a 50 wt % aqueous solution of sodium hydroxide was added while maintaining the internal reaction temperature below 25° C. The resulting pale-green solution (pH 12.7) turned purplish-brown and finally orange upon addition of 200 g of toluene. The mixture was stirred for 30 minutes before allowing to stand and phase separate to 30 minutes. The phases were separated and the organic phase azeotropically dried by vacuum distillation (29 in Hg, bath 60° C.). The solution was concentrated to approximately 40% of its original volume affording the title compound (16) as a pale orangish-brown solution (17.35 g, 14.6 wt % solution, 80% yield).

EXAMPLE 111

Scheme M, step a: 4-[1-Hydroxy-1-(2,3-dimethoxyphenyl)methyl]-N-2-(4-fluorophen-1-oxo-ethyl) piperidine (20)

A 100-mL, four-necked, round-bottomed flask, equipped with a reflux condenser, mechanical stirrer, addition funnel, thermocouple, and nitrogen bubbler, was charged with 3.23 g (13.1 mmol) of 4-[1-hydroxy-1-(2,3-dimethoxyphenyl)methyl]piperidine (11) and 50 mL of toluene. The 4-[1-hydroxy-1-(2,3-dimethoxyphenyl)methyl]piperidine -did not completely dissolve in the toluene. The reaction vessel was then charged with 4 mL of a 5N solution of sodium hydroxide (20 mmol). The reaction mixture was cooled to 2° C. with an ice bath. The addition funnel was charged with 2.71 g (15.7 mmol) of 4-fluorophenylacetyl chloride dissolved in 15 mL of toluene. The solution of acid chloride was added to the reaction vessel over 12 minutes. The temperature of the reaction mixture was maintained at less than 4° C. during the addition. As the acid chloride was added, the 4-[1-hydroxy-1-(2,3-dimethoxyphenyl)methyl]piperidine appeared to be dissolving. However, before the acid chloride was completely added, a gummy ball of solid formed in the reaction vessel. In order to dissolve the solid, 10 mL of water was added to the reaction vessel. It took approximately 15 minutes for the gummy solid to dissolve. The reaction mixture was allowed to stir for 1 hour at room temperature.

The reaction mixture was diluted with 25 mL of a 20% aqueous solution of sodium chloride and transferred to a separatory funnel. The organic phase was dried over anhydrous magnesium sulfate, filtered through a medium sintered glass funnel, and evaporated to dryness using a rotary evaporator and vacuum oven overnight at room temperature. The isolated product (20) was a pale yellow foam which weighed 5.34 g and was used in Scheme E, step c, without further purification.

EXAMPLE 112

Scheme M, step a: 4-[1-Hydroxy-1-(2,3-dimethoxyphenyl)methyl]-N-2-(4-fluorophen-1-oxo-ethyl) piperidine (20)

Into a suitable reactor is charged 4-fluorophenylacetic acid (122.5 kg, 795 mol), N,N-dimethylformamide (0.37 kg, 5.1 mol), and toluene (490 kg). Oxalyl chloride (105.2 kg, 829 mol) is added at a rate to maintain the temperature at about 35° C. The solution is stirred for at least 7 hours at about 25° C., typically affording a solution of about 22.1 wt % 4-fluorophenylacetyl chloride (99% yield as determined by HPLC assay).

A suitable inert reactor is charged with 4-[1-hydroxy-1-(2,3-dimethoxyphenyl)methyl]piperidine (11) (45.6 kg, 181 mol, about 6 wt % solution in methanol) and the concentration of 4-[1-hydroxy-1-(2,3-dimethoxyphenyl)methyl]piperidine (11) is adjusted to about 20 wt % or higher by atmospheric distillation[1]. Toluene (about 550 kg) is added and distillation is continued until the temperature reaches about 110° C. Toluene is added[2] while at reflux to adjust the mixture to about a 9 wt % solution of 4-[1-hydroxy-1-(2,3-dimethoxyphenyl)methyl]piperidine (11). The reaction mixture is cooled to about 30° C., causing precipitation of 4-[1-hydroxy-1-(2,3-dimethoxyphenyl)methyl]piperidine (11)[3] before 50 wt % solution of sodium hydroxide (17.4 kg, 217 mol) and about 182 kg of water are added. The 4-fluorophenylacetyl chloride/toluene solution (32.8 kg, 190 mol) is added at a rate to maintain the temperature at about 25° C. The addition line is flushed with 10 kg of toluene.[4] The phases are separated and the organic phase is washed with about 180 kg of water. The organic phase is concentrated and dried by atmospheric distillation[5]. The concentration of 4-[1-hydroxy-1-(2,3-dimethoxyphenyl)methyl]-N-2-(4-fluorophen-1-oxo-ethyl)piperidine (20) is about 18 wt % as determined by HPLC assay, affording about 67 kg of 4-[1-hydroxy-1-(2,3-dimethoxyphenyl)methyl]-N-2-(4-fluorophen-1-oxo-ethyl)piperidine (20) (95% yield).[6]

[1] The approximate wt % of 4-[1-hydroxy-1-(2,3-dimethoxyphenyl)methyl]piperidine (11) is arrived at by removal of approximately two-thirds of initial solvent. An exact wt % can be obtained by HPLC analysis of the solution.
[2] The amount of toluene back added is determined by weighing the distillate and knowing the amount of toluene initially added.
[3] 4-[1-Hydroxy-1-(2,3-dimethoxyphenyl)methyl]piperidine (11) can be isolated at this stage is desired to increase its purity by cooling to about 20° C. and isolation by filtration.
[4] The mixture is sampled and analyzed by HPLC assay to confirm the formation of 4-[1-hydroxy-1-(2,3-dimethoxyphenyl)methyl]-N-2-(4-fluorophen-1-oxo-ethyl)piperidine (20). The reaction is complete if less than 3% of 4-[1-hydroxy-1-(2,3-dimethoxyphenyl)methyl]piperidine (11) (by area percent) is detected.
[5] The solution is sampled and the water content is determined by Karl Fischer titration. If the water content is above 500 ppm, additional toluene may be added and the distillation continued.
[6] The 4-[1-hydroxy-1-(2,3-dimethoxyphenyl)methyl]-N-2-(4-fluorophen-1-oxo-ethyl)piperidine (20)/toluene solution is filtered through a cartridge filter and stored in drums for use in Scheme I, step c.

EXAMPLE 113a

Scheme M, step a: 4-[1-Hydroxy-1-(2,3-dimethoxyphenyl)methyl]-N-2-(4-fluorophen-1-oxo-ethyl) piperidine (20)

Into a 1-L three-neck flask equipped with a mechanical stirrer, an addition funnel, and a nitrogen bubbler vented to a water scrubber was placed 60.0 g (0.389 mol) of 4-fluorophenylacetic acid, 0.18 g, 0.002 mol) of N,N-dimethylformamide and 250 g of toluene. The addition funnel was charged with 50.4 g (0.397 mol) of oxalyl chloride and added to the reaction mixture over a 10 minute period resulting in gas evolution (4.7° C. exotherm was observed). The reaction mixture was stirred at ambient temperature for 2.5 hours (gas evolution complete) and the head space of the reaction flask was sparged with nitrogen for 10 minutes before storing the material. HPLC assay of the solution indicated that 19.1 wt % of the solution was 4-fluoroacetyl chloride, thus affording a 99% yield. Purification of crude 4-fluorophenylacetyl chloride by vacuum distillation (57-58° C., 0.15 mm Hg) affords 4-fluorophenylacetyl chloride as a clear liquid in 90% yield.

$^1$H NMR (CDCl$_3$) δ 7.25-7.21 (m, 2H, aromatic), 7.05 (t, 2H, J=8.6 Hz, aromatic), 4.11 (s, 2H, —CH$_2$);

$^{13}$C NMR (CDCl$_3$) δ 171.6, 164.2, 160.9, 131.2, 131.1, 127.1, 127.0, 116.4, 115.7, 52.1.

Into a 250-mL jacketed-bottom drain resin pot equipped with a thermowell with thermocouple and a four-joint head fitted with a mechanical stirrer, a distillation head with receiver, and two stoppers was placed 108.4 g (0.027 mol) of a 6.2 wt % solution of 4-[1-hydroxy-1-(2,3-dimethoxyphenyl)methyl]piperidine (11) in methanol from Example 90, Scheme I. step c. The solution was heated and 81.6 g of methanol distillate was collected. To the slurry was added 80.7 g of toluene and the distillation was continued. The distillation was terminated when both the pot and distillation head temperatures stabilized at 110° C. (141 g of distillate was collected). To the slurry was added an additional 25.9 g of toluene, before warming to 110° C. to completely dissolve all of the 4-[1-hydroxy-1-(2,3-dimethoxyphenyl)methyl]piperidine (11). The solution was allowed to cool and crystallize over a 30 minutes period to 28° C. To the slurry was added 2.55 g (0.032 mol) of a 50 wt % solution of aqueous sodium hydroxide and 26.9 g of water. The flask was equipped with an addition funnel which was charged with 22.2 g (0.028 mol) of a 22.2 wt % solution of 4-fluorophenylacetyl chloride in toluene. After the three-phase mixture had stirred for 15 minutes, the 4-fluorophenylacetyl chloride/toluene solution was added dropwise over a 5 minute period. This resulted in formation of a two-phase solution. The mixture was allowed to stir at ambient temperature under a nitrogen atmosphere for 2 hours before monitoring by HPLC. The reaction was determined to be complete by HPLC, agitation was stopped and the phases were allowed to separate. The phases were separated and the organic phase was washed with 13.4 g of water. The toluene/4-fluorophenylacetyl chloride solution was azeotropically dried and concentrated by distillation until both the pot and distillation-head temperature reached 110° C. Distillation afforded 31.9 g of a pale-yellow solution which contained 30.6 wt % of 4-[1-hydroxy-1-(2,3-dimethoxyphenyl)methyl]-N-2-(4-fluorophen-1-oxo-ethyl)piperidine (20) by HPLC assay (95% yield).

Concentration and purification by flash chromatography on EM silica gel, 230-400 mesh (particle size 0.040-0.063 mm) using heptane and ethyl acetate (4:1) afforded purified 4-[1-hydroxy-1-(2,3-dimethoxyphenyl)methyl]-N-2-(4-fluorophen-1-oxo-ethyl)piperidine (20) as a thick clear oil.

$^1$H NMR (CDCl$_3$) δ 7.20-7.13 (m, 2H, aromatic), 7.05-6.93 (m, 3H, aromatic), 6.87-6.82 (m, 2H, aromatic), 4.61-4.54 (m, 2H, —CH$_2$), 3.91-3.65 (m, 6H, —OCH$_3$), 6.54 (d, 2H, J=9.4 Hz), 3.02-2.71 (m, 1H), 2.63 (s, 1H), 2.60-2.35 (m, 1H), 2.02-1.80 (m, 2H), 1.32-1.09 (m, 4H);

$^{13}$C NMR (CDCl$_3$) δ 169.0, 163.3, 160.0, 152.4, 146.4, 136.1, 135.9, 131.0, 130.2, 130.1, 123.9, 119.4, 119.3, 115.5, 115.2, 111.6, 111.5, 73.5, 73.2, 60.7, 60.3, 55.7, 46.2, 46.1, 43.0, 42.0, 41.9, 40.0, 28.9, 28.7, 28.3, 27.9

EXAMPLE 113b

Scheme M, step a: 4-[1-Hydroxy-1-(2,3-dimethoxyphenyl)methyl]-N-2-(4-fluorophen-1-oxo-ethyl) piperidine (20)

Into a 500-mL four-neck flask equipped with a mechanical stirrer, a thermowell with a thermocouple, a 125-mL addition funnel topped with a nitrogen bubbler, and a distillation head was placed 70.5 g (0.031 mol) of 4-[1-hydroxy-1-(2,3-dimethoxyphenyl)methyl]piperidine (11) as an 11.1 wt % solution in methanol (containing 2.9 wt % of acetic acid). The solution was warmed and approximately ⅔ of the methanol was removed by atmospheric distillation. To the concentrated solution was added 110 g of toluene and the distillation was continued until the distillation head temperature reached 98° C. At the end of the solvent exchange the toluene unit ratio is adjusted to 10. This was accomplished by determining the weight of the distillate and knowing the amount of toluene initially added. The 4-[1-hydroxy-1-(2,3-dimethoxyphenyl )methyl]piperidine (11)/toluene/acetic acid solution was allowed to cool to 60° C. To the solution was added 47 g of water. The resulting slurry was allowed to stir for 15 min and the addition funnel was charged with 27.1 g (0.034 mol) of a 21.7 wt % solution of 4-fluorophenylacetyl chloride in toluene. The 4-fluorophenyl acetyl chloride/toluene solution was added in one portion to the slurry at 40° C., resulting in a 4° C. exotherm. Within minutes of the addition, the three-phase system became a two-phase system. The reaction mixture was allowed to cool to ambient temperature and stir for 2 h. The phases were separated and the organic phase was washed with 15.7 g of a 1N hydrochloric acid solution and 15.7 g of water. The 4-[1-hydroxy-1-(2,3-dimethoxyphenyl)methyl]-N-2-(4-fluorophen-1-oxo-ethyl)piperidine (20)/toluene solution was concentrated and azeotropically dried by rotary evaporation to afford a 95% yield of 4-[1-hydroxy-1-(2,3-dimethoxyphenyl)methyl]-N-2-(4-fluorophen-1-oxo-ethyl) piperidine (20) as an 11.5 wt % solution in toluene.

EXAMPLE 114

Scheme M, step b:4-[1-Hydroxy-1-(2,3-dimethoxyphenyl)methyl]-N-2-(4-fluorophen-1-oxo-ethyl) piperidine (20)

A solution of 4-[1-oxo-1-(2,3-dimethoxyphenyl)methyl]-N-2-(4-fluorophen-1-oxo-ethyl)piperidine (4) (1.0 g, 2.5 mmol), EtOH (10 mL) is treated with 1 drop of 5N NaOH and NaBH$_4$ (0.20 g, 5.2 mmol). The resulting solution is stirred at ambient temperature overnight, quenched with acetone (2 mL) and stirred for an additional 30 minutes. The solution is concentrated at reduced pressure, the residue partitioned between EtOAc (30 mL) and 2 N NaOH (30 mL). The phases are separated and the organic phase is washed with water, then brine (saturated) and dried. The mixture is filtered and the filtrate is concentrated at reduced pressure to provide an oil. Flash chromatography (SiO$_2$, 3:1 EtOAc/toluene) provides the title compound (20) as a semi-solid (0.69 g, 70% yield).

As stated previously, (R)-α-(2,3-dimethoxyphenyl)-1-[2-(4-fluorophenyl)ethyl]-4-piperidinemethanol (3) is a 5HT$_2$ receptor antagonist useful in the treatment of a number of disease states, including schizophrenia, anxiety, variant angina, anorexia nervosa, Raynaud's phenomenon, intermittent claudication, coronary or peripheral vasospasms, fibromyalgia, cardiac arrhythmia's, thrombotic illness and in controlling the extrapyramidal symptoms associated with neuroleptic therapy. The present invention provides methods of treating these diseases comprising administering an effective amount of (R)-α-(2,3-dimethoxyphenyl)-1-[2-(4-fluorophenyl)ethyl]-4-piperidinemethanol (3) having a particle size range of approximately 25 μm to approximately 250 μm, such treatment being in accordance with the techniques and procedures provided in U.S. Pat. No. 5,134,149, issued Jul. 28, 1992; U.S. Pat. No. 5,700,813, issued Dec. 23, 1997, U.S. Pat. No. 5,700,812, issued Dec. 23, 1997, and U.S. Pat. No. 5,561,144, issued Oct. 1, 1996, the disclosure of each of which is hereby incorporated by reference.

In effecting treatment of a patient, effective amounts of (R)-α-(2,3-dimethoxyphenyl)-1-[2-(4-fluorophenyl)ethyl]-4-piperidinemethanol (3) may be administered orally in solid unit dosage forms, including tablets, and the present invention provides pharmaceutical compositions containing effective amounts of (R)-α-(2,3-dimethoxyphenyl)-1-[2-(4-fluorophenyl)ethyl]-4-piperidinemethanol (3) in combination with one or more inert ingredients. These pharmaceutical composition may contain (R)-α-(2,3-dimethoxyphenyl)-1-[2-(4-fluorophenyl)ethyl]-4-piperidinemethanol (3) of unspecified particle size or may contain (R)-α-(2,3-dimethoxyphenyl)-1-[2-(4-fluorophenyl)ethyl]-4-piperidinemethanol (3) having a particle size range of approximately 25 μm to approximately 250 μm.

As used herein, the term "inert ingredient" refers to those therapeutically inert ingredients that are well known in the art of pharmaceutical science which can be used singly or in various combinations, and include, for example, binders, diluents, lubricants, glidants, sweetening agents, antioxidants, solubilizing agents, coating agents and the like, as are disclosed in The United States Pharmacopoeia, XXII, 1990, (1989 The United States Pharmacopoeia Convention, Inc), pages 1857-1859, which is incorporated herein by reference. For example, the following inert ingredients can be utilized singly or in various combinations: binders such as gelatin, polyvinylpyrrolidone (PVP), pregelatinized starch, providone, cellulose derivatives including methyl cellulose, carboxymethyl cellulose, hydroxypropyl methyl cellulose, carboxymethyl cellulose, hydroxypropyl methyl cellulose (HPMC), hydroxy cellulose (HPC), sucrose and the like; diluents such as calcium carbonate, lactose, starch, microcrystalline cellulose, and the like; lubricants such as magnesium stearate, calcium stearate, zinc stearate, stearic acid, talc, hydrogenated vegetable oil and the like; glidants such as silicon dioxide, talc and the like; disintegrants such as alginic acid, methacrylic acid, DVB, cross-linked PVP, microcrystalline cellulose, croscarmellose sodium, crospovidone, polacrilin potassium, sodium starch glycolate, starch, pregelatinized starch and the like. A preferred combination of inert ingredients comprises lactose monohydrate, microcrystalline cellulose, croscarmellose sodium, colloidal silicon dioxide and magnesium stearate.

A preferred pharmaceutical composition according to the present invention is as follows:

| Component | % wt/wt |
|---|---|
| (R)-α-(2,3-dimethoxyphenyl)-1-[2-(4-fluorophenyl)ethyl]-4-piperidinemethanol (3) | from about 3 wt/wt % to about 15 wt/wt % |
| lactose monohydrate | from about 50 wt/wt % to about 90 wt/wt % |
| microcrystalline cellulose | from about 3 wt/wt % to about 15 wt/wt % |
| croscarmellose sodium | from about 2 wt/wt % to about 10 wt/wt % |
| colloidal silicon dioxide | from about 0.1 wt/wt % to about 1 wt/wt % |
| magnesium stearate | from about 0.1 wt/wt % to about 2 wt/wt % |

A more preferred pharmaceutical composition according to the present invention is as follows:

| Component | % wt/wt |
|---|---|
| (R)-α-(2,3-dimethoxyphenyl)-1-[2-(4-fluorophenyl)ethyl]-4-piperidinemethanol (3) | from about 4 wt/wt % to about 11 wt/wt % |
| lactose monohydrate | from about 70 wt/wt % to about 85 wt/wt % |
| microcrystalline cellulose | from about 5 wt/wt % to about 11 wt/wt % |
| croscarmellose sodium | from about 3 wt/wt % to about 6 wt/wt % |
| colloidal silicon dioxide | from about 0.2 wt/wt % to about 0.5 wt/wt % |
| magnesium stearate | from about 0.4 wt/wt % to about 0.8 wt/wt % |

A still more preferred pharmaceutical composition according to the present invention is as follows:

| Component | % wt/wt |
|---|---|
| (R)-α-(2,3-dimethoxyphenyl)-1-[2-(4-fluorophenyl)ethyl]-4-piperidinemethanol (3) | about 5 wt/wt % |
| lactose monohydrate | about 79 wt/wt % |
| microcrystalline cellulose | about 10 wt/wt % |
| croscarmellose sodium | about 5 wt/wt % |
| colloidal silicon dioxide | about 0.4 wt/wt % |
| magnesium stearate | about 0.5 wt/wt % |

Another more preferred pharmaceutical composition according to the present invention is as follows:

| Component | % wt/wt |
|---|---|
| (R)-α-(2,3-dimethoxyphenyl)-1-[2-(4-fluorophenyl)ethyl]-4-piperidinemethanol (3) | about 10 wt/wt % |
| lactose monohydrate | about 74 wt/wt % |
| microcrystalline cellulose | about 10 wt/wt % |
| croscarmellose sodium | about 5 wt/wt % |
| colloidal silicon dioxide | about 0.4 wt/wt % |
| magnesium stearate | about 0.5 wt/wt % |

Another more preferred pharmaceutical composition according to the present invention is as follows:

| Component | % wt/wt |
|---|---|
| (R)-α-(2,3-dimethoxyphenyl)-1-[2-(4-fluorophenyl)ethyl]-4-piperidinemethanol (3) | about 6 wt/wt % |

| Component | % wt/wt |
| --- | --- |
| lactose monohydrate | about 83 wt/wt % |
| microcrystalline cellulose | about 6 wt/wt % |
| croscarmellose sodium | about 3 wt/wt % |
| colloidal silicon dioxide | about 0.2 wt/wt % |
| magnesium stearate | about 0.75 wt/wt % |

Another more preferred pharmaceutical composition according to the present invention is as follows:

| Component | % wt/wt |
| --- | --- |
| (R)-α-(2,3-dimethoxyphenyl)-1-[2-(4-fluorophenyl)ethyl]-4-piperidinemethanol (3) | about 7 wt/wt % |
| lactose monohydrate | about 80 wt/wt % |
| microcrystalline cellulose | about 7 wt/wt % |
| croscarmellose sodium | about 4 wt/wt % |
| colloidal silicon dioxide | about 0.3 wt/wt % |
| magnesium stearate | about 0.75 wt/wt % |

Another more preferred pharmaceutical composition according to the present invention is as follows:

| Component | % wt/wt |
| --- | --- |
| (R)-α-(2,3-dimethoxyphenyl)-1-[2-(4-fluorophenyl)ethyl]-4-piperidinemethanol (3) | 5 |
| Lactose Monohydrate | 79.1 |
| Microcrystalline Cellulose | 10 |
| Croscarmellose Sodium | 5 |
| Colloidal Silicon Dioxide | 0.4 |
| Magnesium Stearate | 0.5 |

Another more preferred pharmaceutical composition according to the present invention is as follows:

| Component | % wt/wt |
| --- | --- |
| (R)-α-(2,3-dimethoxyphenyl)-1-[2-(4-fluorophenyl)ethyl]-4-piperidinemethanol (3) | 9.963 |
| Lactose Monohydrate | 74.2 |
| Microcrystalline Cellulose | 9.963 |
| Croscarmellose Sodium | 4.981 |
| Colloidal Silicon Dioxide | 0.3736 |
| Magnesium Stearate | 0.4981 |

Another more preferred pharmaceutical composition according to the present invention is as follows:

| Component | % wt/wt |
| --- | --- |
| (R)-α-(2,3-dimethoxyphenyl)-1-[2-(4-fluorophenyl)ethyl]-4-piperidinemethanol (3) | 6.25 |
| Lactose Monohydrate | 83.39 |
| Microcrystalline Cellulose | 6.25 |
| Croscarmellose Sodium | 3.125 |
| Colloidal Silicon Dioxide | 0.2344 |
| Magnesium Stearate | 0.75 |

Another more preferred pharmaceutical composition according to the present invention is as follows:

| Component | % wt/wt |
| --- | --- |
| (R)-α-(2,3-dimethoxyphenyl)-1-[2-(4-fluorophenyl)ethyl]-4-piperidinemethanol (3) | 7.692 |
| Lactose Monohydrate | 79.73 |
| Microcrystalline Cellulose | 7.692 |
| Croscarmellose Sodium | 3.846 |
| Colloidal Silicon Dioxide | 0.2885 |
| Magnesium Stearate | 0.75 |

As stated previously, in all the above compositions, the (R)-α-(2,3-dimethoxyphenyl)-1-[2-(4-fluorophenyl)ethyl]-4-piperidinemethanol (3) in the composition may have an unspecified particle size or may have a particle size range of approximately 25 μm to approximately 250 μm.

When the pharmaceutical compositions of the present invention are in solid unit dosage form, such a tablets, content uniformity of the composition is desirable. Since improved solid unit dosage form content uniformity results when the particle size distribution of the drug substance approximates the particle size distribution of the excipients used, the most preferred (R)-α-(2,3-dimethoxyphenyl)-1-[2-(4-fluorophenyl)ethyl]-4-piperidinemethanol (3) particle size distribution for formulation into solid unit dosage composition, such as tablets, is one wherein the particle size distribution of the (R)-α-(2,3-dimethoxyphenyl)-1-[2-(4-fluorophenyl)ethyl]-4-piperidinemethanol (3) approximates the particle size distribution of the excipients used in formulating the tablet.

For example, as shown above, the preferred pharmaceutical compositions of the present invention comprise lactose monohydrate as a major component. In any given amount of lactose monohydrate, not less than approximately 50 wt % of the lactose monohydrate is typically present as particles which are between approximately 75 μm and approximately 250 μm in size. Therefore, since improved tablet content uniformity results when the particle size distribution of the drug substance approximates the particle size distribution of the excipients used, it is preferred that, in compositions of the present invention comprising lactose monohydrate as a major component, not less than approximately 50 wt % of the (R)-α-(2,3-dimethoxyphenyl)-1-[2-(4-fluorophenyl)ethyl]-4-piperidinemethanol (3) have a particle size between approximately 75 μm and approximately 250 μm.

Therefore, the present invention also provides an optional crystallization techniques whereby (R)-α-(2,3-dimethoxyphenyl)-1-[2-(4-fluorophenyl)ethyl]-4-piperidinemethanol (3) with a particle size range of from about 25 μm and approximately 250 μm, including (R)-α-(2,3-dimethoxyphenyl)-1-[2-(4-fluorophenyl)ethyl]-4-piperidinemethanol (3) with not less than approximately 50 wt % of its particles within the size range between approximately 75 μm and approximately 250 μm in size, may be prepared.

This crystallization technique typically provides (R)-α-(2,3-dimethoxyphenyl)-1-[2-(4-fluorophenyl)ethyl]-4-piperidinemethanol (3) having a particle size range of from approximately 25 μm to approximately 250 μm, more typically having a particle size range of from approximately 30 μm to approximately 240 μm, and most typically and most preferred, having a particle size range of from approximately 38 μm to approximately 224 μm. The (R)-α-(2,3-dimethoxyphenyl)-1-[2-(4-fluorophenyl)ethyl]-4-piperidinemethanol (3) so crystallized also typically demonstrates a particle size distribution wherein typically, approximately 3 wt % to approximately 60 wt % of the material has a particle size of less than about 45 µm, approximately 0.5 wt % to approximately 60 wt % of the material has a particle size of greater than about 90 µm, and approximately 25 wt % to approximately 85 wt % of the material has a particle size range of from about 45 µm to about 90 µm. More typically, the distribution is approximately 5 wt % to approximately 55 wt % of the material having a particle size of less than about 40 µm, approximately 1 wt % to approximately 55 wt % of the material having a particle size of greater than 95 µm, and approximately 30 wt % to approximately 80 wt % of the material having a particle size range of from about 40 µm to about 95 µm. Most typically and most preferred, the distribution is approximately 8 wt % to approximately 53 wt % of the material having a particle size range less than about 38 µm; from approximately 33 wt % to approximately 78 wt % of the material having a particle size range between about 38 µm to about 101 µm, and approximately 2 wt % to approximately 50 wt % of the material having a particle size range of from about 101 µm to about 224 µm.

This crystallization procedure is performed in two stages. First, about 4% to about 20% of the (R)-α-(2,3-dimethoxyphenyl)-1-[2-(4-fluorophenyl)ethyl]-4-piperidinemethanol (3) is used to produce seed crystals through crystallization at high supersaturation and the solvent composition is adjusted (without dissolving the seed crystals) so that as the remaining (R)-α-(2,3-dimethoxyphenyl)-1-[2-(4-fluorophenyl)ethyl]-4-piperidinemethanol (3) is added it crystallizes on the existing seed crystals. Second, a concentrated solution of (R)-α-(2,3-dimethoxyphenyl)-1-[2-(4-fluorophenyl)ethyl]-4-piperidinemethanol (3) is added to the seed crystals such that the solvent composition and temperature change generate supersaturation which is relieved by crystallization on the existing seeds.

For example, first, in one vessel, using from approximately 4% to approximately 20% of the (R)-α-(2,3-dimethoxyphenyl)-1-[2-(4-fluorophenyl)ethyl]-4-piperidinemethanol (3) to be crystallized, a saturated solution of (R)-α-(2,3-dimethoxyphenyl)-1-[2-(4-fluorophenyl)ethyl]-4-piperidinemethanol (3) containing seed crystals of the (R)-α-(2,3-dimethoxyphenyl)-1-[2-(4-fluorophenyl)ethyl]-4-piperidinemethanol (3) is formed (Solution 1). Next, the remainder of the (R)-α-(2,3-dimethoxyphenyl)-1-[2-(4-fluorophenyl)ethyl]-4-piperidinemethanol (3) is thermally dissolved in a solvent wherein the (R)-α-(2,3-dimethoxyphenyl)-1-[2-(4-fluorophenyl)ethyl]-4-piperidinemethanol (3) exhibits a high degree of solubility at moderate temperature (i.e., temperatures from about 35° C. to about 75° C.) such that the solvent chosen will produce a supersaturated solution when combined with the seed crystals present in Solution 1 and which is otherwise suitable for recrystallization of the (R)-α-(2,3-dimethoxyphenyl)-1-[2-(4-fluorophenyl)ethyl]-4-piperidinemethanol (3), such as aqueous isopropanol, thereby forming Solution 2. Next, Solution 2 is added to Solution 1, adjusting the solvent composition as needed by the addition of a suitable antisolvent, such as water, to maintain an acceptable yield by minimizing solubility at the isolation temperature. The dissolved (R)-α-(2,3-dimethoxyphenyl)-1-[2-(4-fluorophenyl)ethyl]-4-piperidinemethanol (3) is then allowed to grow on the existing seed crystals. As used herein, the term "antisolvent" refers to a poor solvent for the substance in question which, when added to a solution of the substances, causes the substance to precipitate or otherwise become less soluble.

Solution 1 may be prepared by first dissolving approximately 1% to approximately 6% of the (R)-α-(2,3-dimethoxyphenyl)-1-[2-(4-fluorophenyl)ethyl]-4-piperidinemethanol (3) to be crystallized in a suitable solvent wherein the (R)-α-(2,3-dimethoxyphenyl)-1-[2-(4-fluorophenyl)ethyl]-4-piperidinemethanol (3) exhibits a relatively high level of solubility, such as methanol (Solution 3). Solution 3 and a suitable antisolvent, such as water, are then merged, preferably by continuously feeding both Solution 3 and the antisolvent into a separate vessel, preferably at constant rate and constant ratio, thereby forming Solution 4. Secondly, in a separate vessel, approximately 3% to approximately 12% of the (R)-α-(2,3-dimethoxyphenyl)-1-[2-(4-fluorophenyl)ethyl]-4-piperidinemethanol (3) to be crystallized is dissolved in a solvent wherein the (R)-α-(2,3-dimethoxyphenyl)-1-[2-(4-fluorophenyl)ethyl]-4-piperidinemethanol (3) exhibits a lesser degree of solubility than the solvent used in Solution 2, such as isopropanol, thereby forming Solution 5. Thirdly, Solution 5 is added to Solution 4, forming the saturated solution containing seed crystals (Solution 1).

Alternatively, Solution 1 may be prepared by first dissolving approximately 1% to approximately 6% of the (R)-α-(2,3-dimethoxyphenyl)-1-[2-(4-fluorophenyl)ethyl]-4-piperidinemethanol (3) to be crystallized in a suitable solvent wherein the (R)-α-(2,3-dimethoxyphenyl)-1-[2-(4-fluorophenyl)ethyl]-4-piperidinemethanol (3) exhibits a relatively high level of solubility, such as methanol (Solution 3). Solution 3 and a suitable antisolvent, such as water, are then merged, preferably by continuously feeding both Solution 3 and the antisolvent into a separate vessel, preferably at constant rate and constant ratio, thereby forming Solution 4. The precipitate of small crystals which forms in Solution 4 is isolated by filtration. Secondly, in a separate vessel, approximately 3% to approximately 12% of the (R)-α-(2,3-dimethoxyphenyl)-1-[2-(4-fluorophenyl)ethyl]-4-piperidinemethanol (3) to be crystallized is dissolved in a solvent wherein the (R)-α-(2,3-dimethoxyphenyl)-1-[2-(4-fluorophenyl)ethyl]-4-piperidinemethanol (3) exhibits a lesser degree of solubility than the solvent used in Solution 2, such as isopropanol, thereby forming Solution 5. Thirdly, the seed crystals isolated from Solution 4 are added to Solution 5, forming the saturated solution containing seed crystals (Solution 1).

In a typical manufacturing process, tablets containing (R)-α-(2,3-dimethoxyphenyl)-1-[2-(4-fluorophenyl)ethyl]-4-piperidinemethanol (3) may be prepared by the following procedure, all components being screened prior to manufacturing: 1) a preblend comprised of (R)-α-(2,3-dimethoxyphenyl)-1-[2-(4-fluorophenyl)ethyl]-4-piperidinemethanol (3) and a portion of the total lactose is prepared by addition of (R)-α-(2,3-dimethoxyphenyl)-1-[2-(4-fluorophenyl)ethyl]-4-piperidinemethanol (3) and the lactose to a suitable blender and blending; 2) adding approximately one half of the remaining lactose to another suitable blender and adding croscarmellose sodium, cellulose (preferably microcrystalline cellulose), and the preblend mixture to the blender, followed by the remaining lactose; 3) blending the excipients and the preblend; 4) adding magnesium stearate and colloidal silicon dioxide to the blender; 5) blending the ingredients; and 6) compressing the final blend into tablets. A film coat may then be applied to the tablets. The portion of total lactose utilized in step 1) is typically from about 15 wt/wt % to about 40 wt/wt % and is more typically from about 20 wt/wt % to about 30 wt/wt % of the total lactose utilized in the composition.

For example, about 28 wt/wt % of the total lactose is added in step 1) and the remaining approximate 51 wt/wt % of the approximate 79 wt/wt % total is added in step 2) in the following composition:

| Component | % wt/wt |
| --- | --- |
| (R)-α-(2,3-dimethoxyphenyl)-1-[2-(4-fluorophenyl)ethyl]-4-piperidinemethanol (3) | about 5 wt/wt % |
| lactose monohydrate | about 79 wt/wt %<br>(about 28 wt/wt % in step 1)<br>and about 51% in step 2) |
| microcrystalline cellulose | about 10 wt/wt % |
| croscarmellose sodium | about 5 wt/wt % |
| colloidal silicon dioxide | about 0.4 wt/wt % |
| magnesium stearate | about 0.5 wt/wt % |

In another example, about 23 wt/wt % of the total lactose is added in step 1) and the remaining approximate 51 wt/wt % of the approximate 74 wt/wt % total is added in step 2) in the following composition:

| Component | % wt/wt |
| --- | --- |
| (R)-α-(2,3-dimethoxyphenyl)-1-[2-(4-fluorophenyl)ethyl]-4-piperidinemethanol (3) | about 10 wt/wt % |
| lactose monohydrate | about 74 wt/wt %<br>(about 23 wt/wt % in step 1)<br>and about 51% in step 2) |
| microcrystalline cellulose | about 10 wt/wt % |
| croscarmellose sodium | about 5 wt/wt % |
| colloidal silicon dioxide | about 0.4 wt/wt % |
| magnesium stearate | about 0.5 wt/wt % |

In another typical manufacturing process, tablets containing (R)-α-(2,3-dimethoxyphenyl)-1-[2-(4-fluorophenyl) ethyl]-4-piperidinemethanol (3) may be prepared by the following procedure, all components being screened prior to manufacturing: 1) a preblend comprised of (R)-α-(2,3-dimethoxyphenyl)-1-[2-(4-fluorophenyl)ethyl]-4-piperidinemethanol (3), lactose, microcrystalline cellulose, croscarmellose sodium and colloidal silicon dioxide is prepared by addition of (R)-α-(2,3-dimethoxyphenyl)-1-[2-(4-fluorophenyl)ethyl]-4-piperidinemethanol (3), lactose, microcrystalline cellulose, croscarmellose sodium and colloidal silicon dioxide to a suitable blender and blending; 2) screening the preblend through a sieve into another blender and blending; 3) screening magnesium stearate into the blender containing the screened preblend and blending; and 4) compressing the final blend into tablets. A film coat may then be applied to the tablets.

What is claimed is:

1. A process for preparing 4-[1-hydroxy-1-(2,3-dimethoxyphenyl)methyl]-N-2-(4-fluorophen-1-oxo-ethyl)piperidine comprising the steps of:

a) subjecting 4-[1-hydroxy-1-(2,3-dimethoxyphenyl)methyl]pyridine to catalytic hydrogenation to provide 4-[1-hydroxy-1-(2,3-dimethoxyphenyl)methyl]piperidine; and b) reacting 4-[1-hydroxy-1-(2,3-dimethoxyphenyl)methyl]piperidine with a suitable 4-fluorophenylacetylating reagent, in the presence of a suitable base and a suitable solvent to provide 4-[1-hydroxy-1-(2,3-dimethoxyphenyl)methyl]-N-2-(4-fluorophen-1-oxo-ethyl)piperidine.

2. A compound which is 4-[1-hydroxy-1-(2,3-dimethoxyphenyl)methyl]-N-2-(4-fluorophen-1-oxo-ethyl)piperidine.

* * * * *